(12) United States Patent
Hui et al.

(10) Patent No.: US 10,174,038 B2
(45) Date of Patent: *Jan. 8, 2019

(54) COMPOUNDS AND METHODS FOR ANTIVIRAL TREATMENT

(71) Applicant: Gilead Sciences, Inc., Foster City, CA (US)

(72) Inventors: Hon Chung Hui, Foster City, CA (US); Jay P. Parrish, El Dorado Hills, CA (US); Michael Sangi, San Mateo, CA (US); Dustin Siegel, Half Moon Bay, CA (US); David Sperandio, Palo Alto, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,974

(22) Filed: Jun. 9, 2017

(65) Prior Publication Data

US 2017/0342079 A1 Nov. 30, 2017

Related U.S. Application Data

(60) Continuation of application No. 15/191,974, filed on Jun. 24, 2016, now abandoned, which is a continuation of application No. 14/635,830, filed on Mar. 2, 2015, now Pat. No. 9,504,689, which is a division of application No. 13/865,069, filed on Apr. 17, 2013, now Pat. No. 8,980,878.

(60) Provisional application No. 61/625,480, filed on Apr. 17, 2012.

(51) Int. Cl.
| | | |
|---|---|---|
| *A61K 31/397* | (2006.01) | |
| *C07D 487/04* | (2006.01) | |
| *C07D 519/00* | (2006.01) | |
| *C07D 471/04* | (2006.01) | |
| *A61K 45/06* | (2006.01) | |
| *A61K 31/4545* | (2006.01) | |
| *A61K 31/5025* | (2006.01) | |
| *A61K 31/519* | (2006.01) | |
| *A61K 31/53* | (2006.01) | |
| *A61K 31/5377* | (2006.01) | |

(52) U.S. Cl.
CPC ........ *C07D 487/04* (2013.01); *A61K 31/4545* (2013.01); *A61K 31/5025* (2013.01); *A61K 31/519* (2013.01); *A61K 31/53* (2013.01); *A61K 31/5377* (2013.01); *A61K 45/06* (2013.01); *C07D 471/04* (2013.01); *C07D 519/00* (2013.01)

(58) Field of Classification Search
CPC .................................................. C07D 401/12
USPC .............. 514/210.2; 544/281, 230
See application file for complete search history.

(56) References Cited

U.S. PATENT DOCUMENTS

| | | | |
|---|---|---|---|
| 6,342,501 B1 | 1/2002 | Townsend et al. | |
| 7,304,068 B2 | 12/2007 | Gudmundsson et al. | |
| 8,486,938 B2 | 7/2013 | Babaoglu et al. | |
| 8,809,330 B2 | 8/2014 | Babaoglu et al. | |
| 8,946,238 B2 | 2/2015 | Boojamra et al. | |
| 8,980,878 B2 * | 3/2015 | Siegel ................... | C07D 487/04 514/210.2 |
| 9,238,039 B2 | 1/2016 | Babaoglu et al. | |
| 9,278,975 B2 | 3/2016 | Sangi | |
| 9,504,689 B2 * | 11/2016 | Siegel ................... | C07D 487/04 |
| 2004/0038993 A1 | 2/2004 | Shipps et al. | |
| 2007/0287700 A1 | 12/2007 | Bond et al. | |
| 2010/0215616 A1 | 8/2010 | Romine et al. | |
| 2010/0316607 A1 | 12/2010 | Or et al. | |
| 2011/0319412 A1 | 12/2011 | Sakagami et al. | |
| 2013/0164280 A1 | 6/2013 | Boojamra et al. | |
| 2013/0273037 A1 | 10/2013 | Siegel et al. | |
| 2014/0072554 A1 | 3/2014 | Babaoglu et al. | |
| 2014/0154240 A1 | 6/2014 | Babaoglu et al. | |
| 2015/0166546 A1 | 6/2015 | Boojamra et al. | |

FOREIGN PATENT DOCUMENTS

| | | |
|---|---|---|
| CN | 1297447 A | 5/2001 |
| DE | 10247271 A1 | 8/2004 |
| WO | WO-95/23151 A1 | 8/1995 |
| WO | WO-1996/00730 A1 | 1/1996 |
| WO | WO-1999/41253 A1 | 8/1999 |
| WO | WO-2000/42043 A1 | 7/2000 |
| WO | WO-2001/46189 A1 | 6/2001 |
| WO | WO-2003/078435 A1 | 9/2003 |
| WO | WO-2003/095455 A2 | 11/2003 |
| WO | WO 2005/061513 A1 | 7/2005 |
| WO | WO-2007/077186 A1 | 7/2007 |

(Continued)

OTHER PUBLICATIONS

"Chemivate Limited Screening Compounds," Chemivate Limited, Jun. 2007 (Jun. 2007) XP002708502, retrieved from the Internet: URL:http://chemivate.com/chemivate/Downloads/ChemivateJun07.pdf [retrieved on Aug. 1, 2013].
2nd Notice of Allowance and Fee(s) Due dated Apr. 14, 2014 for U.S. Appl. No. 14/069,685.
2nd Notice of Allowance and Fee(s) Due dated Jan. 21, 2015 for U.S. Appl. No. 13/905,410.
Asinex Compounds (Nov. 2008-Mar. 2011) Aisnex Ltd., 20 Geroev Panfilovtzev Str., Bldg. 1, Moscow 125480, Russia, 27 pages.
Boulatov, Roman et al., "Functional Analogues of the Dioxygen Reduction Site in Cytochrome Oxidase: Mechanistic Aspects and Possible Effects of CuB," J. Am. Soc. 124(10):11923-11935, 2002.
Chapman, J. et al. (2007) "RSV604, a Novel Inhibitor of Respiratory Syncytial Virus Replication", *Antimicrobial Agents and Chemotherapy*, vol. 51, No. 9, pp. 3346-3353.

(Continued)

*Primary Examiner* — Rei Tsang Shiao

(57) ABSTRACT

Compounds and pharmaceutically acceptable salts and esters and compositions thereof, for treating viral infections are provided. The compounds and compositions are useful for treating Pneumovirinae virus infections. The compounds, compositions, and methods provided are particularly useful for the treatment of Human respiratory syncytial virus infections.

20 Claims, No Drawings

(56) References Cited

FOREIGN PATENT DOCUMENTS

| WO | WO-2008/070447 A2 | 6/2008 |
|---|---|---|
| WO | WO-2009/076679 A2 | 6/2009 |
| WO | WO-2009/079011 A1 | 6/2009 |
| WO | WO-2009/106539 A1 | 9/2009 |
| WO | WO-2009/126691 A1 | 10/2009 |
| WO | WO-2010/033701 A2 | 3/2010 |
| WO | WO-2010/048950 A1 | 5/2010 |
| WO | WO-20101065674 A1 | 6/2010 |
| WO | WO 2010/075376 A2 | 7/2010 |
| WO | WO-2010/080357 A1 | 7/2010 |
| WO | WO-2010099527 A1 | 9/2010 |
| WO | WO-2010101246 A | 9/2010 |
| WO | WO-2010144646 A2 | 12/2010 |
| WO | WO-2010148006 A1 | 12/2010 |
| WO | WO-2011/015658 A1 | 2/2011 |
| WO | WO-2011059887 A1 | 5/2011 |
| WO | WO-2011099832 A2 | 8/2011 |
| WO | WO-2011/149856 A1 | 12/2011 |
| WO | WO-2011/163518 A1 | 12/2011 |
| WO | WO-2012/012776 A1 | 1/2012 |
| WO | WO-2013/096681 A1 | 6/2013 |
| WO | WO-2013/158776 A1 | 10/2013 |

OTHER PUBLICATIONS

Cihlar, T. et al. (2008) "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131", *Antimicrobial Agents and Chemotherapy*, vol. 52, No. 2, pp. 655-665.
Cockerill, G. Stuart et al., "The discovery and development of a novel inhibitor of RSV," Division of Medicinal Chemistry Program, 231st ACS National Meeting, Atlanta, GA, 2006.
Communication pursuant to Article 94(3), dated Jan. 18, 2017, for EP Patent Application No. 15195216.5.
Communication pursuant to Article 94(3) EPC for EP Application No. 11729018.9, dated May 23, 2014.
Communication pursuant to Article 94(3), dated Jul. 14. 2017, for EP Application No. 15195216.5.
Communication pursuant to Rules 161(1) and 162 EPC dated Aug. 7, 2014, for EP Patent Application No. 12814092.8.
Communication under Rule 71(3) EPC for EP Application No. 11729018.9, dated Jul. 8, 2015.
Completion of final requirements dated Dec. 23, 2014, for Philippines Application No. 1-2012-502528.
Completion of final requirements dated Mar. 12, 2015, for Philippines Application No. 1-2012-502528.
Dall'Aqua, William F. et al. "Properties of Human IgG1s Engineered for Enhanced Binding to the Neonatal Fc Receptor (FcRn)," *The Journal of Biological Chemistry*; 281(33):23514-23524, 2006.
Dominy, Jr., John E, "Synthesis of Amino Acid Cofactor in Cysteine Dioxygenase Is Regulated by Substrate and Represents a Novel Post-translational Regulation of Activity," Journal of Biological Chemistry, 283(18):12188-12201, 2008.
Douglas et al., "Small Molecules VP-14637 and JNJ-2408068 Inhibit Respiratory Syncytial Virus Fusion by Similar Mechanisms," Antimicrobial Agents and Chemotherapy 49(6):2460-2468, 2005.
EPO Communication in EP Application No. EP 13718996.5 dated Dec. 23, 2014.
Eurasian 2nd Office Action for EA Patent Application No. 201291172 (with English translation), dated Jun. 10, 2014.
Eurasian 3rd Office Action for EA Patent Application No. 201291172 (with English translation), dated Jan. 16, 2015.
Eurasian Office Action for EA Patent Application No. 201291172, dated Feb. 3, 2015.
Eurasian Office Action for EA Patent Application No. 201591390, dated Sep. 15, 2017.
Eurasian Office Action for EA Patent Application No. 201291172 (with English translation), dated Jan. 10, 2014.
Final Office Action dated Aug. 11, 2016, for U.S. Appl. No. 14/995,486.
Final Rejection, dated Aug. 4, 2014, for U.S. Appl. No. 13/865,069.
First Examination Report dated Feb. 27, 2015 for New Zealand Application No. 704655.
First Examination Report dated Jun. 28, 2016 for New Zealand Application No. 720869.
First Examination Report for New Zealand Application No. 625737 dated Mar. 27, 2015.
First Examination Report for NZ Patent Application No. 604345, dated Aug. 9, 2013.
First Examination Report for NZ Patent Application No. 704655, dated Feb. 27, 2015.
Further Examination Report dated Jun. 28, 2016 for New Zealand Application No. 704655.
Further Examination Report for NZ Patent Application No. 604345, dated Nov. 24, 2014.
Grimes, K., e.t al., (2010), "Copper(II)-Catalyzed Conversion of Aryl/Heteroaryl Boronic Acids, Boronates, and Trifluoroborates into the Corresponding Azides: Substrate Scope and Limitations", *Synthesis*, 9:1441-1448.
International Preliminary Report on Patentability for PCT International Application No. PCT/US2011/041688, dated Dec. 28, 2012.
International Preliminary Report on Patentability for PCT International Application No. PCT/US2012/071065, dated Jul. 3, 2014 (9 pages).
International Preliminary Report on Patentability for PCT International Application No. PCT/US2013/037001, dated Oct. 30, 2014. (10 pages).
International Search Report and Written Opinion for International Patent Application No. PCT/US2011/041688, dated Sep. 30, 2011.
International Search Report and Written Opinion for PCT International Application No. PCT/US2013/037001, dated Aug. 29, 2013 (13 pages).
International Search Report for PCT International Application No. PCT/US2012/071065, dated Mar, 11, 2013 (3 pages).
JP Application No. 2013-516776, Office Action dated Apr. 15, 2015 (English translation).
Morrison et al., "Salts of Amines," Organic Chemistry, 6th Edition, p. 823, 1992.
Notice of Allowability dated Jun. 18, 2013 for U.S. Appl. No. 13/167,618.
Notice of Allowability dated May 27, 2014 for U.S. Appl. No. 14/069,685.
Notice of Allowance and Fee(s) Due dated Dec. 13, 2013 for U.S. Appl. No. 14/069,685.
Notice of Allowance and Fee(s) Due dated Nov. 10, 2014 for U.S. Appl. No. 13/905,410.
Notice of Allowance and Fee(s) Due dated Sep. 10, 2014 for U.S. Appl. No. 13/722,962.
Notice of Allowance and Fees Due, dated Jan. 21, 2015, for U.S. Appl. No. 13/905,410.
Notice of Allowance and Fees Due, dated Oct. 22, 2014, for U.S. Appl. No. 13/865,069.
Notice of Allowance dated Mar. 12, 2013 for U.S. Appl. No. 13/167,618.
Notice of Allowance and Fee(s) Due dated Jun. 29, 2015 for U.S. Appl. No. 14/566,340.
Notice of Reasons for Rejection, dated Apr. 15, 2015, for Japanese Application No. 2013-516776.
Notification of Defects in Patent Application No. 223253, dated Aug. 11, 2014.
Notification of readiness to grant a Eurasian Patent for EA Patent Application No. 2012291172, dated Apr. 20, 2015.
Notification of the First Office Action, dated Mar. 3, 2014, for CN Patent Application No. 201180030620.4 (with English translation).
Notification of the Second Office Action, dated Nov. 4, 2014, for CN Patent Application No. 201180030620.4 (with English translation).
Notification of the Third Office Action, dated Apr. 27, 2015 for CN Patent Application No. 201180030620.4 (with English translation), 11 pages.
Notification Prior to Examination for Israeli Patent Application No. 235062, dated Jan. 1, 2015.

(56) References Cited

OTHER PUBLICATIONS

Office Action dated Feb. 9, 2016 for Chilean App. No. 3632-12.
Office Action dated Nov. 28, 2016 for Peruvian Application No. 002481-2012.
Office Action for Columbian Patent Application No. 12-217.437 dated Jan. 3, 2014.
Office Action for MX Patent Application No. MX/a/2012/015292, dated Mar. 31, 2014.
Office Action issued by the Bolivian Patent Office for Application No. Application No. SP-0188-2011, dated Apr. 21, 2015—Non-English w/Agent Summary.
Office action Issued by the Ukranian Patent Office for Application No. Application No. a 2012 13827, dated Jul. 7, 2015; 6 pages (with English translation).
Office Action dated Apr. 11, 2017 for U.S. Appl. No. 15/347,494, 19 pages.
Office Action dated Apr. 20, 2016, for U.S. Appl. No. 14/995,486.
Office Acton dated Dec. 4, 2012 for U.S. Appl. No. 13/167,618.
Office Action dated Mar. 12, 2014 for U.S. Appl. No. 13/905,410.
Office Action dated Nov. 23, 2016 for TW Application No. 105109583.
Office Action dated Oct. 16, 2015 for TW Application No. 103145818.
Office Action dated Sep. 2, 2014 for U.S. Appl. No. 13/905,410.
Office Action, dated Jul. 13, 2017, for Canadian Patent Application No. 2880834.
Office Action, dated Jul. 28, 2016, for Chilean Application No. 2012-003632.
Office Action, dated Mar. 17, 2014, for U.S. Appl. No. 13/865,069.
Office Action, dated Apr. 2, 2015 for CL Application No. CL3632-2012 (5 pages) (in SP).
Office Action, dated Jul. 7, 2015, for Ukranian Application No. 2012-13827.
Pakistan Examination Report for Pakistan Patent Application No. 469/2011, dated Jul. 26, 2012 (2 pages).
Pandey, Gunjart et al., "Branching of o-nitrobenzoate degradation pathway in Arthrobacter protophormiae RKJI 00: identification of new intermediates," *FEMS Microbiology Letters* 229(2):231-236, 2003.
Patent Examination Report No. 1, dated Mar. 7, 2014, for Australian Patent Application No. 2011270798.
Patent Examination Report No. 1, dated Oct. 28, 2015, for Australian Patent Application No. 2015200638.
Patent Examination Report No. 1, dated Sep. 26, 2017, for Australian Patent Application No. 2016247174.
Patent Examination Report No. 2, dated Aug. 26, 2014, for Australian Patent Application No. 2011270798.
Restriction Requirement, dated Dec. 6, 2013, for U.S. Appl. No. 13/865,069.
Restriction Requirement, dated May 16, 2014, for U.S. Appl. No. 13/722,962.
Roymans, D., et al., (2011), "Treatment of Respiratory Synctial Virus infection: Past, Present and Future", Human Respiratory Syncytial Virus Infection, http://cdn.intechopen.com/pdfs-wm/24399.pdf, 197-234.
Sandritter, et al., (1997), "Part 1: Respiratory syncytial virus-immunoglobulin intravenous (RSV-IGIV) for respiratory syncytial viral infections", *J. Pediatric Health Care*, 11:6:284-91.
Sin, N., et al., (2009), "Part 7: Structure-Activity relationships associated with a series of isatin oxirnes that demonstrate antiviral activity in vivo", *Bioorganic & Medicinal Chemistry Letters*, 19:4857-4862.
Statement of Bolivian Opposition, Jan. 29, 2013, for BO Patent Application No. SP-0188-2011.
Substantive Examination Report for PH Patent Application No. 1/2012/502528, dated Jul. 16, 2014.
Substantive Examination Report Stage II for ID Application No. W-00201205282, dated Mar. 1, 2017.
Sun, Z. et al., (2013), "Respiratory Syncytial Virus Entry Inhibitors Targeting the F Protein", *Viruses*, 5:211-25.
Taiwan Office Action for TW Patent Application No. 100122237, dated Jun. 13, 2014.
Taiwan Office Action with Search Report (+ English translation) for TW Patent Application No. 100122237, dated Jan. 7, 2014.
Technical Report for OM Patent Application No. OM/P/2012/00246, dated Nov. 5, 2017 with English translation.
The Random House Dictionary of the English Language, Second Edition, Definition of "obligate" (1987).
Vietnam National Office of intellectual Property (NOIP)'s Opinion dated Jun. 30, 2014, with English translation for Vn Patent Application No. 1-2013-00161.
Written Opinion for PCT International Application No. PCT/US2012/071065, dated Mar. 11, 2013 (7 pages).
Wu, H. et al., In: Current Topics in Microbiology and Immunology, Dessain, S.K. (ed.), Springer-Verlag Berlin Heidelberg, p. 118, 2008.
Notification of the First office action dated May 3, 2017 for CN Application No. 2016100043400.
Database Chemcats [Online], Accession No. 0056408351, Chemical Abstract Service, Columbus, Ohio US XP0026583.04, 15 pages, 2011.
Substantive Examination Report Stage II for ID Application No. W-00201205282, dated Oct. 6, 2016.
Search Report for ARIPO Application No. AP/P/2013/006686, dated Nov. 13, 2014.

\* cited by examiner

COMPOUNDS AND METHODS FOR ANTIVIRAL TREATMENT

CROSS REFERENCE TO RELATED APPLICATION

This Application is a Continuation of application Ser. No. 15/191,974 filed on Jun. 24, 2016. Application Ser. No. 15/191,974 is a Continuation of application Ser. No. 14/635,830 filed on Mar. 2, 2015. Application Ser. No. 14/635,830 is a Division of application Ser. No. 13/865,069 filed on Apr. 17, 2013. Application Ser. No. 13/865,069 claims the benefit of U.S. Provisional Application 61/625,480 filed on Apr. 17, 2012. The entire contents of these applications are incorporated herein by reference in their entirety.

BACKGROUND OF THE INVENTION

Pneumovirinae viruses are negative-sense, single-stranded, RNA viruses that are responsible for many prevalent human and animal diseases. The Pneumovirinae sub-family of viruses is a part of the family Paramyxoviridae and includes human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (www.cdc.gov/rsv/index.html). No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, the nucleoside analog ribavirin has been approved as the only antiviral agent to treat HRSV infections but has limited efficacy. Therefore, there is a need for anti-Pneumovirinae therapeutics.

SUMMARY OF THE INVENTION

Provided herein are methods and compounds for the treatment of infections caused by the Pneumovirinae virus family.

Accordingly, one embodiment provides a compound of formula I:

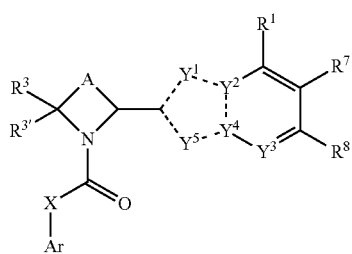

Formula I or a pharmaceutically acceptable salt thereof;
wherein:
a) $Y^1$ is N, NH or CH, $Y^2$ is C, $Y^3$ is N or $CR^{8'}$, $Y^4$ is N or C and $Y^5$ is N, $NR^{2'}$ or $CR^2$, wherein at least two of $Y^1$, $Y^2$, $Y^3$, $Y^4$ and $Y^5$ are independently N, NH or $NR^{2'}$; or b) $Y^1$ is N, NH or CH, $Y^2$ is N or C, $Y^3$ is N or $CR^{8'}$, $Y^4$ is N or C, and $Y^5$ is N or $NR^{2'}$, wherein at least two of $Y^1$, $Y^2$, $Y^3$, $Y^4$ and $Y^5$ are independently N, NH or $NR^{2'}$, or c) $Y^1$ is N, NH or CH, $Y^2$ is N or C, $Y^3$ is $CR^{8'}$, $Y^4$ is N or C, and $Y^5$ is N, $NR^{2'}$ or $CR^2$, wherein at least two of $Y^1$, $Y^2$, $Y^3$, $Y^4$ and $Y^5$ are independently N, NH or $NR^{2'}$;

the dashed bonds ---- are selected from single bonds and double bonds so as to provide an aromatic ring system;

A is $-(CR^4R^{4'})_n-$ wherein any one $CR^4R^{4'}$ of said $-(CR^4R^{4'})_n-$ may be optionally replaced with $-O-$, $-S-$, $-S(O)_p-$, NH or $NR^a$;

n is 3, 4, 5 or 6;

each p is 1 or 2;

Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1 to 5 $R^6$;

X is $-C(R^{13})(R^{14})-$, $-N(CH_2R^{14})-$ or $-NH-$, or X is absent;

$R^1$ is H, $-OR^{11}$, $-NR^{11}R^{12}$, $-NR^{11}C(O)R^{11}$, $-NR^{11}C(O)OR^{11}$, $-NR^{11}C(O)NR^{11}R^{12}$, $N_3$, CN, $NO_2$, $-SR^{11}$, $-S(O)_pR^a$, $NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $-NR^{11}C(=NR^{11})NR^{11}R^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

$R^2$ is H, CN, $NO_2$, halogen or ($C_1$-$C_8$)alkyl;

$R^{2'}$ is H or ($C_1$-$C_8$)alkyl;

$R^3$ is H, $-OR^{11}$, $-NR^{11}R^{12}$, $-NR^{11}C(O)R^{11}$, $-NR^{11}C(O)OR^{11}$, $-NR^{11}C(O)NR^{11}R^{12}$, $N_3$, CN, $NO_2$, $-SR^{11}$, $-S(O)_pR^a$, $-NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $-NR^{11}C(=NR^{11})NR^{11}R^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

$R^{3'}$ is H, $-OR^{11}$, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

each $R^4$ is independently H, $-OR^{11}$, $-NR^{11}R^{12}$, $-NR^{11}C(O)R^{11}$, $-NR^{11}C(O)OR^{11}$, $-NR^{11}C(O)NR^{11}R^{12}$, $N_3$, CN, $NO_2$, $-S(O)_pR^a$, $-NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $NR^{11}C(=NR^{11})NR^{11}R^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl; and each $R^{4'}$ is independently H, $OR^{11}$, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

or two $R^4$ on adjacent carbon atoms, when taken together, may form a double bond between the two carbons to which they are attached or may form a ($C_3$-$C_7$)cycloalkyl ring wherein one carbon atom of said ($C_3$-$C_7$)cycloalkyl ring may be optionally replaced by $-O-$, $-S-$, $-S(O)_p-$, $-NH-$ or $-NR^a-$;

or two $R^4$ on non-adjacent carbon atoms, when taken together, may form a ($C_3$-$C_7$)cycloalkyl ring wherein one carbon atom of said $(C_3-C_7)$cycloalkyl ring may be optionally replaced by —O—, —S—, —S(O)$_p$—, —NH— or —NR$^a$—;

or two R$^4$ and two R$^{4'}$ on adjacent carbon atoms, when taken together, may form an optionally substituted C$_6$ aryl ring;

or one R$^4$ and one R$^{4'}$ on the same carbon atom, when taken together, may form a $(C_3-C_7)$cycloalkyl ring wherein one carbon atom of said $(C_3-C_7)$cycloalkyl ring may be optionally replaced by —O—, —S—, —S(O)$_p$—, —NH— or —NR$^a$—;

each R$^5$ is independently H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl;

each R$^{5'}$ is independently H, —OR$^{11}$, $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl;

each R$^6$ is independently H, oxo, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl;

or two R$^6$ on adjacent carbon atoms, when taken together, may form a $(C_3-C_7)$cycloalkyl ring wherein one carbon atom of said $(C_3-C_7)$cycloalkyl ring may be optionally replaced by —O—, —S—, —S(O)$_p$—, —NH— or —NR$^a$—;

or any R$^6$ adjacent to the obligate carbonyl group of said Ar, when taken together with R$^3$, may form a bond or a —(CR$^5$R$^{5'}$)$_m$— group wherein m is 1 or 2;

or any R$^6$ adjacent to the obligate carbonyl group of said Ar, when taken together with R$^2$ or R$^{2'}$ may form a bond;

R$^7$ is H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl;

R$^8$ is H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl;

R$^{8'}$ is H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, $(C_1-C_8)$alkyl, $(C_2-C_8)$alkenyl, $(C_2-C_8)$alkynyl, aryl$(C_1-C_8)$ alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl;

each R$^a$ is independently $(C_1-C_8)$alkyl, $(C_1-C_8)$haloalkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl wherein any $(C_1-C_8)$alkyl, $(C_1-C_8)$haloalkyl, $(C_2-C_8)$alkenyl or $(C_2-C_8)$alkynyl of R$^a$ is optionally substituted with one or more OH, NH$_2$, CO$_2$H, C$_2$-C$_{20}$ heterocyclyl, and wherein any aryl$(C_1-C_8)$alkyl, C$_6$-C$_{20}$ aryl, C$_2$-C$_{20}$ heterocyclyl, $(C_3-C_7)$cycloalkyl or $(C_3-C_7)$cycloalkyl$(C_1-C_8)$alkyl of R$^a$ is optionally substituted with one or more —OH, —NH$_2$, CO$_2$H, C$_2$-C$_{20}$ heterocyclyl or $(C_1-C_8)$alkyl;

each R$^{11}$ or R$^{12}$ is independently H, $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, $(C_3-C_7)$cycloalkyl, $(C_3-C_7)$cycloalkyl$(C_1-C_8)$alkyl, —C(=O)R$^a$ or —S(O)$_p$R$^a$; or when R$^{11}$ and R$^{12}$ are attached to a nitrogen they may optionally be taken together with the nitrogen to which they are both attached to form a 3 to 7 membered heterocyclic ring wherein any one carbon atom of said heterocyclic ring can optionally be replaced with —O—, —S—, —S(O)$_p$—, —NH—, —NR$^a$— or —C(O)—;

R$^{13}$ is H or $(C_1-C_8)$alkyl;

R$^{14}$ is H, $(C_1-C_8)$alkyl, NR$^{11}$R$^{12}$, NR$^{11}$C(O)R$^{11}$, NR$^{11}$C(O)OR$^{11}$, NR$^{11}$C(O)NR$^{11}$R$^{12}$, NR$^{11}$S(O)$_p$R$^a$, —NR$^{11}$S(O)$_p$(OR$^{11}$) or NR$^{11}$SO$_p$NR$^{11}$R$^{12}$; and wherein each $(C_1-C_8)$alkyl, $(C_2-C_8)$alkenyl, $(C_2-C_8)$alkynyl, aryl$(C_1-C_8)$alkyl, C$_6$-C$_{20}$ aryl, C$_2$-C$_{20}$ heterocyclyl, C$_2$-C$_{20}$ heterocyclyl$(C_1-C_8)$alkyl, $(C_3-C_7)$cycloalkyl or $(C_3-C_7)$cycloalkyl$(C_1-C_8)$alkyl of each R$^1$, R$^2$, R$^{2'}$, R$^3$, R$^{3'}$, R$^4$, R$^{4'}$, R$^5$, R$^{5'}$, R$^6$, R$^7$, R$^8$, R$^{8'}$, R$^{11}$ or R$^{12}$ is independently, optionally substituted with one or more oxo, halogen, hydroxy, —NH$_2$, CN, N$_3$, —N(R$^a$)$_2$, —NHR$^a$, —SH, —SR$^a$, —S(O)$_p$R$^a$, —OR$^a$, $(C_1-C_8)$alkyl, $(C_1-C_8)$haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, —NHS(O)$_p$R$^a$, —NR$^a$S(O)$_p$R$^a$, —NHC(O)R$^a$, —NR$^a$C(O)R$^a$, —NHC(O)OR$^a$, —NR$^a$C(O)OR$^a$, —NR$^a$C(O)NHR$^a$, —NR$^a$C(O)N(R$^a$)$_2$, —NR$^a$C(O)NH$_2$, —NHC(O)NHR$^a$, —NHC(O)N(R$^a$)$_2$, —NHC(O)NH$_2$, =NH, =NOH, =NOR$^a$, —NR$^a$S(O)$_p$NHR$^a$, —NR$^a$S(O)$_p$N(R$^a$)$_2$, —NR$^a$S(O)$_p$NH$_2$, —NHS(O)$_p$NHR$^a$, —NHS(O)$_p$N(R$^a$)$_2$, —NHS(O)$_p$NH$_2$, —OC(=O)R$^a$, —OP(O)(OH)$_2$ or R$^a$.

One embodiment provides a compound of formulas 1-103 (i.e., compounds 1-103 as described in examples 117-218), or a salt or ester thereof.

One embodiment provides a compound of formula I (including compounds 104-122 of examples 219-237) or a stereoisomer (e.g., enantiomer, diasteromer, atropisomer) or a salt or ester thereof or a compound of formulas 1-103 or a stereoisomer (e.g., enantiomer, diasteromer, atropisomer) or a salt or ester thereof.

One embodiment provides a pharmaceutical composition comprising a compound disclosed herein or a pharmaceutically acceptable salt or ester thereof (e.g., a compound of formula I or a pharmaceutically acceptable salt thereof or ester thereof, or a compound of formulas 1-103 or a pharmaceutically acceptable salt or ester thereof), and a pharmaceutically acceptable carrier.

One embodiment provides a method of treating a Pneumovirinae infection in a mammal (e.g., a human) in need thereof by administering a therapeutically effective amount of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof).

One embodiment provides a method of treating a Pneumovirinae infection in a mammal (e.g., a human) in need thereof by administering a therapeutically effective amount of a tautomer, polymorph, pseudopolymorph, amorphous form, hydrate or solvate of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof).

One embodiment provides a method of treating a respiratory syncytial virus infection in a mammal (e.g., a human) in need thereof by administering a therapeutically effective amount of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof).

One embodiment provides a method of treating a respiratory syncytial virus infection in a mammal (e.g., a human) in need thereof by administering a therapeutically effective amount of a tautomer, polymorph, pseudopolymorph, amorphous form, hydrate or solvate of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof).

One embodiment provides a method of treating a Pneumovirinae infection (e.g., a respiratory syncytial virus infection) in a mammal (e.g., a human) in need thereof by administering a therapeutically effective amount of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof), and a pharmaceutically acceptable diluent or carrier.

One embodiment provides a method of treating a Pneumovirinae infection (e.g., a respiratory syncytial virus infection) in a mammal (e.g., a human) in need thereof by administering a therapeutically effective amount of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof), in combination with at least one additional therapeutic agent.

One embodiment provides a method of treating a Pneumovirinae infection in a mammal (e.g., a human) in need thereof, by administering a therapeutically effective amount of a combination pharmaceutical agent comprising:
a) a first pharmaceutical composition comprising a compound disclosed herein or a pharmaceutically acceptable salt or ester thereof (e.g., a compound a of formula I or a pharmaceutically acceptable salt or ester thereof, or a compound of formulas 1-103 or a pharmaceutically acceptable salt or ester thereof); and
b) a second pharmaceutical composition comprising at least one additional therapeutic agent active against infectious Pneumovirinae viruses.

One embodiment provides a method of treating a Pneumovirinae infection in a mammal (e.g., a human) in need thereof, by administering a therapeutically effective amount of a combination pharmaceutical agent comprising:
a) a therapeutic agent selected from a compound disclosed herein or a pharmaceutically acceptable salt or ester thereof (e.g., a compound a of formula I and pharmaceutically acceptable salts and esters thereof, and a compound of formulas 1-103 and pharmaceutically acceptable salts or esters thereof; and
b) a therapeutic agent active against infectious Pneumovirinae viruses.

One embodiment provides a method of treating a respiratory syncytial virus infection in a mammal (e.g., a human) in need thereof, by administering a therapeutically effective amount of a combination pharmaceutical agent comprising:
a) a first pharmaceutical composition comprising a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof); and
b) a second pharmaceutical composition comprising at least one additional therapeutic agent active against infectious respiratory syncytial viruses.

One embodiment provides a method of treating a respiratory syncytial virus infection in a mammal (e.g., a human) in need thereof, by administering a therapeutically effective amount of a combination pharmaceutical agent comprising:
a) a therapeutic agent selected from a compound disclosed herein or a pharmaceutically acceptable salt or ester thereof (e.g., a compound a of formula I and pharmaceutically acceptable salts and esters thereof and a compound of formulas 1-103 and pharmaceutically acceptable salts or esters thereof; and
b) a therapeutic agent active against infectious Pneumovirinae viruses.

One embodiment provides compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof) for use in medical therapy.

One embodiment provides a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof for use in the prophylactic or therapeutic treat a viral infection caused by a Pneumovirinae virus or a respiratory syncytial virus.

One embodiment provides the use of a compound disclosed herein or a pharmaceutically acceptable salt or ester thereof (e.g., a compound of formula I or a pharmaceutically acceptable salt or ester thereof, or a compound of formulas 1-103 or a pharmaceutically acceptable salt or ester thereof) for the manufacture of a medicament useful for the treatment of a viral infection caused by a Pneumovirinae virus or a respiratory syncytial virus.

One embodiment provides processes and novel intermediates disclosed herein which are useful for preparing a compound disclosed herein (e.g., a compound of formula I or a compound of formulas 1-103).

One embodiment provides novel methods for synthesis, analysis, separation, isolation, purification, characterization, and testing of the compounds disclosed herein.

DETAILED DESCRIPTION OF THE INVENTION

Definitions

Unless stated otherwise, the following terms and phrases as used herein are intended to have the following meanings:

When trade names are used herein, applicants intend to independently include the tradename product and the active pharmaceutical ingredient(s) of the tradename product.

The term "alkyl" refers to a straight or branched hydrocarbon. For example, an alkyl group can have 1 to 20 carbon atoms (Le, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, and octyl (—($CH_2$)$_7CH_3$).

The term "alkoxy" refers to a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—OCH$_2$CH$_3$ or —OEt), t-butoxy (—O—C($CH_3$)$_3$ or —OtBu) and the like.

The term "haloalkyl" refers to an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

The term "alkenyl" refers to a straight or branched hydrocarbon with at least one site of unsaturation, i.e., a carbon-carbon, sp$^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

The term "alkynyl" refers to a straight or branched hydrocarbon with at least one site of unsaturation, i.e., a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halogen" or "halo" refers to F, Cl, Br, or I.

The term "aryl" refers to an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

The term "arylalkyl" refers to an acyclic alkyl radical as described herein in which one of the hydrogen atoms bonded to a carbon atom, is replaced with an aryl radical as described herein. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl", unless otherwise indicated, means alkyl, alkylene, aryl, arylalkyl, heterocyclyl, carbocyclyl, respectively, in which one or more hydrogen atoms are each independently replaced with a non-hydrogen substituent. Typical substituents include, but are not limited to, —X, —$R^b$, —$O^-$, =O, —$OR^b$, —$SR^b$, —$S^-$, —$NR^b_2$, —$N^+R^b_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b_2$, —S(=O)$_2$—, —S(=O)$_2$OH, —S(=O)$_2R^b$, —OS(=O)$_2OR^b$, —S(=O)$_2NR^b_2$, —S(=O)$R^b$, —OP(=O)(O$R^b$)$_2$, —P(=O)(O$R^b$)$_2$, —P(=O)(O$^-$)$_2$, —P(=O)(OH)$_2$, —P(O)(O$R^b$)(O$^-$), —C(=O)$R^b$, —C(=O)X, —C(S)$R^b$, —C(O)O$R^b$, —C(O)O$^-$, —C(S)O$R^b$, —C(O)S$R^b$, —C(S)S$R^b$, —C(O)NR$^b_2$, —C(S)NR$^b_2$, —C(=N$R^b$)NR$^b_2$, where each X is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "heterocycle" or "heterocyclyl" as used herein includes by way of example and not limitation those heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g., 1, 2, 3, or 4) carbon atoms have been replaced with a heteroatom (e.g., O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

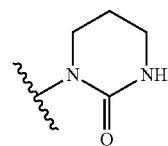 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

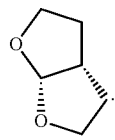

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "heterocyclyl" refers to a monocyclic heterocyclyl ring or a polycyclic heterocyclyl ring, wherein the monocyclic heterocyclyl ring or polycyclic heterocyclyl ring has between 2-20 carbon atoms in the ring system and 1, 2, 3 or 4 heteroatoms selected from oxygen, nitrogen and sulfur in the ring system, which heterocyclyl is also referred to as a $C_2$-$C_{20}$ heterocyclyl. The $C_2$-$C_{20}$ heterocyclyl can be saturated, partially unsaturated or aromatic. The rings of a polycyclic $C_2$-$C_{20}$ heterocyclyl can be connected to one another by fused, bridged or spiro bonds.

The term "heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

The term "heterocyclylalkyl" refers to an acyclic alkyl radical as described herein in which one of the hydrogen atoms bonded to a carbon atom is replaced with a heterocyclyl radical as described herein. It is to be understood that the hetereocyclyl can be connected to the alkyl group at any acceptable carbon or heteroatom of the hetereocyclyl. Typical, but non-limiting, examples of heterocyclylalkyl groups include pyridylmethyl, pyrimidinylethyl, piperidinylmethyl and 1-imidazolylethyl.

The term "carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

The term "cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 7 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, bicyclo [3.1.0]hex-6-yl and the like.

The term "cycloalkylalkyl" refers to an acyclic alkyl radical as described herein in which one of the hydrogen atoms bonded to a carbon atom is replaced with a cycloalkyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

The term "carbocyclylalkyl" refers to an acyclic alkyl radical as described herein in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

The term "optionally substituted" in reference to a particular moiety of the compound of formula I (e.g., an optionally substituted aryl or alkyl group) refers to a moiety wherein all substitutents are hydrogen or wherein one or more of the hydrogens of the moiety may be replaced by substituents such as those listed under the definition of "substituted" or as otherwise indicated.

Selected substituents comprising the compounds of formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with, for example any phosphate or phosphonate prodrug compounds of the invention, include but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

It is to be noted that all tautomers, polymorphs, pseudopolymorphs of compounds within the scope of formula I and pharmaceutically acceptable salts and esters thereof and compounds of formulas 1-103 and pharmaceutically acceptable salts and esters thereof are embraced by the present invention.

It is also to be noted that all stereoisomers (e.g., enantiomers, diastereomers, atropisomers etc.) of compounds within the scope of formula I and pharmaceutically acceptable salts and esters thereof and compounds of formulas 1-103 and pharmaceutically acceptable salts and esters thereof are embraced by the present invention.

A compound of formula I or a compound of formulas 1-103, and their pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I and formulas 1-103, and their pharmaceutically acceptable salts.

A compound of formula I or a compound of formulas 1-103 and their pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I and formulas 1-103 and their pharmaceutically acceptable salts.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of formula I or a compound of formulas 1-103 present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of formula I or the compound of formulas 1-103, the specific activity of the composition, the delivery device employed, the physical characteristics of the composition, its intended use, as well as patient considerations such as severity of the disease state, patient cooperation, etc., and can readily be determined by one skilled in the art and in reference to the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

Any reference to the compounds of the invention described herein also includes a reference to a physiologically acceptable salt (e.g., pharmaceutically acceptable salt) thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$. In one embodiment each R is independently H or $(C_1-C_6)$alkyl.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

It is to be understood that the compositions herein comprise compounds of the invention in their un-ionized, as well as zwitterionic form, and combinations with stoichiometric amounts of water as in hydrates.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds disclosed herein, exemplified by formula I and formulas 1-103 may have chiral centers, e.g. chiral carbon. The compounds of the invention include enriched or resolved optical isomers at any or all asymmetric, chiral atoms. In other words, the chiral centers apparent from the depictions are provided as the chiral isomers. Individual enantiomers or diasteromers, isolated or synthesized, substantially free of their enantiomeric or diastereomeric partners, are all within the scope of the invention. The stereoisomeric mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography. Enantiomers" refer to two stereoisomers of a compound which are non-superimposable mirror images of one another.

It is to be understood that for compounds disclosed herein including compounds of the invention (e.g., compounds of formula I (compounds 104-122) and compounds 1-103) when a bond is drawn in a non-stereochemical manner (e.g., flat) the atom to which the bond is attached includes all stereochemical possibilities. It is also to understood that when a bond is drawn in a stereochemical manner (e.g., bold, bold-wedge, dashed or dashed-wedge) the atom to which the stereochemical bond is attached has the stereochemistry as shown unless otherwise noted.

Accordingly, in one embodiment, the compounds of the invention are greater than 50% a single enantiomer. In another embodiment, the compounds of the invention are at least 51% a single enantiomer. In another embodiment, the compounds of the invention are at least 60% a single enantiomer. In another embodiment, the compounds of the invention are at least 70% a single enantiomer. In another embodiment, the compounds of the invention are at least 80% a single enantiomer. In another embodiment, the compounds of the invention are at least 90% a single enantiomer. In another embodiment, the compounds of the invention are at least 95% a single enantiomer. In another embodiment, the compounds of the invention are at least 98% a single enantiomer. In another embodiment, the compounds of the invention are at least 99% a single enantiomer. In another embodiment, the compounds of the invention are greater than 50% a single diasteromer. In another embodiment, the compounds of the invention are at least 51% a single diasteromer. In another embodiment, the compounds of the invention are at least 60% a single diastereomer. In another embodiment, the compounds of the invention are at least 70% a single diastereomer. In another embodiment, the compounds of the invention are at least 80% a single diastereomer. In another embodiment, the compounds of the invention are at least 90% a single diastereomer. In another embodiment, the compounds of the invention are at least 95% a single diastereomer. In another embodiment, the compounds of the invention of are at least 98% a single diastereomer. In another embodiment, the compounds of the invention are at least 99% a single diastereomer.

Certain compounds disclosed herein including compounds of the invention are represented by formula Ic (and salts and esters, thereof) as shown below wherein a position of chirality is marked with an asterisk.

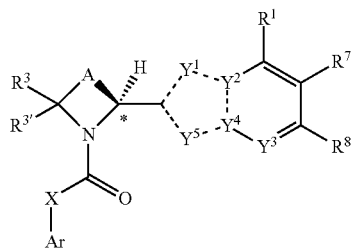

Ic

The chirality at the asterisk position is a feature of these certain compounds of formula Ic (as well as compounds of related formulas). The stereochemistry at the carbon marked with an asterisk as shown above for formula Ic is the (S) stereochemistry provided that A is ranked the lowest (3) or highest (1) of the three substituents of the asterisk carbon following the Cahn-Ingold-Prelog system or the (R) stereochemistry provided that A is ranked number 2 of the three substituents of the asterisk carbon following the Cahn-Ingold-Prelog system (March, J., Advanced Organic Chemistery, 4$^{th}$ Addition, John Wiley and Sons, pages 109-111). For example, the stereochemistry at the carbon marked with an asterisk as shown above for formula Ic wherein A is for example, an alkyl group (e.g., —$(CH_2)_{3-6}$—), is the (S) stereochemistry. In one embodiment, the compounds of the invention of formula Ic are greater than 50% a single stereoisomer at the asterisk position. In another embodiment, the compounds of the invention of formula Ic are at least 60% a single stereoisomer at the asterisk position. In another embodiment, the compounds of the invention of formula Ic are at least 70% a single stereoisomer at the asterisk position. In another embodiment, the compounds of the invention of formula Ic are at least 80% a single stereoisomer at the asterisk position. In another embodiment, the compounds of the invention of formula Ic are at least 90% a single stereoisomer at the asterisk position. In another embodiment, the compounds of the invention of formula Ic are at least 95% a single stereoisomer at the asterisk position.

Certain compounds disclosed herein including compounds of the invention can be represented by formula II (and salts and esters, thereof) as shown below wherein a position of chirality is marked with an asterisk. This formula is representative of compounds 1-103 wherein the R, X and Ar groups in formula II represent the corresponding groups of the compounds 1-103.

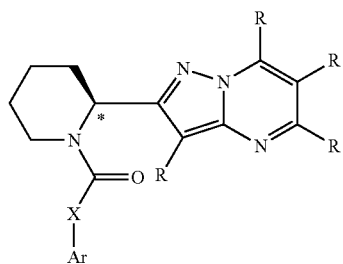

II

The chirality at the asterisk position is a feature of these certain compounds of the invention of formula II (as well as compounds of related formulas). The stereochemistry at the carbon marked with an asterisk as shown above for formula II is the (S) stereochemistry. In one embodiment, the compounds of the invention represented by formula II are greater than 50% a single stereoisomer at the asterisk position. In another embodiment, the compounds of the invention represented by formula II are at least 60% a single stereoisomer at the asterisk position. In another embodiment, the compounds of the invention represented by formula II are at least 70% a single stereoisomer at the asterisk position. In another embodiment, the compounds of the invention represented by formula II are at least 80% a single stereoisomer at the asterisk position. In another embodiment, the compounds of the invention represented by formula II are at least 90% a single stereoisomer at the asterisk position. In another embodiment, the compounds of the invention represented by formula II are at least 95% a single stereoisomer at the asterisk position.

Compounds disclosed herein including compounds of formula I and formulas 1-103 also include molecules that incorporate isotopes of the atoms specified in the particular molecules. Non-limiting examples of these isotopes include D, T, $^{14}C$, $^{13}C$ and $^{15}N$.

Whenever a compound described herein is substituted with more than one of the same designated group, e.g., "R" or "$R^1$", then it will be understood that the groups may be the same or different, i.e., each group is independently selected. Wavy lines, ∿∿∿, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention.

Detailed Description of Exemplary Embodiments

Reference will now be made in detail to certain embodiments of the invention, examples of which are illustrated in the accompanying description, structures and formulas. While the invention will be described in conjunction with the embodiments, it will be understood that they are not intended to limit the invention to those embodiments. On the contrary, the invention is intended to cover all alternatives, modifications, and equivalents, which may be included within the full scope of the present invention as described herein.

Specific values listed below for radicals, substituents, and ranges, are for illustration only; they do not exclude other defined values or other values within defined ranges for the radicals and substituents. Specific values listed are values for compounds of formula I as well as all related formulas (e.g., formulas Ia, Ib, Ic, Id, Ie, If, Ig, Ih, Ii, Ij, Ik, Im, In, Ip1, Ip2, Ip3, Ip4, Iq1, Iq2, Iq3, Iq4, Ir1, Ir2, Ir3, Ir4, Is1, Is2, Is3, Is4, It1, It2, It3, It4, Iu1, Iu2, Iu3, Iu4, Iv1, Iv2, Iv3, Iv4, Iw1, Iw2, Iw3, Iw4, Ix1, Ix2, Ix3 or Ix4)

A specific group of compounds of formula I are compounds of formula Ia:

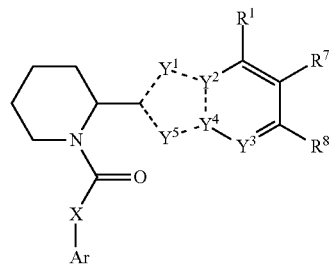

and salts and esters, thereof.

Another specific group of compounds of formula I are compounds of formula Ib:

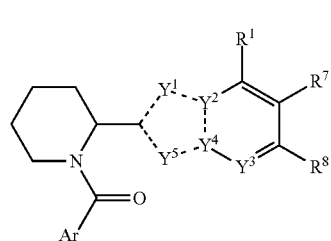

and salts and esters, thereof.

Another specific group of compounds of formula I are compounds of formula Ic:

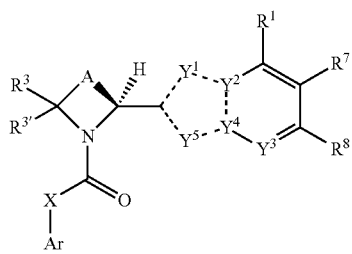

and salts and esters, thereof.

Another specific group of compounds of formula I are compounds of formula Id:

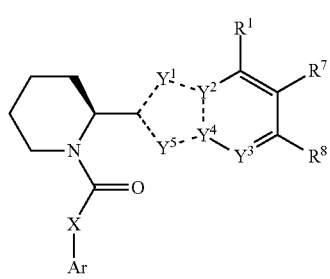

and salts and esters, thereof.

Another specific group of compounds of formula I are compounds of formula Ie:

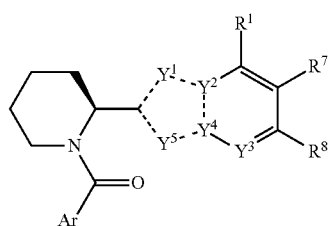

Another specific group of compounds of formula I are compounds of formula If:

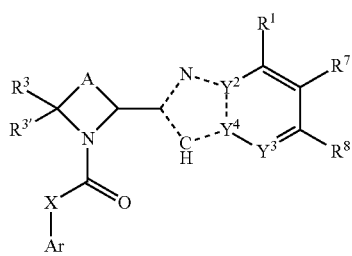

and salts and esters, thereof.

Another specific group of compounds of formula I are compounds of formula Ig:

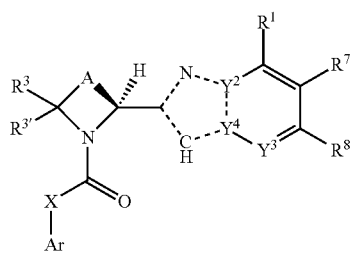

Ig and salts and esters, thereof.

Another specific group of compounds of formula I are compounds of formula Ih:

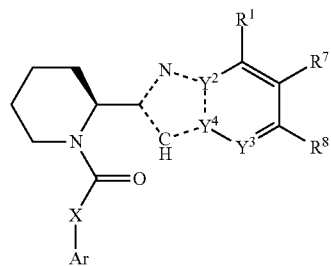

Ih and salts and esters, thereof.

Another specific group of compounds of formula I are compounds of formula Ii:

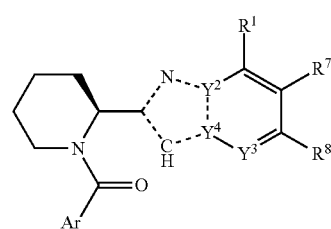

Ii and salts and esters, thereof.

Another specific group of compounds of formula I are compounds of formula Ij:

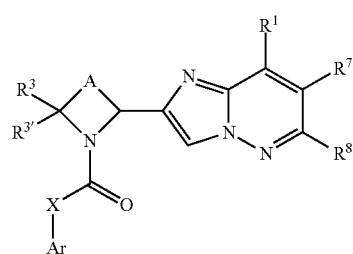

Ij and salts and esters, thereof.

Another specific group of compounds of formula I are compounds of formula Ik:

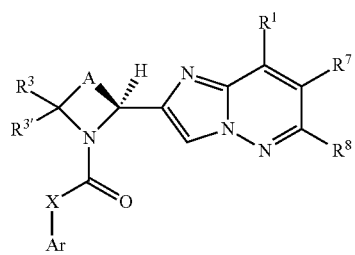

Ik and salts and esters, thereof.

Another specific group of compounds of formula I are compounds of formula Im:

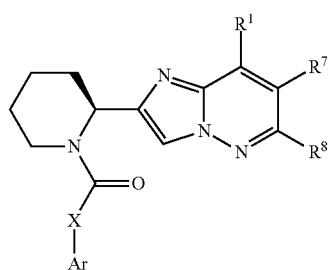

Im and salts and esters, thereof.

Another specific group of compounds of formula I are compounds of formula In:

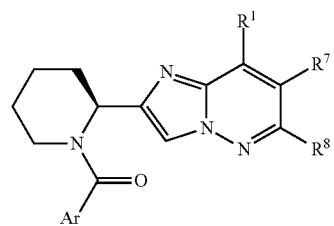

In and salts and esters, thereof.

Additional specific groups of compounds of formula I are compounds of formula Ip1, Ip2, Ip3 or Ip4:

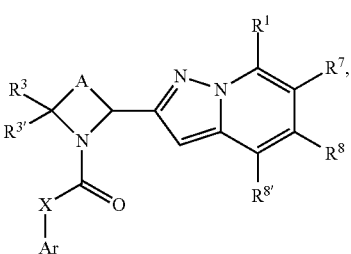

Ip1

-continued
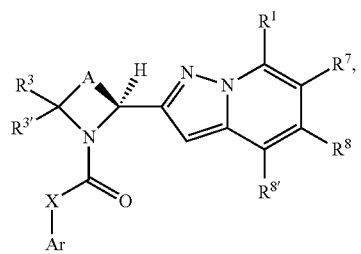
Ip2
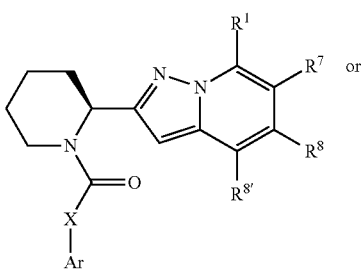
Ip3 or
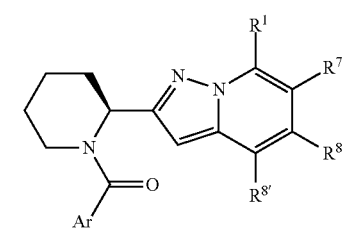
Ip4
or a salt or ester, thereof.
Additional specific groups of compounds of formula I are compounds of formula Iq1, Iq2, Iq3 or Iq4:
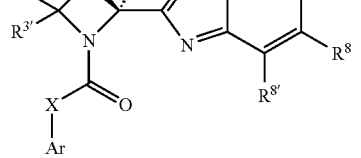
Iq1
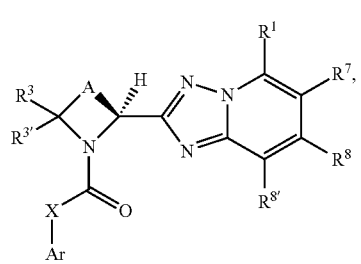
Iq2
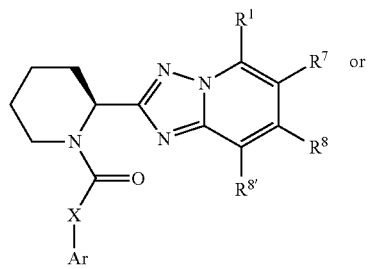
Iq3 or
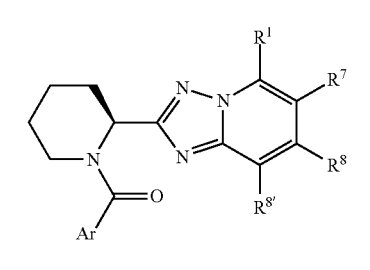
Iq4
or a salt or ester, thereof.
Additional specific groups of compounds of formula I are compounds of formula Ir1, Ir2, Ir3 or Ir4:
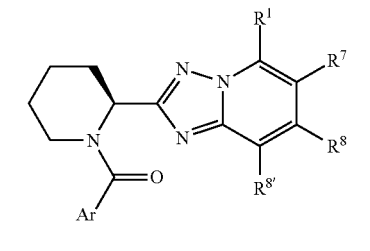
Ir1
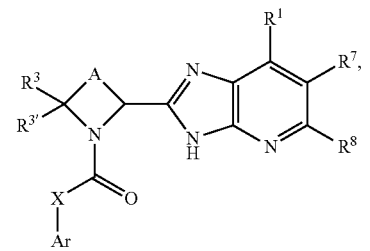
Ir2
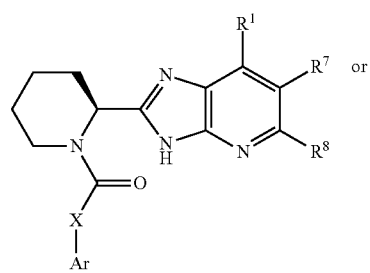
Ir3 or -continued

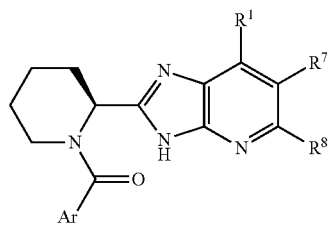
Ir4 or a salt or ester, thereof.

Additional specific groups of compounds of formula I are compounds of formula Is1, Is2, Is3 or Is4:

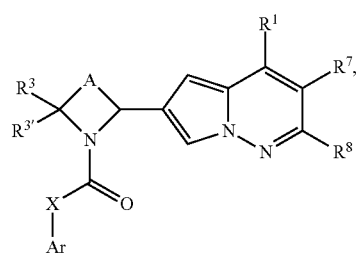
Is1

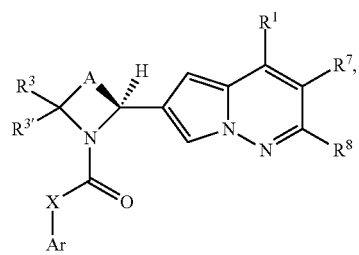
Is2

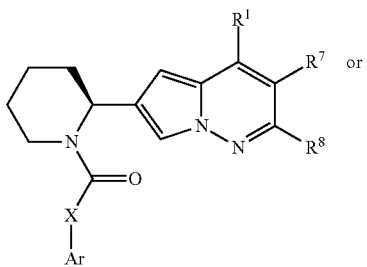
Is3

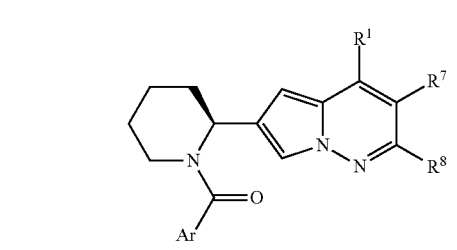
Is4 or a salt or ester, thereof.

Additional specific groups of compounds of formula I are compounds of formula It1, It2, It3 or It4:

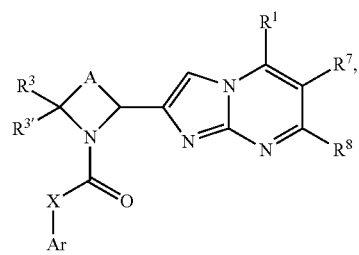
It1

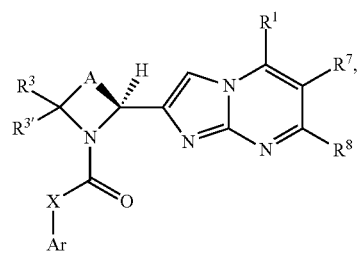
It2

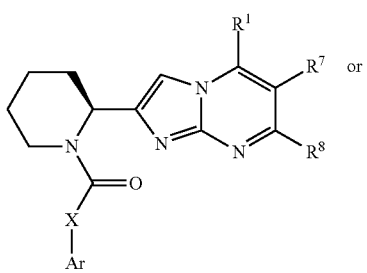
It3

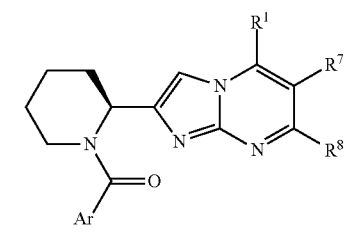
It4 or a salt or ester, thereof.

Additional specific groups of compounds of formula I are compounds of formula Iu1, Iu2, Iu3 or Iu4:

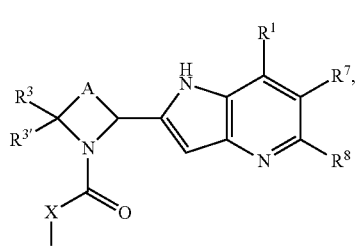
Iu1

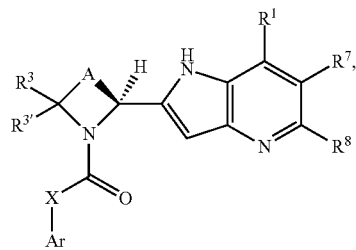
Iu2
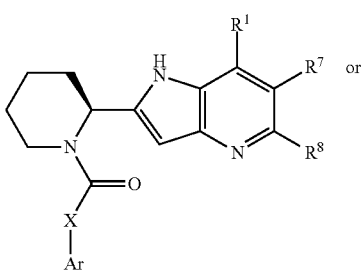
Iu3
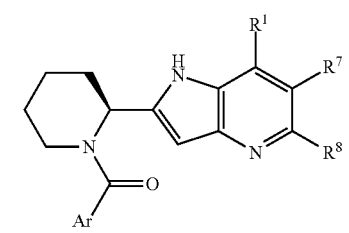
Iu4
or a salt or ester, thereof.
Additional specific groups of compounds of formula I are compounds of formula Iv1, Iv2, Iv3 or Iv4:
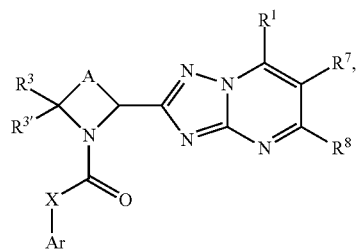
Iv1
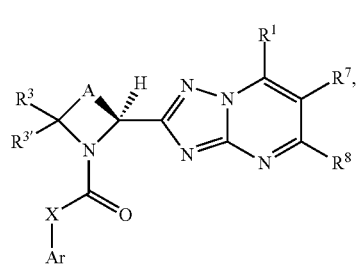
Iv2
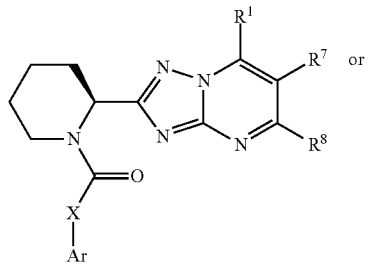
Iv3
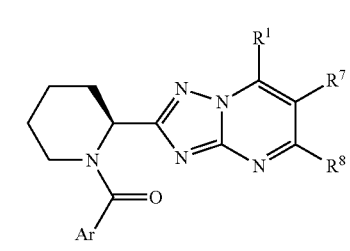
Iv4
or a salt or ester, thereof.
Additional specific groups of compounds of formula I are compounds of formula Iw1, Iw2, Iw3 or Iw4:
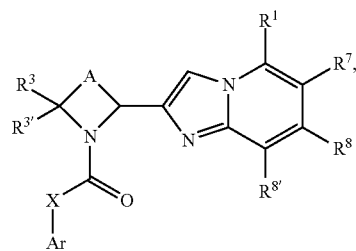
Iw1
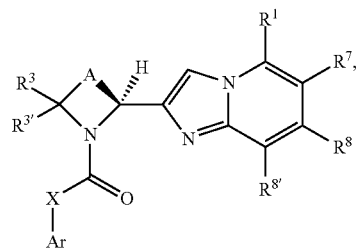
Iw2
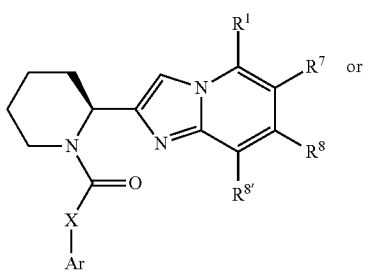
Iw3

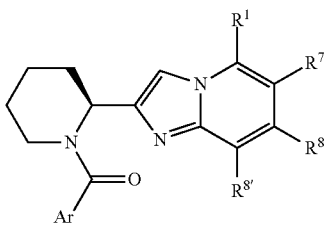

or a salt or ester, thereof.

Additional specific groups of compounds of formula I are compounds of formula Ix1, Ix2, Ix3 or Ix4:

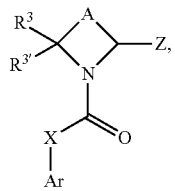

Ix1

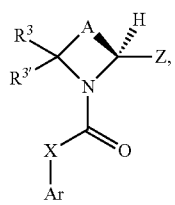

Ix2

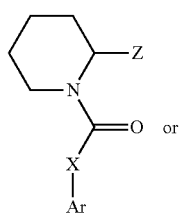

Ix3

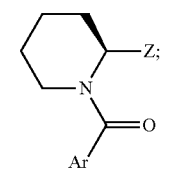

Ix4 wherein Z is:

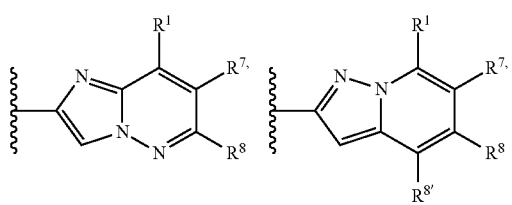

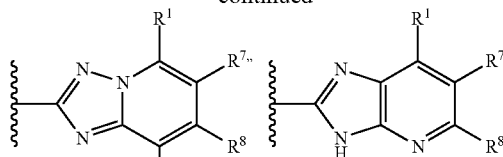

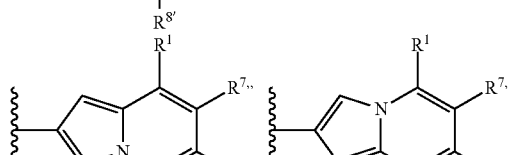

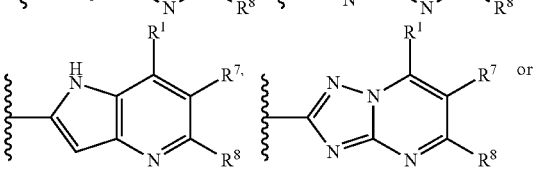

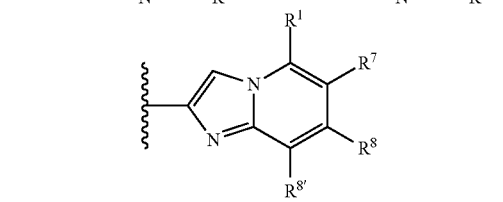

or a salt or ester, thereof.

A specific group of compounds of formula I are compounds wherein each $R^3$ and each $R^{3'}$ is H.

A specific value for $R^3$ is H.

A specific value for $R^{3'}$ is H.

A specific value for n is 3.

A specific group of compounds of formula I are compounds wherein each p is 2.

A specific group of compounds of formula I are compounds wherein each $R^4$ and each $R^{4'}$ is H.

A specific value for $R^4$ is H.

A specific value for $R^{4'}$ is H.

A specific value for A is —$(CH_2)_3$—.

A specific group of compounds of formula I are compounds wherein:

a) $Y^1$ is N, NH or CH, $Y^2$ is C, $Y^3$ is N or $CR^{8'}$, $Y^4$ is N or C, and $Y^5$ is N, $NR^{2'}$ or $CR^2$, wherein at least two of $Y^1$, $Y^2$, $Y^3$, $Y^4$ and $Y^5$ are independently N, NH or $NR^{2'}$; or b) $Y^1$ is N, NH or CH, $Y^2$ is N or C, $Y^3$ is $CR^{8'}$, $Y^4$ is N or C, and $Y^5$ is N, $NR^{2'}$ or $CR^2$, wherein at least two of $Y^1$, $Y^2$, $Y^3$, $Y^4$ and $Y^5$ are independently N, NH or $NR^{2'}$.

Another specific group of compounds of formula I are compounds wherein:

a) $Y^1$ is N, $Y^2$ is C, $Y^3$ is N, $Y^4$ is N and $Y^5$ is $CR^2$; or b) $Y^1$ is CH, $Y^2$ is C, $Y^3$ is N, $Y^4$ is N and $Y^5$ is $CR^2$; or c) $Y^1$ is N, $Y^2$ is N, $Y^3$ is $CR^{8'}$, $Y^4$ is C and $Y^5$ is N; or d) $Y^1$ is N, $Y^2$ is N, $Y^3$ is $CR^{8'}$, $Y^4$ is C and $Y^5$ is $CR^2$; or e) $Y^1$ is N, $Y^2$ is N, $Y^3$ is N, $Y^4$ is C and $Y^5$ is N; or f) $Y^1$ is CH, $Y^2$ is N, $Y^3$ is N, $Y^4$ is C and $Y^5$ is N; or g) $Y^1$ is N, $Y^2$ is C, $Y^3$ is N, $Y^4$ is C and $Y^5$ is $NR^{2'}$; or h) $Y^1$ is CH, $Y^2$ is N, $Y^3$ is $CR^{8'}$, $Y^4$ is C and $Y^5$ is N; or i) $Y^1$ is NH, $Y^2$ is C, $Y^3$ is N, $Y^4$ is C and $Y^5$ is $CR^2$.

Another specific group of compounds of formula I are compounds wherein:

a) $Y^1$ is N or CH, $Y^2$ is C, $Y^3$ is N, $Y^4$ is N and $Y^5$ is $CR^2$; or b) $Y^1$ is N, $Y^2$ is N, $Y^3$ is $CR^{8'}$, $Y^4$ is C and $Y^5$ is N or $CR^2$; or c) $Y^1$ is N or CH, $Y^2$ is N, $Y^3$ is N, $Y^4$ is C and $Y^5$ is N; or d) $Y^1$ is N, $Y^2$ is C, $Y^3$ is N, $Y^4$ is C and $Y^5$ is $NR^{2'}$, or e) $Y^1$ is CH, $Y^2$ is N, $Y^3$ is $CR^{8'}$, $Y^4$ is C and $Y^5$ is N; or f) $Y^1$ is NH, $Y^2$ is C, $Y^3$ is N, $Y^4$ is C and $Y^5$ is $CR^2$.

Another specific group of compounds of formula I are compounds wherein:

a) $Y^1$ is N, $Y^2$ is C, $Y^3$ is N, $Y^4$ is N and $Y^5$ is $CR^2$; or b) $Y^1$ is N, $Y^2$ is N, $Y^3$ is $CR^{8'}$, $Y^4$ is C and $Y^5$ is $CR^2$.

Another specific group of compounds of formula I are compounds wherein:

a) $Y^1$ is N, NH or CH, $Y^2$ is C, $Y^3$ is N, $Y^4$ is N or C and $Y^5$ is $NR^{2'}$ or $CR^2$, wherein at least two of $Y^1$, $Y^2$, $Y^3$, $Y^4$ and $Y^5$ are independently N, NH or $NR^{2'}$; or b) $Y^1$ is N, NH or CH, $Y^2$ is N or C, $Y^3$ is N or $CR^{8'}$, $Y^4$ is N or C and $Y^5$ is N, wherein at least two of $Y^1$, $Y^2$, $Y^3$, $Y^4$ and $Y^5$ are independently N or NH; or c) $Y^1$ is N, NH or CH, $Y^2$ is N or C, $Y^3$ is $CR^{8'}$, $Y^4$ is N or C and $Y^5$ is $NR^{2'}$ or $CR^2$, wherein at least two of $Y^1$, $Y^2$, $Y^3$, $Y^4$ and $Y^5$ are independently N, NH or $NR^{2'}$.

It is to be understood that the values for $Y^1$, $Y^2$, $Y^3$, $Y^4$ and $Y^5$ are each selected so that the ring formed by $Y^1$, $Y^2$, $Y^4$, $Y^5$ and the carbon atom connected to $Y^1$ and $Y^5$ is an aromatic ring.

It is to be understood that the values for $Y^1$, $Y^2$, $Y^3$, $Y^4$ and $Y^5$ are each selected so that the ring formed by $Y^1$, $Y^2$, $Y^4$, $Y^5$ and the carbon atom connected to $Y^1$ and $Y^5$ is an aromatic ring, and the dashed bonds (----) are selected from single bonds and double bonds so that the ring formed by $Y^1$, $Y^2$, $Y^4$, $Y^5$ along with the carbon atom connected to $Y^1$ and $Y^5$ is an aromatic ring.

A specific value for $Y^1$ is N.

A specific value for $Y^5$ is $CR^2$.

A specific value for $R^2$ is H.

A specific value for $R^{2'}$ is H.

A specific value for $R^{8'}$ is H.

A specific group of compounds of formula I are compounds wherein $R^{2'}$, $R^2$ and $R^{8'}$ are each H.

A specific value for $R^7$ is H or $(C_1-C_8)$alkyl, wherein $(C_1-C_8)$alkyl is optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$alkyl, $(C_1-C_8)$haloalkyl, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $-NHS(O)_pR^a$, $-NR^aS(O)_pR^a$, $-NHC(O)R^a$, $-NR^aC(O)R^a$, $-NHC(O)OR^a$, $-NR^aC(O)OR^a$, $-NR^aC(O)NHR^a$, $-NR^aC(O)N(R^a)_2$, $-NR^aC(O)NH_2$, $-NHC(O)NHR^a$, $-NHC(O)N(R^a)_2$, $-NHC(O)NH_2$, $=NH$, $=NOH$, $=NOR^a$, $-NR^aS(O)_pNHR^a$, $-NR^aS(O)_pN(R^a)_2$, $-NR^aS(O)_pNH_2$, $-NHS(O)_pNHR^a$, $-NHS(O)_pN(R^a)_2$, $-NHS(O)_pNH_2$, $-OC(=O)R^a$, $-OP(O)(OH)_2$ or $R^a$.

Another specific value for $R^7$ is H or $(C_1-C_8)$alkyl.

Another specific value for $R^7$ is H or $(C_1-C_2)$alkyl.

Another specific value for $R^7$ is H or methyl.

A specific value for $R^1$ is H, $-NR^{11}R^{12}$, $(C_1-C_8)$alkyl or $C_2-C_{20}$ heterocyclyl, wherein $(C_1-C_8)$alkyl or $C_2-C_{20}$ heterocyclyl is optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$alkyl, $(C_1-C_8)$haloalkyl, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $-NHS(O)_pR^a$, $-NR^aS(O)_pR^a$, $-NHC(O)R^a$, $-NR^aC(O)R^a$, $-NHC(O)OR^a$, $-NR^aC(O)OR^a$, $-NR^aC(O)NHR^a$, $-NR^aC(O)N(R^a)_2$, $-NR^aC(O)NH_2$, $-NHC(O)NHR^a$, $-NHC(O)N(R^a)_2$, $-NHC(O)NH_2$, $=NH$, $=NOH$, $=NOR^a$, $-NR^aS(O)_pNHR^a$, $-NR^aS(O)_pN(R^a)_2$, $-NR^aS(O)_pNH_2$, $-NHS(O)_pNHR^a$, $-NHS(O)_pN(R^a)_2$, $-NHS(O)_pNH_2$, $-OC(=O)R^a$, $-OP(O)(OH)_2$ or $R^a$.

Another specific value for $R^1$ is H, $-NR^{11}R^{12}$, $(C_1-C_8)$alkyl or $C_2-C_{20}$ heterocyclyl.

Another specific value for $R^1$ is H, $(C_1-C_8)$alkyl or $C_2-C_{20}$ heterocyclyl.

Another specific value for $R^1$ is H, $-NR^{11}R^{12}$ or $(C_1-C_8)$alkyl.

Another specific value for $R^1$ is H, $(C_1-C_3)$alkyl or $-NR^{11}R^{12}$, wherein each $R^{11}$ or $R^{12}$ is independently H or $(C_1-C_3)$alkyl; or $R^{11}$ and $R^{12}$ together with the nitrogen to which they are both attached to form a 3 to 7 membered heterocyclic ring wherein any one carbon atom of said heterocyclic ring can optionally be replaced with $-O-$, $-S-$, $-S(O)_p-$, $-NH-$, $-NR^a-$ or $-C(O)-$.

Another specific value for $R^1$ is H, $(C_1-C_3)$alkyl or $-NR^{11}R^{12}$, wherein each $R^{11}$ or $R^{12}$ is independently H or $(C_1-C_3)$alkyl; or $R^{11}$ and $R^{12}$ together with the nitrogen to which they are both attached to form a 4 to 5 membered heterocyclic ring.

Another specific value for $R^1$ is H, methyl or azetidinyl.

Another specific value for $R^1$ is H, $(C_1-C_8)$alkyl or $C_2-C_{20}$ heterocyclyl, wherein $C_2-C_{20}$ heterocyclyl is optionally substituted with one or more oxo, halogen, hydroxy, $-NH_2$, CN, $N_3$, $-N(R^a)_2$, $-NHR^a$, $-SH$, $SR^a$, $-S(O)_pR^a$, $-OR^a$, $(C_1-C_8)$alkyl, $(C_1-C_8)$haloalkyl, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $-NHS(O)_pR^a$, $-NR^aS(O)_pR^a$, $-NHC(O)R^a$, $-NR^aC(O)R^a$, $-NHC(O)OR^a$, $-NR^aC(O)OR^a$, $-NR^aC(O)NHR^a$, $-NR^aC(O)N(R^a)_2$, $-NR^aC(O)NH_2$, $-NHC(O)NHR^a$, $-NHC(O)N(R^a)_2$, $-NHC(O)NH_2$, $=NH$, $=NOH$, $=NOR^a$, $-NR^aS(O)_pNHR^a$, $-NR^aS(O)_pN(R^a)_2$, $-NR^aS(O)_pNH_2$, $-NHS(O)_pNHR^a$, $-NHS(O)_pN(R^a)_2$, $-NHS(O)_pNH_2$, $-OC(=O)R^a$, $-OP(O)(OH)_2$ or $R^a$.

Another specific value for $R^1$ is H, $(C_1-C_8)$alkyl or $C_2-C_{20}$ heterocyclyl.

Another specific value for $R^1$ is H, $(C_1-C_8)$alkyl or 3-7 membered monocyclic saturated heterocyclyl.

Another specific value for $R^1$ is H, $(C_1-C_8)$alkyl or 3-7 membered monocyclic saturated heterocyclyl wherein the 3-7 membered monocyclic saturated heterocyclyl includes 2-6 carbon atoms in the ring and 1-3 heteroatoms selected from oxygen, sulfur and nitrogen in the ring.

Another specific value for $R^1$ is H, $(C_1-C_3)$alkyl or 3-7 membered monocyclic saturated heterocyclyl wherein the 3-7 membered monocyclic saturated heterocyclyl includes 2-6 carbon atoms in the ring and 1-3 heteroatoms selected from oxygen, sulfur and nitrogen in the ring.

Another specific value for $R^1$ is H, $(C_1-C_3)$alkyl or 4-5 membered monocyclic saturated heterocyclyl wherein the 4-5 membered monocyclic saturated heterocyclyl includes 3-4 carbon atoms in the ring and 1 heteroatom selected from oxygen, sulfur and nitrogen in the ring.

A specific value for $R^8$ is $NR^{11}R^{12}$, $C_8)$alkyl or $C_2-C_{20}$ heterocyclyl wherein $(C_1-C_8)$alkyl or $C_2-C_{20}$ heterocyclyl is optionally substituted with one or more oxo, halogen, hydroxy, $-NH_2$, CN, $N_3$, $-N(R^a)_2$, $-NHR^a$, $-SH$, $-SR^a$, $-S(O)_pR^a$, $-OR^a$, $(C_1-C_8)$alkyl, $(C_1-C_8)$haloalkyl, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $-NHS(O)_pR^a$, $-NR^aS(O)_pR^a$, $-NHC(O)R^a$, $-NR^aC(O)R^a$, $-NHC(O)OR^a$, $-NR^aC(O)OR^a$, $-NR^aC(O)NHR^a$, $-NR^aC(O)N(R^a)_2$, $-NR^aC(O)NH_2$, $-NHC(O)NHR^a$, $-NHC(O)N(R^a)_2$, $-NHC(O)NH_2$, $=NH$, $=NOH$, $=NOR^a$, $-NR^aS(O)_pNHR^a$, $-NR^aS(O)_pN(R^a)_2$, $-NR^aS$ (O)$_p$NH$_2$, —NHS(O)$_p$NHR$^a$, —NHS(O)$_p$N(R$^a$)$_2$, —NHS(O)$_p$NH$_2$, —OC(=O)R$^a$, —OP(O)(OH)$_2$ or R$^a$.

Another specific value for R$^8$ is (C$_1$-C$_8$)alkyl or 3-7 membered monocyclic saturated heterocyclyl wherein (C$_1$-C$_8$)alkyl or 3-7 membered monocyclic saturated heterocyclyl is optionally substituted with one or more oxo, halogen, hydroxy, —NH$_2$, CN, N$_3$, —N(R$^a$)$_2$, —NHR$^a$, —SH, —SR$^a$, —S(O)$_p$R$^a$, —OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, —NHS(O)$_p$R$^a$, —NR$^a$S(O)$_p$R$^a$, —NHC(O)R$^a$, —NR$^a$C(O)R$^a$, —NHC(O)OR$^a$, —NR$^a$C(O)OR$^a$, —NR$^a$C(O)NHR$^a$, —NR$^a$C(O)N(R$^a$)$_2$, —NR$^a$C(O)NH$_2$, —NHC(O)NHR$^a$, —NHC(O)N(R$^a$)$_2$, —NHC(O)NH$_2$, =NH, =NOH, =NOR$^a$, —NR$^a$S(O)$_p$NHR$^a$, —NR$^a$S(O)$_p$N(R$^a$)$_2$, —NR$^a$S(O)$_p$NH$_2$, —NHS(O)$_p$NHR$^a$, —NHS(O)$_p$N(R$^a$)$_2$, —NHS(O)$_p$NH$_2$, —OC(=O)R$^a$, —OP(O)(OH)$_2$ or R$^a$.

Another specific value for R$^8$ is (C$_1$-C$_8$)alkyl or 3-7 membered monocyclic saturated heterocyclyl, wherein the 3-7 membered monocyclic saturated heterocyclyl includes 2-6 carbon atoms in the ring and 1-3 heteroatoms selected from oxygen, sulfur and nitrogen in the ring, and wherein (C$_1$-C$_8$)alkyl or 3-7 membered monocyclic saturated heterocyclyl is optionally substituted with one or more oxo, halogen, hydroxy, —NH$_2$, CN, N$_3$, —N(R$^a$)$_2$, —NHR$^a$, —SH, —SR$^a$, —S(O)$_p$R$^a$, —OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, —NHS(O)$_p$R$^a$, —NR$^a$S(O)$_p$R$^a$, —NHC(O)R$^a$, —NR$^a$C(O)R$^a$, —NHC(O)OR$^a$, —NR$^a$C(O)OR$^a$, —NR$^a$C(O)NHR$^a$, —NR$^a$C(O)N(R$^a$)$_2$, —NR$^a$C(O)NH$_2$, —NHC(O)NHR$^a$, —NHC(O)N(R$^a$)$_2$, —NHC(O)NH$_2$, =NH, =NOH, =NOR$^a$, —NR$^a$S(O)$_p$NHR$^a$, —NR$^a$S(O)$_p$N(R$^a$)$_2$, —NR$^a$S(O)$_p$NH$_2$, —NHS(O)$_p$NHR$^a$, —NHS(O)$_p$N(R$^a$)$_2$, —NHS(O)$_p$NH$_2$, —OC(=O)R$^a$, —OP(O)(OH)$_2$ or R$^a$.

Another specific value for R$^8$ is (C$_1$-C$_8$)alkyl or 3-7 membered monocyclic saturated heterocyclyl, wherein the 3-7 membered monocyclic saturated heterocyclyl is optionally substituted with one or more hydroxy, NH$_2$ or CN.

Another specific value for R$^8$ is (C$_1$-C$_8$)alkyl or 3-7 membered monocyclic saturated heterocyclyl, wherein the 3-7 membered monocyclic saturated heterocyclyl includes 2-6 carbon atoms in the ring and 1-3 heteroatoms selected from oxygen, sulfur and nitrogen in the ring, and wherein the 3-7 membered monocyclic saturated heterocyclyl is optionally substituted with one or more hydroxy, NH$_2$ or CN.

Another specific value for R$^8$ is (C$_1$-C$_3$)alkyl or 3-7 membered monocyclic saturated heterocyclyl wherein 3-7 membered monocyclic saturated heterocyclyl is optionally substituted with one or more hydroxy, NH$_2$ or CN.

Another specific value for R$^8$ is (C$_1$-C$_3$)alkyl or 3-7 membered monocyclic saturated heterocyclyl, wherein the 3-7 membered monocyclic saturated heterocyclyl includes 2-6 carbon atoms in the ring and 1-3 heteroatoms selected from oxygen, sulfur and nitrogen in the ring, and wherein 3-7 membered monocyclic saturated heterocyclyl is optionally substituted with one or more hydroxy, NH$_2$ or CN.

Another specific value for R$^8$ is (C$_1$-C$_2$)alkyl or 4-5 membered monocyclic saturated heterocyclyl, wherein the 4-5 membered monocyclic saturated heterocyclyl includes 3-4 carbon atoms in the ring and one nitrogen atom in the ring, and wherein the 4-5 membered monocyclic saturated heterocyclyl is optionally substituted with one or more hydroxy, NH$_2$ or CN.

Another specific value for R$^8$ is (C$_1$-C$_8$)alkyl, azetidinyl or pyrrolidinyl, wherein azetidinyl or pyrrolidinyl is optionally substituted with one or more oxo, halogen, hydroxy, —NH$_2$, CN, N$_3$, —N(R$^a$)$_2$, —NHR$^a$, —SH, —SR$^a$, —S(O)$_p$R$^a$, —OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, —NHS(O)$_p$R$^a$, —NR$^a$S(O)$_p$R$^a$, —NHC(O)R$^a$, —NR$^a$C(O)R$^a$, —NHC(O)OR$^a$, —NR$^a$C(O)OR$^a$, —NR$^a$C(O)NHR$^a$, —NR$^a$C(O)N(R$^a$)$_2$, —NR$^a$C(O)NH$_2$, —NHC(O)NHR$^a$, —NHC(O)N(R$^a$)$_2$, —NHC(O)NH$_2$, =NH, =NOH, =NOR$^a$, —NR$^a$S(O)$_p$NHR$^a$, —NR$^a$S(O)$_p$N(R$^a$)$_2$, —NR$^a$S(O)$_p$NH$_2$, —NHS(O)$_p$NHR$^a$, —NHS(O)$_p$N(R$^a$)$_2$, —NHS(O)$_p$NH$_2$, —OC(=O)R$^a$, —OP(O)(OH)$_2$ or R$^a$.

Another specific value for R$^8$ is methyl, azetidinyl or pyrrolidinyl, wherein azetidinyl or pyrrolidinyl is optionally substituted with one or more hydroxy, NH$_2$ or CN.

A specific group of compounds of formula I are compounds wherein each R$^a$ is (C$_1$-C$_8$)alkyl.

A specific group of compounds of formula I are compounds wherein each R$^a$ is (C$_1$-C$_3$)alkyl.

A specific group of compounds of formula I are compounds wherein each R$^a$ is (C$_1$-C$_2$)alkyl.

A specific group of compounds of formula I are compounds wherein each R$^a$ is methyl.

A specific group of compounds of formula I are compounds wherein X is —C(R$^{13}$)(R$^{14}$)— or X is absent.

A specific value for R$^{13}$ is H.

A specific value for R$^{14}$ is —NR$^{11}$S(O)$_p$R$^a$.

A specific value for R$^{14}$ is —NHS(O)$_2$(C$_1$-C$_3$)alkyl.

A specific value for R$^{14}$ is —NHS(O)$_2$CH$_3$.

A specific group of compounds of formula I are compounds R$^{13}$ is H and R$^{14}$ is —NR$^{11}$S(O)$_p$R$^a$.

A specific group of compounds of formula I are compounds R$^{13}$ is H and R$^{14}$ is —NHS(O)$_2$(C$_1$-C$_3$)alkyl.

A specific group of compounds of formula I are compounds wherein R$^{13}$ is H and R$^{14}$ is —NHS(O)$_2$CH$_3$.

A specific group of compounds of formula I are compounds wherein X is —C(H)(NHS(O)$_2$CH$_3$)— or X is absent.

A specific group of compounds of formula I are compounds wherein X is absent.

A specific value for Ar is a phenyl or a pyridyl wherein the phenyl or pyridyl is optionally substituted with 1 to 5 R$^6$.

Another specific value for Ar is a phenyl or 5-6 membered monocyclic heteroaryl, wherein phenyl or 5-6 membered monocyclic heteroaryl is optionally substituted with 1 to 5 R$^6$.

Another specific value for Ar is a phenyl, pyridinyl or thienyl, wherein phenyl, pyridinyl or thienyl is optionally substituted with 1 to 5 R$^6$.

Another specific value for R$^6$ is —NR$^{11}$S(O)$_p$R$^a$, halogen, (C$_1$-C$_8$)alkyl or NR$^{11}$C(O)R$^{11}$.

Another specific value for R$^6$ is —NR$^{11}$S(O)$_p$R$^a$, halogen or (C$_1$-C$_8$)alkyl.

Another specific value for R$^6$ is —NHS(O)$_2$(C$_1$-C$_3$)alkyl, halogen or (C$_1$-C$_3$)alkyl.

Another specific value for R$^6$ is —NHS(O)$_2$CH$_3$, chloro, bromo or methyl.

A specific group of compounds of formula I are compounds wherein:
a) Y$^1$ is N, Y$^2$ is C, Y$^3$ is N, Y$^4$ is N and Y$^5$ is CR$^2$; or
b) Y$^1$ is CH, Y$^2$ is C, Y$^3$ is N, Y$^4$ is N and Y$^5$ is CR$^2$; or
c) Y$^1$ is N, Y$^2$ is N, Y$^3$ is CR$^{8'}$, Y$^4$ is C and Y$^5$ is N; or
d) Y$^1$ is N, Y$^2$ is N, Y$^3$ is CR$^{8'}$, Y$^4$ is C and Y$^5$ is CR$^2$; or
e) Y$^1$ is N, Y$^2$ is N, Y$^3$ is N, Y$^4$ is C and Y$^5$ is N; or
f) Y$^1$ is CH, Y$^2$ is N, Y$^3$ is N, Y$^4$ is C and Y$^5$ is N; or
g) Y$^1$ is N, Y$^2$ is C, Y$^3$ is N, Y$^4$ is C and Y$^5$ is NR$^{2'}$; or
h) Y$^1$ is CH, Y$^2$ is N, Y$^3$ is CR$^{8'}$, Y$^4$ is C and Y$^5$ is N; or
i) Y$^1$ is NH, Y$^2$ is C, Y$^3$ is N, Y$^4$ is C and Y$^5$ is CR$^2$.

the dashed bonds ---- are selected from single bonds and double bonds so as to provide an aromatic ring system;

A is —$(CR^4R^{4'})$—;

n is 3;

each p is 2;

Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1 to 5 $R^6$;

X is —$C(R^{13})(R^{14})$—, or X is absent;

$R^1$ is H, —$NR^{11}R^{12}$, $(C_1$-$C_8)$alkyl or $C_2$-$C_{20}$ heterocyclyl;

$R^2$ is H;

$R^{2'}$ is H;

$R^3$ is H;

$R^{3'}$ is H;

each $R^4$ is H;

each $R^{4'}$ is H;

each $R^6$ is independently —$NR^{11}S(O)_pR^a$, halogen or $(C_1$-$C_8)$alkyl;

$R^7$ is H or $(C_1$-$C_8)$alkyl;

$R^8$ is $(C_1$-$C_8)$alkyl or $C_2$-$C_{20}$ heterocyclyl;

$R^{8'}$ is H;

each $R^a$ is independently $(C_1$-$C_8)$alkyl;

each $R^{11}$ or $R^{12}$ is independently H; or when $R^{11}$ and $R^{12}$ are attached to a nitrogen they may optionally be taken together with the nitrogen to which they are both attached to form a 3 to 7 membered heterocyclic ring wherein any one carbon atom of said heterocyclic ring can optionally be replaced with —O—, —S—, —$S(O)_p$—, —NH—, —$NR^a$— or —C(O)—;

$R^{13}$ is H;

$R^{14}$ is $NR^{11}S(O)_pR^a$; and wherein each $C_2$-$C_{20}$ heterocyclyl of each $R^1$ or $R^8$ is independently, optionally substituted with one or more hydroxy, —$NH_2$ or CN.

In one embodiment the compounds of formula I do not include compounds wherein $Y^3$ is N and $R^1$ is OH.

A specific group of compounds of formula I and salts and esters, thereof are compounds wherein:

a) $Y^1$ is N, NH or CH, $Y^2$ is C, $Y^3$ is N or $CR^{8'}$, $Y^4$ is N or C and $Y^5$ is N, $NR^{2'}$ or $CR^2$, wherein at least two of $Y^1$, $Y^2$, $Y^3$, $Y^4$ and $Y^5$ are independently N, NH or $NR^{2'}$; or b) $Y^1$ is N, NH or CH, $Y^2$ is N or C, $Y^3$ is N or $CR^{8'}$, $Y^4$ is N or C and $Y^5$ is N or $NR^2$, wherein at least two of $Y^1$, $Y^2$, $Y^3$, $Y^4$ and $Y^5$ are independently N, NH or $NR^2$; or c) $Y^1$ is N, NH or CH, $Y^2$ is N or C, $Y^3$ is $CR^{8'}$, $Y^4$ is N or C and $Y^5$ is N, $NR^{2'}$ or $CR^2$, wherein at least two of $Y^1$, $Y^2$, $Y^3$, $Y^4$ and $Y^5$ are independently N, NH or $NR^{2'}$;

the dashed bonds ---- are selected from single bonds and double bonds so as to provide an aromatic ring system;

A is —$(CR^4R^{4'})$— wherein any one $CR^4R^{4'}$ of said —$(CR^4R^{4'})_n$— may be optionally replaced with —O—, —S—, —$S(O)_p$—, NH or $NR^a$;

n is 3, 4, 5 or 6;

each p is 1 or 2;

Ar is a $C_2$-$C_{20}$ heterocyclyl group or a $C_6$-$C_{20}$ aryl group, wherein the $C_2$-$C_{20}$ heterocyclyl group or the $C_6$-$C_{20}$ aryl group is optionally substituted with 1 to 5 $R^6$;

X is —$C(R^{13})(R^{14})$—, —$N(CH_2R^{14})$—, —NH— or X is absent;

$R^1$ is H, —$OR^{11}$, —$NR^{11}R^{12}$, —$NR^{11}C(O)R^{11}$, —$NR^{11}C(O)OR^{11}$, —$NR^{11}C(O)NR^{11}R^{12}$, $N_3$, CN, $NO_2$, —$SR^{11}$, —$S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S(O)_p(OR^{11})$, —$NR^{11}SO_pNR^{11}R^{12}$, —$NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^2$ is H, CN, $NO_2$, halogen or $(C_1$-$C_8)$alkyl;

$R^{2'}$ is H or $(C_1$-$C_8)$alkyl;

$R^3$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^{3'}$ is H, $OR^{11}$, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^4$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^{4'}$ is H, $OR^{11}$, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^5$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^{5'}$ is H, $OR^{11}$, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

each $R^6$ is independently H, oxo, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^7$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S(O)_p(OR^{11})$, —$NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^8$ is H, $OR^{11}$, $NR^{11}R^{12}$, $NR^{11}C(O)R^{11}$, $NR^{11}C(O)OR^{11}$, $NR^{11}C(O)NR^{11}R^{12}$, $N_3$, CN, $NO_2$, $SR^{11}$, $S(O)_pR^a$, $NR^{11}S(O)_pR^a$, —$C(=O)R^{11}$, —$C(=O)OR^{11}$, —$C(=O)NR^{11}R^{12}$, —$C(=O)SR^{11}$, —$S(O)_p(OR^{11})$, —$SO_2NR^{11}R^{12}$, —$NR^{11}S$ (O)$_p$(OR$^{11}$), —NR$^{11}$SO$_p$NR$^{11}$R$^{12}$, NR$^{11}$C(=NR$^{11}$)NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

R$^{8'}$ is H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

each R$^a$ is independently (C$_1$-C$_8$)alkyl, (C$_1$-C$_8$)haloalkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_3$-C$_7$)cycloalkyl(C$_1$-C$_8$)alkyl wherein any (C$_1$-C$_8$)alkyl, (C$_1$-C$_8$)haloalkyl, (C$_2$-C$_8$)alkenyl or (C$_2$-C$_8$)alkynyl of R$^a$ is optionally substituted with one or more OH, NH$_2$, CO$_2$H, C$_2$-C$_{20}$ heterocyclyl, and wherein any aryl(C$_1$-C$_8$)alkyl, C$_6$-C$_{20}$ aryl, C$_2$-C$_{20}$ heterocyclyl, (C$_3$-C$_7$)cycloalkyl or (C$_3$-C$_7$)cycloalkyl(C$_1$-C$_8$)alkyl of R$^a$ is optionally substituted with one or more (e.g., 1, 2 3, 4 or 5) OH, NH$_2$, CO$_2$H, C$_2$-C$_{20}$ heterocyclyl or (C$_1$-C$_8$)alkyl;

each R$^{11}$ or R$^{12}$ is independently H, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl, (C$_3$-C$_7$)cycloalkyl(C$_1$-C$_8$)alkyl, —C(=O)R$^a$ or —S(O)$_p$R$^a$; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S—, —S(O)$_p$—, —NH—, —NR$^a$— or —C(O)—;

R$^{13}$ is H or (C$_1$-C$_8$)alkyl;

R$^{14}$ is H, (C$_1$-C$_8$)alkyl, NR$^{11}$R$^{12}$, NR$^{11}$C(O)R$^{11}$, NR$^{11}$C(O)OR$^{11}$, NR$^{11}$C(O)NR$^{11}$R$^{12}$, NR$^{11}$S(O)$_p$R$^a$, —NR$^{11}$S(O)$_p$(OR$^{11}$) or NR$^{11}$SO$_p$NR$^{11}$R$^{12}$; and wherein each (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, (C$_3$-C$_7$)cycloalkyl or (C$_3$-C$_7$)cycloalkyl(C$_1$-C$_8$)alkyl of each R$^1$, R$^2$, R$^{2'}$, R$^3$, R$^{3'}$, R$^4$, R$^{4'}$, R$^5$, R$^{5'}$, R$^6$, R$^7$, R$^8$, R$^{8'}$, R$^{11}$ or R$^{12}$ is independently, optionally substituted with one or more (e.g., 1, 2 3, 4, 5 or more) oxo, halogen, hydroxy, NH$_2$, CN, N$_3$, N(R$^a$)$_2$, NHR$^a$, SH, SR$^a$, S(O)$_p$R$^a$, OR$^a$, (C$_1$-C$_8$)alkyl, (C$_1$-C$_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, =NOH, =NOR$^a$, NR$^a$S(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, —OC(=O)R$^a$, —OP(O)(OH)$_2$ or R$^a$.

In one embodiment the compounds of formula I are selected from compounds compound of formula I, or a salt or ester, thereof;
wherein:

a) Y$^1$ is N, NH or CH, Y$^2$ is C, Y$^3$ is N or CR$^{8'}$, Y$^4$ is N or C and Y$^5$ is N, NR$^{2'}$ or CR$^2$, wherein at least two of Y$^1$, Y$^2$, Y$^3$, Y$^4$ and Y$^5$ are independently N, NH or NR$^{2'}$; or b) Y$^1$ is N, NH or CH; Y$^2$ is N or C; Y$^3$ is N or CR$^{8'}$, Y$^4$ is N or C; and Y$^5$ is N or NR$^{2'}$, wherein at least two of Y$^1$, Y$^2$, Y$^3$, Y$^4$ and Y$^5$ are independently N, NH or NR$^{2'}$; or c) Y$^1$ is N, NH or CH; Y$^2$ is N or C; Y$^3$ is CR$^{8'}$; Y$^4$ is N or C; and Y$^5$ is N, NR$^{2'}$ or CR$^2$, wherein at least two of Y$^1$, Y$^2$, Y$^3$, Y$^4$ and Y$^5$ are independently N, NH or NR$^{2'}$;

the dashed bonds ---- are selected from single bonds and double bonds so as to provide an aromatic ring system;

A is —(CR$^4$R$^{4'}$)— wherein any one CR$^4$R$^{4'}$ of said —(CR$^4$R$^{4'}$)$_n$— may be optionally replaced with —O—, —S—, —S(O)$_p$—, NH or NR$^a$;

n is 3, 4, 5 or 6;

each p is 1 or 2;

Ar is a C$_2$-C$_{20}$ heterocyclyl group or a C$_6$-C$_{20}$ aryl group, wherein the C$_2$-C$_{20}$ heterocyclyl group or the C$_6$-C$_{20}$ aryl group is optionally substituted with 1 to 5 R$^6$;

X is —C(R$^{13}$)(R$^{14}$)—, —N(CH$_2$R$^{14}$)— or —NH—, or X is absent (e.g., Ar is directly attached to the carbonyl of formula I);

R$^1$ is H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

R$^2$ is H, CN, NO$_2$, halogen or (C$_1$-C$_8$)alkyl;

R$^{2'}$ is H or (C$_1$-C$_8$)alkyl;

R$^3$ is H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

R$^{3'}$ is H, OR$^{11}$, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

each R$^4$ is independently H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

each R$^{4'}$ is independently H, OR$^{11}$, (C$_1$-C$_8$)alkyl, (C$_2$-C$_8$)alkenyl, (C$_2$-C$_8$)alkynyl, aryl(C$_1$-C$_8$)alkyl, C$_6$-C$_{20}$ aryl, C$_2$-C$_{20}$ heterocyclyl, C$_2$-C$_{20}$ heterocyclyl(C$_1$-C$_8$)alkyl, (C$_3$-C$_7$)cycloalkyl or (C$_3$-C$_7$)cycloalkyl(C$_1$-C$_8$)alkyl;

or two R$^4$ on adjacent carbon atoms, when taken together, may form a double bond between the two carbons to which they are attached or may form a (C$_3$-C$_7$)cycloalkyl ring wherein one carbon atom of said (C$_3$-C$_7$)cycloalkyl ring may be optionally replaced by —O—, —S—, —S(O)$_p$—, —NH— or —NR$^a$—;

or two R$^4$ on non-adjacent carbon atoms, when taken together, may form a (C$_3$-C$_7$)cycloalkyl ring wherein one carbon atom of said (C$_3$-C$_7$)cycloalkyl ring may be optionally replaced by —O—, —S—, —S(O)$_p$—, —NH— or —NR$^a$—;

or two R$^4$ and two R$^{4'}$ on adjacent carbon atoms, when taken together, may form an optionally substituted C$_6$ aryl ring;

or one $R^4$ and one $R^{4'}$ on the same carbon atom, when taken together, may form a $(C_3$-$C_7)$cycloalkyl ring wherein one carbon atom of said $(C_3$-$C_7)$cycloalkyl ring may be optionally replaced by —O—, —S—, —S(O)$_p$—, —NH— or —NR$^a$—;

each $R^5$ is independently H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

each $R^{5'}$ is independently H, OR$^{11}$, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

each $R^6$ is independently H, oxo, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

or two $R^6$ on adjacent carbon atoms, when taken together, may form a $(C_3$-$C_7)$cycloalkyl ring wherein one carbon atom of said $(C_3$-$C_7)$cycloalkyl ring may be optionally replaced by —O—, —S—, —S(O)$_p$—, —NH— or —NR$^a$—;

or any $R^6$ adjacent to the obligate carbonyl group of said Ar, when taken together with $R^3$, may form a bond or a —(CR$^5$R$^{5'}$)$_m$— group wherein m is 1 or 2;

or any $R^6$ adjacent to the obligate carbonyl group of said Ar, when taken together with $R^2$ or $R^{2'}$ may form a bond;

$R^7$ is H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)N$^{11}$R$^{12}$, —C(=O)SR$^{11}$, —S(O)$_p$(OR$^{11}$), —SO$_2$NR$^{11}$R$^{12}$, NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$ halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^8$ is H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

$R^{8'}$ is H, OR$^{11}$, NR$^{11}$R$^{12}$, NR$^{11}$C(O)R$^{11}$, NR$^{11}$C(O)OR$^{11}$, NR$^{11}$C(O)NR$^{11}$R$^{12}$, N$_3$, CN, NO$_2$, SR$^{11}$, S(O)$_p$R$^a$, NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl;

each $R^a$ is independently $(C_1$-$C_8)$alkyl, $(C_1$-$C_8)$haloalkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl wherein any $(C_1$-$C_8)$alkyl, $(C_1$-$C_8)$haloalkyl, $(C_2$-$C_8)$alkenyl or $(C_2$-$C_8)$alkynyl of $R^a$ is optionally substituted with one or more OH, NH$_2$, CO$_2$H, $C_2$-$C_{20}$ heterocyclyl, and wherein any aryl$(C_1$-$C_8)$alkyl, $C_6$-$C_{20}$ aryl, $C_2$-$C_{20}$ heterocyclyl, $(C_3$-$C_7)$cycloalkyl or $(C_3$-$C_7)$cycloalkyl$(C_1$-$C_8)$alkyl of $R^a$ is optionally substituted with one or more (e.g., 1, 2 3, 4 or 5) OH, NH$_2$, CO$_2$H, $C_2$-$C_{20}$ heterocyclyl or $(C_1$-$C_8)$alkyl;

each $R^{11}$ or $R^{12}$ is independently H, $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $(C_3$-$C_7)$cycloalkyl, $(C_3$-$C_7)$cycloalkyl$(C_1$-$C_8)$alkyl, —C(=O)R$^a$ or —S(O)$_p$R$^a$; or when $R^{11}$ and $R^{12}$ are attached to a nitrogen they may optionally be taken together with the nitrogen to which they are both attached to form a 3 to 7 membered heterocyclic ring wherein any one carbon atom of said heterocyclic ring can optionally be replaced with —O—, —S—, —S(O)$_p$—, —NH—, —NR$^a$— or —C(O)—;

$R^{13}$ is H or $(C_1$-$C_8)$alkyl;

$R^{14}$ is H, $(C_1$-$C_8)$alkyl, NR$^{11}$R$^{12}$, NR$^{11}$C(O)R$^{11}$, NR$^{11}$C(O)OR$^{11}$, NR$^{11}$C(O)NR$^{11}$R$^{12}$, NR$^{11}$S(O)$_p$R$^a$, —NR$^{11}$S(O)$_p$(OR$^{11}$) or NR$^{11}$SO$_p$NR$^{11}$R$^{12}$; and wherein each $(C_1$-$C_8)$alkyl, $(C_2$-$C_8)$alkenyl, $(C_2$-$C_8)$alkynyl, aryl$(C_1$-$C_8)$alkyl, $C_6$-$C_{20}$ aryl, $C_2$-$C_{20}$ heterocyclyl, $C_2$-$C_{20}$ heterocyclyl$(C_1$-$C_8)$alkyl, $(C_3$-$C_7)$cycloalkyl or $(C_3$-$C_7)$cycloalkyl$(C_1$-$C_8)$alkyl of each $R^1$, $R^2$, $R^{2'}$, $R^3$, $R^{3'}$, $R^4$, $R^{4'}$, $R^5$, $R^{5'}$, $R^6$, $R^7$, $R^8$, $R^{8'}$, $R^{11}$ or $R^{12}$ is independently, optionally substituted with one or more (e.g., 1, 2 3, 4, 5 or more) oxo, halogen, hydroxy, NH$_2$, CN, N$_3$, N(R$^a$)$_2$, NHR$^a$, SH, SR$^a$, S(O)$_p$R$^a$, OR$^a$, $(C_1$-$C_8)$alkyl, $(C_1$-$C_8)$haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, NHS(O)$_p$R$^a$, NR$^a$S(O)$_p$R$^a$, NHC(O)R$^a$, NR$^a$C(O)R$^a$, NHC(O)OR$^a$, NR$^a$C(O)OR$^a$, NR$^a$C(O)NHR$^a$, NR$^a$C(O)N(R$^a$)$_2$, NR$^a$C(O)NH$_2$, NHC(O)NHR$^a$, NHC(O)N(R$^a$)$_2$, NHC(O)NH$_2$, =NH, =NOH, =NOR$^a$, NR$^a$S(O)$_p$NHR$^a$, NR$^a$S(O)$_p$N(R$^a$)$_2$, NR$^a$S(O)$_p$NH$_2$, NHS(O)$_p$NHR$^a$, NHS(O)$_p$N(R$^a$)$_2$, NHS(O)$_p$NH$_2$, —OC(=O)R$^a$, —OP(O)(OH)$_2$ or R$^a$.

In one embodiment a compound of formula I is selected from:

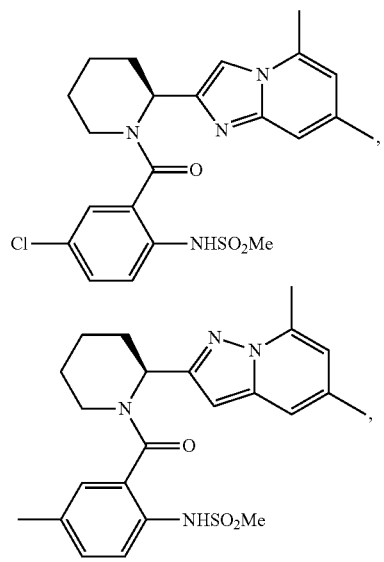

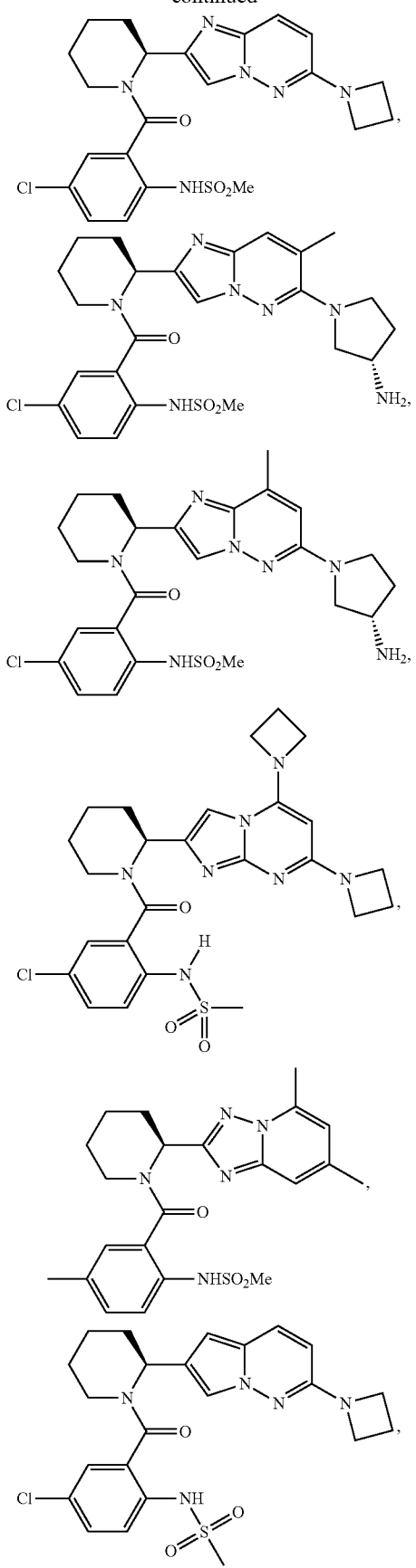
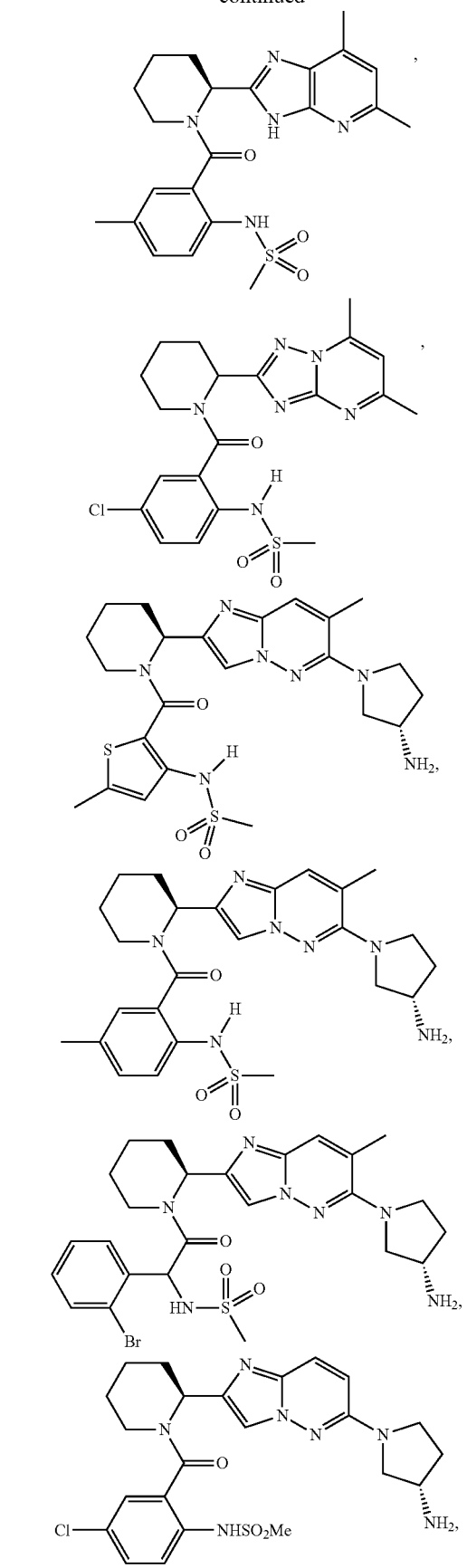

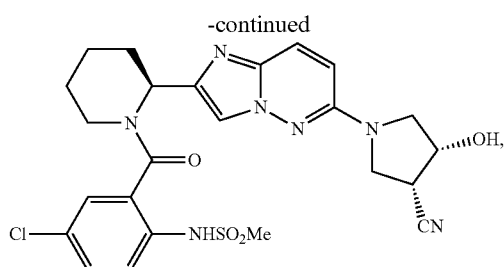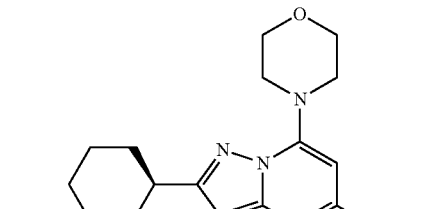
and salts and esters, thereof.
In one embodiment a compound of the invention is selected from:

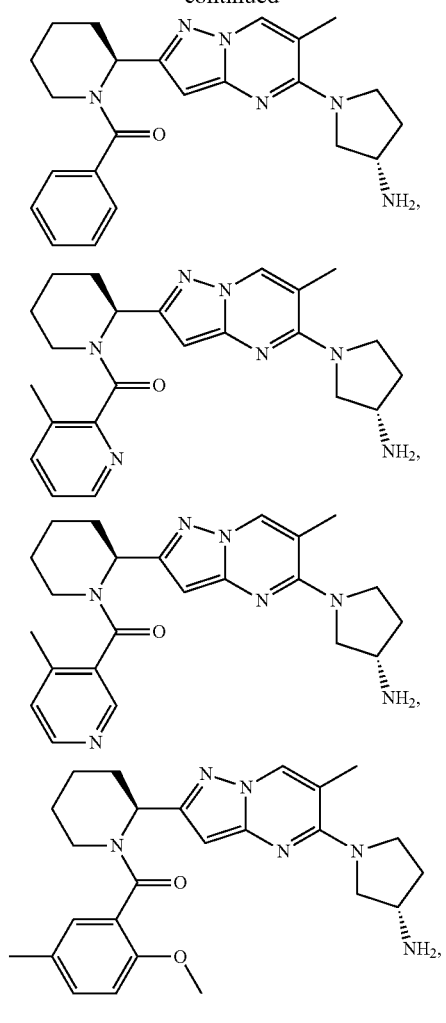
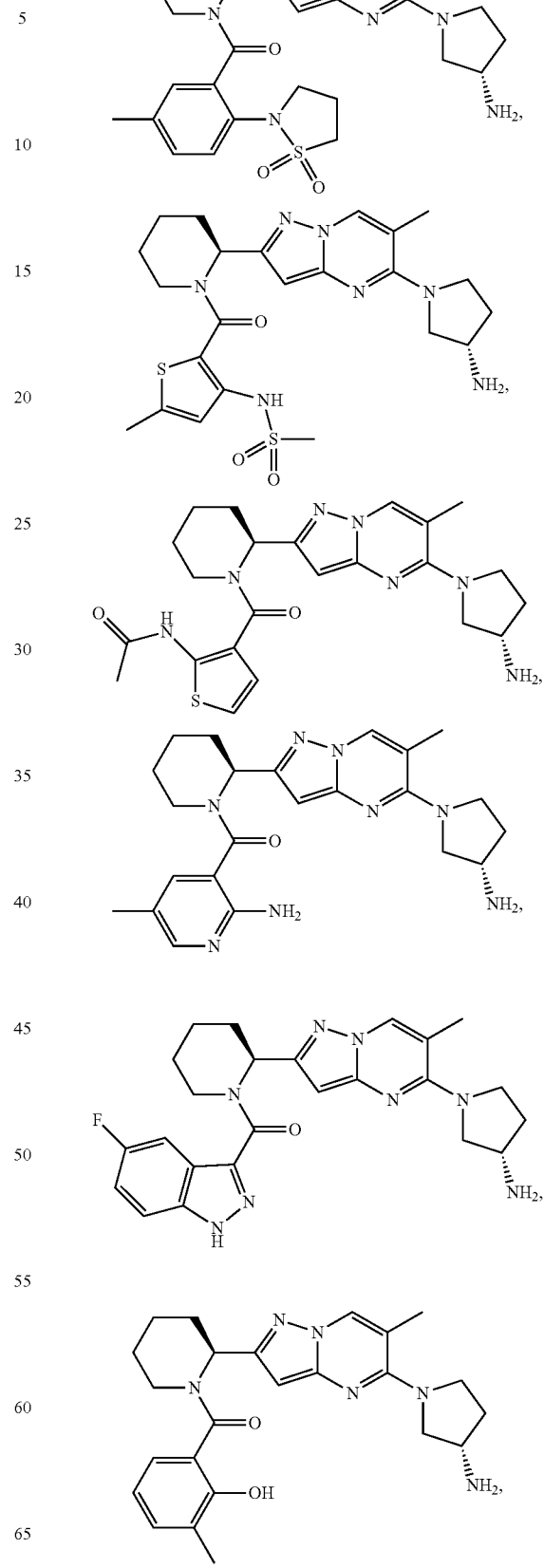

-continued
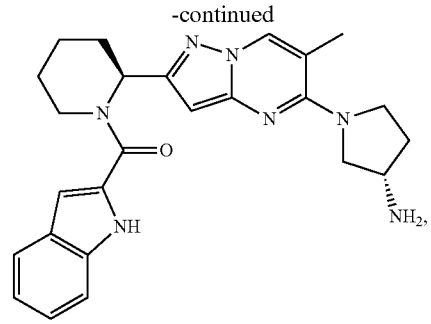
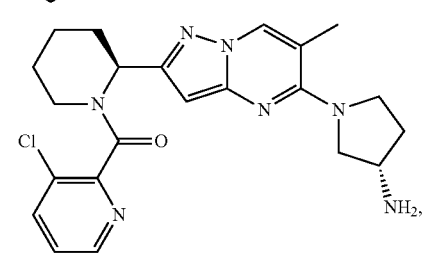
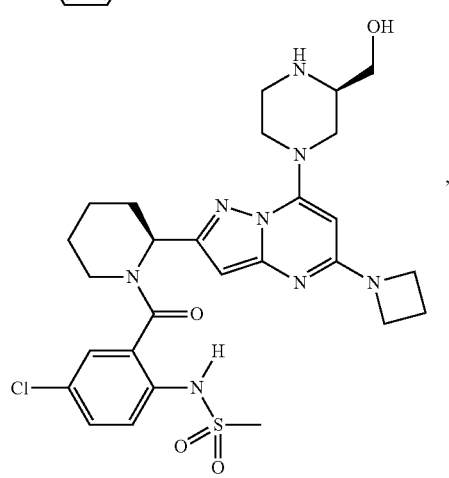
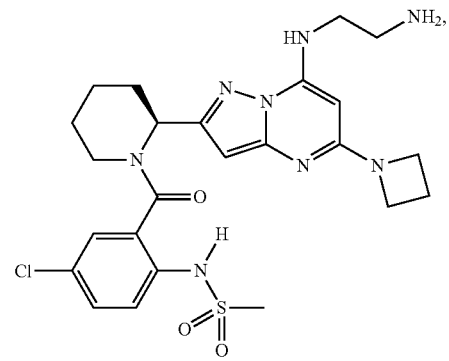
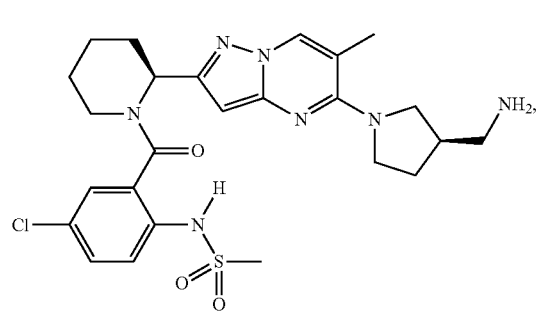
-continued
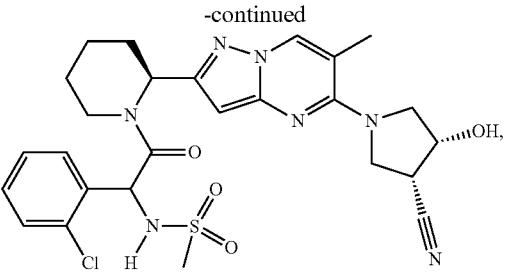
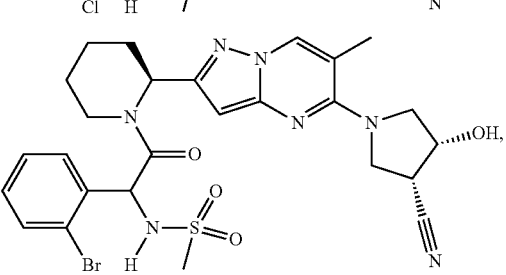
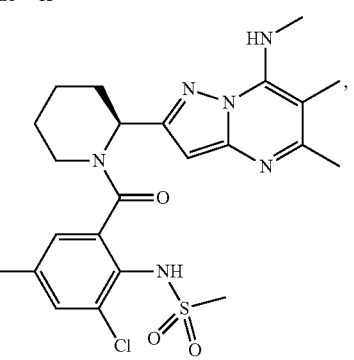
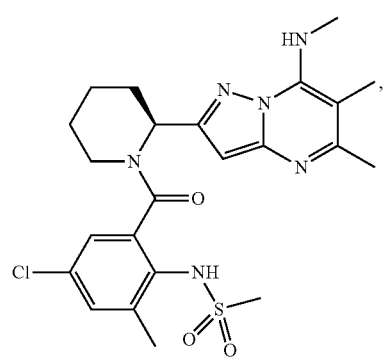
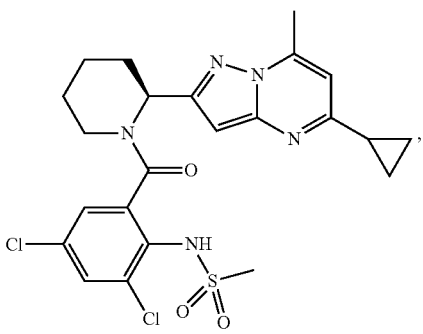

-continued
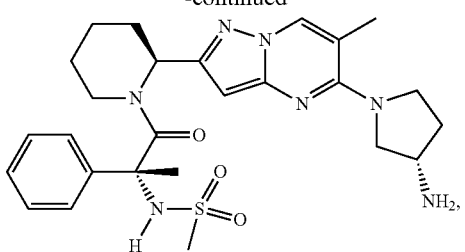
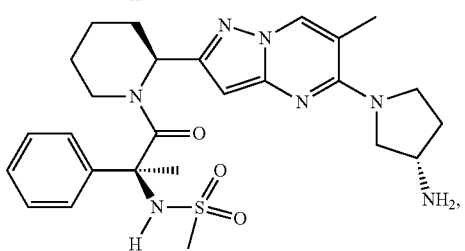
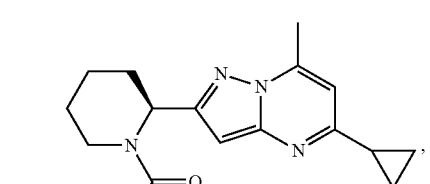
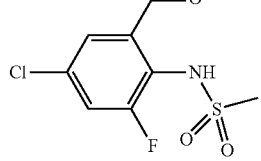
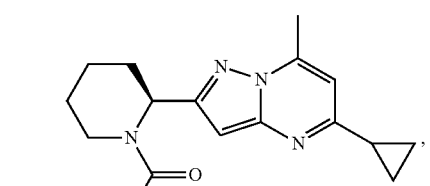
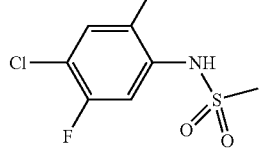
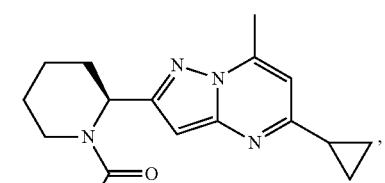
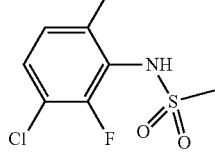
-continued
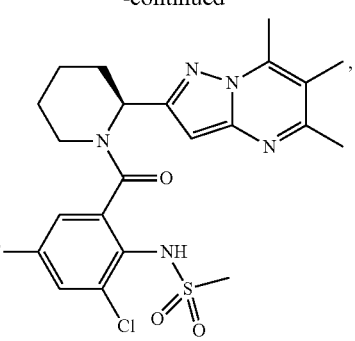
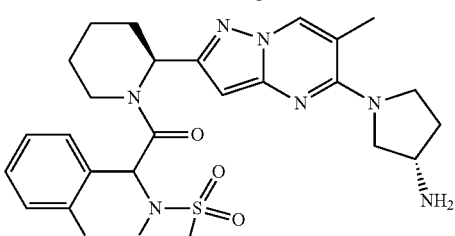
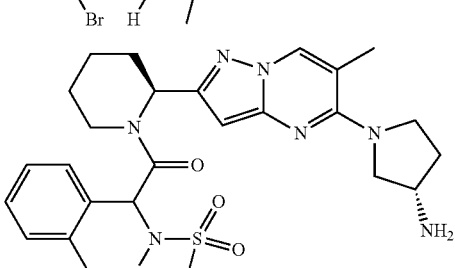
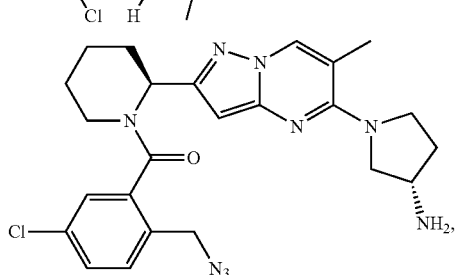
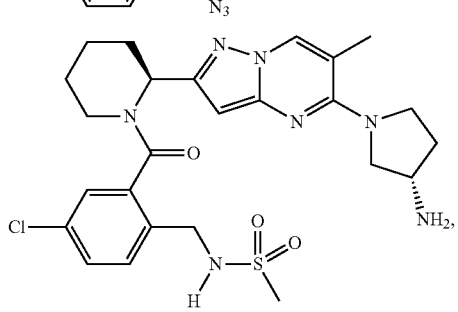
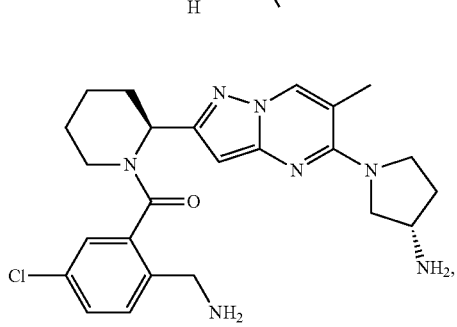

49
-continued
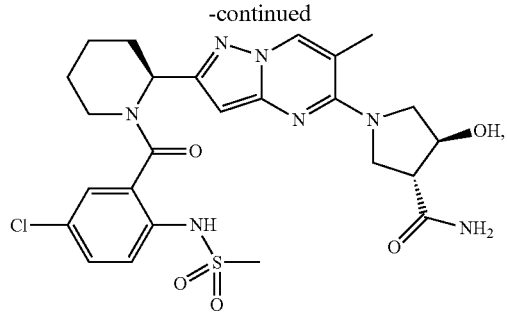
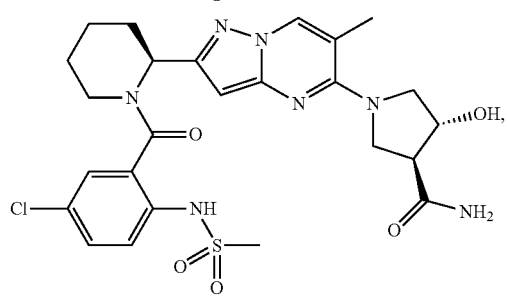
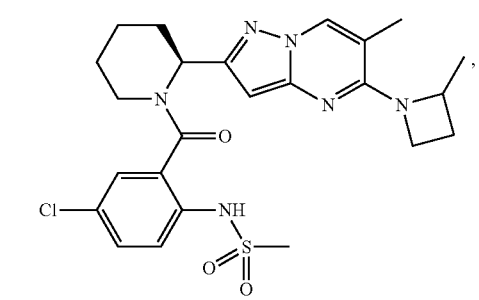
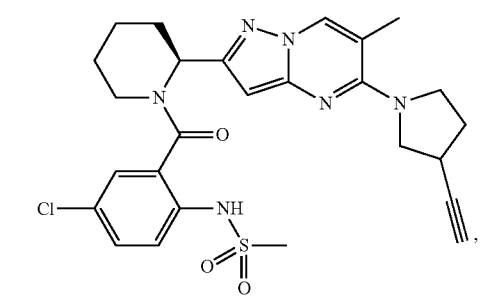
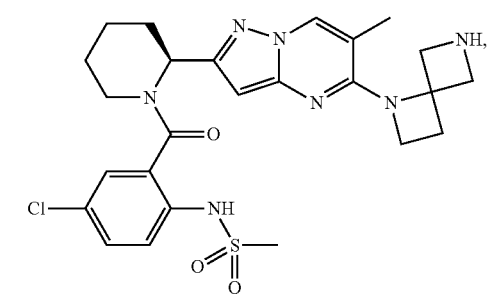
50
-continued
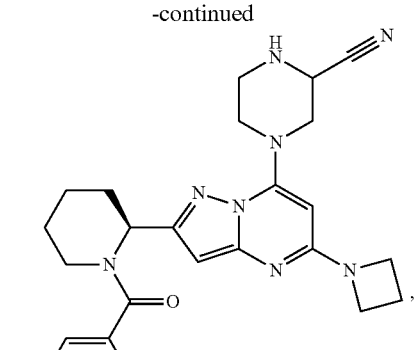
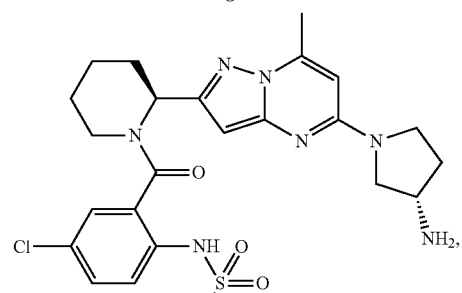
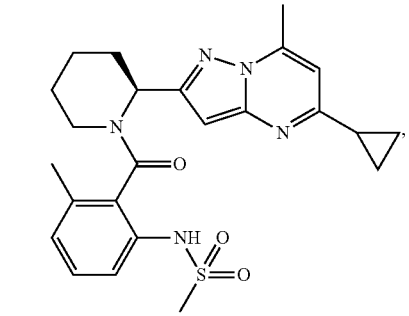
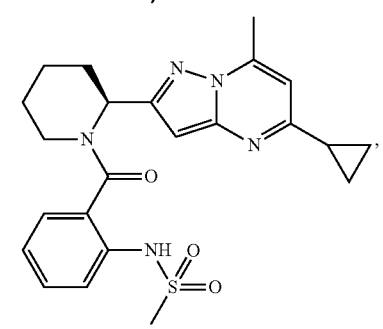
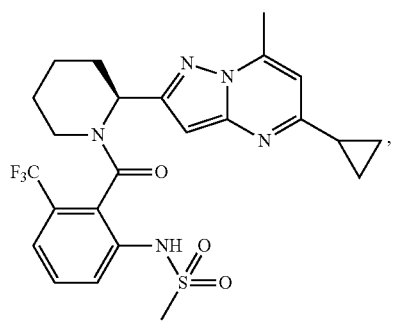

51
-continued
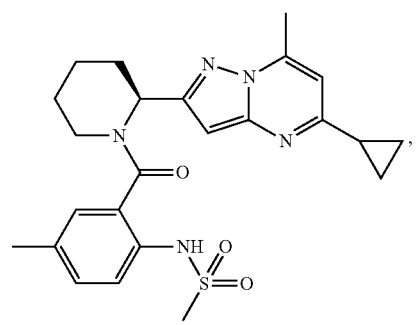
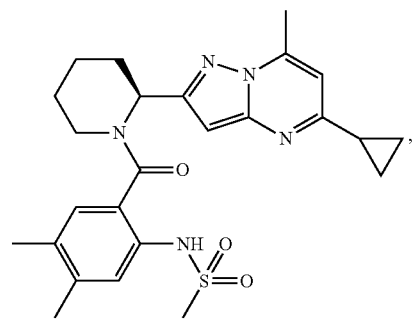
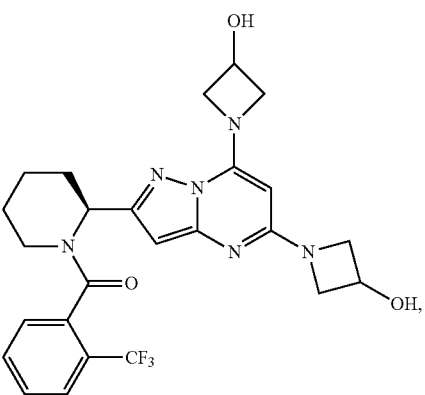
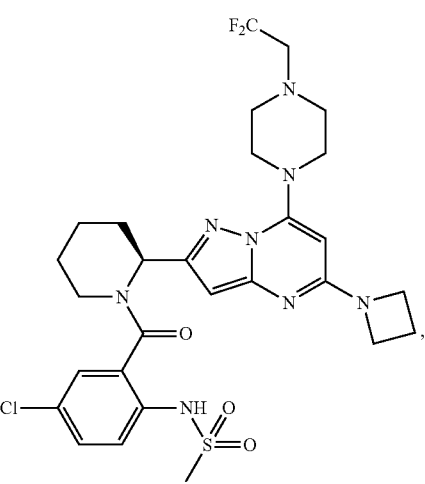
52
-continued
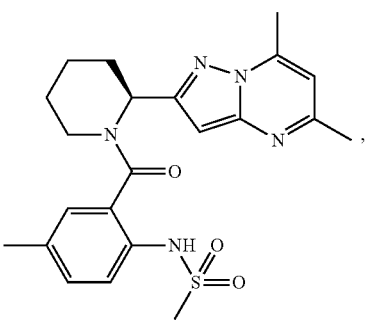
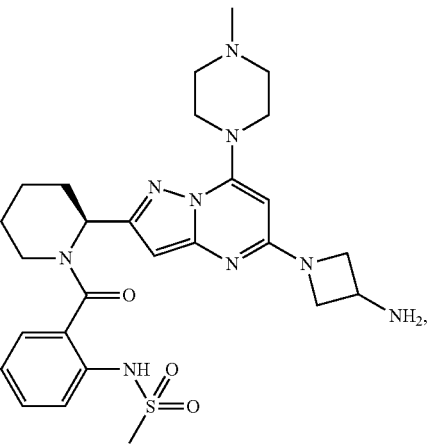
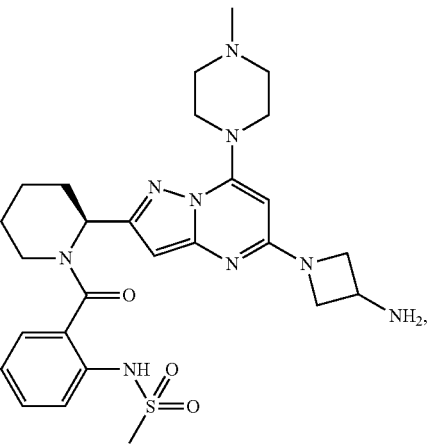
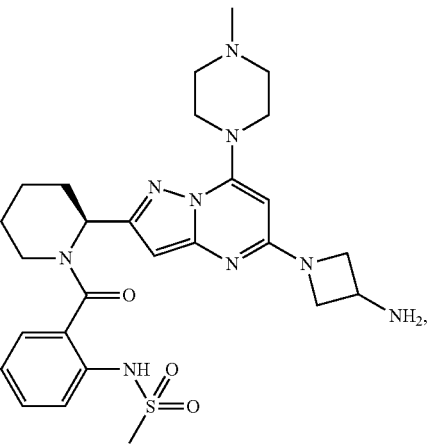

-continued
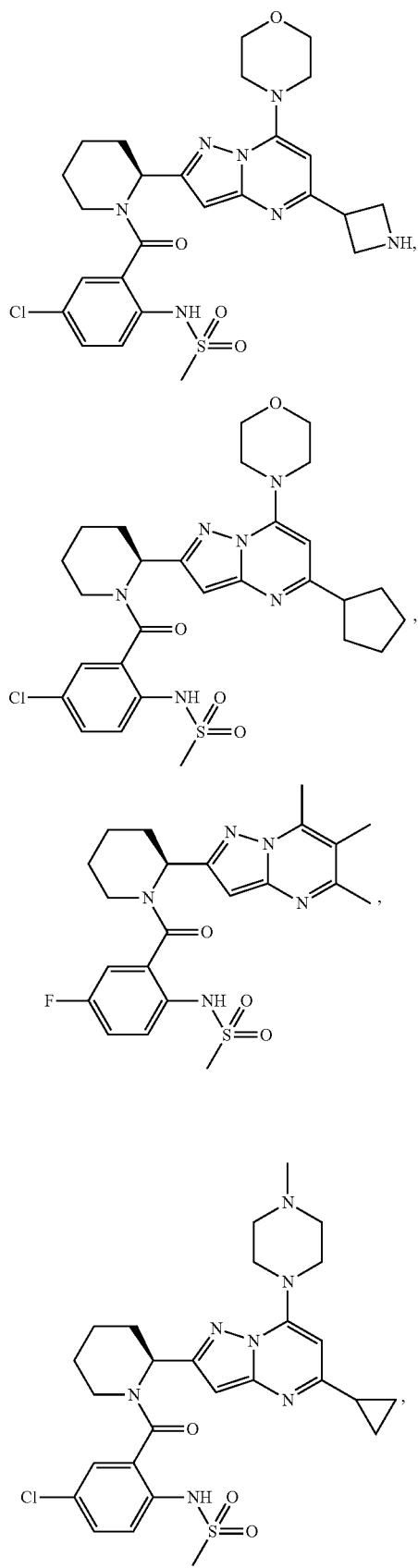
-continued
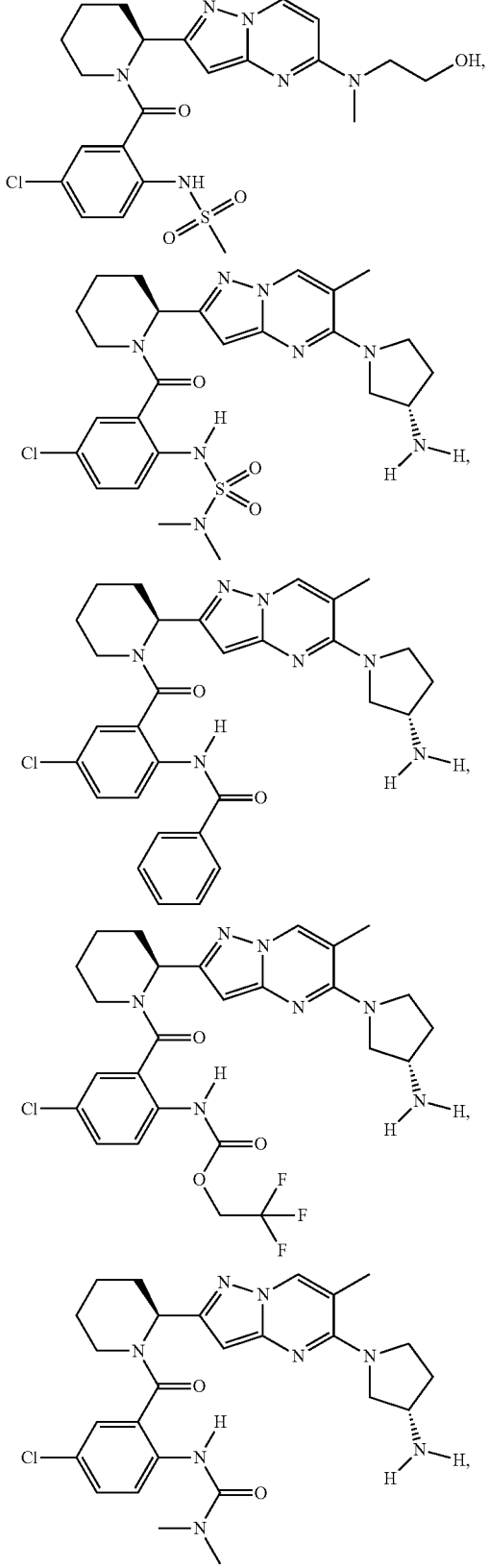

55
-continued
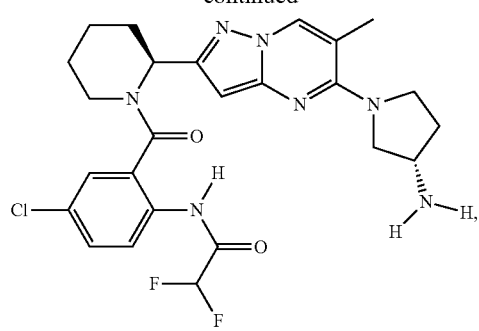
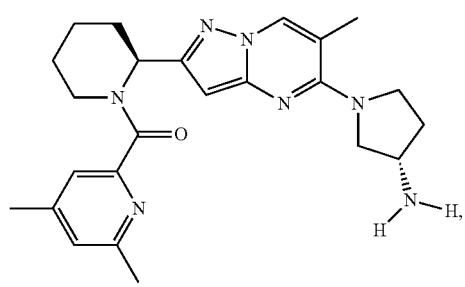
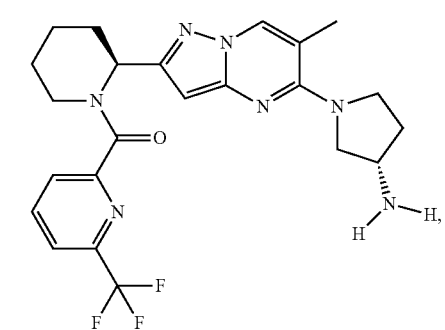
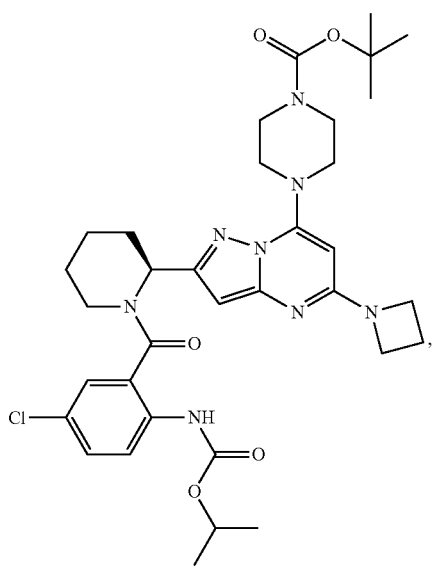
56
-continued
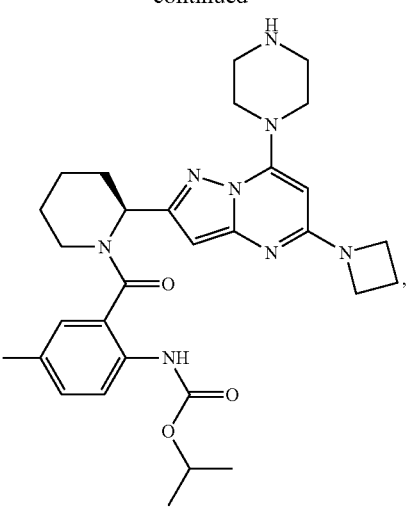
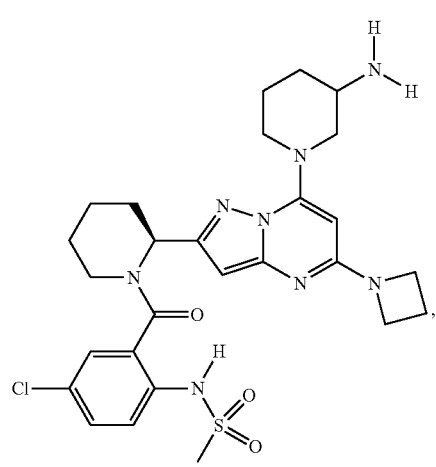
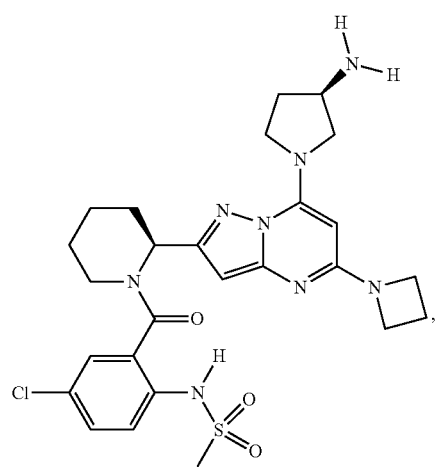

57
-continued
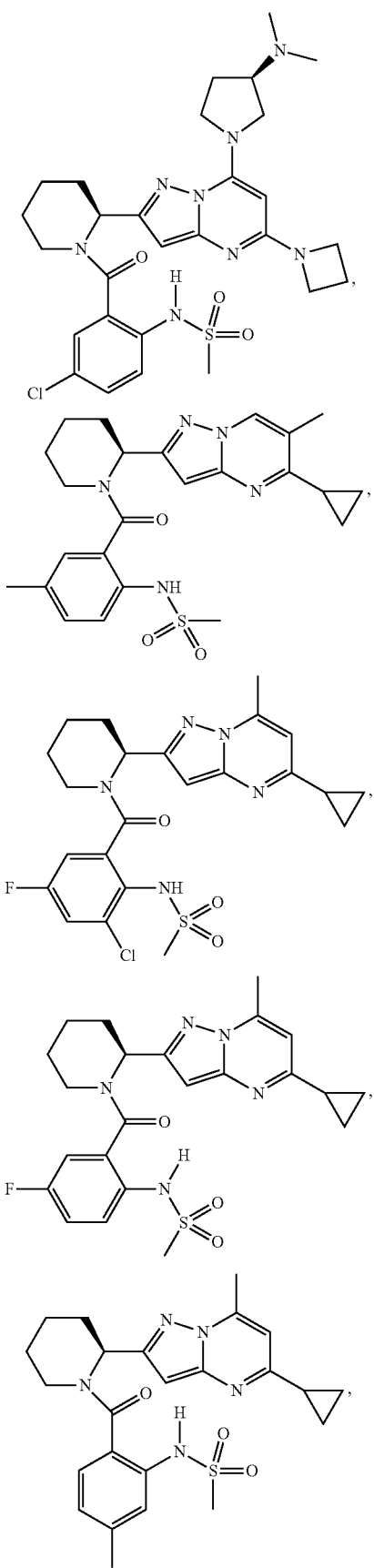
58
-continued
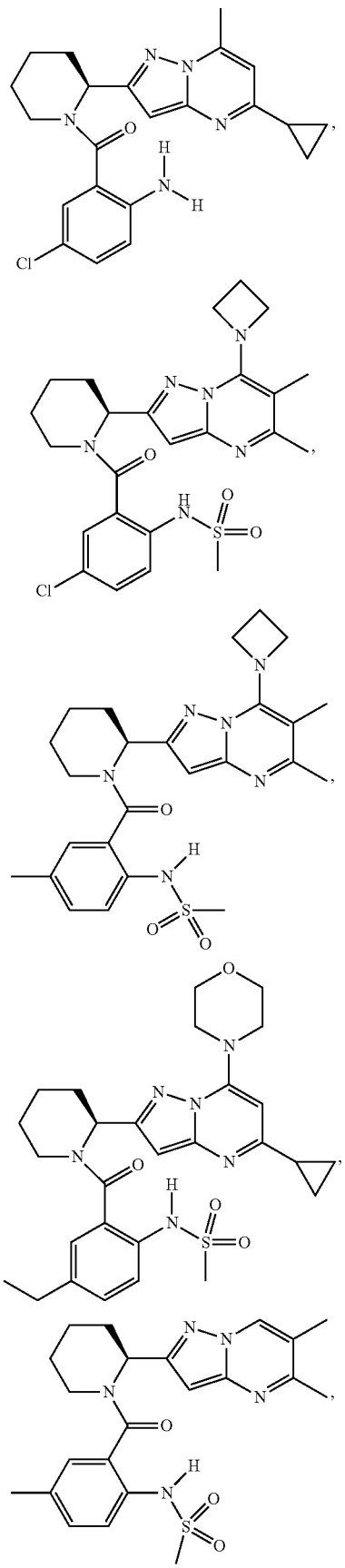

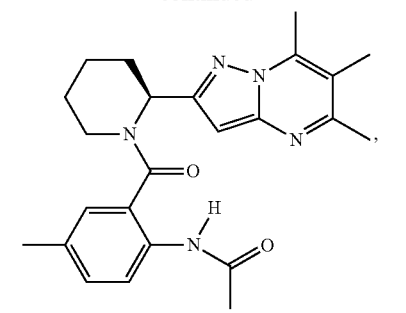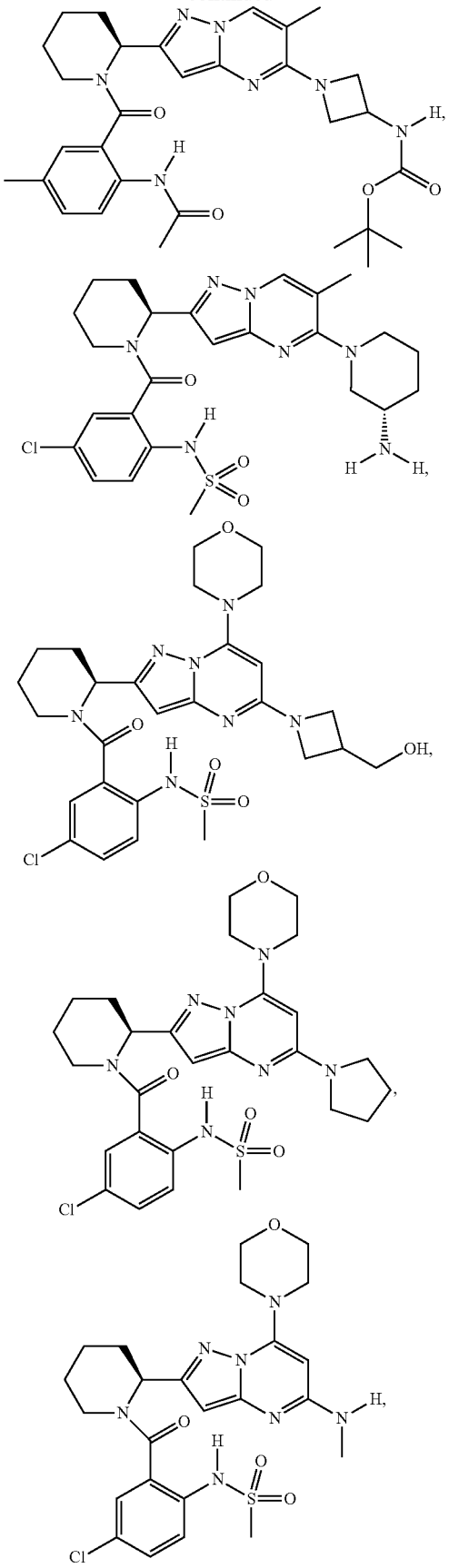

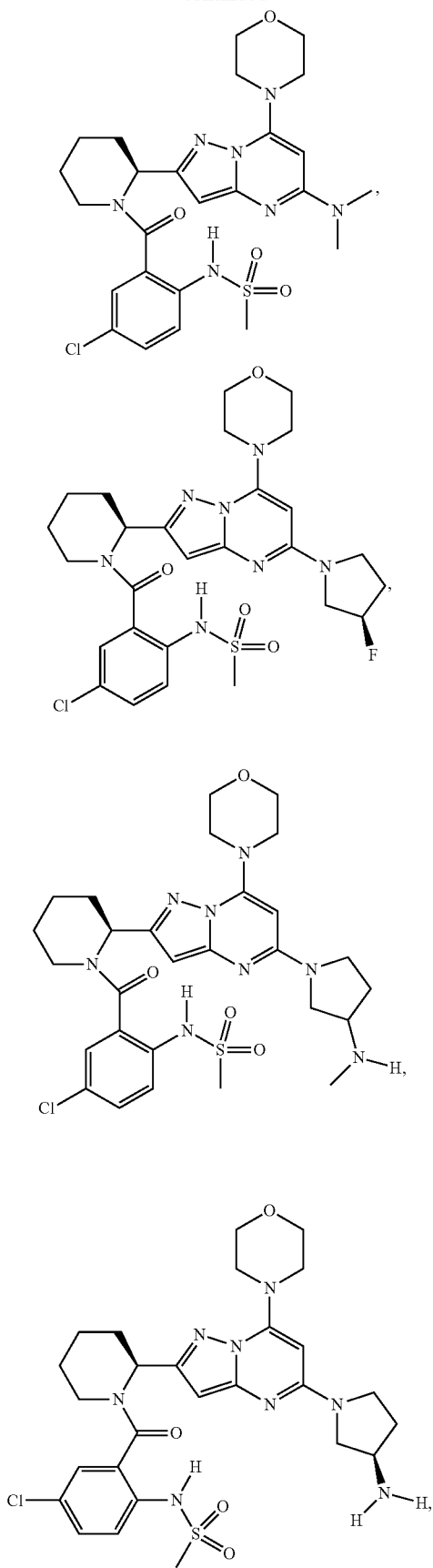
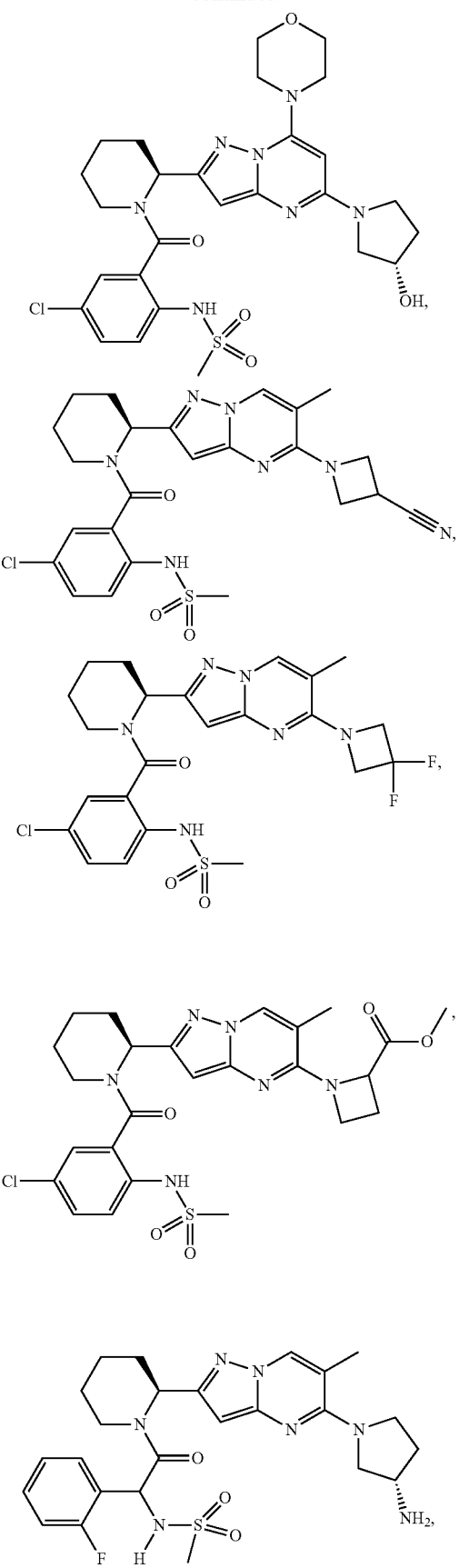

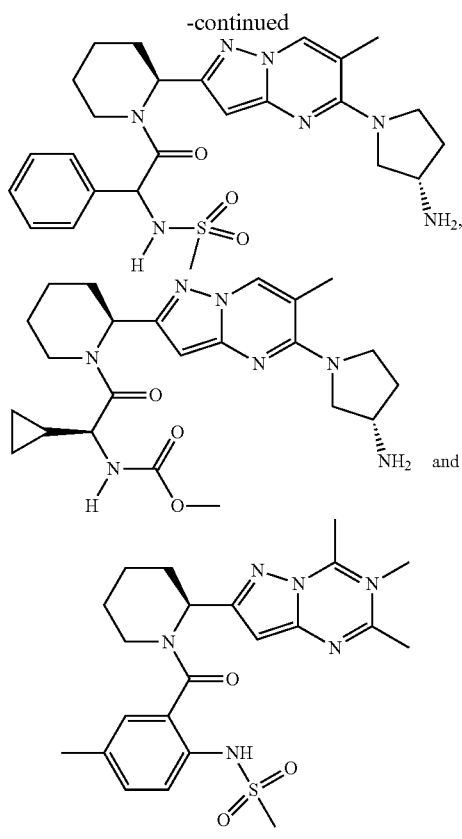

and salts and esters, thereof.

Esters of Compounds of the Invention.

The compounds of the invention also include "esters" of the compounds of the invention. Accordingly, one example of esters of the compounds of the invention include esters wherein a hydroxyl group of the compound of the invention is an ester. These esters of the invention are typically labile and thus the ester may be converted to the corresponding hydroxyl group in vivo (e.g., after administration). Esters include those esters based on carbon and phosphorus.

Typical esters include: $(R^aO)_2P(=O)O-$, $(HO)_2P(=O)O-$, $(C_1-C_8)alkyl(C=O)O-$, $C_6-C_{20}aryl(C=O)O-$, $C_2-C_{20}heterocycyl(C=O)O-$ or $(C_3-C_7)cyclolalkyl(C=O)O-$ wherein each $(C_1-C_8)alkyl(C=O)O-$, $C_6-C_{20}aryl(C=O)O-$, $C_2-C_{20}heterocycyl(C=O)O-$ or $(C_3-C_7)cyclolalkyl(C=O)O-$, is independently, optionally substituted with one or more oxo, halogen, hydroxy, $NH_2$, CN, $N_3$, $N(R^a)_2$, $NHR^a$, SH, $SR^a$, $S(O)_pR^a$, $OR^a$, $(C_1-C_8)$ alkyl, $(C_1-C_8)haloalkyl$, $-C(O)R^a$, $-C(O)H$, $-C(=O)OR^a$, $-C(=O)OH$, $-C(=O)N(R^a)_2$, $-C(=O)NHR^a$, $-C(=O)NH_2$, $NHS(O)_pR^a$, $NR^aS(O)_pR^a$, $NHC(O)R^a$, $NR^aC(O)R^a$, $NHC(O)OR^a$, $NR^aC(O)OR^a$, $NR^aC(O)NHR^a$, $NR^aC(O)N(R^a)_2$, $NR^aC(O)NH_2$, $NHC(O)NHR^a$, $NHC(O)N(R^a)_2$, $NHC(O)NH_2$, $=NH$, $=NOH$, $=NOR^a$, $NR^aS(O)_pNHR^a$, $NR^aS(O)_pN(R^a)_2$, $NR^aS(O)_pNH_2$, $NHS(O)_pNHR^a$, $NHS(O)_pN(R^a)_2$, $NHS(O)_pNH_2$, $-OC(=O)R^a$, $-OP(O)(OH)_2$ or $R^a$; and each $R^a$ is independently $(C_1-C_8)alkyl$, $(C_1-C_8)haloalkyl$, $(C_2-C_8)alkenyl$, $(C_2-C_8)alkynyl$, $aryl(C_1-C_8)alkyl$, $C_6-C_{20}$ aryl, $C_2-C_{20}$ heterocyclyl, $(C_3-C_7)cycloalkyl$ or $(C_3-C_7)cycloalkyl(C_1-C_8)alkyl$, wherein any $(C_1-C_8)alkyl$, $(C_1-C_8)$ haloalkyl, $(C_2-C_8)alkenyl$ or $(C_2-C_8)alkynyl$ of $R^a$ is optionally substituted with one or more OH, $NH_2$, $CO_2H$, $C_2-C_{20}$ heterocyclyl, and wherein any $aryl(C_1-C_8)alkyl$, $C_6-C_{20}$ aryl, $C_2-C_{20}$ heterocyclyl, $(C_3-C_7)cycloalkyl$ or $(C_3-C_7)cycloalkyl(C_1-C_8)alkyl$ of $R^a$ is optionally substituted with one or more OH, $NH_2$, $CO_2H$, $C_2-C_{20}$ heterocyclyl or $(C_1-C_8)$ alkyl.

It is to be understood that the point of connection of the esters $(R^aO)_2P(=O)O-$, $(HO)_2P(=O)O-$, $(C_1-C_8)alkyl(C=O)O-$, $C_6-C_{20}aryl(C=O)O-$. $C_2-C_{20}heterocycyl(C=O)O-$ and $(C_3-C_7)cyclolalkyl(C=O)O-$ to the compound of the invention is through the oxygen of the ester.

Preparation of Compounds of the Invention

The compounds of formula I and compounds 1-103 were be prepared by the procedures described in examples 1-237 presented herein below. It is to be understood that related compounds to those described can be prepared by varying these procedures or using other synthetic procedures and such synthetic variations are well within the grasp of the practitioner. General schemes 1-9 are provided as additional embodiments of the invention and describe methods that can be used to prepare compounds of the invention.

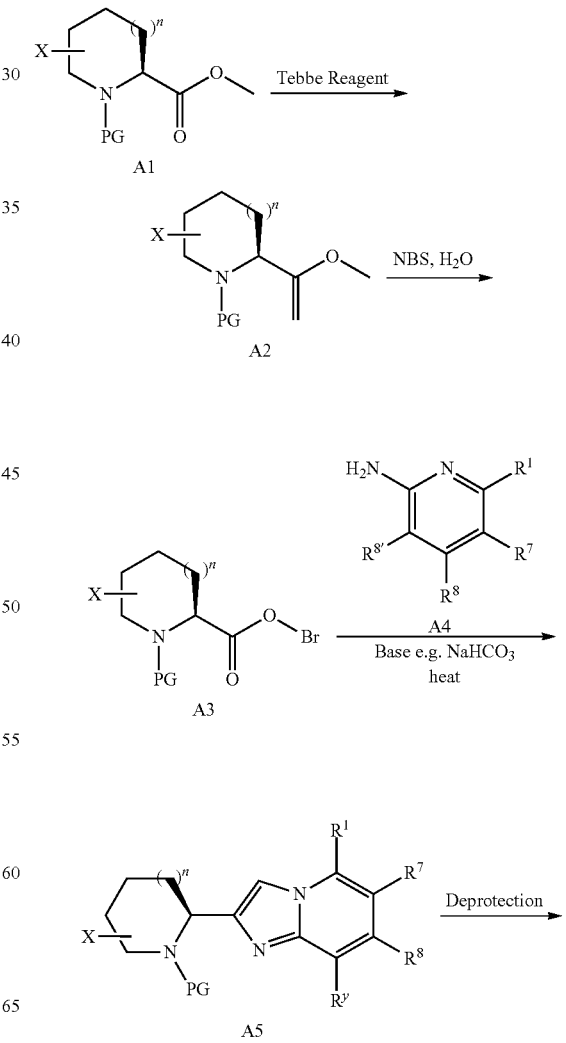

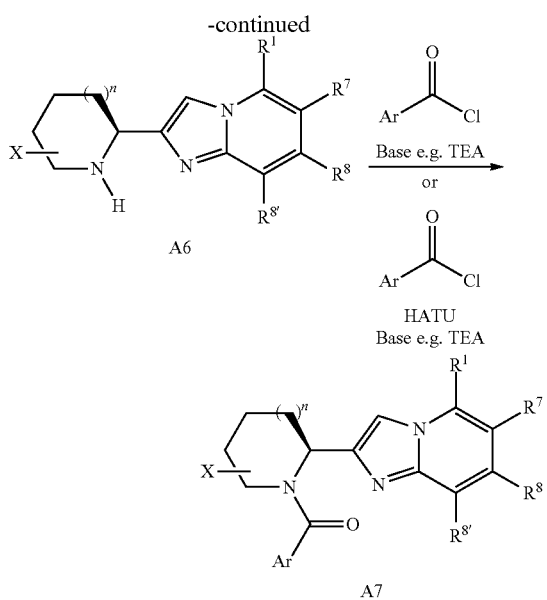

n = 1, 2 or more
X = H, Me, CF₃, etc
PG = protecting group e.g. BOC

General Scheme 1 describes the methods under which the compounds of the invention A7 can be prepared. The starting material is a protected (PG) cycloaminoalkyl ring that can be 6-, 7- or larger size ring and also optionally contain substituents around the ring. This cycloaminoalkyl ring is substituted at the carbon atom adjacent to the nitrogen group with a methyl ester group. In one embodiment the stereochemistry at this position is the (S) stereochemistry.

Protecting groups on the cycloaminoalkyl nitrogen can be removed during the synthesis using methods described in Green and Wutts, Protecting Groups in Organic Synthesis 3rd Edition. In the forward scheme, the carboxylic acid methyl ester group on N-protected cycloaminoalkyl A1 is first converted to the enol ether utilizing a solution of Tebbe Reagent to yield A2. Typically the ester is reacted with the Tebbe reagent at low temperature (−78° C.) and in a suitable solvent (e.g., dry THF). The product A2 is then transformed into alpha-bromo ketone A3 via bromination of enol ether. This transformation is carried out using bromination reagents such as NBS in a mixed solvent (e.g. THF and water). Formation of imidazopyridine A5 is then achieved via condensation of A3 with a 2-aminopyridine e.g. A4 in the presence of a base e.g. sodium bicarbonate under elevated temperatures. Removal of the protecting group on the cycloalkylamine e.g. BOC or CBZ is done using procedures described in Green and Wutts, Protecting Groups in Organic Synthesis 3rd Edition to provide A6. For example BOC groups are removed using TFA in an organic solvent (e.g. dichloromethane), or treatment with phosphoric acid. The unprotected NH in the cycloaminoalkyl ring on A6 is acylated to provide compounds of structure A7 using standard acylation procedures. For example an acid chloride, generated from the corresponding acid using thionyl chloride or oxalyl chloride, is reacted with A6 in the presence of an organic base, e.g. triethylamine, in an organic solvent e.g. dichloromethane. Alternatively, a peptide coupling of A6 with an acid can be performed using a variety of standard coupling agents. For example, A6 is acylated by first, combining HATU and the acid together in an organic solvent e.g. DMF, and then after a short period of time e.g. 30 min adding the amine A6 and an organic base e.g. triethylamine to generate A7

General Scheme 2

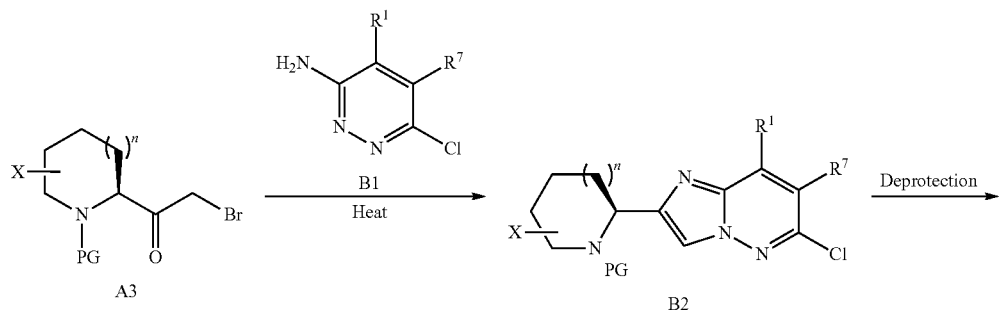

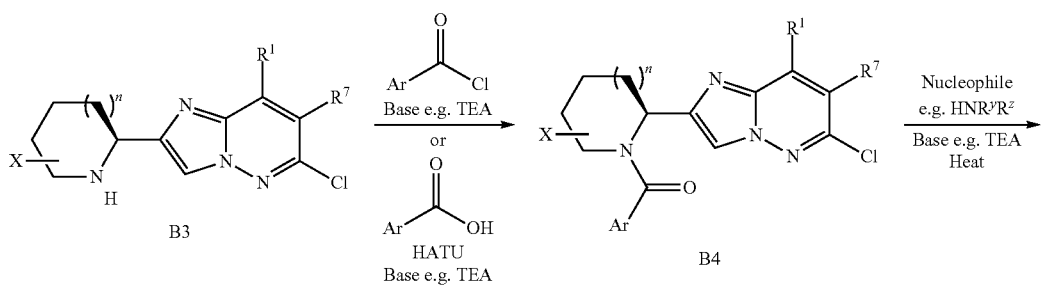

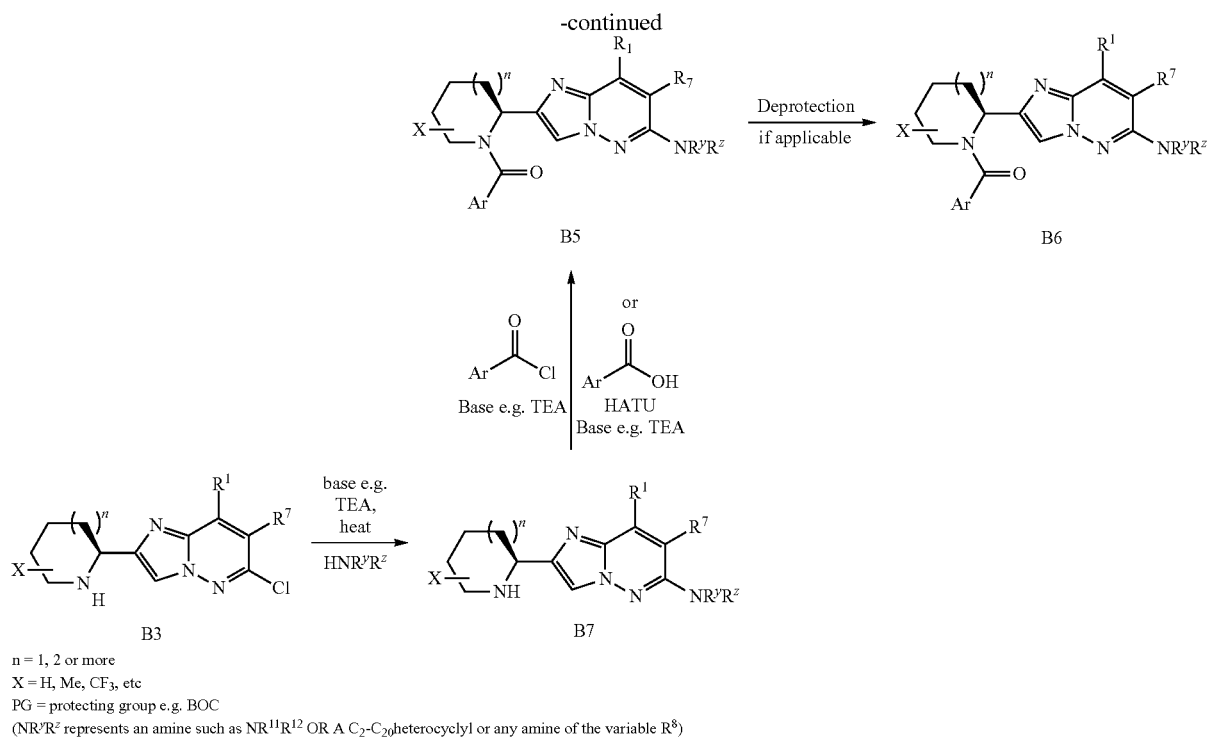

n = 1, 2 or more
X = H, Me, CF₃, etc
PG = protecting group e.g. BOC
(NR^yR^z represents an amine such as NR^11R^12 OR A C₂-C₂₀heterocyclyl or any amine of the variable R⁸)

General Scheme 2 describes the methods under which the compounds of the invention B6 can be prepared. The starting material A3 (general scheme 1) is a protected (PG) cycloaminoalkyl ring that can be 6-, 7- or larger size ring and also optionally contain substituents around the ring. This cycloaminoalkyl ring is substituted at the carbon atom adjacent to the nitrogen group with a halo ketone. In one embodiment the stereochemistry at this position is the (S) stereochemistry. Protecting groups on the cycloaminoalkyl nitrogen can be removed during the synthesis using methods described in Green and Wutts, Protecting Groups in Organic Synthesis 3rd Edition. Condensation of A3 with substituted 6-chloropyridazin-3-amines B1 at elevated temperatures in an organic solvent e.g. ethanol, leads to imidazopyridazine scaffold B2. Removal of the protecting group on the cycloalkylamine e.g. BOC or CBZ is done using procedures described in Green and Wutts, Protecting Groups in Organic Synthesis 3rd Edition to provide B3. For example BOC groups are removed using TFA in an organic solvent (e.g. dichloromethane) or treatment with phosphoric acid. The unprotected NH in the cycloaminoalkyl ring on B3 is acylated to provide compounds of structure B4 using standard acylation procedures. For example an acid chloride, generated from the corresponding acid using thionyl chloride or oxalyl chloride, is reacted with B3 in the presence of an organic base, e.g. triethylamine, in an organic solvent e.g. dichloromethane. Alternatively, a peptide coupling of B3 with an acid can be performed using a variety of standard coupling agents. For example B3 is acylated by first, combining HATU and the acid together in an organic solvent e.g. DMF, and then after a short period of time e.g. 30 min adding the amine B3 and an organic base e.g. triethylamine to generate B4.

Displacement of the chloride in B4 with nucleophilic amines is then performed to form B5. Typically treatment of B4 in the presence of a base e.g. triethylamine and the appropriate amine at elevated temperatures above 50° C. forms B5. If necessary, any protecting groups remaining on compounds B5 are then removed using conditions as described in Green and Wutts, Protecting Groups in Organic Synthesis 3rd Edition to yield compounds of type B6.

An alternative sequence of steps can also be utilized to convert B3 to B5. Imidazo-chloropyridazine B3 is reacted with an amine in the presence of a base e.g. triethylamine at elevated temperatures above 50 C to displace the chloride and form B7. The unprotected NH in the cycloaminoalkyl ring on B7 is then acylated as described above to provide compounds of structure B5.

General Scheme 3

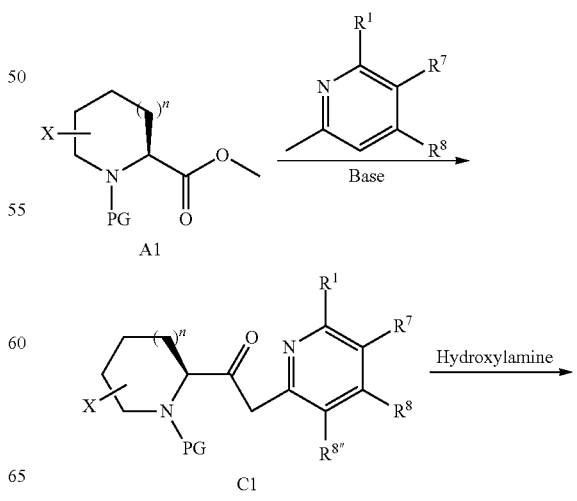

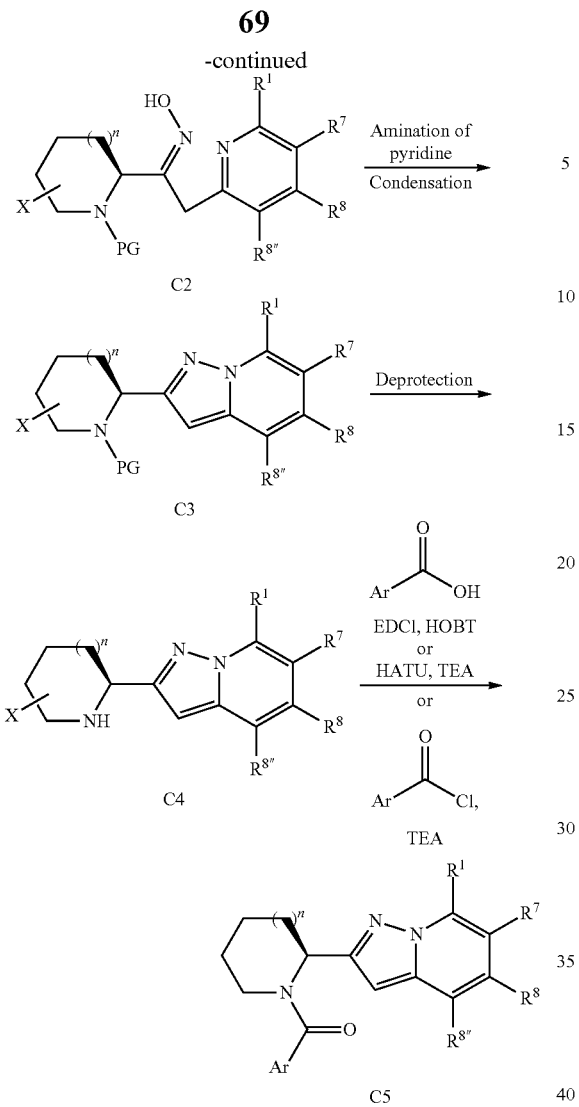

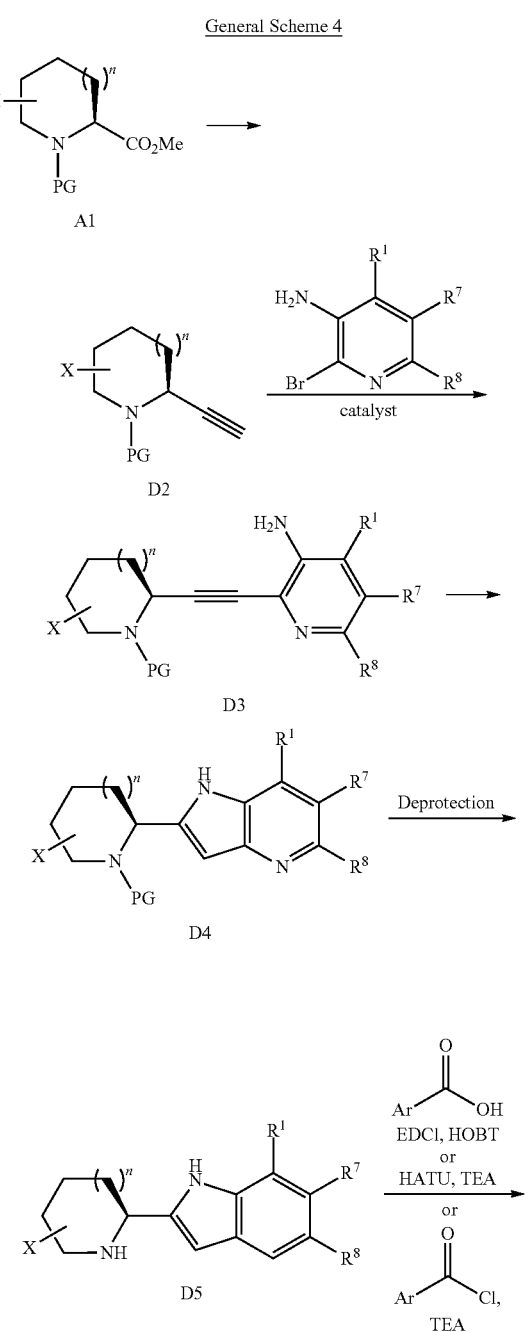

n = 1, 2 or more
X = H, Me, CF$_3$, etc
PG = protecting group e.g. BOC

General scheme 3 describes the methods under which the compounds of the invention C5 can be prepared. The starting material is a protected (PG) cycloaminoalkyl ring A1 that can be 6-, 7- or larger size ring and also optionally contain substituents around the ring. This cycloaminoalkyl ring is substituted at the carbon atom adjacent to the nitrogen group with an ester group. In one embodiment the stereochemistry at this position is the (S) stereochemistry. Protecting groups on the cycloaminoalkyl nitrogen can be removed during the synthesis using methods described in Green and Wutts, Protecting Groups in Organic Synthesis 3rd Edition. The N-protected cyclic aminoheterocycle A1 is first reacted with the anion of the alpha-methyl substituted pyridine to form C1. For example, the anion is generated first by treatment of the pyridine reagent in an organic solvent such as THF with base, preferred (but not limited to) are bases such as BuLi, NaHMDS, LDA or KOi-Bu and then adding A1. The intermediate C1 is then converted to C2 by treatment with hydroxylamine. A typical produce includes treatment of the ketone in ethanolic solution with hydroxylamine in the presence of sodium acetate to provide C2. In the next step, the pyridine nitrogen in C2 is aminated by using a variety of reagents described in the literature for this transformation, such as hydroxylamine-o-sulphonic acid, O-(diphenyl-phosphinyl)hydroxylamine/hydrogen iodide, O-(2,4-dinitrophenyl)hydroxylamine and the like. Typically C2 is dissolved in a suitable organic solvent (e.g. acetonitrile) and treated with the amination reagent in the presence of base, e.g. cesium carbonate. The corresponding aminated pyridine, can often be reacted in situ to form the desired cyclised product C3, or alternatively addition of acid or base can facilitate this transformation to C3. The product C3 is then converted to C4 and then C5 as described in Scheme 1 for conversion of A5 to A7 via A6.

-continued

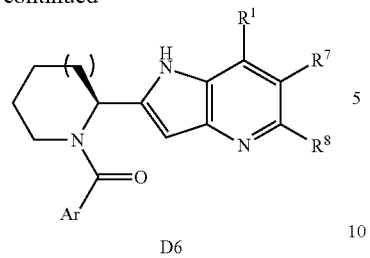

n = 1, 2, or more
X = H, Me, CF$_3$, etc
PG = protecting group e.g. BOC

General scheme 4 describes the methods under which the compounds of the invention D6 can be prepared. The starting material is a protected (PG) cycloaminoalkyl ring that can be 6-, 7- or larger size ring and also optionally contain substituents around the ring. This cycloaminoalkyl ring is substituted at the carbon atom adjacent to the nitrogen group with a methyl ester group. In one embodiment the stereochemistry at this position is the (S) stereochemistry. Protecting groups on the cycloaminoalkyl nitrogen can be removed during the synthesis using methods described in Green and Wutts, Protecting Groups in Organic Synthesis 3rd Edition. The ester group on the N-protected cyclic aminoheterocycle A1 is first converted to an alkyne D2 via one of the many methods known in the literature, typically via the corresponding aldehyde analog of A1. The aldehyde for example, is formed through reduction of the ester group, using DIBAL in a suitable organic solvent (e.g. dichloromethane, THF, and the like). Conversion of the aldehyde to the alkyne can be achieved by several efficient methods documented in the literature, Corey-Fuchs, Ohira Bestmann reagent and the like. For example, coupling of the aldehyde with triphenylphosphine and carbon tetrabromide in an organic solvent (e.g. dichloromethane) forms the intermediate dibromoalkene, which is then treated with strong base e.g. nBuLi, in THF at −78 C to generate the alkyne. Alternatively, base-promoted reactions of dialkyl (diazomethyl) phosphonates (Ohira Bestmann) or (diazomethyl)-trimethylsilane with aldehydes and aryl ketones lead directly to the corresponding homologous alkynes. For example, treatment of the aldehyde with the Ohira-Bestmann phosphonate reagent in the presence of potassium carbonate in an alcoholic solvent generates the alkyne. The alkyne is then reacted with a bromopyridine under typically, but not limited to, Sonogashira-type conditions and their many variations. For example, treatment of the alkyne D2 with the halogenated pyridine in triethylamine in the presence of CuI and a palladium (II) catalyst e.g. PdCl$_2$(PPh$_3$)$_2$ provides D3. The resulting pyridyl alkyne often cyclizes under the reaction conditions to the product D4 or alternatively can be reacted with a fluoride base e.g. TBAF or catalytic amounts of a transition metal to undergo the cyclisation. The product D4 is then converted to D5 and then D6 as described in Scheme 1 for conversion of A5 to A7 via A6.

General Scheme 5

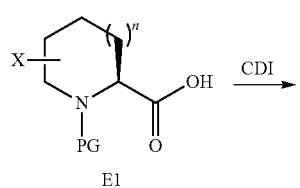

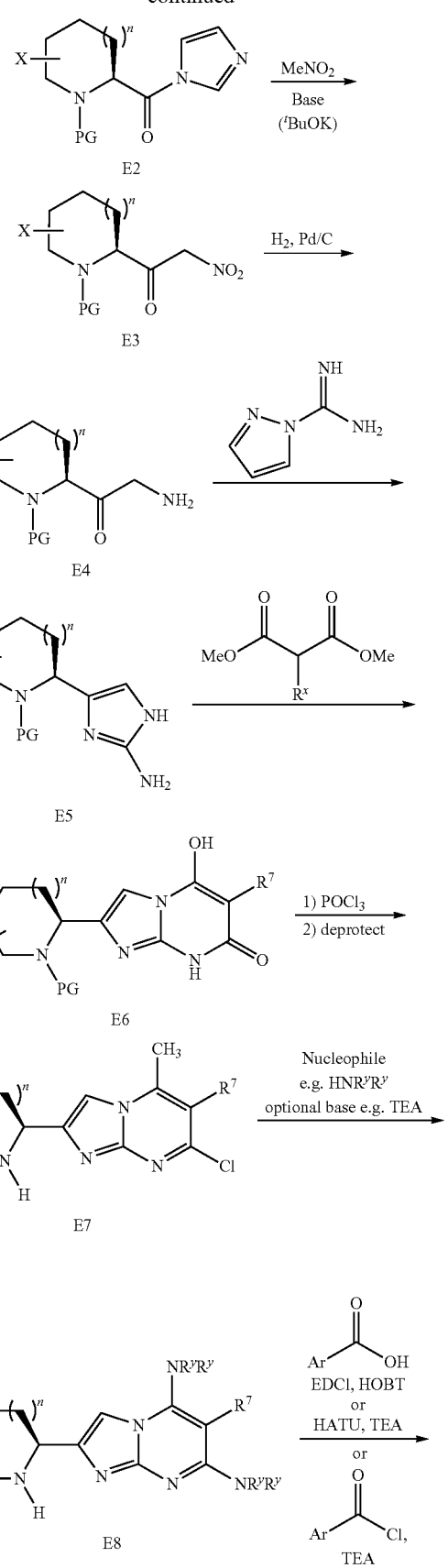

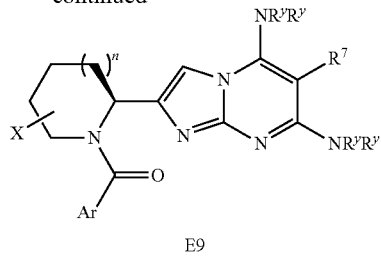

E9 n = 1, 2 or more
X = H, Me, CF₃, etc
PG = protecting group e.g. BOC
(NR<sup>y</sup>R<sup>y</sup> represents an amine such as NR¹¹R¹² or a C₂-C₂₀heterocyclyl or any amine of the variable R¹ or R⁸)

General scheme 5 describes the methods under which the compounds of the invention E9 can be prepared. The starting material is a protected (PG) cycloaminoalkyl ring that can be 6-, 7- or larger size ring and also optionally contain substituents around the ring. This cycloaminoalkyl ring is substituted at the carbon atom adjacent to the nitrogen group with an acid group. In one embodiment the stereochemistry at this position is the (S) stereochemistry. Protecting groups on the cycloaminoalkyl nitrogen can be removed during the synthesis using methods described in Green and Wutts, Protecting Groups in Organic Synthesis 3rd Edition. The carboxylic acid E1 is first activated with a suitable leaving group, for example imidazole. The imidazole product E2 is typically generated by treatment of the carboxylic acid with carbonyldiimidazole in an inert organic solvent. Once the acid is activated as the acylimidazole E2, the addition to nitromethane anion is performed. The anion is generated from nitromethane and a strong base (e.g. potassium tert-butoxide), in a solvent such as DMSO, to which E2 is then added to form E3. Reduction of the nitro ketone is then performed to provide E4 using one of a variety of methods described in the literature for reduction of nitro groups. For example, a solution of the nitro compound in ethanol and acetic acid, is reduced with hydrogen gas in the presence of palladium on carbon to generate the amino ketone intermediate E4. Reaction of the amino ketone with 1H-pyrazole-1-carboximidamide then generates the amino imidazole intermediate E5. This conversion is carried out in the presence of base e.g. sodium carbonate in organic solvent such as ethanol/acetic acid. Intermediate E5 is used to form bicyclic heterocycle E6 through condensation reactions with unsubstituted and substituted malonates in the presence of a base. For example, dimethyl malonate is added to the intermediate E5 in ethanol and treated with sodium ethoxide, followed by heating to provide E6 where Rx is H. Treatment of E6 with neat POCl₃ under elevated temperature then affords the dichloride E7. Under the POCl₃ conditions acidic labile protecting groups e.g. BOC are typically removed, but if this is partial, further treatment with acid e.g. 4N HCl in dioxane can be used to remove remaining BOC protected material. If other protecting groups are utilized then procedures described in Green and Wutts, Protecting groups in Organic Synthesis 3rd Edition can be used to remove the protecting group. Displacement of the aromatic chlorides is then effected with a variety of nucleophiles. A typical nucleophile would be an amine for example that can be reacted in the absence or presence of a base such as triethylamine to form E8. The unprotected NH in the cycloaminoalkyl ring is then acylated to E9 as described in general Scheme 1 for formation of A7 from A6. If E9 requires subsequent removal of a protecting group, this is achieved using conditions as described in Green and Wutts, Protecting groups in Organic Synthesis 3rd Edition.

General Scheme 6

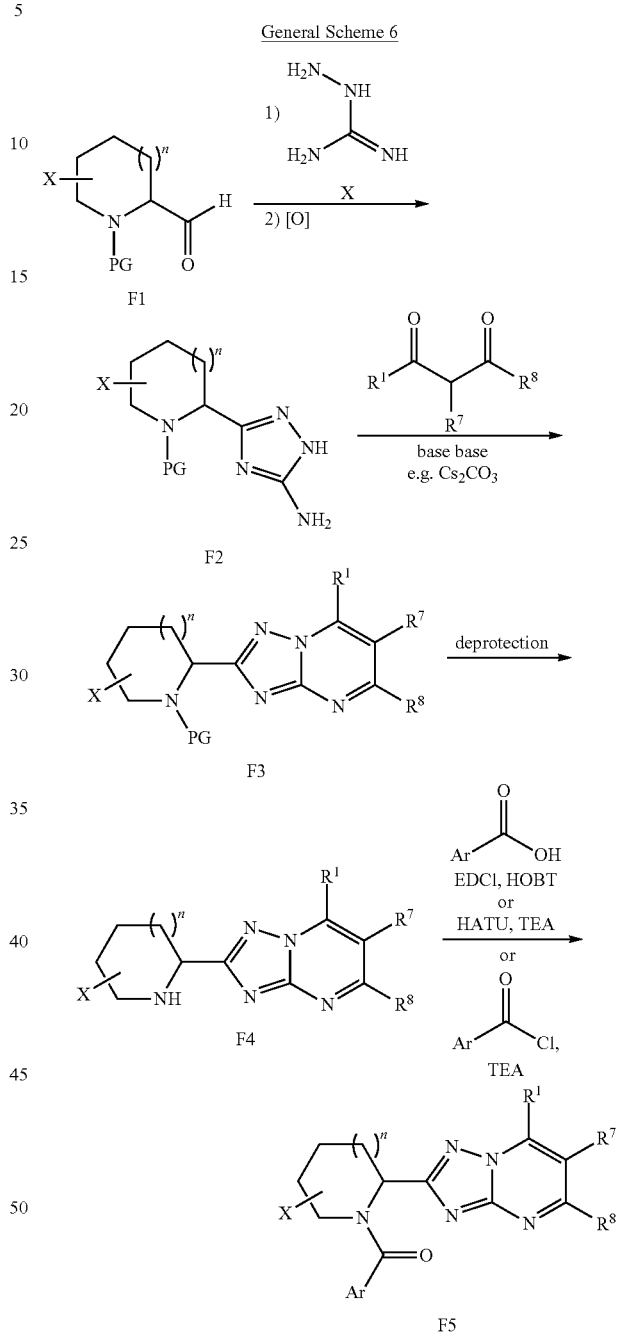

n = 1, 2 or more
X = H, Me, CF₃, etc
PG = protecting group e.g. BOC

Scheme 1 describes the methods under which the compounds of the invention F5 can be prepared. The starting material is aldehyde F1 described above. The aldehyde F1 is first condensed with a hydrazinecarboximidamide and after auto-oxidation generates the amino triazole F2. In one embodiment the stereochemistry of the carbon bearing the aldehyde for F1 is the (S) stereochemistry. Typically this is performed in an organic solvent e.g. DMF. This key intermediate F2 is then used to form the bicyclic heterocycle F3 with different side chains through different condensation reactions. For example, condensation with a 1,3-dicarbonyl compound to form the heterocycle F3 where $R^1$, $R^8$=Me and $R^7$=H. Typically, the amino triazole F2 is heated with acetyl acetone in an organic solvent e.g. DMF in the presence of a base e.g. cesium carbonate. The product F3 is then converted to F4 and then F5 as described in Scheme 1 for conversion of A5 to A7 via A6.

General Scheme 7

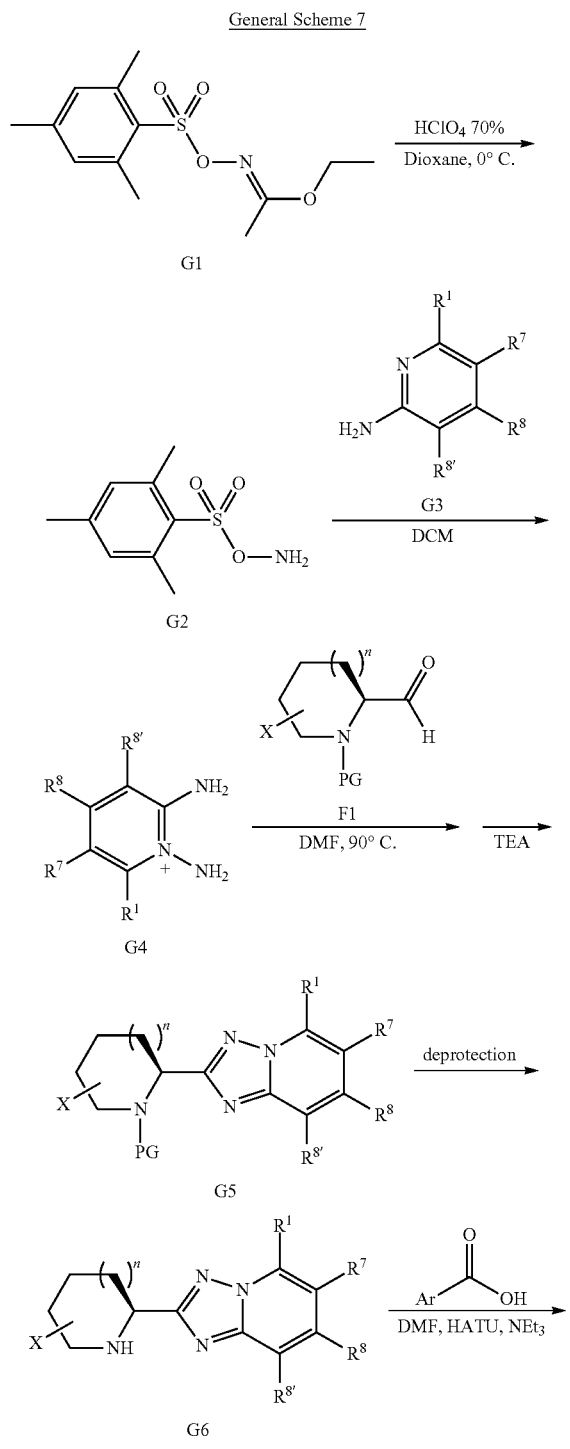

-continued

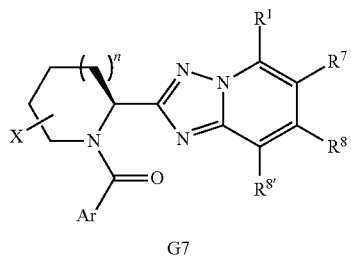

n = 1, 2 or more
X = Me, $CF_3$, etc
PG = protecting group e.g. BOC, CBZ

General scheme 7 describes the methods under which the compounds of the invention G7 can be prepared. The starting material is aldehyde F1 described above and is treated with aminopyridinium intermediates and then cyclised to form the target heterocycles. For example, ethyl O-mesityl sulfonyl acetohydroxanate is treated with 70% $HClO_4$ in dioxane to form the sulfonic acid ammonium salt G2, which is then reacted with an aminopyridine G3 to form the aminopyridinium salt G4. Typically G3 is treated with the reagent G2 in an organic solvent such as dichloromethane to form G4. Condensation of G4 with aldehyde F1 affords triazolopyridine G5. In this step a typical procedure is to heat the mixture in an organic solvent e.g. DMF in the presence of base e.g. triethylamine. The product G5 is then converted to G6 and then G7 as described in Scheme 1 for conversion of A5 to A7 via A6.

General Scheme 8

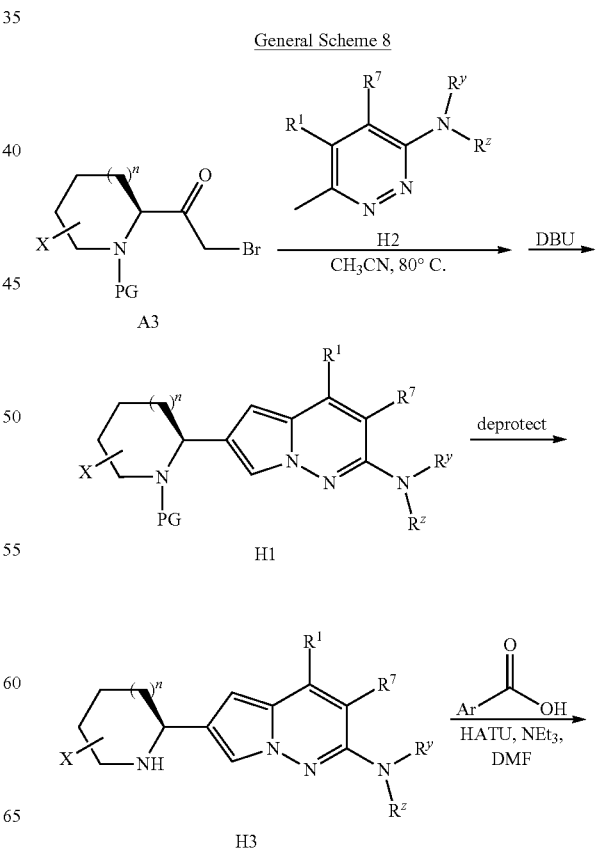

-continued

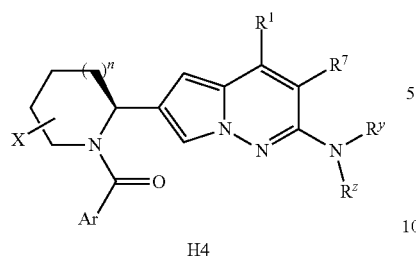

H4 n = 1, 2 or more
X = H, Me, CF$_3$, etc
PG = protecting group e.g. BOC, CBZ
(NR$^y$R$^z$ represents an amine such as NR$^{11}$R$^{12}$ or a C$_2$-C$_{20}$heterocyclyl or any amine of the variable R$^8$)

General scheme 8 describes the methods under which the compounds of the invention H4 can be prepared. The starting material is bromo ketone A3 described above. Compound A3 is reacted with a pyridazine H2. Typically, treatment of the bromo ketone A3 in organic solvent e.g. acetonitrile at elevated temperature effects the initial condensation, and then addition of DBU followed by further heating effects the cyclization to afford H1. The product H1 is then converted to H3 and then H4 as described in Scheme 1 for conversion of A5 to A7 via A6.

General Scheme 9

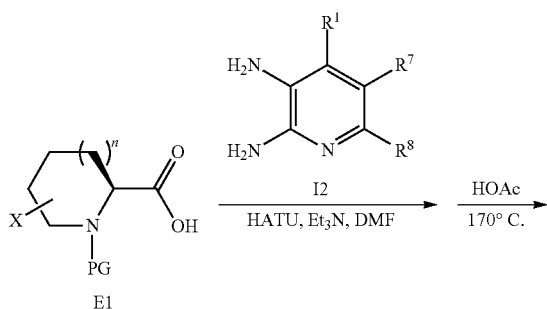

E1

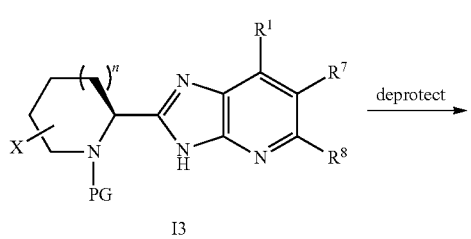

I3

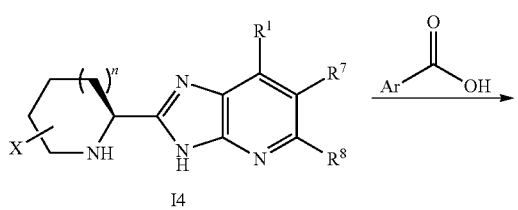

I4

-continued

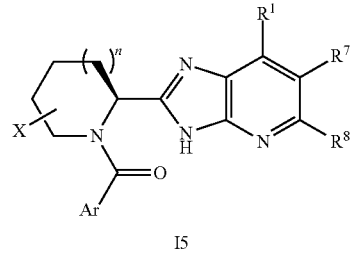

I5 n = 1, 2 or more
X = H, Me, CF$_3$, etc
PG = protecting group e.g. BOC, CBZ

General scheme 9 describes the methods under which the compounds of the invention I5 can be prepared. The starting material is acid E1 described above. Acid E1 is first coupled to a diaminopyridine I2 in the presence of an amide coupling reagent followed by subsequent cyclization in the presence of acid to form heterocycle I3. Typically, compound E1 is reacted with diamino pyridine I2 in an organic solvent e.g. DMF, and in the presence of a coupling reagent, e.g. HATU and base, e.g. triethylamine. The mixture is then treated with acid e.g. HOAc and heated at elevated temperature 170° C. to form I3. The product I3 is then converted to I4 and then I5 as described in Scheme 1 for conversion of A5 to A7 via A6.

Pharmaceutical Formulations

The compounds disclosed herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumovirinae infections as described below.

In another aspect, the invention is a novel, efficacious, safe, nonirritating and physiologically compatible inhalable composition comprising a compound disclosed herein, or a pharmaceutically acceptable salt thereof (e.g., a compound of formula I or a pharmaceutically acceptable salt thereof or a compound of formulas 1-103 or a pharmaceutically acceptable salt thereof), suitable for treating Pneumovirinae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 μm. Preferably, the compound disclosed herein, or a pharmaceutically acceptable salt thereof (e.g., a compound of formula I or a pharmaceutically acceptable salt thereof or a compound of formulas 1-103 or a pharmaceutically acceptable salt thereof) is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 μm and about 5 μm using a nebulizer able to aerosolize the formulation of a compound disclosed herein, or a pharmaceutically acceptable salt thereof (e.g., a compound of formula I or a pharmaceutically acceptable salt thereof or a compound of formulas 1-103 or a pharmaceutically acceptable salt thereof) into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µm, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method of the invention, the aerosol formulation for nebulization delivers a therapeutically efficacious dose of a compound disclosed herein, or a pharmaceutically acceptable salt thereof (e.g., a compound of formula I or a pharmaceutically acceptable salt thereof or a compound of formulas 1-103 or a pharmaceutically acceptable salt thereof) to the site of Pneumovirinae infection sufficient to treat the Pneumovirinae infection. The amount of drug administered must be adjusted to reflect the efficiency of the delivery of a therapeutically efficacious dose of a compound disclosed herein, or a pharmaceutically acceptable salt thereof. In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of a compound disclosed herein, or a pharmaceutically acceptable salt thereof (e.g., a compound of formula I or a pharmaceutically acceptable salt thereof or a compound of formulas 1-103 or a pharmaceutically acceptable salt thereof). In a preferred embodiment, at least about 30 to about 50% of the active compound is delivered. More preferably, about 70 to about 90% of the active compound is delivered.

In another embodiment, a compound disclosed herein, or a pharmaceutically acceptable salt thereof (e.g., a compound of formula I or a pharmaceutically acceptable salt thereof or a compound of formulas 1-103 or a pharmaceutically acceptable salt thereof), is delivered as a dry inhalable powder. The compounds of the invention are administered endobronchially as a dry powder formulation to efficacious deliver fine particles of compound into the endobronchial space using dry powder or metered dose inhalers. For delivery by DPI, the compound disclosed herein is processed into particles with, predominantly, MMAD between about 1 µm and about 5 lam by milling spray drying, critical fluid processing, or precipitation from solution. Media milling, jet milling and spray-drying devices and procedures capable of producing the particle sizes with a MMAD between about 1 µm and about 5 µm are well known in the art. In one embodiment, excipients are added to the compound disclosed herein, or a pharmaceutically acceptable salt thereof (e.g., a compound of formula I or a pharmaceutically acceptable salt thereof or a compound of formulas 1-103 or a pharmaceutically acceptable salt thereof) before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, compound disclosed herein, or a pharmaceutically acceptable salt thereof (e.g., a compound of formula I or a pharmaceutically acceptable salt thereof or a compound of formulas 1-103 or a pharmaceutically acceptable salt thereof) is delivered as a dry powder using a device such as a dry powder inhaler or other dry powder dispersion devices. Non-limiting examples of dry powder inhalers and devices include those disclosed in U.S. Pat. No. 5,458,135; U.S. Pat. No. 5,740,794; U.S. Pat. No. 5,775,320; U.S. Pat. No. 5,785,049; U.S. Pat. No. 3,906,950; U.S. Pat. No. 4,013,075; U.S. Pat. No. 4,069,819; U.S. Pat. No. 4,995,385; U.S. Pat. No. 5,522,385; U.S. Pat. No. 4,668,218; U.S. Pat. No. 4,667,668; U.S. Pat. No. 4,805,811 and U.S. Pat. No. 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm, and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, compound disclosed herein, or a pharmaceutically acceptable salt thereof (e.g., a compound of formula I or a pharmaceutically acceptable salt thereof or a compound of formulas 1-103 or a pharmaceutically acceptable salt thereof), is delivered as a dry powder using either type of dry powder inhaler as described herein, wherein the MMAD of the dry powder, exclusive of any excipients, is predominantly in the range of 1 µm to about 5 µm.

In another preferred embodiment, compound disclosed herein, or a pharmaceutically acceptable salt thereof (e.g., a compound of formula I or a pharmaceutically acceptable salt thereof or a compound of formulas 1-103 or a pharmaceutically acceptable salt thereof) is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234. In preferred embodiments, a compound disclosed herein, or a pharmaceutically acceptable salt thereof (e.g., a compound of formula I or a pharmaceutically acceptable salt thereof or a compound of formulas 1-103 or a pharmaceutically acceptable salt thereof), is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. For the treatment of Pneumovirinae virus infections, preferably, the other active therapeutic agent is active against Pneumovirinae virus infections, particularly respiratory syncytial virus infections. Non-limiting examples of these other active therapeutic agents are ribavirin, palivizumab, motavizumab, RSV-IGIV (RespiGam®), MEDI-557, A-60444 (also known as RSV604), MDT-637, BMS-433771, ALN-RSV01, ALX-0171 and mixtures thereof.

Many of the infections of the Pneumovirinae viruses are respiratory infections. Therefore, additional active therapeutics used to treat respiratory symptoms and sequelae of infection may be used in combination with the compounds disclosed herein, or a pharmaceutically acceptable salt thereof (e.g., a compound of formula I or a pharmaceutically acceptable salt thereof or a compound of formulas 1-103 or a pharmaceutically acceptable salt thereof). The additional agents are preferably administered orally or by direct inhalation. For example, other preferred additional therapeutic agents in combination with the compounds disclosed herein for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compound disclosed herein, or a pharmaceutically acceptable salt thereof (e.g., a compound of formula I or a pharmaceutically acceptable salt thereof or a compound of formulas 1-103 or a pharmaceutically acceptable salt thereof) are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflamatory agents working through anti-inflamatory cascade mechanisms are also useful as additional therapeutic agents in combination with the compounds disclosed herein, or a pharmaceutically acceptable salt thereof (e.g., compounds of formula I or a pharmaceutically acceptable salt thereof or compound of formulas 1-103 or a pharmaceutically acceptable salt thereof) for the treatment of viral respiratory infections. Applying "anti-inflammatory signal transduction modulators" (referred to in this text as AISTM), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloropyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxyphenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with a compound disclosed herein, or a pharmaceutically acceptable salt thereof (e.g., a compound of formula I or a pharmaceutically acceptable salt thereof or a compound of formulas 1-103 or a pharmaceutically acceptable salt thereof) are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds disclosed herein are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with a compound disclosed herein, or a pharmaceutically acceptable salt thereof (e.g., a compound of formula I or a pharmaceutically acceptable salt thereof or a compound of formulas 1-103 or a pharmaceutically acceptable salt thereof) for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl -acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester.

The compounds of formula I or a compound of formulas 1-103 may also be combined with mucolytic agents to treat both the infection and symptoms of respiratory infections. A non-limiting example of a mucolytic agent is ambroxol. Similarly, the compounds of formula I or the compounds of formulas 1-103 may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). The compounds of formula I or the compounds of formulas 1-103 may also be combined with nebulized hypertonic saline particularly when the Pneumovirinae virus infection is complicated with bronchiolitis. The combination of the compounds of formula I or the compounds of formulas 1-103 with hypertonic saline may also comprise any of the additional agents discussed above. In a preferred aspect, nebulized about 3% hypertonic saline is used.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

One embodiment provides for methods of treating a Pneumovirinae virus infection (e.g., a Human respiratory syncytial virus infection) in a patient (e.g., a human), comprising administering to the patient a therapeutically effective amount of a compound of formula I or a compound of formulas 1-103, or a pharmaceutically acceptable salt, solvate, and/or ester thereof.

One embodiment provides for methods of treating a Pneumovirinae virus infection in a patient (e.g., a human), comprising administering to the patient a therapeutically effective amount of a compound of formula I or a compound of formulas 1-103, or a pharmaceutically acceptable salt, solvate, and/or ester thereof, and at least one additional active therapeutic agent.

One embodiment provides for methods of treating Human respiratory syncytial virus infection in a patient (e.g., a human), comprising: administering to the patient a therapeutically effective amount of a compound of formula I or a compound of formulas 1-103, or a pharmaceutically acceptable salt, solvate, and/or ester thereof, and at least one additional active therapeutic agent.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}$C or $^{3}$H) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver, lung or other metabolic organ, or within cells in general.

Tissue Distribution

It has also been discovered that certain compounds disclosed herein of the invention show high lung to plasma ratios which may be beneficial for therapy. One particular group of compounds of the invention that demonstrate this property are compounds that include an amine functional group.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| Ac$_2$O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4, 4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH$^+$ | mass plus 1 |
| MH$^-$ | mass minus 1 |
| MsOH | methanesulfonic acid |
| MS or ms | mass spectrum |

TABLE 1-continued

List of abbreviations and acronyms.

| Abbreviation | Meaning |
| --- | --- |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

The invention will now be illustrated by the preparation of the following non-limiting compounds of the invention. It is to be understood that certain intermediates described herein may also be compounds of the invention.

Example 1a: Preparation of Intermediate 1

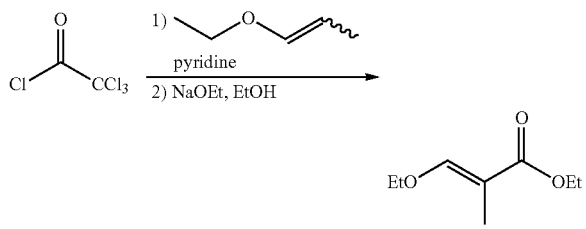

A solution of 1-ethoxy-propene (5.1 mL, 46 mmol) in pyridine (3.4 mL) was added slowly via addition funnel (~1 drop/sec) to neat trichloroacetyl chloride (4.7 mL, 42 mmol) at −10° C. under an argon atmosphere. The reaction mixture was then allowed to slowly warm to 23° C. After 20 h, the reaction mixture was diluted with dichloromethane (50 mL) and the resulting mixture was washed with 0.01N HCl (3×50 mL) and brine (50 mL), was dried over anhydrous sodium sulfate, and was concentrated under reduced pressure. To the crude residue was added sodium ethoxide (21 wt % in ethanol, 7.1 g, 44 mmol) slowly via syringe. After 30 min, the reaction mixture was partitioned between dichloromethane (500 mL) and water (500 mL). The phases were split and the aqueous layer was extracted with dichloromethane (500 mL). The combined organic extracts were dried over anhydrous sodium sulfate, and were concentrated to afford intermediate 1 (6.8 g, 95%) as an orange oil.

$^1$H-NMR (CDCl$_3$, 400 MHz): 7.28 (app s, 1H), 4.09 (q, J=7.1 Hz, 2H), 3.96 (q, J=7.1 Hz, 2H), 1.66 (s, 3H), 1.25 (t, J=7.1 Hz, 3H), 1.20 (t, J=7.1 Hz, 3H).

Example 1b: Preparation of Intermediate 2

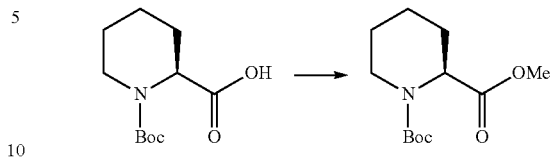

N-Boc-(S)-piperidine-2-carboxylic acid (5.0 g, 22 mmol) in DMF (100 mL) was treated with Cs$_2$CO$_3$ (3.5 g, 10.9 mmol) and MeI (1.5 mL, 24 mmol). The mixture was stirred for 4 hours and diluted with MTBE (250 mL). The mixture was washed with water (twice with 100 mL) and saturated sodium chloride solution (100 mL). The solution was dried over anhydrous sodium sulfate and concentrated to afford the ester intermediate 2 (5.1 g crude, 96%) as an oil which was used without further purification $^1$H NMR (CDCl$_3$, 300 MHz): δ 4.80 (m, 1H), 3.97 (m, 1H), 3.73 (s, 3H), 2.93 (m, 1H), 2.18 (app d, J=13.2 Hz, 1H), 1.67 (m, 2H), 1.45 (br s, 10H), 1.20 (app t, J=13.5 Hz, 1H).

R$_f$=0.90 (30% EtOAc-hexanes);

Example 2: Preparation of Intermediate 3

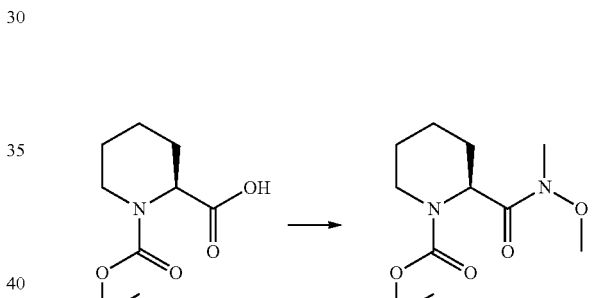

(S)-1-Boc-piperidine-2-carboxylic acid (25 g, 109 mmol, Sigma-Aldrich) in DMF (500 mL) was treated sequentially with MeNHOMe.HCl (11.2 g, 115 mmol), N-methylmorpholine (36 mL, 327 mmol), HOBt (16.2 g, 120 mmol), and EDCI (23 g, 120 mmol) and stirred for 18 h. The solution was diluted with EtOAc (1000 mL) and washed with H$_2$O (twice with 500 mL) and saturated NaCl solution (500 mL). The solution was dried over MgSO$_4$, filtered and concentrated. The residue was subjected to a 330 g SiO$_2$ Combiflash High Performance Gold column (0-100% EtOAc-hexanes gradient) to afford the Weinreb amide intermediate 3 (18.4 g, 61%) as a clear oil:

$^1$H NMR (CDCl$_3$, 300 MHz): δ 5.06 (br m, 1H), 3.93 (br m, 1H), 3.77 (br s, 3H), 3.18 (s, 3H), 2.01 (app d, J=13.5 Hz, 1H), 1.71 (m, 4H), 1.45 (s, 9H);

LCMS (ESI) m/z 273 [M+H]$^+$, t$_R$=2.31 min;

HPLC (RP: 6-98% MeCN—H$_2$O gradient, 0.05% TFA modifier) t$_R$=4.423 min.

R$_f$=0.60 (50% EtOAc-hexanes);

Example 3: Preparation of Intermediate 4

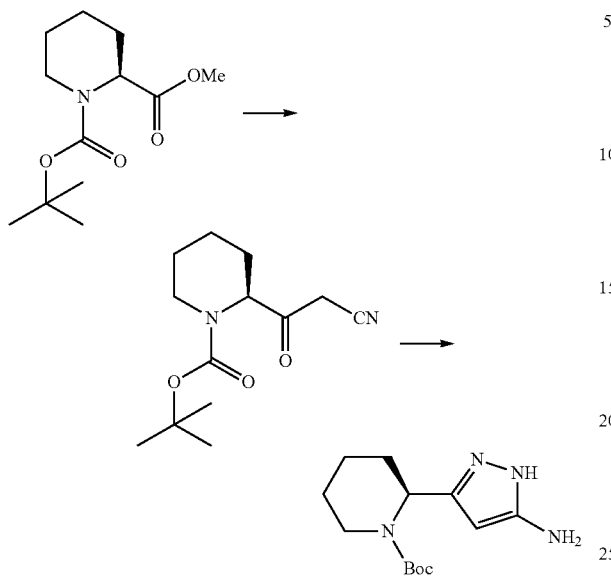

Example 4: Preparation of Intermediate 4 Via Weinreb Amide

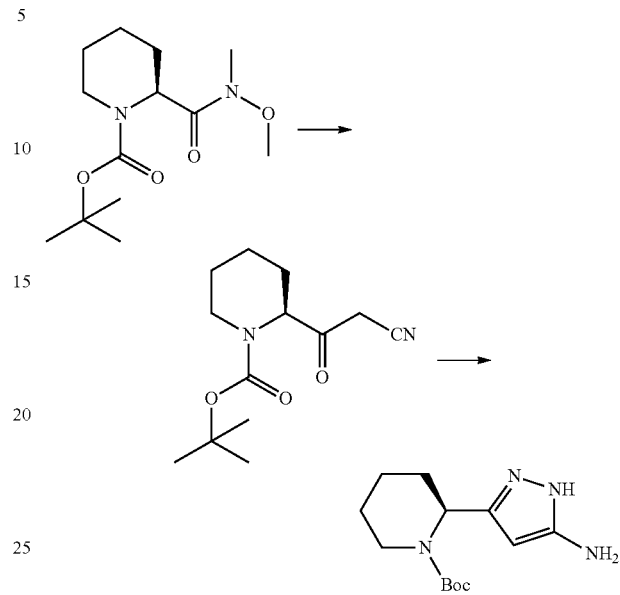

To a solution of acetonitrile (5 ml, 93.8 mmol) in dry THF (50 ml) at −78° C. was added dropwise NaN(TMS)$_2$ (34 ml, 68 mmol, 2M in hexanes). The solution was warmed to −40° C. and stirred for 20 min. The solution was then cooled to −78° C. and a solution of the ester (Intermediate 2) (7.6 g, 31.1 mmol) in THF (20 ml) was added dropwise. The solution was warmed up to −40° C. and stirred for 2 h. The solution was then cooled to −78° C. and a solution of acetic acid (4.8 ml, 80 mmol) in THF (20 ml) was added dropwise. The solution was then warmed to room temperature and volatiles were removed under reduced pressure at 40° C. The resulting residue was dissolved in EtOAc (300 mL) and the organic phase was washed 2× each with brine. Volatiles were removed under reduced pressure at 40° C.

$^1$H NMR (DMSO, 300 MHz): δ 4.63 (br s, 1H), 4.18-4.13 (m, 1H), 3.82-3.78 (m, 1H), 3.65 (s, 2H), 2.85-2.63 (m, 1H), 1.65-1.52 (m, 9H), 1.38 (s, 9H).

LCMS m/z: 153 [M-Boc group+H], $t_R$=2.50 min.

The residue was dissolved in EtOH (150 ml) and hydrazine acetate (4.5 g, 47 mmol) was added. The solution was stirred for 16 h at room temperature. Volatiles were removed under reduced pressure at 40° C., EtOAc added (200 ml) and the organic phase washed with aqueous dilute NaHCO$_3$, then H$_2$O followed by brine. Volatiles were removed under reduced pressure at 40° C., the resulting residue was purified by silica gel column (DCM/MeOH, gradient from 0% to 20%) to afford the product intermediate 4 (7.5 g, 90%) as an oil.

LCMS m/z [M+H]$^+$ C$_{13}$H$_{22}$N$_4$O$_2$ requires: 266.34. Found 266.84.

HPLC (min, purity) $t_R$=2.13, 100%

$^1$H NMR (DMSO, 300 MHz): δ 11.20 (br s, 1H), 5.09 (m, 1H), 5.07 (s, 1H), 4.67 (br s, 2H), 3.81 (app d, J=12.0 Hz, 1H), 2.72 (app br t, J=12.0 Hz, 1H), 2.08 (app d, J=12.9 Hz, 1H), 1.57 (m, 4H), 1.39 (s, 9H); MS (ESI) m/z 267 [M+H]$^+$, $t_R$=1.97 min. (3.5 min method); HPLC (Chiral: Chiralpak AD-H, isocratic n-heptane-isopropanol 70:30). $t_R$ (desired)= 22.42 min, $t_R$ (enantiomer of desired isomer)=25.67 min; % ee=93.

MeCN (3.20 mL, 60.7 mmol) in THF (50 mL) was cooled to −78° C. under Ar. A NaHMDS solution (1.0 M in THF, 36.8 mL, 36.8 mmol) was added dropwise over 5 min, during which time an off-white suspension had formed. The suspension was warmed to −20° C. and stirred for 20 min. The suspension was cooled to −78° C. and transferred via cannula to the Weinreb amide intermediate 3 (5.02 g, 18.4 mmol) in THF (50 mL) at −78° C. over 5 min. The suspension is warmed to −45° C. and stirred for 3 h, during which time the suspension became a yellow solution. The solution was cooled to −78° C. and AcOH (4.2 mL in 10 mL THF, 73.6 mmol) was added dropwise. The solution was warmed to room temperature and diluted with EtOAc (100 mL). The solution was washed with H$_2$O (50 mL) and saturated NaCl solution (50 mL). The solution was dried over MgSO$_4$ and concentrated to afford the cyano ketone as a yellow oil which was used without further purification.

The crude α-cyano ketone was used in the next reaction with hydrazine acetate to synthesize desired amino pyrazole intermediate 4 as described above.

MS (ESI) m/z 267 [M+H]$^+$, $t_R$=1.81 min.

HPLC (RP: 6-98% MeCN—H$_2$O gradient, 0.05% TFA modifier) $t_R$=3.212 min (>95% purity @ 254 nM).

HPLC (Chiral: Chiralpak AD-H 250×4.6 mm, 5 micron; isocratic n-heptane-isopropanol 70:30) $t_R$ (a isomer, desired) =22.35 min, $t_R$ (b isomer)=25.78 min; α=1.15; % ee=>90%.

Example 5: Preparation of Intermediate 5

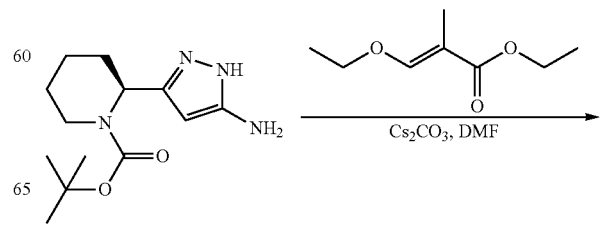

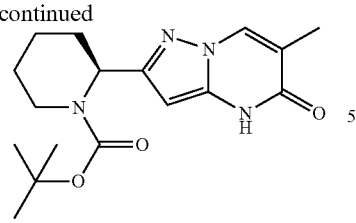

Intermediate 1, (11.8 g, 67.6 mmol) and Cs₂CO₃ (22.0 g, 67.6 mmol) were added to a solution of intermediate 4 (12.0 g, 45.1 mmol) at room temperature and the reaction mixture was heated to 130° C. After 17 h, the reaction mixture was allowed to cool to room temperature and was concentrated under reduced pressure. The crude residue was diluted with ethyl acetate (250 mL) and was filtered. The resulting filtrate was concentrated under reduced pressure and the residue was purified via SiO₂ column chromatography (330 g SiO₂ Combiflash HP Gold Column, 0-100% ethyl acetate/hexanes) to afford intermediate 5 (8.58 g, 57%) as a light yellow solid.

¹H NMR (CDCl₃, 400 MHz): δ 12.01 (br s, 1H), 7.99 (s, 1H), 5.73 (s, 1H), 5.42 (br s, 1H), 4.01 (br d, J=12.2 Hz, 1H), 2.81 (br t, J=11.2 Hz, 1H), 2.29 (d, J=13.5 Hz, 1H), 2.07 (d, J=1.1 Hz, 3H), 1.87-1.69 (m, 1H), 1.68-1.41 (m, 4H), 1.48 (s, 9H).

¹³C NMR (CDCl₃, 100 MHz): δ 162.87, 156.34, 155.43, 140.16, 135.00, 113.29, 86.50, 79.75, 28.41, 27.79, 25.27, 21.00, 19.88, 13.38.

LCMS (ESI) m/z 333.0 [M+H]⁺, $t_R$=2.24 min.
HPLC $t_R$ (min), purity %: 3.969, 99%.
$R_f$=0.50 (EtOAc).
Chiral HPLC, 98% ee (Chiralpak IC 5 mM, 4.6×150 mm, 10-95% MeCN/H₂O, 0.05% trifluoroacetic acid modifier) (S)-isomer $t_R$=22.234 min, (R)-isomer $t_R$=20.875 min.

Example 6: Preparation of Intermediate 6

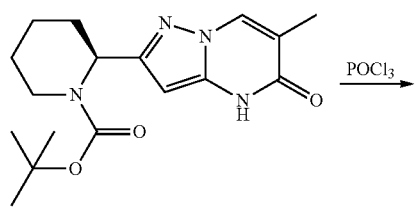

POCl₃ (5.60 mL, 59.8 mmol) was added to intermediate 5 (993.4 mg, 2.99 mmol) at room temperature and the reaction mixture was heated to 100° C. After 2 h, the reaction mixture was allowed to cool to room temperature and was concentrated under reduced pressure to afford intermediate 6 as an orange semi-solid, which was used directly in the following step.

¹H NMR (DMSO-d₆, 400 MHz): δ 9.40 (br d, J=7.6 Hz, 1H), 9.27-9.16 (m, 2H), 6.85 (s, 1H), 4.54 (t, J=112.4 Hz, 1H), 3.32 (d, J=12.8 Hz, 1H), 3.08 (q, J=8.81 Hz, 1H), 2.33 (s, 3H), 2.23-2.14 (m, 1H), 1.92-1.61 (m, 5H).
LCMS (ESI) m/z 251.1 [M+H]⁺, $t_R$=0.21 min.
HPLC $t_R$=2.35 min.

Example 7: Preparation of Intermediate 7

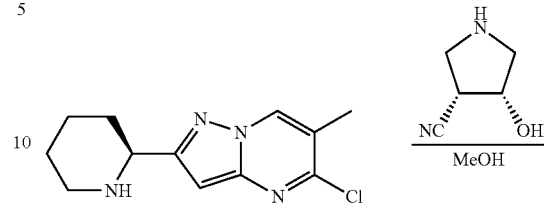

A solution of intermediate 10 (prepared from 1 g of the BOC intermediate using formic acid as described in the synthesis of intermediate 10 of Example 11) was dissolved in MeOH (10 ml). To the solution was added intermediate 6 (944 mg, 3.76 mmol) and NEt₃ (2 ml). The reaction mixture was heated at 70° overnight. The solvent was evaporated and the residue was purified by combi-flash column chromatography (0-100% MeOH/DCM) to afford intermediate 7 (922 mg, 60%).

LCMS (m/z) 327.40[M+H]⁺
MW 326.19

Example 8: Preparation of Intermediate 8 (Cis Mixture of Isomers)

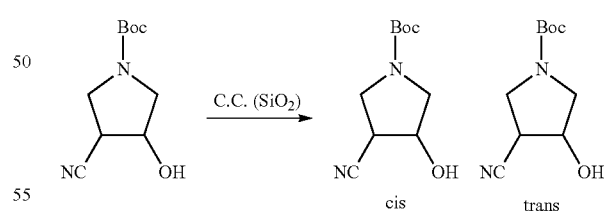

A mixture of cis/trans tert-butyl 3-cyano-4-hydroxypyrrolidine-1-carboxylate was separated on a silica column (200-300) eluting with EA:PE=1:10, EA:PE=1:5 to give intermediate 8 (cis mixture of isomers as the earlier eluting peak, 30 g, 46%) as white solid. TLC (Eluent: PE:EA=1:1): Starting material cis/trans mixture ($R_f$=0.4 and 0.45)

¹H NMR: (400 MHz DMSO): δ 4.60-4.48 (m, 1H), 3.8-3.65 (m, 1H), 3.51-3.63 (m, 1H), 3.5-3.3 (m, 2H), 2.9-3.1 (m, 1H), 2.70 (s, 1H), 1.3-1.45 (s, 9H).

Example 9: Preparation of Intermediate 9

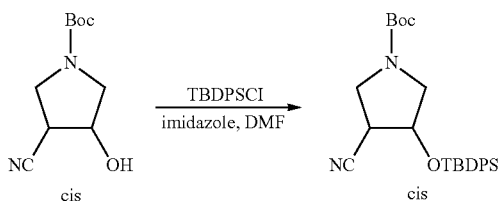

To a mixture of intermediate 8 (10 g, 0.047 mol) and imidazole (6.4 g, 0.094 mol) in DMF (100 ml) was added TBDPSCl (14.2 g, 0.05 mol) dropwise and the mixture was stirred at room temperature overnight. Citric acid (10%) was added and extracted with EA, dried, concentrated and purified by silica gel column chromatography (EA:PE=1:50 to 1:25) to give intermediate 9 as colorless oil (9 g, 60%).

TLC Information (Eluent: PE:EA=1:1), starting material $R_f$=0.40, product $R_f$=0.90

$^1$H NMR (400 MHz DMSO) δ 7.74-7.62 (m, 4H), 7.47-7.41 (m, 6H), 4.51 (m, 1H), 3.8-3.65 (m, 1H), 3.51-3.63 (m, 1H), 3.5-3.3 (m, 2H), 2.9-3.1 (m, 1H), 1.3-1.45 (s, 9H)

Example 10: Preparation of Intermediate 9a and 9b

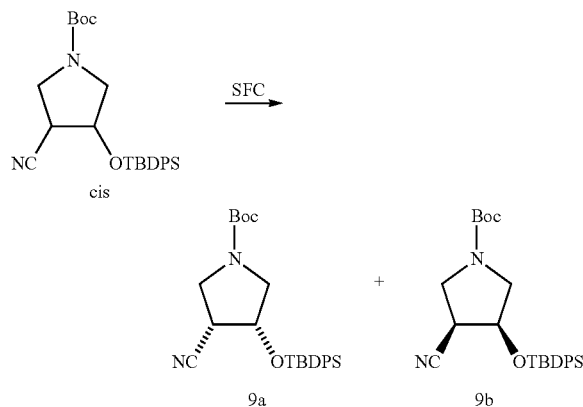

Intermediate 9 was separated by chiral SFC (see below) to give intermediate 9a (earlier eluting, 16.3 g, 41%) and intermediate 9b (later eluting, 16.7 g, 41%) as white solids.

Column: ChiralPak IC-H, 250×50 mmI.D, mobile Phase: CO$_2$/iPrOH (35% isocratic), retention time (9a) 1.94 min, retention time (9b): 2.73 min.

Example 11: Preparation of Intermediate 10

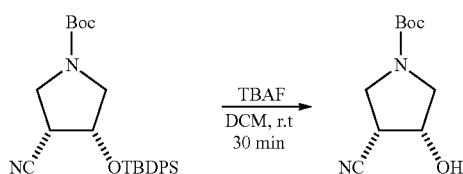

To a solution of intermediate 9a (16.3 g, 0.036 mol) in CH$_2$Cl$_2$ (200 mL) at room temperature was added TBAF (8.0 g, 0.025 mol). The reaction mixture was stirred at room temperature for 30 min, then diluted with CH$_2$Cl$_2$ (500 mL) and washed with saturated aq. NH$_4$Cl and brine, dried over MgSO$_4$, filtered and concentrated. The crude product was purified by silica gel chromatography (PE:EA=10:1 to 2:1) to afford the BOC pyrrolidine intermediate as a single cis isomer (5.9 g, yield: 76%) as a white solid.

TLC Information (10a) (Eluent: PE:EA=1:1)
1. Starting material ($R_f$=0.90)
2. Reaction Mixture (Product: $R_f$=0.4)

$^1$H NMR: 400 MHz DMSO: δ 4.60-4.58 (m, 1H), 3.87-3.79 (m, 1H), 3.69-3.64 (m, 1H), 3.56-3.49 (m, 2H), 2.9-3.1 (m, 1H), 1.4-1.5 (s, 9H)

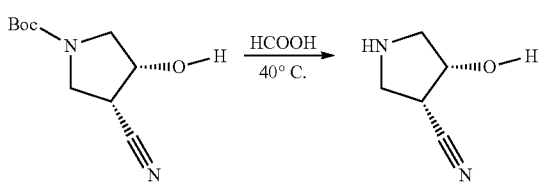

The BOC pyrollidine intermediate (1 g, 4.7 mmol) was added to HCOOH (5 ml) and was heated at 40° C. for 2 h. The solvent was evaporated under reduced pressure and preheated IPA (100° C.) was added to dissolve the residue; white precipitate formed after the IPA solution cooled down. The product was filtered and washed with IPA to give intermediate 10 (470 mg, 63%) that was used without further purification in subsequent reactions.

Example 12: Preparation of Intermediate 11

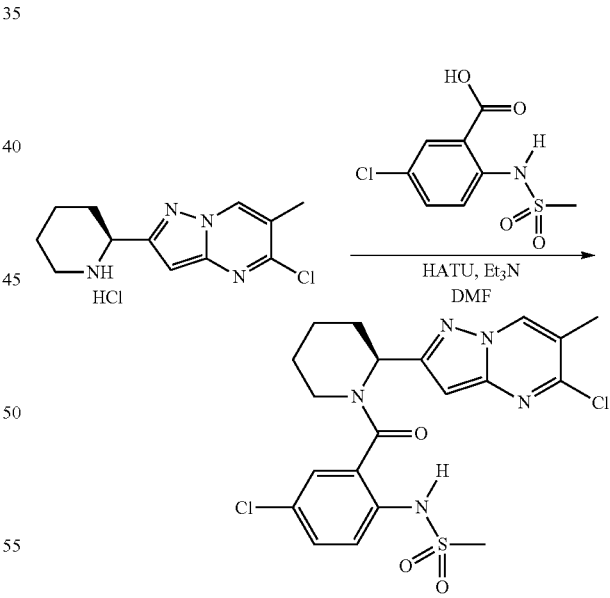

HATU (1.37 g, 3.59 mmol) was added to a solution of 5-chloro-2-(methylsulfonamido)benzoic acid (823 mg, 3.29 mmol) in DMF (15.0 mL), and the reaction mixture was stirred at room temperature. After 1 h, a solution of crude intermediate 6 (220 mg, 2.99 mmol) in DMF (1 mL) was added followed by the addition of triethylamine (2.00 mL, 14.3 mmol), and the reaction mixture was stirred at room temperature for 19 h. The reaction mixture was partitioned between ethyl acetate (250 mL) and saturated aqueous sodium bicarbonate solution (200 mL), and the layers were separated. The organic layer was washed with saturated aqueous sodium bicarbonate solution (200 mL) and saturated sodium chloride solution (200 mL), was dried over Na$_2$SO$_4$, and was concentrated under reduced pressure. The crude residue was purified via SiO$_2$ column chromatography (12 g SiO$_2$ Combiflash HP Gold Column, 0-100% ethyl acetate/hexanes) to afford intermediate 11 (736.2 mg, 51% (2-steps)) as a white solid.

$^1$H NMR (CDCl$_3$, 400 MHz): δ 10.05 (br s, 0.2H), 9.13 (br s, 1H), 8.95 (br s, 1H), 8.81 (br s, 0.2H), 7.70 (d, J=8.8 Hz, 1H), 7.56 (d, J=8.8 Hz, 0.2H), 7.40 (dd, J=8.8, 2.4 Hz, 1H), 7.33 (d, J=2.4 Hz, 1H), 7.31 (d, J=4.4 Hz, 0.2H), 6.45 (s, 1H), 6.40 (br s, 0.2H), 6.28 (br d, J=4.4 Hz, 1H), 5.01 (br s, 0.2H), 4.54 (br d, J=14.0 Hz, 0.2H), 3.35 (br d, J=13.2 Hz, 1H), 3.15-3.03 (m, 1H), 2.92 (s, 3H), 2.39 (s, 3H), 2.13-1.98 (m, 1H), 1.90-1.59 (m, 2H), 1.59-1.31 (m, 3H).

$^{13}$C NMR (CDCl$_3$, 100 MHz): δ 167.09, 156.12, 153.13, 147.86, 135.68, 131.79, 131.66, 131.38, 130.12, 125.91, 125.44, 117.08, 93.74, 47.65, 44.07, 39.81, 27.83, 25.47, 19.78, 16.90.

LCMS (ESI) m/z 482.1 [M+H]$^+$, t$_R$=2.79 min.

HPLC t$_R$ (min), purity %: 5.438, 99%

R$_f$=0.47 (50% EtOAc/hexanes).

Chiral HPLC, 99% ee (Chiralpak IC 5 mM, 4.6×150 mm, 10-95% MeCN/H$_2$O, 0.05% trifluoroacetic acid modifier) (S)-isomer t$_R$=29.739 min, (R)-isomer t$_R$=29.495 min.

Example 13: Preparation of Intermediate 12

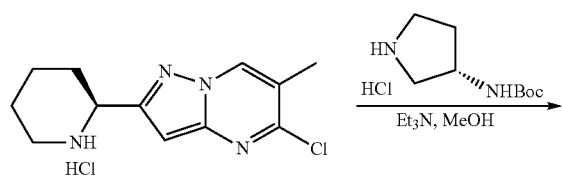

To a solution of intermediate 6 (100.0 mg, 0.35 mmol) in MeOH (1.74 mL) was added (S)-tert-butyl pyrrolidin-3-ylcarbamate (648 mg, 3.48 mmol) and triethylamine (970 µL, 6.96 mmol) at room temperature, and the reaction mixture was heated to 70° C. After 4 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford intermediate 12 (169 mg, 95%) as an orange solid.

LCMS (ESI) m/z 401.23 [M+H]$^+$, t$_R$=1.86 min.

Example 14: Preparation of Intermediate 14

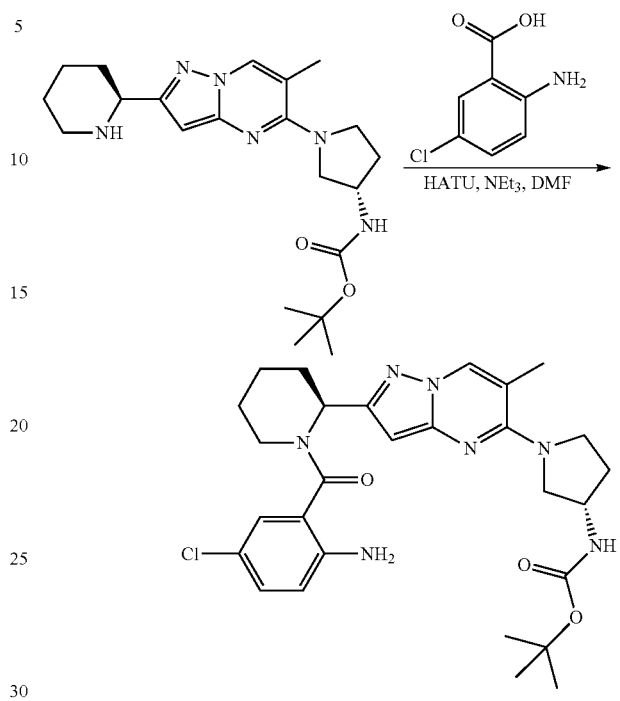

2-Amino-5-chlorobenzoic acid (82 mg, 0.48 mmol) and HATU (228 mg, 0.6 mmol) were dissolved in anhydrous DMF (2 ml). After activation for 1 hour, intermediate 12 (120 mg, 0.3 mmol) and triethylamine (0.17 ml) were added to the above solution. The reaction was stirred under nitrogen for 2 hours. The solvents were removed by rotary evaporation. The residue was purified with silica gel column chromatography to provide intermediate 14. (Yield 134 mg, 81%).

LCMS m/z [M+H]$^+$ C$_{28}$H$_{36}$ClN$_7$O$_3$ requires: 554.26. Found 554.18.

HPLC Tr (min), purity %: 2.00, 98%

Example 15: Preparation of Intermediate 15

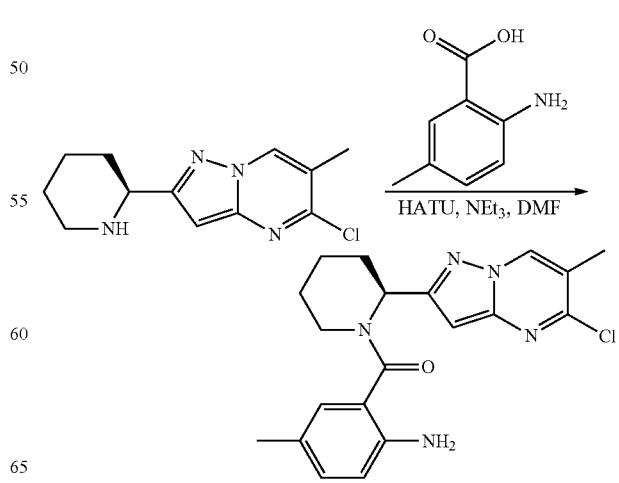

2-Amino-5-methylbenzoic acid (316 mg, 2.09 mmol) and HATU (992 mg, 2.61 mmol) were dissolved in anhydrous DMF (2 ml). After activation for 1 hour, intermediate 6 (500 mg, 1.74 mmol) and triethylamine (0.7 ml) were added to the above solution. The reaction was stirred under nitrogen for 2 hours. The solvents were removed by rotary evaporation. The residue was purified with silica gel column chromatography to provide intermediate 15. (Yield 320 mg, 42%).

LCMS m/z [M+H]$^+$ C$_{20}$H$_{22}$ClN$_5$O requires: 384.15. Found 383.99.

HPLC Tr (min), purity %: 2.00, 98%

Example 16: Preparation of Intermediate 16

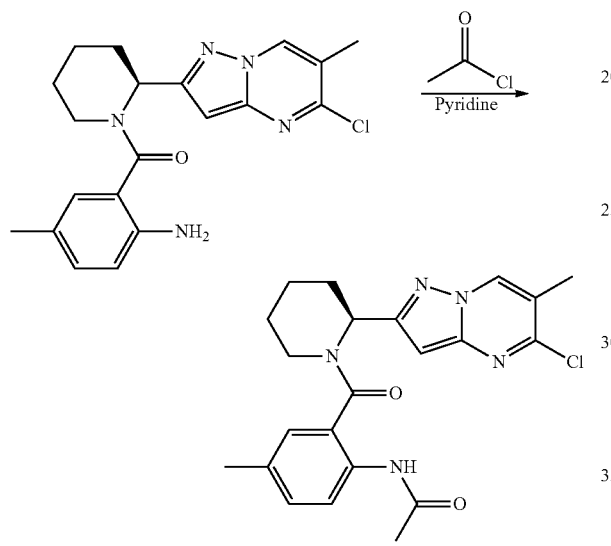

Intermediate 15 (320 mg, 0.84 mmol) was dissolved in pyridine (2 ml). Then acetyl chloride (78 mg, 1.0 mmol) was added to the above solution. The reaction was stirred under nitrogen for 30 min. The solvents were removed by rotary evaporation. The residue was purified with silica gel column chromatography to provide intermediate 16. (Yield 305 mg, 86%).

LCMS m/z [M+H]$^+$ C$_{22}$H$_{24}$ClN$_5$O$_2$ requires: 426.16. Found 425.89.

HPLC Tr (min), purity %: 2.40, 98%

Example 17: Preparation of Intermediate 18

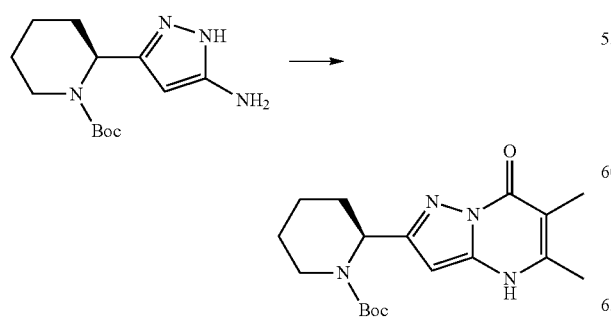

To a solution of the pyrazole intermediate 4 (7.2 g, 27.1 mmol) in acetic acid (100 ml) was added 2-methyl acetoacetate (3.9 ml, 27.1 nM) and the solution stirred at 100° C. for 45 min. The volatiles were removed under reduced pressure at 40° C. and the resulting residue was purified by silica gel column (DCM/MeOH, gradient from 0% to 20%) to afford intermediate 18 (7.23 g, 77%) as an oil.

$^1$H-NMR (DMSO, 400 MHz): δ 7.26 (s, 1H), 5.79 (s, 1H), 5.42 (s, 1H), 3.99 (m, 1H), 2.81 (m, 1H), 2.56 (m, 1H), 2.36 (m, 3H), 2.08 (m, 3H), 1.76 (m, 3H), 1.53-1.28 (m, 14H).

LCMS m/z [M+H]$^+$ C$_{18}$H$_{26}$N$_4$O$_3$ requires: 346.42. Found 347.07.

HPLC Tr (min), purity %: 1.45, 100%.

Example 18: Preparation of Intermediate 19

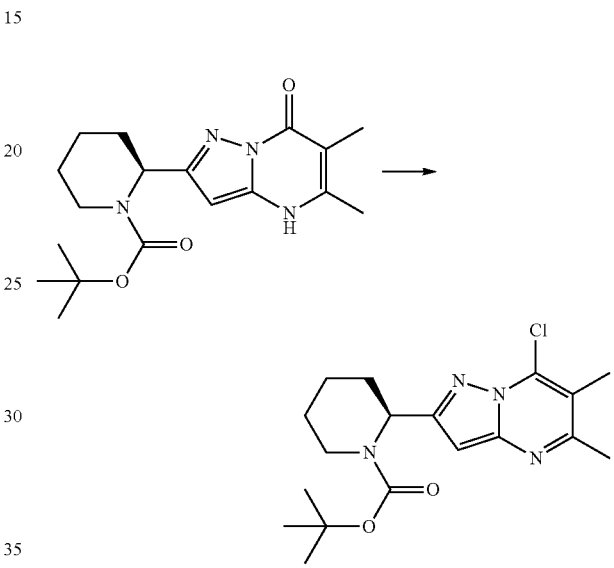

The intermediate 18 (0.3 g, 0.867 mmol), and DMAP (0.117 g, 0.958 mmol) were dissolved in anhydrous pyridine (15 mL) and placed under nitrogen with stirring. POCl$_3$ (0.567 ml, 6.07 mmol) was added neat and the reaction was heated to 100° C. for 2 hours. The reaction was monitored by LC/MS. When it was complete in about 2 hours the reaction was cooled to room temperature and solvents were removed by rotary evaporation. The residue was redissolved in 200 ml DCM and washed with 200 ml water. The organic layer was collected dried over MgSO$_4$ (anhydrous), filtered and then evaporated. The product was purified by column chromatography using ethyl acetate (25%) in hexanes to elute intermediate 19 (0.234 g, 0.643 mmol, 74%)

$^1$H-NMR (CD$_3$CN, 300 MHz): δ 1.45 (m, 11H), 1.64 (m, 2H), 1.87 (m 1H), 2.39 (m 4H), 2.55 (s, 3H), 2.95 (t, 1H), 4.04 (d, 1H), 5.57 (d, 1H), 6.39 (s, 1H).

Example 19: Preparation of Intermediate 20

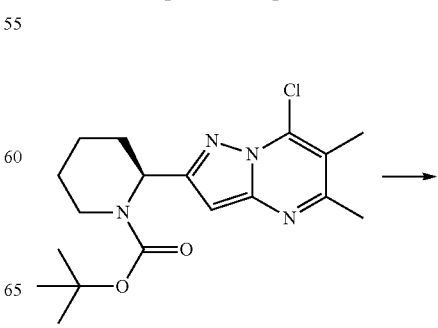

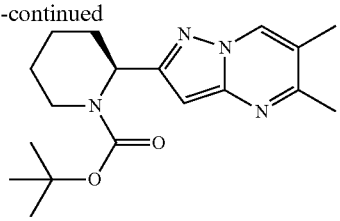

The starting intermediate 19 (0.06 g, 0.165 mmol), along with sodium acetate (0.027 g, 0.330 mmol) were dissolved in absolute ethanol (10 mL). Solid Pd/C (5% by wt) (0.030 g) was added and the reaction was placed under a balloon of hydrogen for 20 minutes. Catalyst was filtered off using a 40 micron syringe filter. The solvent was removed by rotary evaporation. The residue was taken up in DCM and loaded onto a silica gel column. The intermediate 20 was eluted with a 0 to 50% EtOAc in hexanes gradient. (Yield 40 mg, 0.121 mmol, 73%).

$^1$H-NMR (CD$_3$CN, 300 MHz): δ 1.45 (m, 11H), 1.64 (m, 2H), 1.87 (m, 1H), 2.25 (s, 3H), 2.38 (d, 1H), 2.51 (s, 3H), 2.95 (t, 1H), 4.02 (d, 1H), 5.55 (d, 1H), 6.25 (s, 1H), 8.41 (s, 1H)

Example 20: Preparation of Intermediate 21

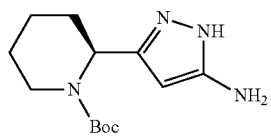

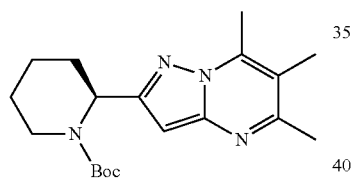

To a solution of the pyrazole intermediate 4 (0.5 g, 2.2 mmol) in acetic acid (5 ml) was added 3-methylpentane-2,4-dione (0.25 g, 2.2 mmol) and the solution stirred at 90° C. for 30 min. Volatiles were removed under reduced pressure at 40° C., and the resulting residue was purified by silica gel column (DCM/MeOH, gradient from 0% to 10%) to afford the product intermediate 21 (0.353 g, 47%) as a viscous oil.

$^1$H-NMR (DMSO, 400 MHz): δ 6.31 (s 1H), 5.58 (s 1H), 4.06 (d, J=12.8, 1H), 2.92 (m 1H), 2.79 (m 3H), 2.58 (s, 3H), 2.52 (m 1H), 2.30 (s 3H), 1.91 (m 1H), 1.57-1.40 (m, 12H).

LCMS m/z [M+H]$^+$ C$_{19}$H$_{28}$N$_4$O$_2$ requires: 344.45. Found 345.20.

HPLC Tr (min), purity %: 5.96, 95%.

Example 21: Preparation of Intermediate 22

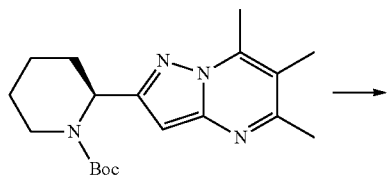
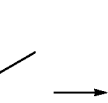

Intermediate 21 (56 mg, 0.16 mmol) was dissolved in 1,4-dioxane (2 mL) and to the solution was added concentrated HCl (0.5 mL). The reaction mixture was stirred at room temperature for 1 h and then the solvent was evaporated. The residue, intermediate 22 was used without further purification.

Example 22: Preparation of Intermediate 23

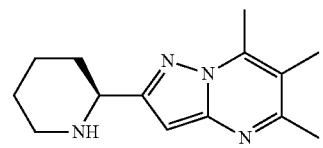

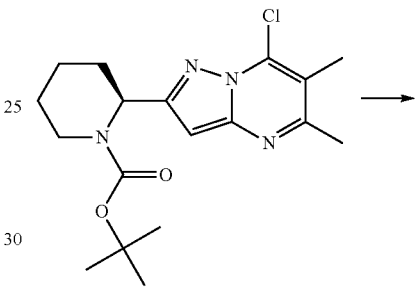

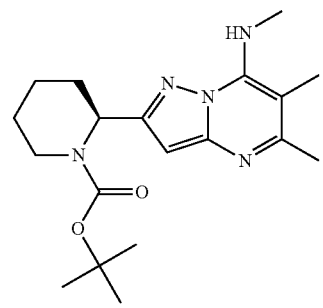

The intermediate 19 (0.110 g, 0.301 mmol), was dissolved in 1,4-dioxane 5 ml. Methyl amine (40% in water) (2 mL) was added and the reaction was stirred for 2 hr. Solvents were removed by rotary evaporation. The residue was taken up in DCM and loaded onto a silica gel column. Intermediate 23 was eluted with a 0 to 80% EtOAc in hexanes gradient (98 mg, 0.272 mmol, 90%).

$^1$H-NMR (CD$_3$CN, 300 MHz): δ 1.45 (m, 11H), 1.60 (m, 2H), 1.82 (m, 1H), 2.30 (s, 3H), 2.40 (m, 1H), 2.42 (s, 3H), 2.95 (t, 1H), 3.35 (d, 3H), 4.01 (d, 1H), 5.49 (m, 1H), 6.00 (s, 1H), 6.29 (bs, 1H).

Example 23: Preparation of Intermediate 24

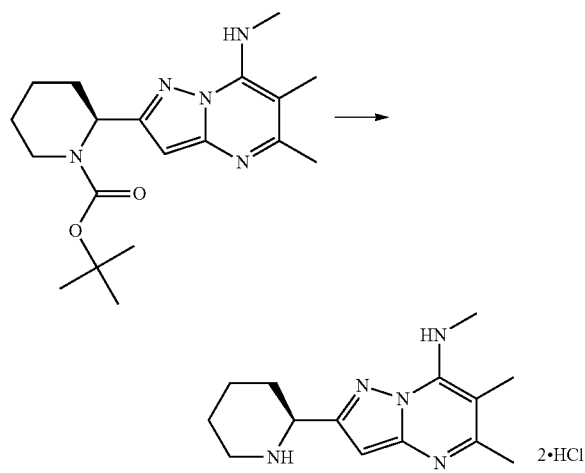

The intermediate 23 (0.10 g, 0.28 mmol), was dissolved in anhydrous 1,4-dioxane (6 ml). With stirring under nitrogen 4N HCl in dioxane (3 ml) was added via syringe. The reaction was stirred for 2 hours at room temperature while monitoring by LC/MS. When the reaction was complete the solvent was removed by rotary evaporation. The product, intermediate 24, was taken forward without further purification after it was characterized by LC/MS (Yield~73 mg, 0.28 mmol, 100%).

LCMS m/z [M+H]$^+$ 261

Example 24: Preparation of Intermediate 25

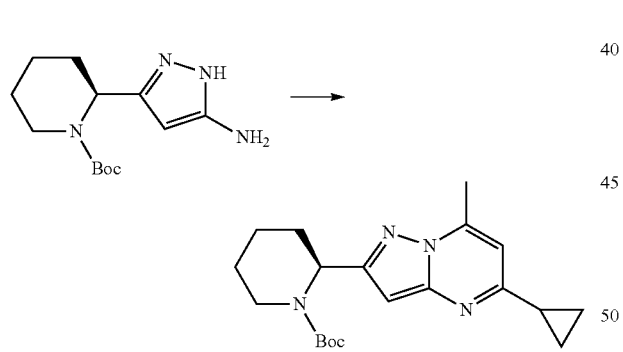

To a solution of the pyrazole intermediate 4 (3.22 g, 12.08 mmol) in acetic acid (25 ml) was added 1-cyclopropyl-1,3-butanedione (2.28 g, 18.13 mmol) and the solution was stirred at 120° C. for 30 min. The volatiles were removed under reduced pressure at 40° C., and the resulting residue was purified by silica gel column (hexane/EtOAc, gradient from 0% to 50%) to afford intermediate 25 (1.72 g, 26%).

$^1$H-NMR (CDCl$_3$, 400 MHz): δ 6.44 (s 1H), 6.28 (s 1H), 5.58 (s, 1H), 4.13-4.04 (m, 1H), 2.96-2.92 (m, 1H), 2.67 (s, 3H), 2.46-2.42 (m, 1H), 2.14-1.85 (m, 4H), 1.47 (s, 9H), 1.13-1.02 (m, 6H).

LCMS m/z [M+H]$^+$ C$_{20}$H$_{28}$N$_4$O$_2$ requires: 357.46. Found 357.13.

Example 25: Preparation of Intermediate 26

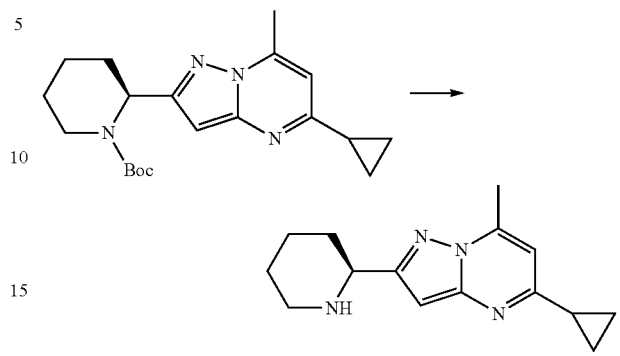

Intermediate 25 (0.60 g, 1.68 mmol), was dissolved in anhydrous 1,4-dioxane (6 ml). With stirring under nitrogen 4N HCl in dioxane (3 ml) was added via syringe. The reaction was stirred for 2 hours at room temperature while monitoring by LC/MS. When the reaction was complete solvent was removed by rotary evaporation. The product, intermediate 26 was taken forward without further purification (Yield 0.55 g, 100%).

$^1$H-NMR (CH$_3$OD, 400 MHz): δ 6.95 (d, J=1.2 Hz, 1H), 6.73 (s, 1H), 4.64 (d, J=12 Hz, 1H), H), 3.52-3.51 (m, 1H), 3.23-3.20 (m, 1H), 2.86 (s 3H), 2.40-2.02 (m, 2H), 2.26-1.81 (m, 5H), 1.41-1.30 (m, 4H).

LCMS m/z [M+H]$^+$ C$_{15}$H$_{20}$N$_4$ requires: 257.35. Found 257.15.

HPLC Tr (min), purity %: 1.65, 98%.

Example 26: Preparation of Intermediate 27

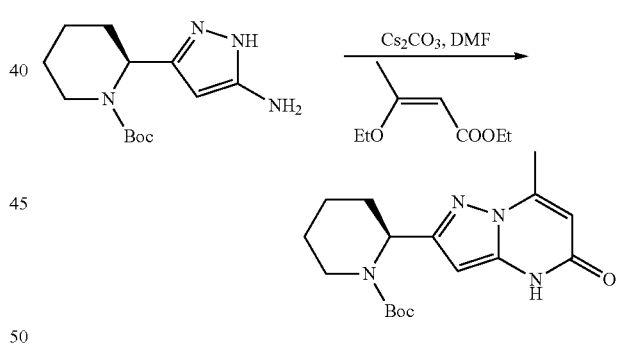

Intermediate 4 (10 g, 37.5 mmol) was dissolved in anhydrous DMF (60 mL). Ethyl 3-ethoxy-2-butenoate (11 g, 67.5 mmol) and cesium carbonate (18 g, 56.3 mmol) were added. The reaction was stirred at 110° C. for 48 h and cooled to room temperature. The reaction was diluted with ethyl acetate and washed with saturated aqueous sodium bicarbonate solution and saturated aqueous sodium chloride solution. The organic extract was dried over anhydrous sodium sulfate and then concentrated under reduced pressure. The crude material was purified with silica gel column (0-80% EtOAc in hexanes) to give intermediate 27 (9.55 g, 77% yield).

$^1$H NMR (400 MHz, CD$_3$OD): δ 5.86 (s, 1H), 5.73 (s, 1H), 5.40 (m, 1H), 4.00 (m, 1H), 2.91 (m, 1H), 2.54 (s, 3H), 2.36 (m, 1H), 1.80 (m, 1H), 1.63 (m, 2H), 1.58-1.45 (m, 11H).

LC/MS (m/z): 333.1 [M+H]$^+$

Example 27: Preparation of Intermediate 28

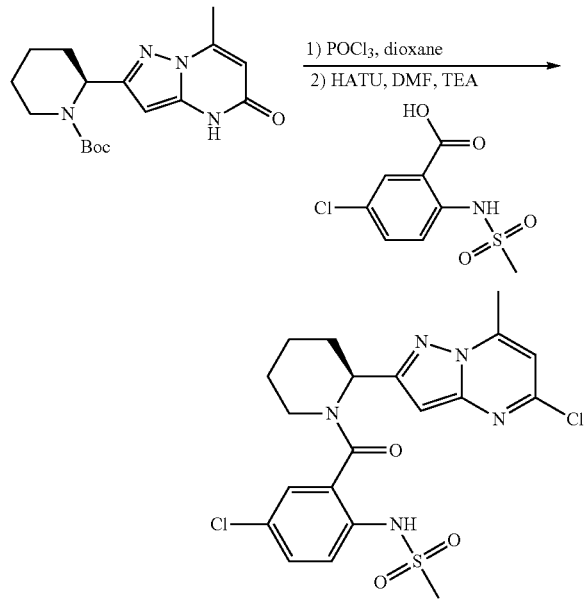

Intermediate 27 (S)-tert-butyl-2-(7-methyl-5-oxo-4,5-dihydropyrazolo[1,5-a]pyrimidin-2-yl) piperidine-1-carboxylate (100 mg, 0.3 mmol) with POCl$_3$ (1 mL) were mixed and stirred at 110° C. for 1 h. The material was concentrated under reduced pressure and then dissolved in acetonitrile and a small amount of MeOH was added. The reaction was stirred at 0° C. for 30 min. The solid was collected and dried under high vacuum.

5-Chloro-2-(methylsulfonamido)benzoic acid (47 mg, 0.187 mmol) with HATU (71 mg, 0.187 mmol) were mixed and dissolved in anhydrous DMF (1 mL) and stirred for 1 h. The amine hydrogen chloride (49 mg, 0.17 mmol) was dissolved in in anhydrous DMF (1 mL) and added to the reaction TEA (71 uL, 0.51 mmol) was added and the material was stirred for 16 hrs. The reaction material was diluted with ethyl acetate and washed with saturated aqueous sodium chloride solution twice. The organic extract was dried over anhydrous sodium sulfate and then concentrated under reduced pressure and purified with silica gel column (0-50% EtOAc in hexanes) to give intermediate 28 (57 mg, 39% yield).

LC/MS (m/z): 482.2 [M+H]$^+$

Example 28: Preparation of Intermediate 29

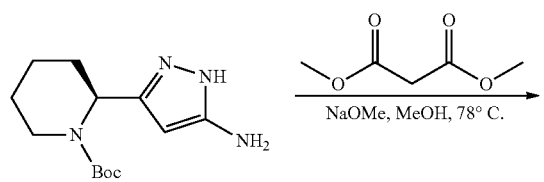

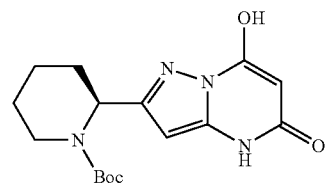

Intermediate 4 (3 g, 0.02 mol) was dissolved in MeOH (30 ml), to the solution was added dimethyl malonate (2.6 ml, 0.02 mmol) and 10% NaOMe in MeOH (25 ml, 0.1 mmol). The reaction mixture was heated at 78° C. for 5 h. Solvent was evaporated, the residue was redissolved in EtOAc (20 mL), HOAc was added to make the solution slightly acidic, washed with brine, organic solvent was evaporated, the residue was purified by silica gel column chromatography to afford intermediate 29 (3 g, 78%).

LCMS m/z [M+H]$^+$ C$_{16}$H$_{22}$N$_4$O$_4$ requires: 335.16. Found 335.05.

HPLC Tr (min), purity %: 2.82, 98%

Example 29: Preparation of Intermediate 30

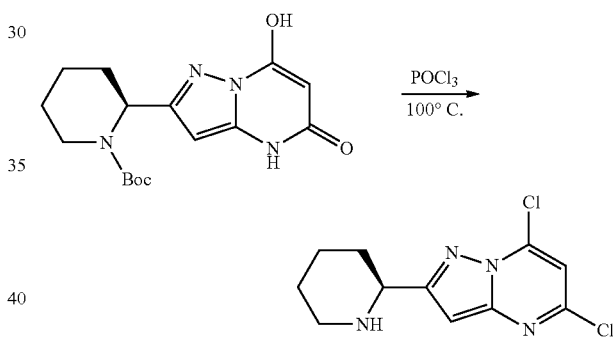

Intermediate 29 (10 g) was added to neat POCl$_3$ (25 ml), the reaction mixture was heated at 100° C. for 3 h. The solvent was evaporated and to the residue was added MeOH until no bubble formed. Then, 30 mL of acetonitrile was added to the above residue and orange solid precipitated out of mixture to afford intermediate 30 (7.4 g, 92%).

LCMS m/z [M+H]$^+$ C$_{11}$H$_{12}$N$_4$Cl$_2$ requires: 271.04. Found 271.07.

HPLC Tr (min), purity %: 1.78, 98%

Example 30: Preparation of Intermediate 31

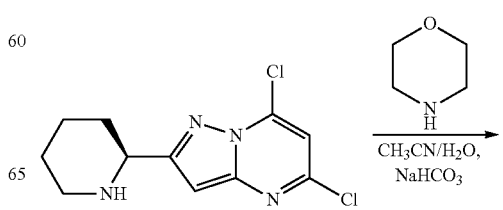

109
-continued

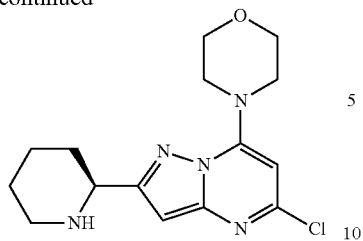

Intermediate 30 (4.2 g, 15.5 mmol) was added to CH₃CN (40 ml) and H₂O (40 ml), to the above mixture was added NaHCO₃ (2.6 G, 31 mmol) and morpholine (1.35 g, 15.5 mmol). The reaction mixture was stirred at room temperature for 30 mins, solvents were evaporated and to the residue was added 20 ml of DCM, the mixture was filtered and filtrate was evaporated to give intermediate 31 (4.5 g, 91%).

LCMS m/z [M+H]⁺ $C_{15}H_{20}ClN_5O$ requires: 322.14. Found 322.10.

HPLC Tr (min), purity %: 1.81, 98%

Example 31: Preparation of Intermediate 32

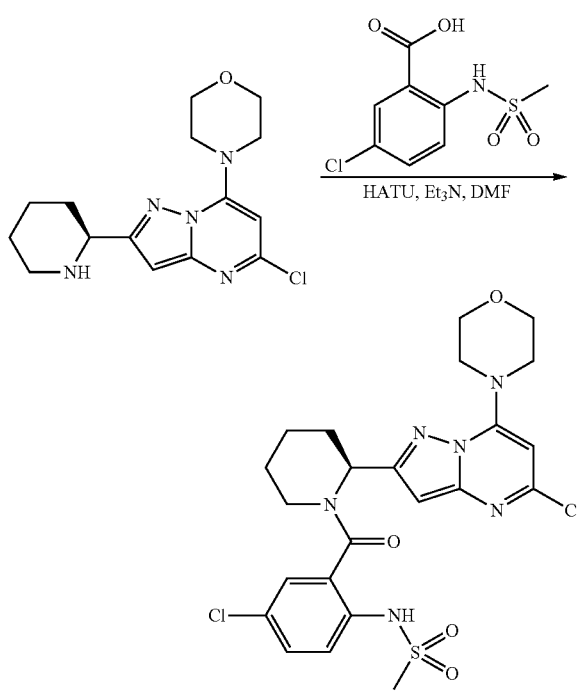

The 5-chloro-2-(methylsulfonamido)benzoic acid (5 g, 19.94 mmol) and HATU (9.5, 24.92 mmol) were dissolved in anhydrous DMF (50 ml). After activation for 1 hour, to the above solution was added intermediate 31 (4 g, 12.46 mmol) and triethylamine (6.93 ml). The reaction was stirred under nitrogen for 2 hours. The solvents were removed by rotary evaporation. The residue was purified with silica gel column chromatography to provide intermediate 32. (Yield 4.7 g, 68%).

LCMS m/z [M+H]⁺ $C_{23}H_{26}Cl_2N_6O_4S$ requires: 553.11. Found 553.16.

HPLC Tr (min), purity %: 2.72, 98%

110

Example 32: Preparation of Intermediate 33

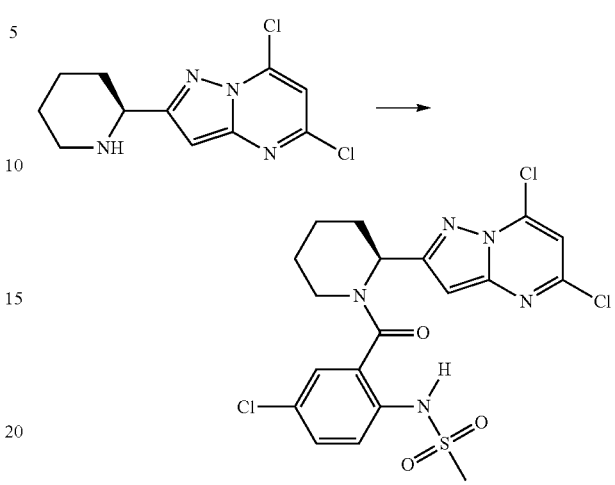

To a suspension of (5-chloro-2-(methylsulfonamido)benzoic acid) (0.7 g, 2.8 mmol) in DCM (6 ml) was added oxalylchloride (2 M in DCM, 6 ml, 12 mmol) and DMF (5 microliter) and the stirred for 3 h at room temperature. Volatiles were removed under vacuum and the residue dissolved in DCM (20 ml). With ice-water bath cooling, the amine intermediate 30 (0.78 g, 2.54 mmol) and ET₃N (0.55 g) was added and stirred for 10 min, then 30 min at room temperature. The reaction mixture was diluted with DCM (100 ml) and washed 3× with water. Volatiles were remove and the residue purified on silica gel (hexane/AcOEt=1/1). The product, intermediate 33, was obtained as a colorless oil in 75% purity and used without further purification in the next step.

Example 33: Preparation of Intermediate 34

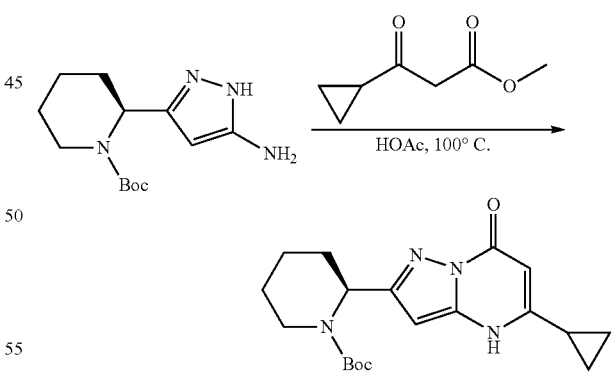

Intermediate 4 (5 g, 0.02 mol) in HOAc (20 mL) was treated with 3-cyclopropyl-3-oxopropanoic acid methyl ester (14 g, 0.1 mmol) and the mixture was stirred overnight at 100° C. The mixture was concentrated and purified via SiO₂ column chromatography (40 g SiO₂ Combiflash HP Gold Column, 0-100% EtOAc/hexanes gradient) to afford intermediate 34 (4 g, 83%).

LCMS m/z [M+H]⁺ $C_{19}H_{26}N_4O_3$ requires: 359.20. Found 359.10.

HPLC Tr (min), purity %: 2.45, 98%

Example 34: Preparation of Intermediate 35

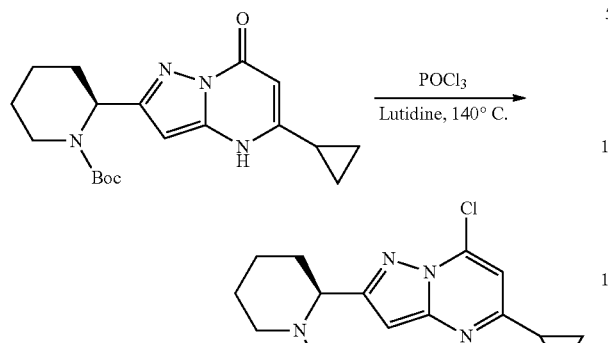

Starting material intermediate 34 (400 mg, 1.1 mol) was dissolved in lutidine (5 ml), to the mixture was added POCl₃ (340 mg, 2.2 mmol) and the mixture was heated at 140° C. The reaction was completed in 30 mins. The mixture was concentrated and purified via SiO₂ column chromatography (40 g SiO₂ Combiflash HP Gold Column, 0-100% EtOAc/hexanes gradient) to afford intermediate 35 (388 mg, 92%).

LCMS m/z [M+H]⁺ $C_{19}H_{25}ClN_4O_2$ requires: 377.17. Found 377.11.

HPLC Tr (min), purity %: 3.21, 98%

Example 35: Preparation of Intermediate 36

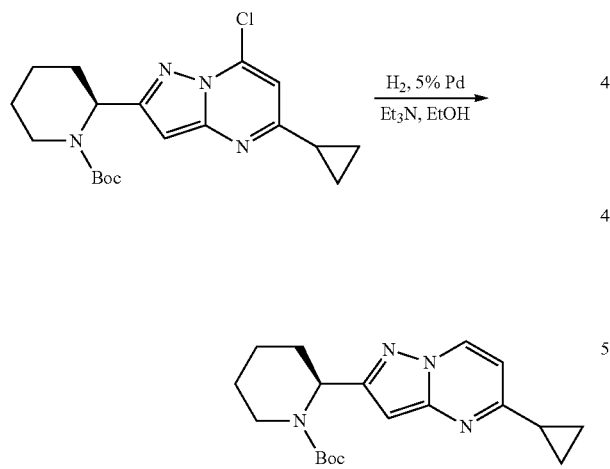

Starting material intermediate 35 (400 mg, 1.1 mmol) was dissolved in EtOH (10 ml), to the mixture was added 5% Pd on carbon (20 mg, 0.053 mmol) and Et₃N (0.5 ml). The mixture was heated under hydrogen balloon at room temperature for 1.5 h. The mixture was filtered and filtrate was concentrated and purified via SiO₂ column chromatography to afford intermediate 36 (283 mg, 80%).

LCMS m/z [M+H]⁺ $C_{19}H_{26}N_4O_2$ requires: 343.21. Found 343.13.

HPLC Tr (min), purity %: 2.93, 98%

Example 36: Preparation of Intermediate 37

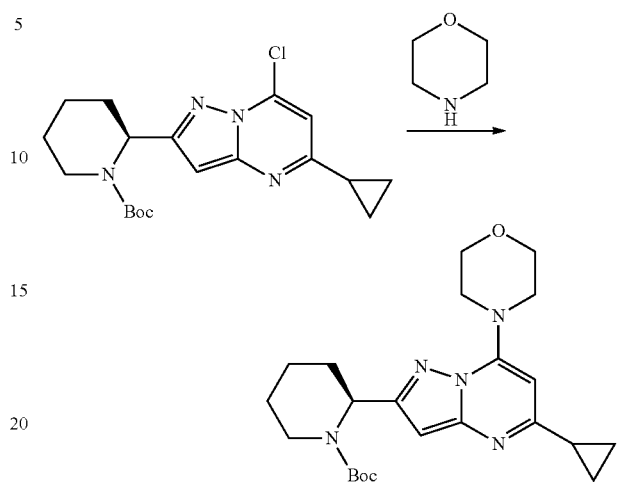

Starting material intermediate 35 (200 mg, 0.55 mmol) was dissolved in morpholine (10 ml), the mixture was stirred at room temperature for 30 mins. The mixture was concentrated and purified via SiO₂ column chromatography to afford intermediate 37 (200 mg, 88%).

LCMS m/z [M+H]⁺ $C_{23}H_{33}N_5O_3$ requires: 428.26. Found 428.17.

HPLC Tr (min), purity %: 2.90, 98%

Example 37: Preparation of Intermediate 38

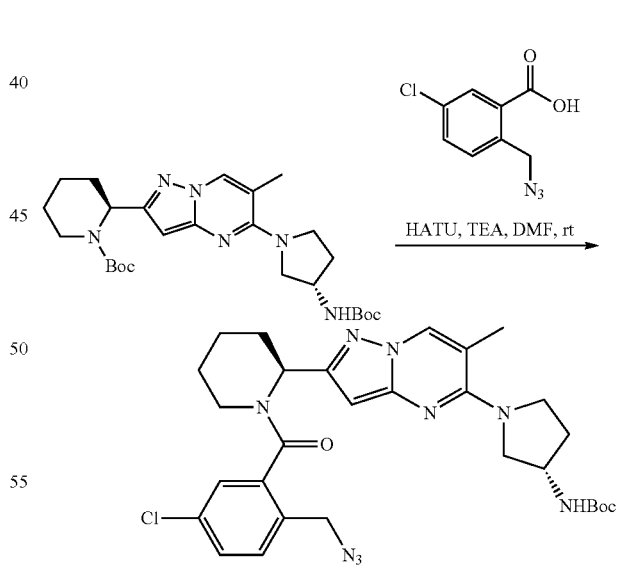

Following the procedure for the synthesis of compound 32, beginning with intermediate 115 (54 mg, 0.255 mmol) and tert-butyl (S)-1-(6-methyl-2-((S)-piperidin-2-yl)pyrazolo[1,5-a]pyrimidin-5-yl)pyrrolidin-3-ylcarbamate (intermediate 12 (79 mg, 0.198 mmol), intermediate 38 was synthesized as a white solid (107 mg, 90%) after silica gel column chromatography (15-75% ethyl acetate in hexanes).

Example 38: Preparation of Intermediate 39

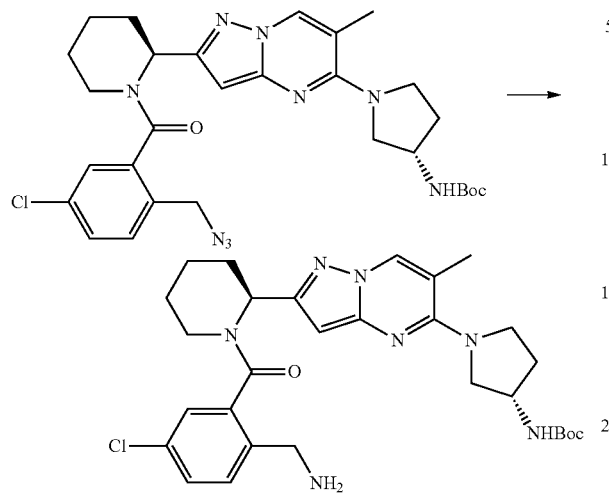

Triphenylphosphine (87 mg, 0.332 mmol) was added to a solution of intermediate 38 (97 mg, 0.163 mmol) in 5 mL of THF at room temperature. After 90 minutes, 0.2 mL of water was added and mixture was heated at 60° C. overnight. The reaction mixture was concentrated under reduced pressure and purified by silica gel column chromatography (0-10% methanol in dichloromethane) to yield intermediate 39 (44 mg, 48%).

Example 39: Preparation of Intermediate 40

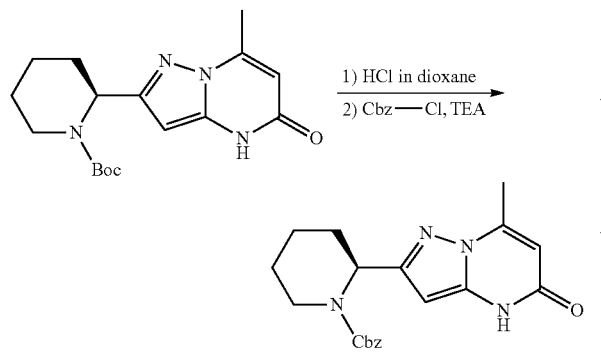

Intermediate 27 (1.68 g, 5 mmol) was dissolved in 4N HCl in dioxane (5 mL) and stirred for 1 h. The material was concentrated under reduced pressure and dried under high vacuum to give solid which was then mixed with THF (10 mL) and TEA (2.1 mL, 15 mmol). Cbz-Cl (739 uL, 5.25 mmol) was added dropwise and stirred for 1 h. The material was diluted with ethyl acetate and washed with saturated aqueous sodium bicarbonate solution and saturated aqueous sodium chloride solution. The organic extract was over anhydrous sodium sulfate and then concentrated under reduced pressure. The material was purified with silica gel column (0-80% EtOAc in hexanes) to give intermediate 40 (929 mg, 51% yield).

$^1$H NMR (400 MHz, CD$_3$OD): δ 7.31 (m, 5H), 5.85 (s, 1H), 5.74 (s, 1H), 5.47 (m, 1H), 5.20-5.10 (m, 2H), 4.08 (m, 1H), 3.05 (m, 1H), 2.50 (s, 3H), 2.34 (m, 1H), 1.85 (m, 1H), 1.63-1.51 (m, 4H).

LC/MS (m/z): 367.2 [M+H]$^+$

Example 40: Preparation of Intermediate 41

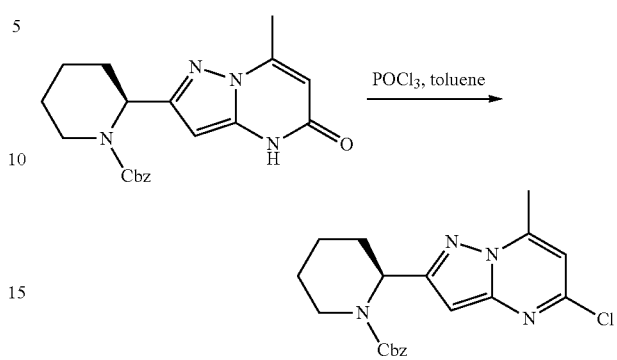

Intermediate 40 (848 mg, 2.3 mmol) was mixed with toluene (7 mL). POCl$_3$ (635 uL, 6.94 mmol) was added and stirred at 110° C. for 1.5 h. The material was concentrated under reduced pressure. The material was dissolved with ethyl acetate and washed with saturated aqueous sodium bicarbonate solution twice and saturated aqueous sodium chloride solution. The organic extract was dried over anhydrous sodium sulfate and then concentrated under reduced pressure. The material was purified with silica gel column (0-30% EtOAc in hexanes) to give intermediate 41 (425 mg, 48% yield).

$^1$H NMR (400 MHz, CD$_3$OD): δ 7.29 (m, 5H), 6.88 (s, 1H), 6.40 (s, 1H), 5.64 (m, 1H), 5.21-5.10 (m, 2H), 4.12 (m, 1H), 3.08 (m, 1H), 2.68 (s, 3H), 2.41 (m, 1H), 1.94 (m, 1H), 1.67-1.49 (m, 4H).

LC/MS (m/z): 385.0 [M+H]$^+$

Example 41: Preparation of Intermediate 42

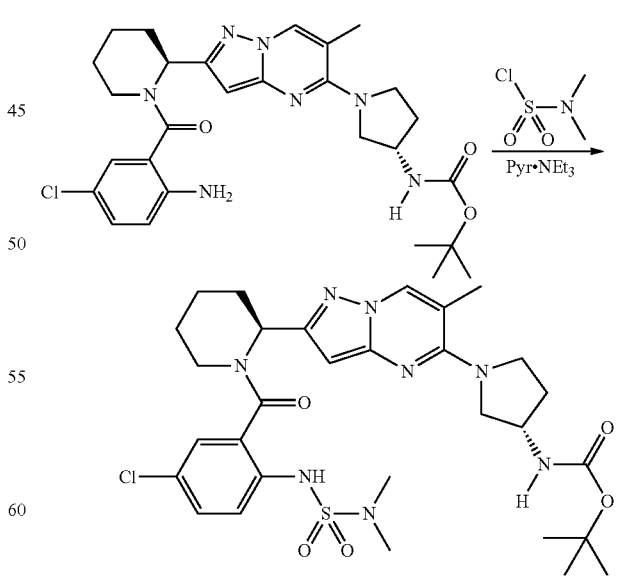

To a solution of intermediate 14 (100 mg, 0.18 mmol) in pyridine (2.00 mL) was added N,N-dimethylsulfamoyl chloride (258 mg, 0.19 mmol) and triethylamine (500 μl, 3.6 mmol), and the reaction mixture was stirred at 90° C. overnight. Then the reaction mixture was allowed to cool to room temperature and was concentrated under reduced pressure. The crude residue was purified by combi-flash column chromatography (0-100% EtOAc/Hexane) to afford intermediate 42 (20 mg, 17%).

LCMS (m/z) 661.09 [M+H]⁺

MW 660.26

Example 42: Preparation of Intermediate 43

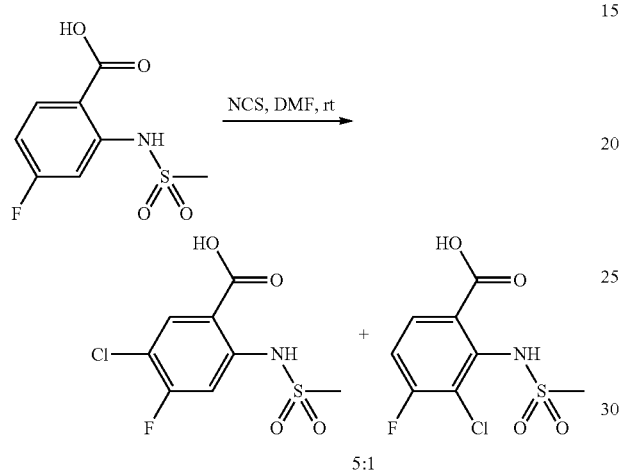

5:1

N-chlorosuccinimide (239 mg, 1.79 mmol) was added to a solution of 4-fluoro-2-(methylsulfonamido)benzoic acid (351 mg, 1.51 mmol) in 9 mL of DMF at room temperature. After stirring overnight, mixture was poured into 90 mL of water and extracted three times with ethyl acetate. The combined organics were washed with water and brine, dried (MgSO₄), filtered, and concentrated under reduced pressure to yield intermediate 43 (384 mg, 95%) as a 5:1 mixture of 5-chloro-4-fluoro-2-(methylsulfonamido)benzoic acid to 3-chloro-4-fluoro-2-(methylsulfonamido)benzoic acid, which was used without further purification.

LCMS m/z [M+H]⁻ C₈H₇ClFNO₄S requires: 265.98. Found 266.07.

Example 43: Preparation of Intermediate 44

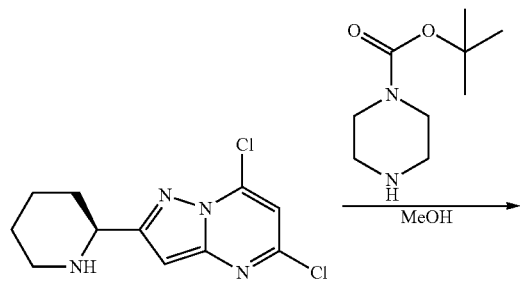

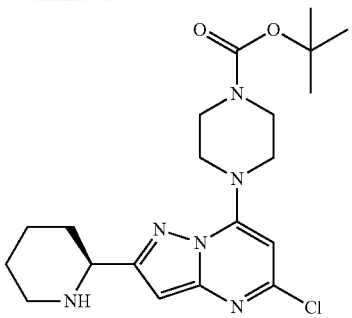

Intermediate 30 (1 g, 3.7 mmol) was dissolved in MeOH (5 ml) and to the solution was added 1-N-Boc-piperazine (0.83 g, 4.4 mmol). The reaction mixture was stirred at room temperature for 10 mins. The solvent was evaporated with reduced pressure and the residue was purified with combi-flash column chromatography (0-50% MeOH/DCM) to afford intermediate 44 (1.7 g, 100%).

LCMS (m/z) 421.05 [M+H]⁺

MW 420.20

Example 44: Preparation of Intermediate 45

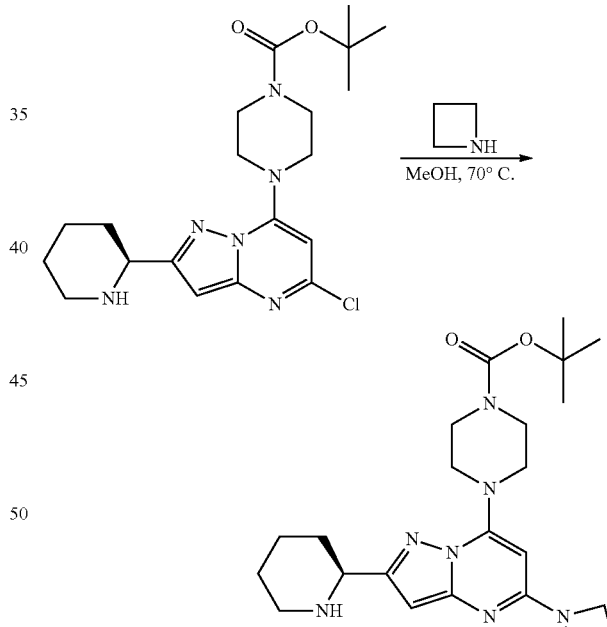

Intermediate 44 (800 mg, 1.9 mmol) was dissolved in MeOH (3 ml) and to the solution was added azetidine (1 g, 19 mmol). The reaction mixture was heated at 70° C. overnight. The solvent was evaporated with reduced pressure and the residue was purified with combi-flash column chromatography (0-60% MeOH/DCM) to afford intermediate 45 (0.54 g, 65%).

LCMS (m/z) 442.39 [M+H]⁺

MW 441.57

Example 45: Preparation of Intermediate 46

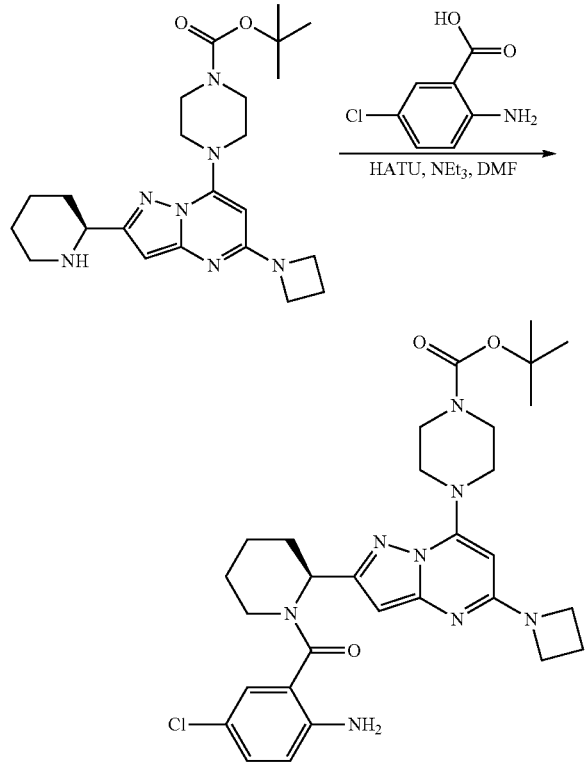

2-Amino-5-chlorobenzoic acid (340 mg, 1.96 mmol) and HATU (930 mg, 2.44 mmol) were dissolved in DMF (3 ml). The reaction mixture was stirred at room temperature for 10 mins. To the above solution was added intermediate 45 (500 mg, 1.22 mmol) and NEt₃ (680 µl). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with combi-flash column chromatography (0-100% EtOAc/Hexane) to afford intermediate 46 (0.5 g, 75%).

LCMS (m/z) 595.28 [M+H]⁺
MW 594.14

Example 46: Preparation of Intermediate 47

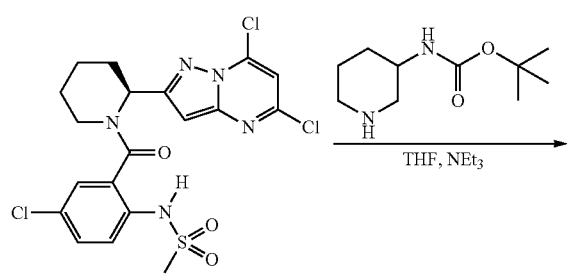

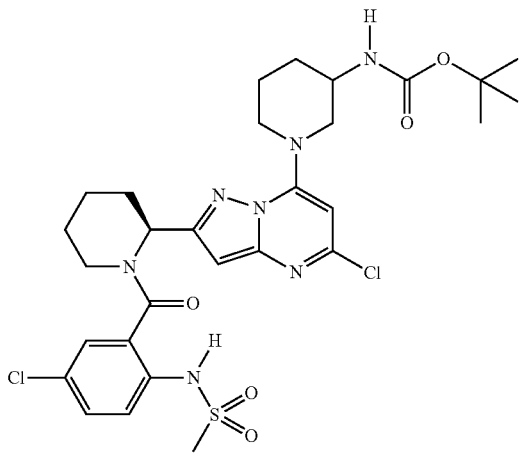

Intermediate 33 (50 mg, 0.1 mmol) was dissolved in THF (2 mL), to the solution was added (S)-3-(Boc-amino)piperidine (22 mg, 0.11 mmol) and NEt₃ (27 µl). The reaction mixture was stirred at room temperature overnight. The solvent was removed under reduced pressure and the residue was purified with combi-flash column chromatography (0-50% MeOH/DCM) to afford intermediate 47 (29 mg, 44%).

Example 47: Preparation of Intermediate 48

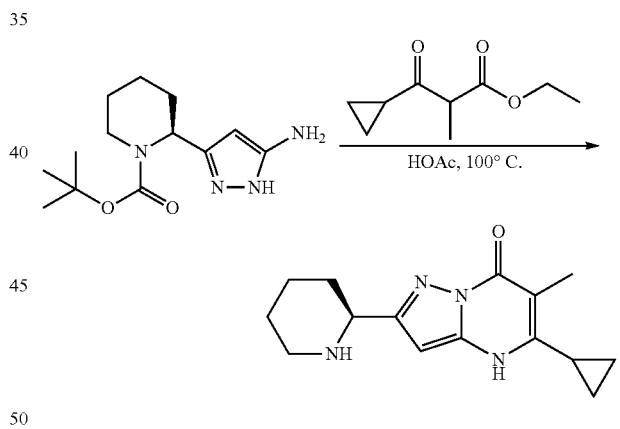

3-(5-Amino-1H-pyrazol-3-yl)-morpholine-4-carboxylic acid tert-butyl ester and intermediate 4 (100 mg, 0.37 mmol) were dissolved in HOAc (2 ml) and 3-cyclopropyl-2-methyl-3-oxo-propionic acid ethyl ester (0.24 ml, 1.88 mmol) was added. The material was stirred at reflux for 1 hour and concentrated under reduced pressure. The material was diluted with ethyl acetate and washed with saturated aqueous sodium bicarbonate solution and saturated aqueous sodium chloride solution. The organic extract was dried over anhydrous sodium sulfate and then concentrated under reduced pressure. The material was purified with Combi-flash silica gel column (linear gradient from 0-80% MeOH in DCM) to yield intermediate 48 (78 mg, 71%).

LCMS (m/z) 273.25 [M+H]⁺
MW 272.16

Example 48: Preparation of Intermediate 49

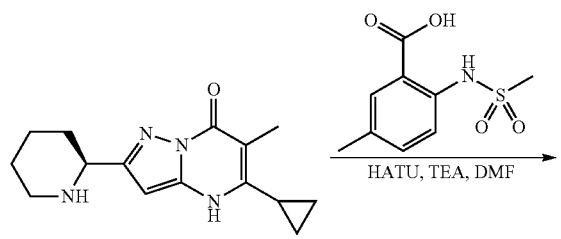

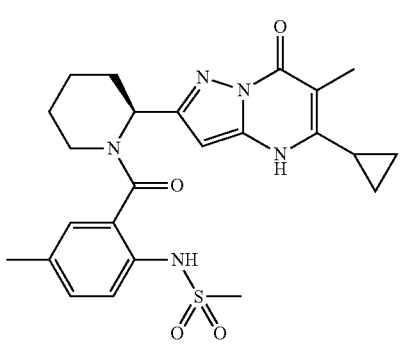

To a solution of 5-methyl-2-[(methylsulfonyl)amino]benzoic acid (126 mg, 0.55 mmol) in DMF (3 ml) was added HATU (281 mg, 0.74 mmol) and stirred for 20 mins at room temperature. To the above solution was added intermediate 48 in DMF (1 ml) followed by addition of TEA (0.1 ml). The reaction was stirred at room temperature for 1 h. Diluted with ethyl acetate and washed with saturated aqueous sodium chloride solution. Dried organic extract over anhydrous sodium sulfate and then concentrated under reduced pressure. The residue was purified with Prep HPLC to yield intermediate 49 (110 mg, 62%).

LCMS (m/z) 474.23 [M+H]+

MW 483.19

Example 49: Preparation of Intermediate 50

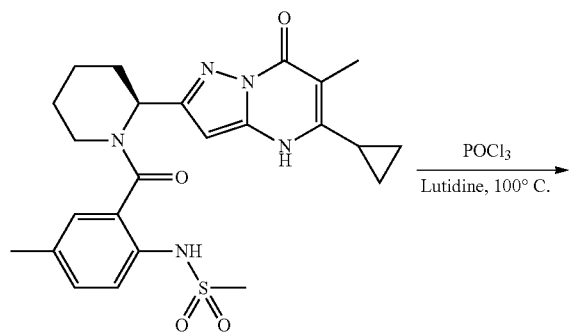

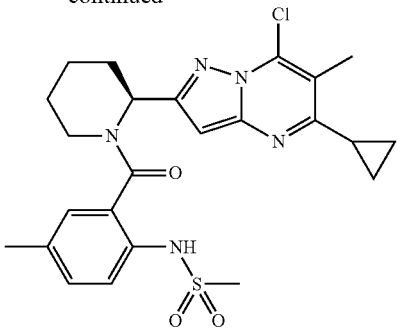

Intermediate 49 (30 mg, 0.06 mmol) with POCl$_3$ (30 uL) was mixed in lutidine (2 mL) and stirred at 100° C. for 3 h and then concentrated under reduced pressure. The material was dissolved in DCM and purified with Combiflash silica gel column (linear gradient from 0-80% EtOAc in hexane) to yield intermediate 50 (15 mg, 48%).

LCMS (m/z) 502.10 [M+H]+

MW 501.03

Example 50: Preparation of Intermediate 51

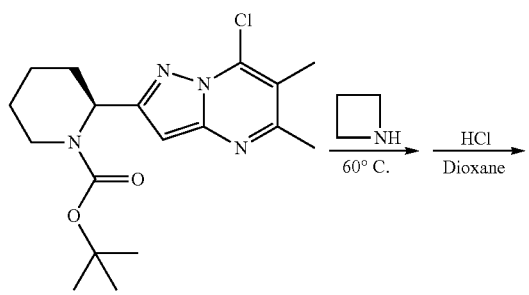

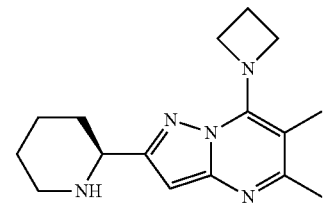

Intermediate 19 (200 mg, 0.55 mmol) was dissolved in azetidine (1 ml) and the reaction mixture was heated to 60° C. for 30 min. The solvent was evaporated and the residue was redissolved in 1,4-dioxane and 4N HCl (1 ml) was added to the above solution. The reaction mixture was stirred at room temperature for 2 h. The solvent was removed under reduced pressure and the residue was purified with prep HPLC (0-100% CH$_3$CN/H$_2$O) to afford intermediate 51 (144 mg, 92%).

LCMS (m/z) 286.21 [M+H]+

MW 285

Example 51: Preparation of Intermediate 52

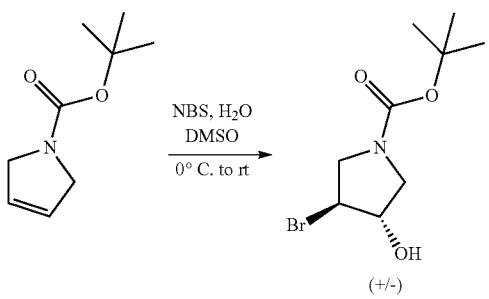

A solution of tert-butyl 2,5-dihydro-1H-pyrrole-1-carboxylate (955 mg, 5.64 mmol) in 7 mL of DMSO and 0.3 mL of water was cooled to 0° C. NBS (1.51 g, 8.44 mmol) was added slowly over eight minutes and then reaction mixture was warmed to room temperature. After four hours, the mixture was poured into 100 mL of ice water and extracted with ethyl acetate (2×70 mL). The combined organics were washed with 100 mL of water and 100 mL of brine, then dried (MgSO$_4$), filtered, and concentrated under reduced pressure to yield intermediate 52 (1.48 g, 99%) as a yellow film, which was used in the next step without further purification.

$^1$H NMR (CDCl$_3$, 400 MHz): δ 4.46 (m, 1H), 4.15 (m, 1H), 4.02 (dd, J=5.2 Hz, 13 Hz), 3.81 (m, 2H), 3.40 (m, 1H), 1.46 (s, 9H)

Example 52: Preparation of Intermediate 53

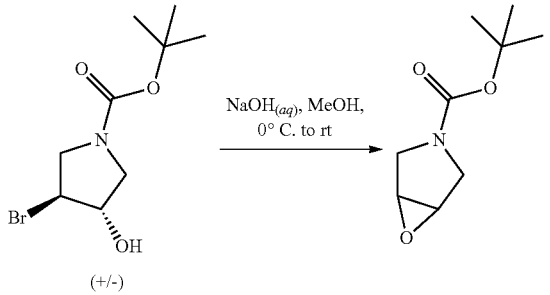

To a solution of intermediate 52 (467 mg, 1.75 mmol) in 7 mL of methanol at 0° C., was slowly added a 1.0 N aqueous solution of NaOH (2.4 mL, 2.4 mmol). The reaction mixture was warmed to room temperature and stirred overnight. Methanol was then concentrated under reduced pressure and 20 mL of water was added. The aqueous was extracted with ethyl acetate (3×25 mL) and combined organics were washed with 50 mL of brine, then dried (MgSO$_4$), filtered, and concentrated under reduced pressure to yield intermediate 53 (1.48 g, 99%) as a colorless oil, which was used in the next step without further purification.

$^1$H NMR (CDCl$_3$, 400 MHz): δ 3.80 (d, J=12.8 Hz, 1H), 3.73 (d, J=12.8 Hz), 3.65 (d, J=3.2 Hz, 2H), 3.31 (d, J=4.8 Hz, 1H), 3.28 (d, J=4.8 Hz, 1H), 1.43 (s, 9H)

Example 53: Preparation of Intermediate 54

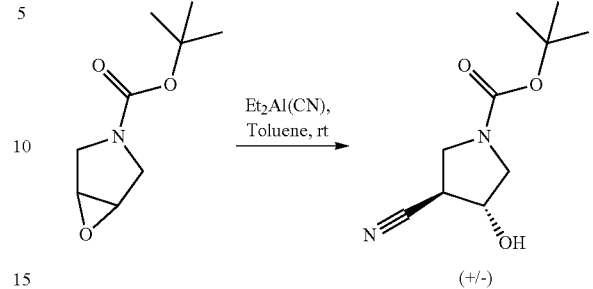

A solution of diethylaluminum cyanide in toluene (1.0 M, 3.3 mL, 3.3 mmol) was added slowly to a solution of intermediate 53 (298 mg, 1.61 mmol) in 9 mL of toluene at room temperature. After stirring overnight, the reaction mixture was quenched carefully (caution: exothermic) by slow addition of 1.0 N solution of NaOH$_{(aq)}$ and then diluted with 15 mL of water. The aqueous was extracted with ethyl acetate (2×60 mL) and the combined organics were washed with water (2×60 mL) and 60 mL of brine, then dried (MgSO$_4$), filtered, and concentrated under reduced pressure to yield intermediate 54 (314 mg, 85%) as a light yellow oil, which was used without further purification.

$^1$H NMR (CDCl$_3$, 400 MHz): δ 4.63 (m, 1H), 3.80-3.61 (m, 3H), 3.36 (m, 1H), 3.05 (m, 1H), 2.64 (br s, 1H), 1.47 (s, 9H)

Example 54: Preparation of Intermediate 55

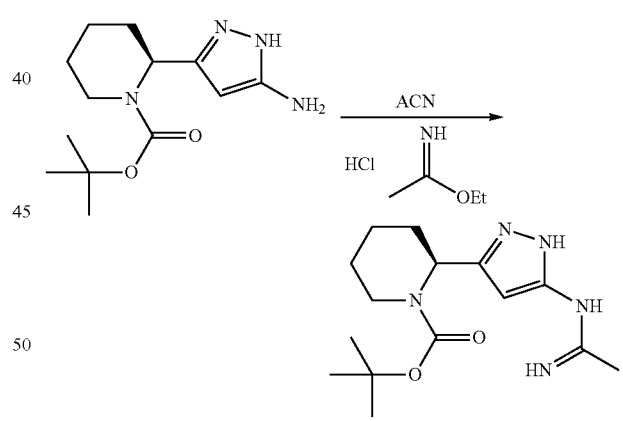

Intermediate 4 (266 mg, 1 mmol) was dissolved in acetonitrile (5 mL). Ethyl acetimidate hydrochloride (247 mg, 2 mmol) was then added followed by dropwise addition of acetic acid (57 µL, 1 mmol). Ethanol (1 mL) was added and the reaction mixture was stirred for 48 h. The resulting solid was filtered and washed with acetonitrile. Filtrate was concentrated under reduced pressure and purified with prep HPLC (5-95% Acetonitrile in water, 0.1% acetic acid buffer) to give intermediate 55 (185 mg, 60%).

$^1$H NMR (400 MHz, CD$_3$OD): δ 5.93 (s, 1H), 5.45 (m, 1H), 4.05 (m, 1H), 2.78 (m, 1H), 2.40 (s, 3H), 2.18 (m, 1H), 1.78 (m, 1H), 1.70-1.60 (m, 2H), 1.47 (m, 12H).

LC/MS (m/z): 308.1 [M+H]$^+$

Example 55: Preparation of Intermediate 56

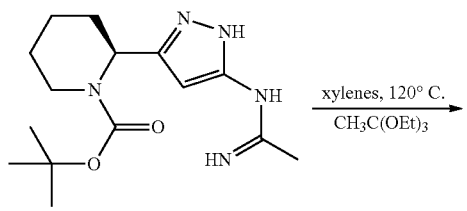

Intermediate 55 (31 mg, 0.1 mmol) was mixed with xylenes (2 mL). Triethyl orthoacetate (60 µL, 0.33 mmol) was added and reaction mixture was stirred at 120° C. for 24 h. After cooling to room temperature, mixture was concentrated under reduced pressure and purified with silica gel column chromatography (40% EtOAc in hexanes) to give intermediate 56 (16 mg, 48%).

$^1$H NMR (400 MHz, CD$_3$OD): δ 6.30 (s, 1H), 5.54 (m, 1H), 4.04 (m, 1H), 2.95 (m, 1H), 2.87 (s, 3H), 2.58 (s, 3H), 2.47 (m, 1H), 1.89 (m, 1H), 1.65 (m, 2H), 1.47 (m, 12H).

LC/MS (m/z): 332.1 [M+H]$^+$

Example 56: Preparation of Intermediate 57

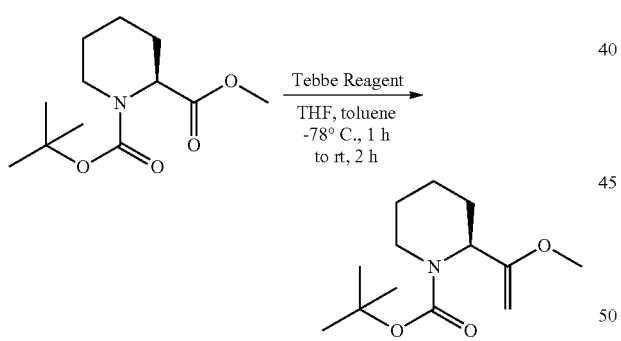

A solution of intermediate 2 (1.52 g, 6.26 mmol) in 15 mL of anhydrous THF was cooled to −78° C. under argon. A solution of Tebbe Reagent (0.5 M in toluene, 15 mL, 7.5 mmol) was added dropwise and reaction mixture stirred at −78° C. for one hour and was then warmed to room temperature. After two hours, reaction mixture was placed in a dropping funnel and then added dropwise to a 500 mL round bottom flask containing a stirring solution of 1N NaOH$_{(aq)}$ at 0° C. After complete addition, 75 mL of ethyl acetate was added and mixture was stirred vigorously overnight (yellow precipitate). Mixture was then filtered over a medium frit and filtrate was added to a separatory funnel. After separating the aqueous layer, the remaining organic layer was washed with brine (2×125 mL), dried (Na$_2$SO$_4$), filtered and concentrated under reduced pressure leaving a yellow oily residue. Hexane was added to crash out more solid and mixture was filtered. Filtrate was concentrated and remaining residue was purified via silica gel column chromatography (0-25% ethyl acetate in hexanes) to yield intermediate 57 (332 mg, 22%) as a clear oil.

$^1$H-NMR (CDCl$_3$, 400 MHz): δ 4.74 (m, 1H), 4.06 (m, 1H), 3.95 (m, 1H), 3.91 (m, 1H), 3.54 (s, 3H), 2.91 (m, 1H), 2.07 (m, 1H), 1.65-1.50 (m, 3H), 1.47 (s, 9H), 1.45-1.32 (m, 2H).

Example 57: Preparation of Intermediate 58

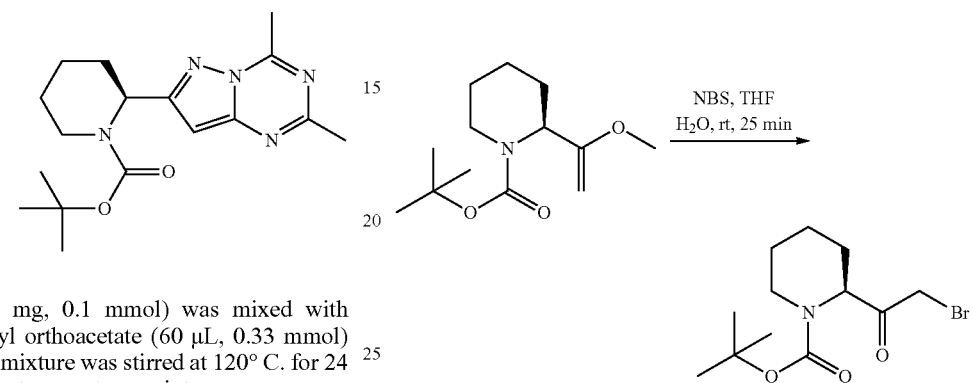

NBS (339 mg, 1.89 mmol) was added slowly to a solution of intermediate 57 (454 mg, 1.88 mmol) in 10 mL of THF and 3 mL of water at room temperature. After 25 minutes, reaction mixture was poured into 45 mL of saturated NaHCO$_{3(aq)}$. Aqueous was extracted with ethyl acetate (3×30 mL). Combined organics were washed with 75 mL of brine, dried (Na$_2$SO$_4$), filtered, and concentrated under reduced pressure. Resulting residue was purified via silica gel column chromatography (5-20% ethyl acetate in hexanes) to yield intermediate 58 (219 mg, 40%) as a clear oil.

$^1$H-NMR (CDCl$_3$, 400 MHz): δ 4.89 (m, 1H), 4.03 (s, 2H), 3.05-2.75 (m, 1H), 2.14 (m, 1H), 1.75-1.61 (m, 3H), 1.47 (s, 9H), 1.44-1.33 (m, 2H).

Example 58: Preparation of Intermediate 59

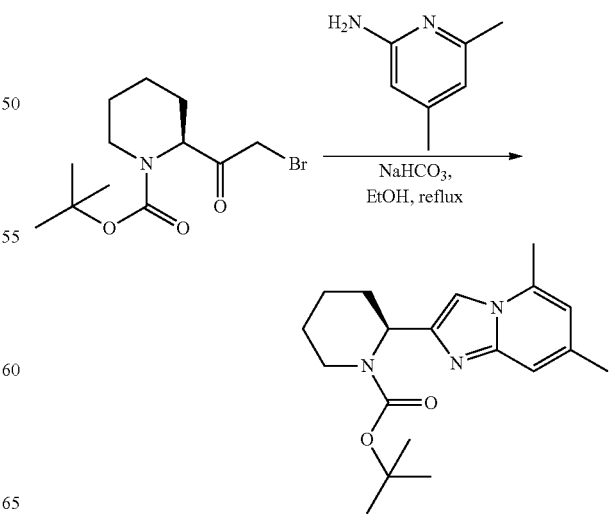

A mixture of intermediate 58 (73 mg, 0.238 mmol), NaHCO₃ (41 mg, 0.488 mmol), and 2,4-dimethyl-6-aminopyridine (60 mg, 0.491 mmol) in 3 mL of ethanol was heated at reflux overnight. After cooling to room temperature the reaction mixture was concentrated under reduced pressure and purified by prep HPLC (15-100% acetonitrile (with 0.1% trifluoroacetic acid) in water (with 0.1% trifluoroacetic acid)) to yield intermediate 59 (6.0 mg, 7.6%) as a solid, trifluoroacetic acid salt, after lyophilization.

LCMS m/z [M+H]⁺ $C_{19}H_{27}N_3O_2$ requires: 330.21. Found 330.38.

Example 59: Preparation of Intermediate 60

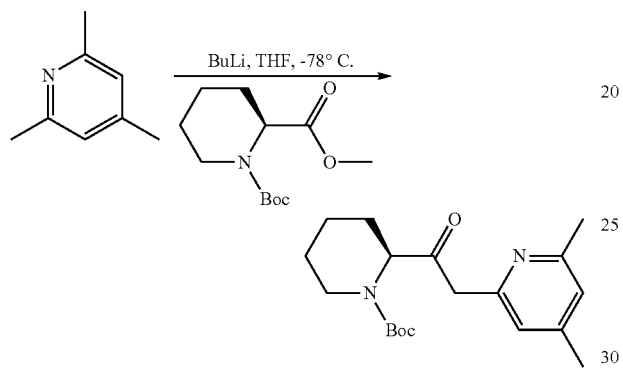

A solution of collidine (1 g, 8.25 mmol) in THF (5 mL) was cooled to −78° C. and BuLi (5.15 mL, 1.6 M in hexanes) was added dropwise. A dark red color formed immediately. The solution was stirred for 10 minutes at −78° C. Intermediate 2 (0.5 g, 0.2 mmol) in THF (5 mL) was added dropwise and stirred at −78° C. for 15 minutes. The solution was quenched with acetic acid (0.5 mL) in THF (2 mL) and warmed to room temperature. The volatiles were partially removed under reduced pressure and EtOAc (50 mL) was added. The organic layer was washed with brine (2×50 mL), dried, and concentrated under reduced pressure. Silica gel column chromatography (0-60% EtOAc in hexanes) afforded intermediate 60 as a colorless oil (1.36 g, 91%).

LCMS m/z [M+H]⁺332.99.
HPLC Tr (min), purity %: 2.34, 60%

Example 60: Preparation of Intermediate 61

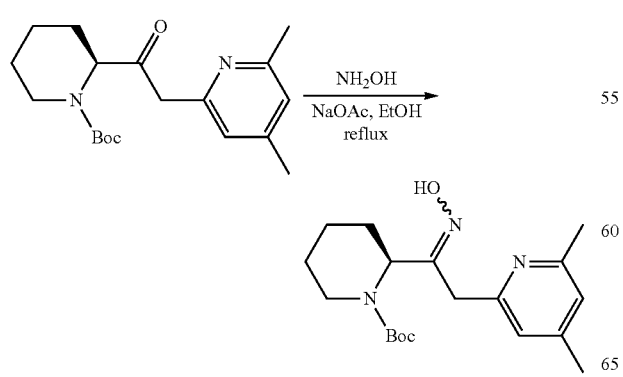

Intermediate 60 (1.3 g, 3.91 mmol), hydroxylamine (1.35 g, 19.5 mmol) and NaOAc (1.92 g, 23.46 mmol) were stirred at reflux in EtOH (20 mL) for 1 h. The volatiles were partially removed under reduced pressure. EtOAc (50 mL) was added and the organic layer was washed with brine (2×50 mL), dried, and concentrated under reduced pressure. The compound was purified by silica gel column chromatography (0-60% EtOAc in hexanes) to afford intermediate 61 as a colorless oil (1.10 g, 81%).

LCMS m/z [M+H]⁺ 348.04
HPLC Tr (min), purity %: 2.28, 80%

Example 61: Preparation of Intermediate 62

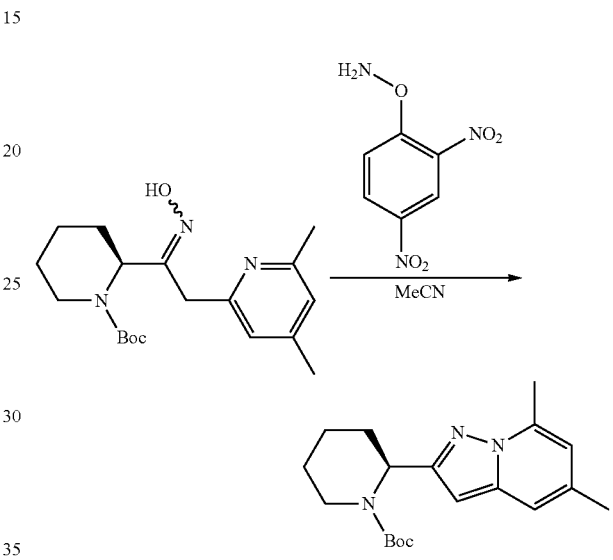

Intermediate 61 (0.348 g, 1.0 mmol) and O-(2,4-dinitrophenyl)-hydroxylamine (0.239 g, 1.2 mmol) were stirred in MeCN under nitrogen for 16 h. Cs₂CO₃ (0.5 g) was added and the suspension stirred at room temperature for 2 h. The volatiles were removed under reduced pressure and the residue was dissolved in MeCN/water and purified by preparatory HPLC (5-95% H₂O/MeCN, 0.1% TFA) to afford intermediate 62 as a colorless powder (0.119 g, 34%).

LCMS m/z [M+H]⁺329.95
HPLC Tr (min), purity %: 2.81, 98%

Example 62: Preparation of Intermediate 63

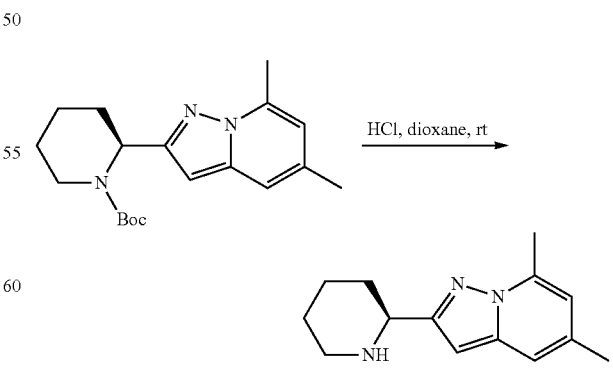

Intermediate 62 (0.119 g, 0.362 mmol) was stirred in dioxane (2 mL) and HCl (4 mL, 4 M in dioxane) was added at room temperature and stirred for 1 h. The volatiles were removed under reduced pressure to afford the HCl salt of intermediate 63 as an off-white powder (0.125 g, >100%).

LCMS m/z [M+H]$^+$ 230.16

$^1$H NMR (CDCl$_3$, 400 MHz): δ 9.44 (s, 2H), 7.36 (s, 1H), 6.73 (s, 1H), 6.70 (s, 1H), 4.46 (m, 1H), 3.28 (d, 12.4 Hz, 1H), 3.04 (m, 1H), 2.62 (s, 3H), 2.30 (s, 3H), 2.10 (d, 13.6 Hz), 1.93-1.78 (m, 4H), 1.66 (m, 1H).

HPLC Tr (min), purity %: 1.34, 98%

Example 63: Preparation of Intermediate 64

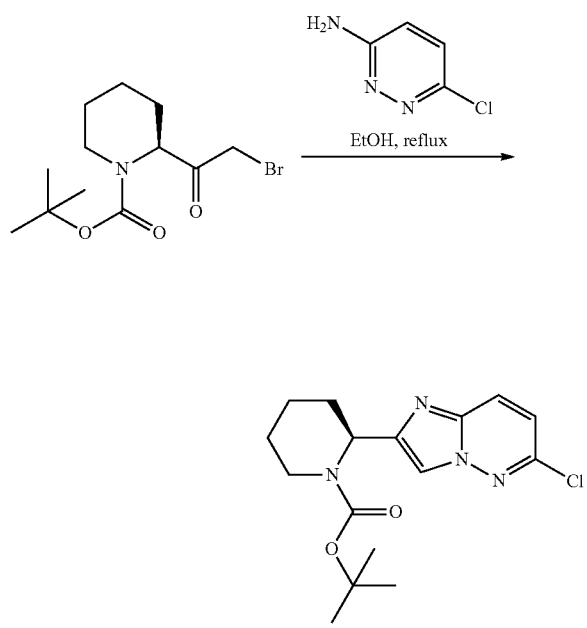

A mixture of intermediate 58 (14 mg, 0.046 mmol) and 6-chloropyridazin-3-amine (17 mg, 0.131 mmol) in 1.2 mL of ethanol was heated a reflux overnight. After cooling to room temperature the reaction mixture was concentrated under reduced pressure and purified via silica gel column chromatography (5-50% ethyl acetate in hexanes) to yield intermediate 64 as a clear film (9 mg, 60%).

LCMS m/z [M+H]$^+$ C$_{17}$H$_{22}$ClN$_3$O$_2$ requires: 337.14. Found 337.04.

Example 64: Preparation of Intermediate 65

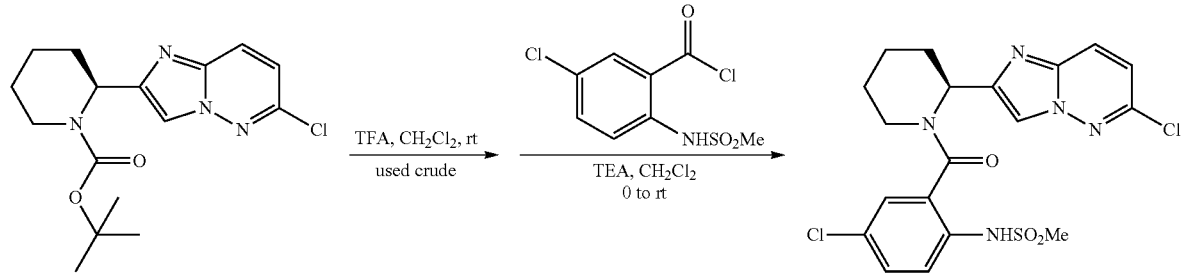

Trifluoroacetic acid (0.070 mL, 0.831 mmol) was added to a solution of intermediate 64 (8 mg, 0.024 mmol) in 1 mL of CH$_2$Cl$_2$. After stirring overnight, LC/MS indicated full removal of Boc group. The reaction mixture was concentrated under reduced pressure and dried in-vacuo for two hours. To a solution of the resulting residue dissolved in 1.5 mL of anhydrous CH$_2$Cl$_2$ was added 5-chloro-2-(methylsulfonamido)benzoyl chloride (6.5 mg, 0.0252 mmol). The mixture was cooled to 0° C., triethylamine (7.0 μL, 0.049 mmol) was added, and the resulting mixture was warmed to room temperature and stirred overnight. LC/MS monitoring indicated full conversion to intermediate 65 (11.5 mg, 99%). The reaction mixture was concentrated under reduced pressure and used without further purification.

LCMS m/z [M+H]$^+$ C$_{19}$H$_{19}$Cl$_2$N$_5$O$_3$S requires: 468.06. Found 467.89.

Example 65: Preparation of Intermediate 66

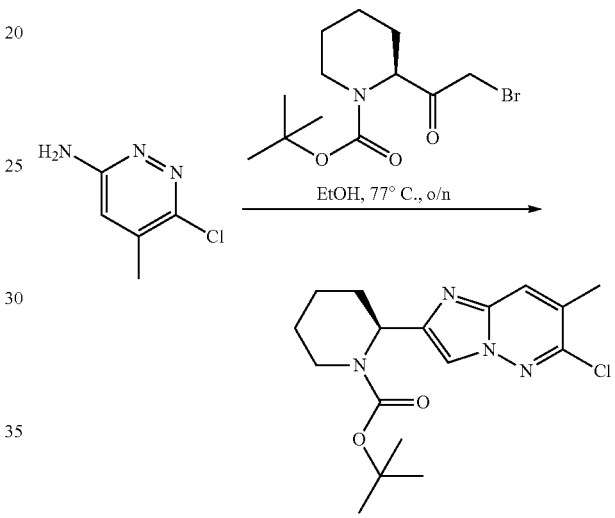

A mixture of intermediate 58 (293 mg, 0.958 mmol) and 6-chloro-5-methylpyridazin-3-amine (195 mg, 1.35 mmol) in 16 mL of ethanol was heated at 77° C. overnight. After cooling to room temperature the reaction mixture was concentrated under reduced pressure and the residue was purified via silica gel column chromatography (5-100% ethyl acetate in hexanes) to yield intermediate 66 (125 mg, 38%) as a white solid.

LCMS m/z [M+H]$^+$ C$_{17}$H$_{23}$ClN$_4$O$_2$ requires: 351.15. Found 351.12.

$^1$H-NMR (CDCl$_3$, 400 MHz): δ 7.76 (s, 1H), 7.62 (s, 1H), 5.57 (m, 1H), 4.09 (m, 1H), 2.89 (m, 1H), 2.52 (m, 1H), 2.45 (s, 3H), 1.86 (m, 1H), 1.70-1.30 (m, 4H), 1.47 (s, 9H).

Example 66: Preparation of Intermediate 67

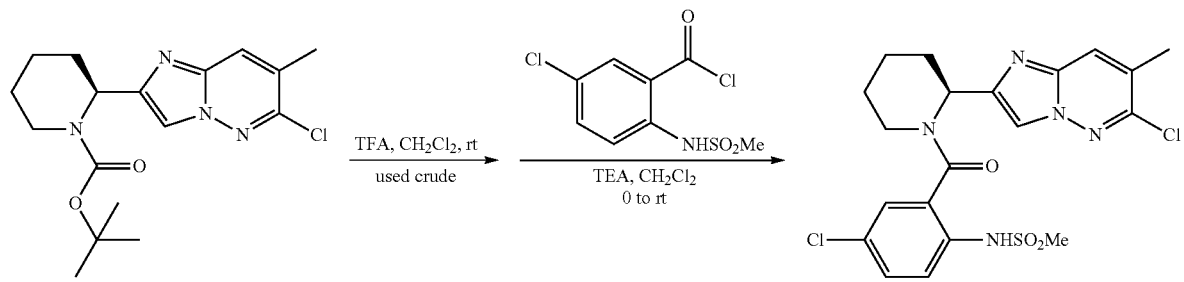

Following the procedure for the synthesis of intermediate 65, beginning with intermediate 66 (120 mg, 0.343 mmol), intermediate 67 (129 mg, 78%) was synthesized as a white solid.

LCMS m/z [M+H]$^+$ C$_{20}$H$_{21}$Cl$_2$N$_5$O$_3$S requires: 482.07. Found 481.86.

$^1$H-NMR (CDCl$_3$, 400 MHz): δ 10.0 (s, 1H), 8.34 (s, 1H), 7.73-7.53 (m, 2H), 7.37-7.30 (m, 1H), 6.27 (s, 1H), 3.31 (m, 1H), 2.95 (s, 3H), 2.46 (s, 3H), 2.27 (m, 2H), 1.77 (m, 2H), 1.68-1.38 (m, 4H).

Example 67: Preparation of Intermediate 68

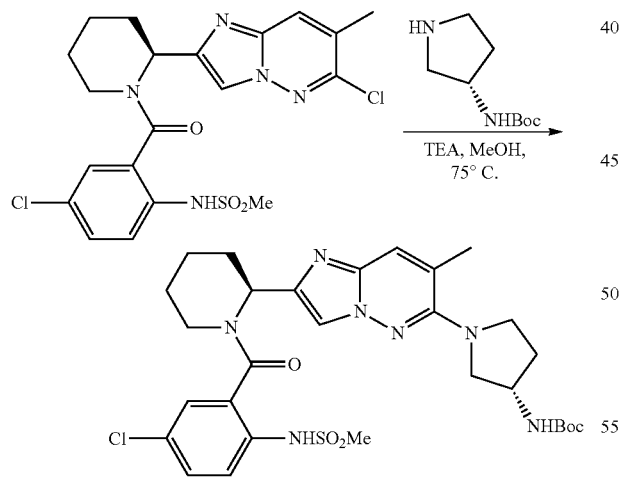

Triethylamine (0.35 mL, 2.51 mmol) was added to a mixture of intermediate 67 (109 mg, 0.226 mmol) and (S)-tert-butyl pyrrolidin-3-ylcarbamate (469 mg, 2.52 mmol) in 9 mL of anhydrous methanol. The mixture was heated at 75° C. overnight. Analytical HPLC indicated about 15% conversion to intermediate 68. Additional (S)-tert-butyl pyrrolidin-3-ylcarbamate (1.81 g) was added along with triethylamine (0.9 mL) and mixture was heated again for five days. The reaction mixture was cooled to room temperature, concentrated under reduced pressure, and the resulting residue was purified by silica gel column chromatography (10-50% ethyl acetate in hexanes) to yield intermediate 68 (91 mg, 64%) as a white solid.

LCMS m/z [M+H]$^+$ C$_{29}$H$_{38}$ClN$_7$O$_5$S requires: 632.23. Found 632.55.

Example 68: Preparation of Intermediate 69

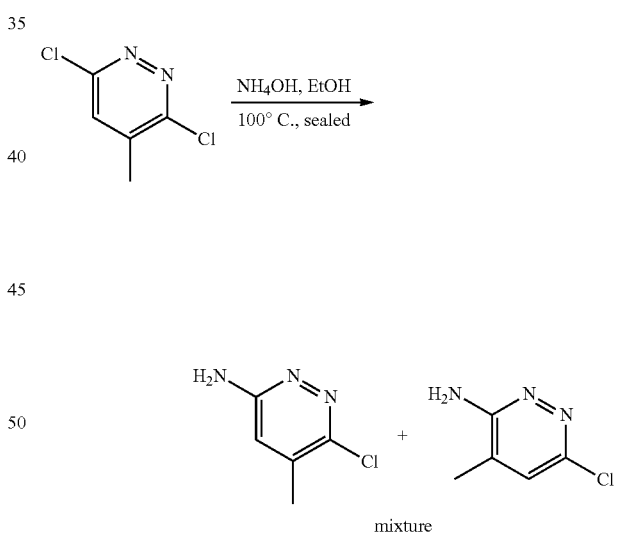

mixture

A mixture of 3,6-dichloro-4-methylpyridazine (333 mg, 2.04 mmol) in 3.3 mL of 28% NH$_4$OH and 2 mL of ethanol was heated at 100° C. in a sealed tube for 48 hours. After cooling to room temperature, the reaction mixture was concentrated under reduced pressure. The resulting solid was washed with ether and decanted (5×) yielding a light yellow solid (123 mg, 42%) as a 55/45 mixture of 6-chloro-5-methylpyridazin-3-amine and intermediate 69 by analytical HPLC.

LCMS m/z [M+H]$^+$ C$_5$H$_6$ClN$_3$ requires: 144.03. Found 144.10.

Example 69: Preparation of Intermediate 70

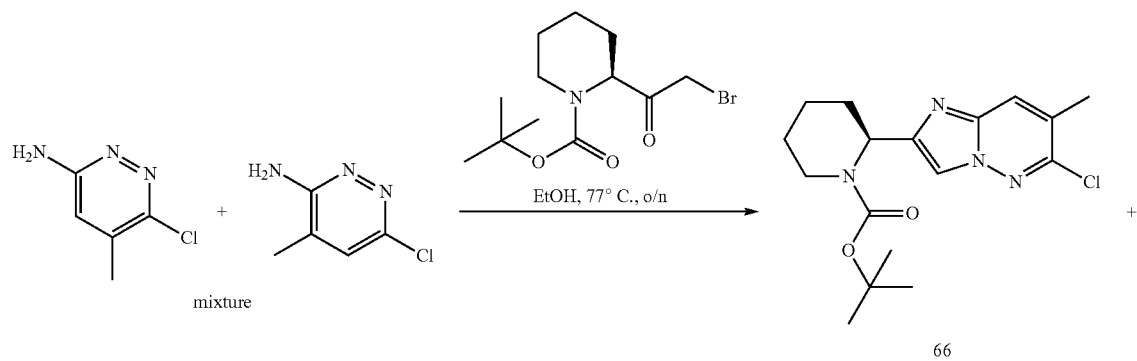

A mixture of intermediate 58 (105 mg, 0.343 mmol) and the mixture of 6-chloro-5-methylpyridazin-3-amine and intermediate 69 (75 mg, 0.521 mmol) in 6 mL of ethanol was heated at 77° C. overnight. After cooling to room temperature, the reaction mixture was concentrated under reduced pressure and the residue was purified via silica gel column chromatography (5-40% ethyl acetate in hexanes) to yield intermediate 70 (7 mg, 6%) as the first eluting product followed by its isomer, intermediate 66 (17 mg, 14%).

Intermediate 70: LCMS m/z [M+H]+ $C_{17}H_{23}ClN_4O_2$ requires: 351.15. Found 351.04.

Example 70: Preparation of Intermediate 72

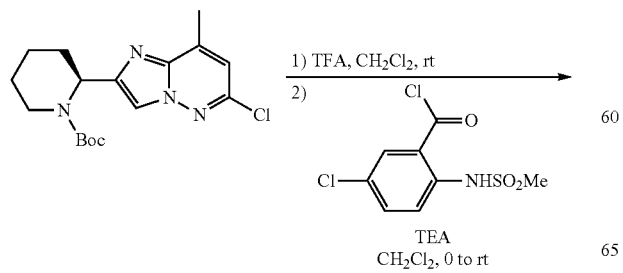

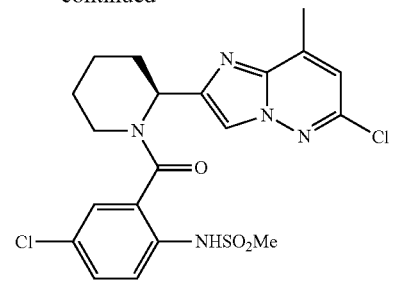

Following the procedure for synthesis of intermediate 65, but beginning with intermediate 70 (7 mg, 0.020 mmol), intermediate 72 was recovered as a clear film (5.8 mg, 60%).

LCMS m/z [M+H]+ $C_{20}H_{21}Cl_2N_5O_3S$ requires: 482.07. Found 481.94.

Example 71: Preparation of Intermediate 73

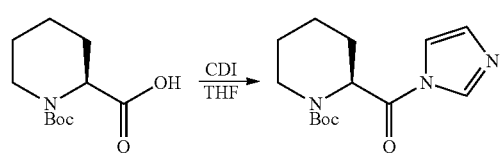

To a solution of (S)-1-(tert-butoxycarbonyl)piperidine-2-carboxylic acid (30.0 g, 130 mmol) in tetrahydrofuran (260 mL) was added carbonyldiimidazole (21.2 g, 130 mmol) at room temperature. After 18 h, the reaction mixture was concentrated under reduced pressure and the crude residue was partitioned between ethyl acetate (600 mL) and water (200 mL). The phases were separated, and the organic layer was washed with water (200 mL), with saturated aqueous sodium bicarbonate solution (200 mL), and with saturated sodium chloride solution (200 mL). The organic layer was dried over $Na_2SO_4$, and was concentrated under reduced pressure to afford intermediate 73 (36 g, 99%) as a white crystalline solid.

$^1$H NMR ($CDCl_3$, 400 MHz): δ 8.21 (br s, 1H), 7.51 (br s, 1H), 7.08 (br s, 1H), 5.45-5.01 (m, 1H), 3.92 (br d, J=13.6 Hz, 1H), 3.39-3.05 (m, 1H), 2.13-1.98 (m, 1H), 1.96-1.82 (m, 1H), 1.78-1.56 (m, 2H), 1.55-1.30 (m, 11H).

$R_f$=0.30 (50% ethyl acetate/hexanes).

Example 72: Preparation of Intermediate 74

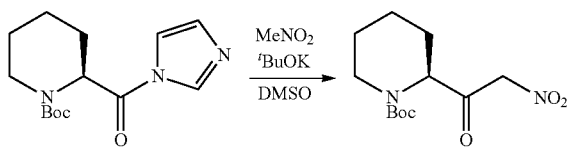 [SMILES: CC(C)(C)OC(=O)N1CCCC[C@H]1C(=O)n1ccnc1 ; CC(C)(C)OC(=O)N1CCCC[C@H]1C(=O)C[N+](=O)[O-]]

To a solution of potassium 2-methylpropan-2-olate (14.5 g, 129 mmol) in dimethylsulfoxide (129 mL) was added nitromethane (6.93 mL, 129 mmol) at room temperature. After 1 h, a solution of intermediate 73 (36.0 g, 129 mmol) in dimethylsulfoxide was added via cannula and the reaction mixture was stirred at room temperature. After 15 h, acetic acid (50 mL) was added and the resulting mixture was partitioned between dichloromethane (400 mL) and water (1 L). The phases were separated, and the aqueous layer was extracted with dichloromethane (3×400 mL). The combined organic layers were dried over $Na_2SO_4$, and were concentrated under reduced pressure. The crude residue was purified via $SiO_2$ column chromatography (330 g $SiO_2$ Combiflash HP Gold Column, 0-100% ethyl acetate/hexanes) to afford intermediate 74 (35.2 g, 99%) as a yellow solid.

$^1$H NMR ($CDCl_3$, 400 MHz): δ 5.36 (s, 2H), 4.73 (br s, 1H), 4.09-3.74 (m, 1H), 3.04-2.69 (m, 1H), 2.14 (br d, J=10.6 Hz, 1H), 1.75-1.55 (m, 3H), 1.54-1.39 (m, 11H).

LCMS (ESI) m/z 271.42 [M−H]$^-$, $t_R$=2.48 min.

$R_f$=0.70 (50% ethyl acetate/hexanes.

Example 73: Preparation of Intermediate 75

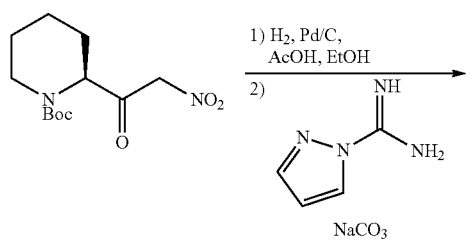

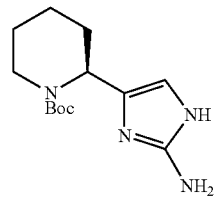

To a suspension of palladium on carbon (10% wt, 78.0 mg, 73.0 μmol) in ethanol (3.6 mL) was added intermediate 74 (400 mg, 1.47 mmol) at room temperature under an argon atmosphere. The reaction vessel was evacuated and refilled with hydrogen gas (3×), and balloon filled with hydrogen gas was appended to the vessel. The reaction mixture was stirred vigorously for 2 h at which point the reaction was filtered through a pad of celite. To the filtrate was added 1H-pyrazole-1-carboximidamide (323 mg, 2.20 mmol) followed by sodium carbonate (233 mg, 2.20 mmol), and the resulting mixture was stirred at room temperature. After 16 h, the reaction mixture was partitioned between ethyl acetate (150 mL) and water (150 mL). The phases were separated, and the aqueous layer was extracted with ethyl acetate (2×150 mL). The combined organic layers were dried over $Na_2SO_4$, and were concentrated under reduced pressure. The crude residue was purified via $SiO_2$ column chromatography (12 g $SiO_2$ Combiflash HP Gold Column, 0-20% methanol/dichloromethane) to afford intermediate 75 (119 mg, 30%) as a yellow oil.

$^1$H NMR ($CD_3OD$, 400 MHz): δ 6.25 (s, 1H), 5.19 (d, J=4.9 Hz, 1H), 3.93 (d, J=10.4 Hz, 1H), 2.91 (t, J=13.4 Hz, 1H), 2.13 (d, J=13.3 Hz, 1H), 1.76-1.62 (m, 1H), 1.62-1.51 (m, 3H), 1.43 (s, 10H).

HPLC $t_R$ (min), purity %: 2.83, 99%.

$R_f$=0.45 (20% methanol/dichloromethane).

Example 74: Preparation of Intermediate 76

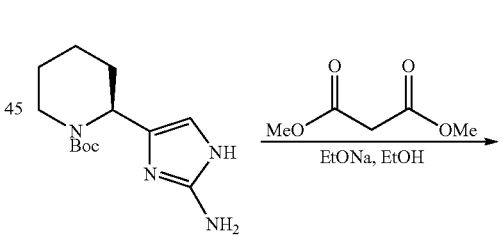

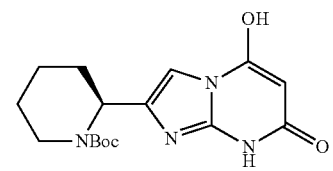

To a solution of intermediate 75 (92 mg, 0.35 mmol), and dimethyl malonate (80 μL, 0.70 mmol), in ethanol (1.7 mL) was added sodium ethoxide (21 wt % in ethanol, 225 mg, 0.70 mmol) at room temperature under an argon atmosphere and the resulting mixture was heated to 70° C. After 19 h, the reaction mixture was allowed to cool to room temperature and acetic acid was added until the mixture was pH=7. The resulting mixture was purified by preparatory HPLC (5-100% $MeCN/H_2O$, 0.1% trifluoroacetic acid modifier) to afford intermediate 76 (80 mg, 69%) as a colorless oil.

¹H NMR (CD₃OD, 400 MHz): δ 7.26 (s, 1H), 7.08 (s, 1H), 5.44 (d, J=4.8 Hz, 1H), 4.04 (d, J=14.0 Hz, 1H), 2.90 (t, J=13.1 Hz, 1H), 2.16 (d, J=14.0 Hz, 1H), 1.94-1.81 (m, 1H), 1.75-1.52 (m, 4H), 1.49 (s, 9H).
LCMS (ESI) m/z 335.14 [M+H]⁺, t_R=2.24 min.

Example 75: Preparation of Intermediate 77

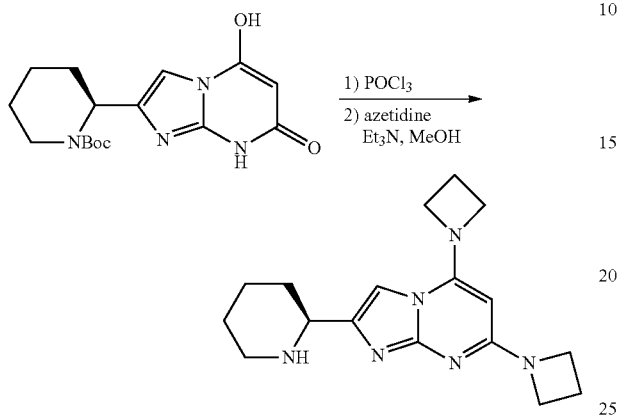

Phosphoryl chloride (1 mL) was added to intermediate 76 (38 mg, 0.11 mmol) at room temperature under an argon atmosphere and the resulting mixture was heated to 100° C. After 7 h, the reaction mixture was allowed to cool to room temperature and was concentrated under reduced pressure. To the resulting residue was added azetidine hydrochloride (106 mg, 1.14 mmol), triethylamine (317 μL, 2.28 mmol), and methanol (2 mL) at room temperature and the reaction mixture was heated to 70° C. After 16 h, the reaction mixture was allowed to cool to room temperature and was purified by preparatory HPLC (5-100% MeCN/H₂O, 0.1% trifluoroacetic acid modifier) to afford intermediate 77 (20.2 mg, 56%) as an orange oil.
LCMS (ESI) m/z 313.13 [M+H]⁺, t_R=1.49 min.

Example 76: Preparation of Intermediate 78

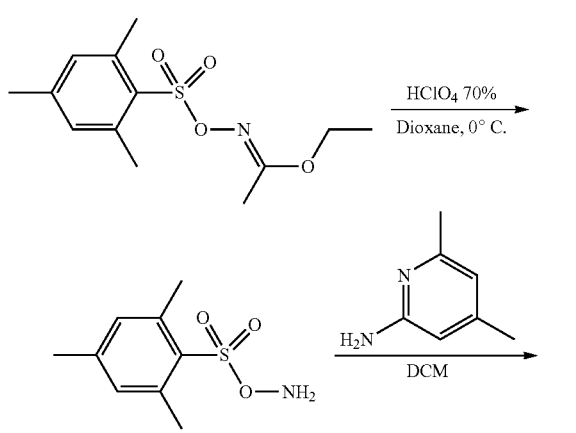

Ethyl O-Mesityl sulfonyl acetohydroxanate (1 g, 3.5 mmol) and dioxane (3 mL) were mixed under argon. The suspension was cooled to 0° C. and then treated with HClO₄ (70% aqueous solution, 0.39 mL). After stirring at 0° C. for 30 minutes, ice-water (7 mL) was added to the reaction mixture. The white precipitate formed was filtered and washed with water, transferred to a round bottom flask while wet, and immediately dissolved in DCM (30 mL). Trace amount of water was removed via separatory funnel and the organic layer was dried over MgSO₄ and filtered. To the above DCM solution was then added a solution of 6-amino-2,4-lutidine in DCM (2 mL) slowly at 0° C. The reaction mixture was then stirred at room temperature for 1 hour. To the reaction mixture was added tert-butyl methyl ether (5 mL). The white precipitate was filtered and washed with DCM/tert-butyl methyl ether (1/1, 40 mL) and dried in vacuo to yield intermediate 78 (0.68 g, 58%).
LCMS m/z [M+H]⁺ C₇H₁₂N₃ requires: 138.19. Found 138.12.
HPLC Tr (min), purity %: 0.39, 95%

Example 77: Preparation of Intermediate 79

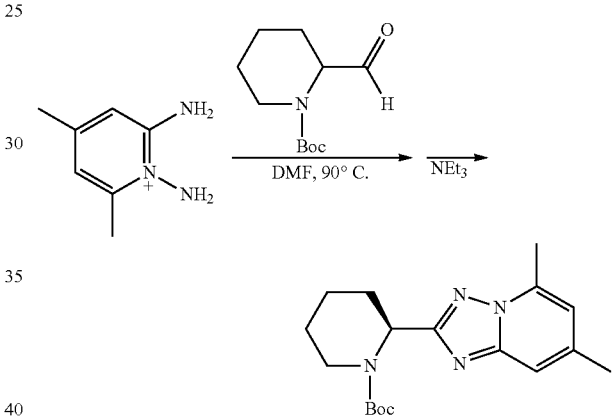

Intermediate 78 (100 mg, 0.3 mmol) and (S)-2-formyl-piperidine-1-carboxylic acid tert-butyl ester (128 mg, 1.2 mmol) were dissolved in DMF (2 mL). The reaction was heated overnight at 90° C. and then triethylamine (0.17 mL, 1.2 mmol) was added. After 1 h, the reaction was diluted with ethyl acetate (20 mL) and washed with brine (3×20 mL). Organic phase was evaporated under vacuum and the residue was purified with silica gel column chromatography (0-100% ethyl acetate in hexanes) to provide intermediate 79 (16 mg, 11%).
LCMS m/z [M+H]⁺ C₁₈H₂₆N₄O₂ requires: 330.42. Found 330.97
HPLC Tr (min), purity %: 2.40, 98%

Example 78: Preparation of Intermediate 80

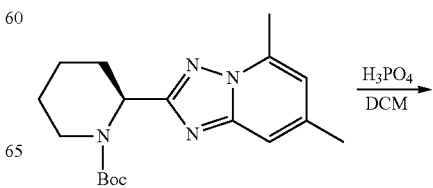

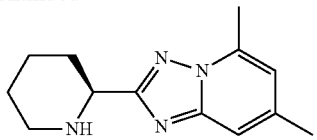

A solution of 85% phosphoric acid in water (0.010 mL) was added to a solution of intermediate 79 (16 mg, 0.05 mmol) in DCM (0.2 mL). After stirring at room temperature for 10 minutes, the reaction mixture was evaporated under reduced pressure and the residue was purified using prep HPLC (0-100% acetonitrile in water) to provide intermediate 80 (9.6 mg, 86%).

LCMS m/z [M+H]$^+$ C$_{13}$H$_{18}$N$_4$ requires: 231.31. Found 231.08.

HPLC Tr (min), purity %: 1.30, 98%

Example 79: Preparation of Intermediate 81

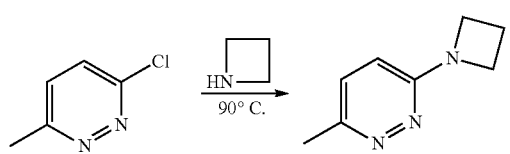

A mixture of 3chloro-6-methylpyridazine (1 g, 7.8 mmol) dissolved in azetidine (4.5 g, 78 mmol) was heated at 90° C. overnight. The reaction mixture was then evaporated under reduced pressure and the residue was purified using silica gel column chromatography (0-10% methanol in dichloromethane) to provide intermediate 81 (980 mg, 84%).

LCMS m/z [M+H]$^+$ C$_8$H$_{11}$N$_3$ requires: 149.19. Found 149.08

HPLC Tr (min), purity %: 1.80, 98%

Example 80: Preparation of Intermediate 82

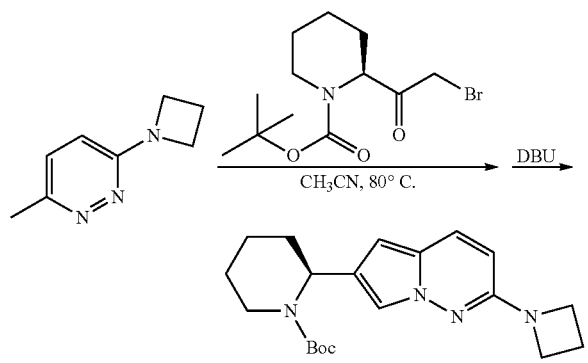

Intermediate 81 (387 mg, 2.6 mmol) and intermediate 58 (200 mg, 0.65 mmol) were dissolved in CH$_3$CN (2 mL). The reaction was heated overnight at 90° C. and then 18-diazabicyclo-[5,4,0]undec-7-ene (0.19 mL, 1.3 mmol) was added. After 1 h, the reaction was diluted with ethyl acetate (20 mL) and washed with brine (3×20 mL). The organic phase was evaporated under reduced pressure and the residue was purified with silica gel column chromatography (0-100% ethyl acetate in hexanes) to provide intermediate 82 (14 mg, 4%).

LCMS m/z [M+H]$^+$ C$_{20}$H$_{28}$N$_4$O$_2$ requires: 356.46. Found 356.94.

HPLC Tr (min), purity %: 2.64, 98%

Example 81: Preparation of Intermediate 83

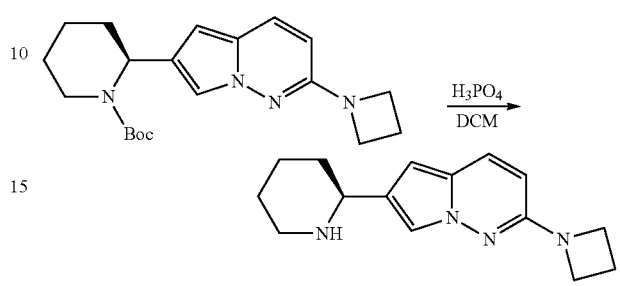

Intermediate 82 (14 mg, 0.04 mmol) was dissolved in DCM (0.2 mL) and a solution of 85% phosphoric acid in water (0.010 mL) was added. After stirring at room temperature for 10 minutes, the reaction mixture was quenched with NaHCO$_3$ and extracted with EtOAc. The organic phase was evaporated under reduced pressure and the residue was purified using prep HPLC (0-100% acetonitrile in water) to provide intermediate 83 (10 mg, 100%).

LCMS m/z [M+H]$^+$ C$_{15}$H$_{20}$N$_4$ requires: 257.35. Found 257.13

HPLC Tr (min), purity %: 1.59, 98%.

Example 82: Preparation of Intermediate 84

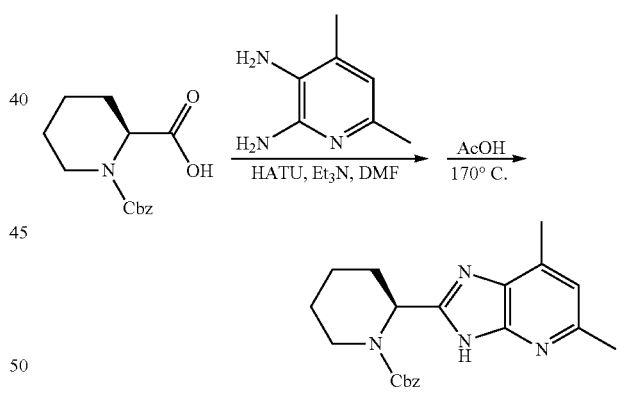

(S)-(−)-1-(carbobenzyloxy)-2-piperidinecarboxylic acid (500 mg, 1.9 mmol) and HATU (1.16 g, 3 mmol) were dissolved in anhydrous DMF (1 mL). After activation for 1 hour, 2,3-diamino-4,6-dimethylpyridine (253 mg, 1.9 mmol) and triethylamine (0.53 mL, 3.80 mmol) were added. The reaction mixture was stirred under nitrogen for 2 hours. The solvents were removed under reduced pressure and the residue was treated with acetic acid (2.5 mL) and heated at 170° C. The solvent was evaporated under reduced pressure and the residue was purified via silica gel column chromatography (0-100% ethyl acetate in hexanes) to provide intermediate 84. (Yield 111 mg, 16%).

LCMS m/z [M+H]$^+$ C$_{21}$H$_{24}$N$_4$O$_2$ requires: 365.19. Found 365.12

HPLC Tr (min), purity %: 2.47, 98%.

Example 83: Preparation of Intermediate 85

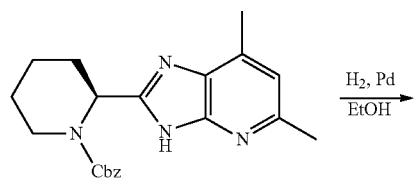

Intermediate 84 (43 mg, 0.118 mmol) was dissolved in EtOH (5 mL) under argon. To the solution was added Pd on carbon (40 mg) and the reaction mixture was stirred under an atmosphere of H₂ at room temperature overnight. The mixture was filtered and the filtrate was concentrated under reduced pressure. The remaining residue was purified with prep HPLC (0-100% acetonitrile in water) to provide intermediate 85 (27 mg, 87%).

LCMS m/z [M+H]⁺ $C_{13}H_{18}N_4$ requires: 231.15. Found 231.07

HPLC Tr (min), purity %: 0.79, 98%

Example 84: Preparation of Intermediate 86

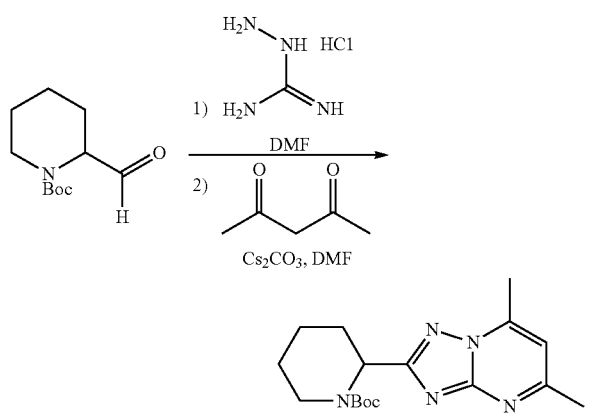

To a solution of hydrazinecarboximidamide hydrochloride (320 mg, 2.81 mmol) in dimethylformamide (14 mL) was added tert-butyl-2-formylpiperidine-1-carboxylate (600 mg, 2.81 mmol) at room temperature open to atmosphere. The resulting mixture was heated to 90° C. and stirred vigorously open to atmosphere. After 16 hours, the reaction mixture was allowed to cool to room temperature and was stirred vigorously open to atmosphere. After 2 days, acetylacetone (290 µL, 2.81 mmol) and cesium carbonate (915 mg, 2.81 mmol) were added and the reaction mixture was heated to 90° C. open to atmosphere. After 6 hours, the reaction was allowed to cool to room temperature and was partitioned between ethyl acetate (250 mL) and water (250 mL). The phases were separated, and the organic layer was washed with saturated sodium chloride solution (3×100 mL). The organic layer was dried over Na₂SO₄, and was concentrated under reduced pressure. The crude residue was purified via SiO₂ column chromatography (12 g SiO₂ Combiflash HP Gold Column, 0-100% ethyl acetate/hexanes) to afford intermediate 86 (67.6 mg, 7%) as a yellow oil.

LCMS (ESI) m/z 332.14 [M–H]⁻, $t_R$=2.38 min.
$R_f$=0.45 (ethyl acetate).

Example 85: Preparation of Intermediate 87

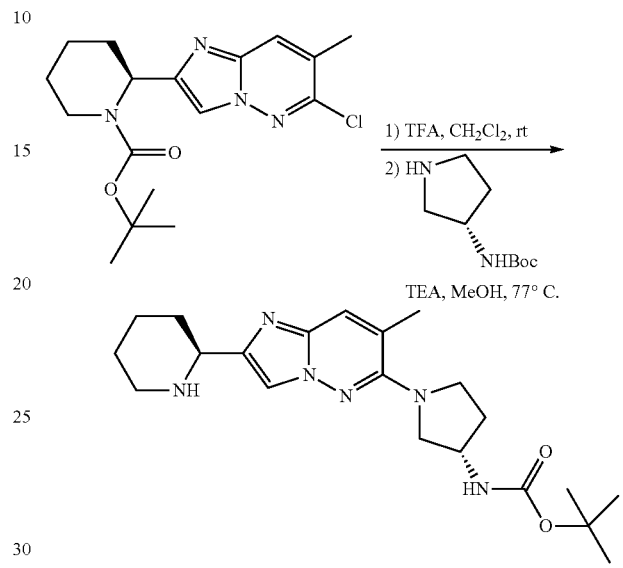

Trifluoroacetic acid (1 mL, 12.9 mmol) was added to a solution of intermediate 66 (131 mg, 0.375 mmol) in 20 mL of dichloromethane at room temperature. After stirring overnight, the reaction mixture was concentrated under reduced pressure and dried in-vacuo for two hours. The resulting film was dissolved in 4 mL of methanol and (S)-tert-butyl pyrrolidin-3-ylcarbamate (710 mg, 3.82 mmol) and triethylamine (0.52 mL, 3.7 mmol) were added. Mixture was heated at 77° C. overnight. LC/MS indicated approximately 25% conversion to desired product. Further (S)-tert-butyl pyrrolidin-3-ylcarbamate (1.1 g, 5.9 mmol) was added and mixture stirred at 77° C. for 72 hours. After cooling to room temperature, the resulting residue was purified via silica gel column chromatography (0-10% methanol in dichloromethane) to yield intermediate 87 (135 mg, 90%) as an off-white film.

LCMS m/z [M+H]⁺ $C_{21}H_{32}N_6O_2$ requires: 401.26. Found 401.24.

Example 86: Preparation of Intermediate 88

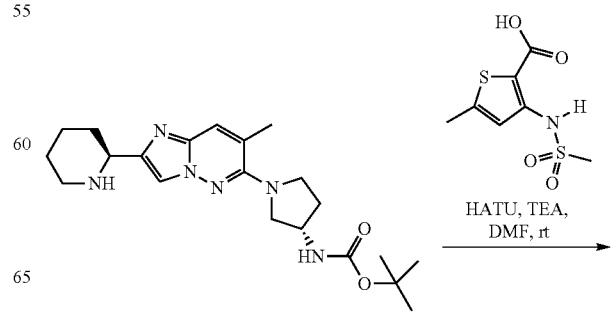

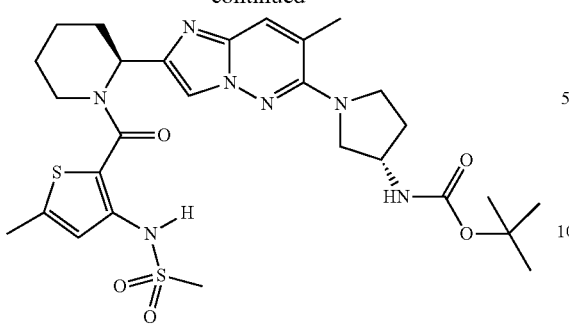

HATU (48 mg, 0.126 mmol) was added to a solution of 5-methyl-3-(methylsulfonamido)thiophene-2-carboxylic acid (24 mg, 0.102 mmol) in 2 mL of anhydrous DMF at room temperature. After 90 minutes, a 0.5 mL acetonitrile solution of intermediate 87 (36 mg, 0.09 mmol) was added, followed by triethylamine (0.030 mL, 0.217 mmol). After stirring overnight, the reaction mixture was poured into a 1:1 solution of water and brine and extracted with ethyl acetate three times. The combined organics were washed with a 1:1 solution of water and brine, dried (MgSO$_4$), filtered and concentrated under reduced pressure. The residue was purified via silica gel column chromatography (5-100% ethyl acetate in hexanes) to yield intermediate 88 (22 mg, 40%) as a clear film.

LCMS m/z [M+H]$^+$ C$_{28}$H$_{39}$N$_7$O$_5$S requires: 618.25. Found 618.28.

Example 87: Preparation of Intermediate 89

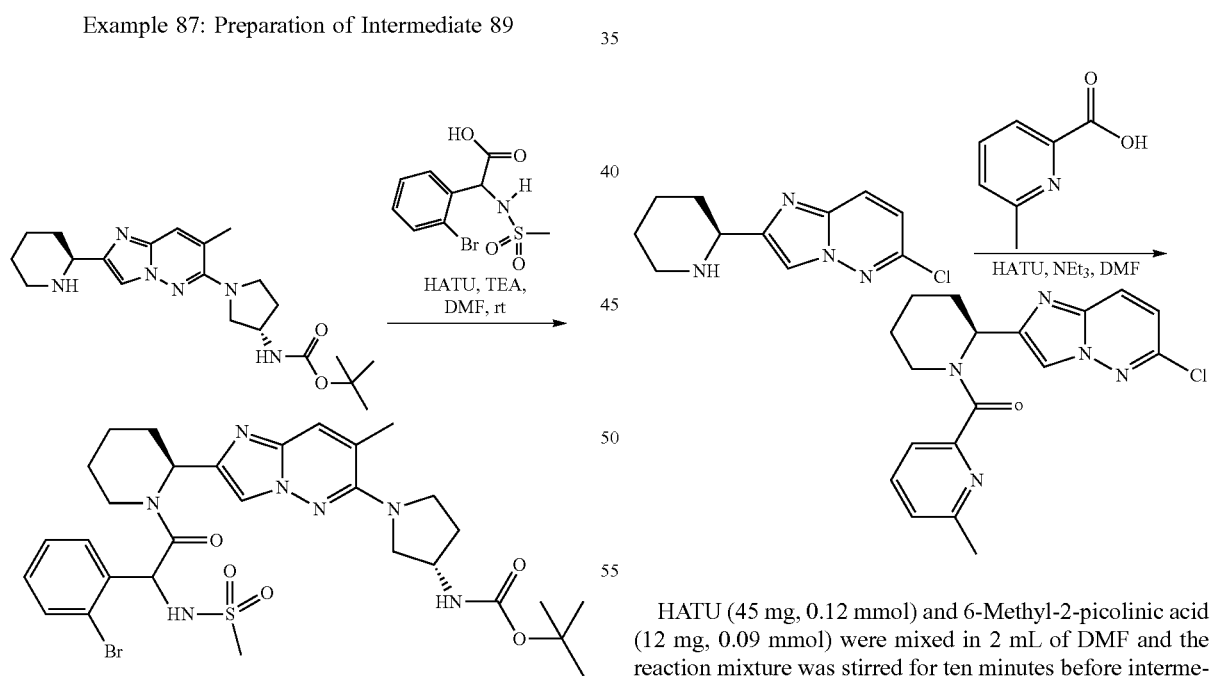

Following the procedure of intermediate 88, beginning with intermediate 87 (38 mg, 0.095 mmol) and intermediate 95 (44 mg, 0.143 mmol), intermediate 89 (12 mg, 18%) was recovered a clear film.

LCMS m/z [M+H]$^+$ C$_{30}$H$_{40}$BrN$_7$O$_5$S requires: 690.20. Found 690.21.

Example 88: Preparation of Intermediate 90

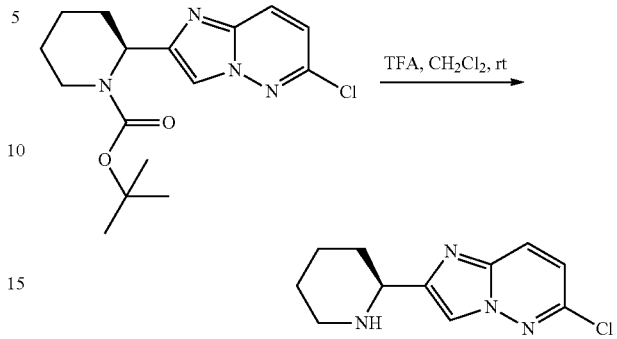

Trifluoroacetic acid (0.070 mL, 0.831 mmol) was added to a solution of intermediate 64 (110 mg, 0.33 mmol) in 5 mL of CH$_2$Cl$_2$. After stirring at room temperature overnight, the reaction mixture was concentrated under reduced pressure and the residue was purified by prep HPLC (15-100% Acetonitrile (with 0.1% trifluoroacetic acid) in water (with 0.1% trifluoroacetic acid)) to yield intermediate 90 (114 mg, 100%) as a solid, trifluoroacetic acid salt, after lyophilization.

LCMS m/z [M+H]$^+$ C$_{11}$H$_{13}$ClN$_4$ requires: 237.08. Found 237.10.

HPLC Tr (min), purity %: 1.36, 95%

Example 89: Preparation of Intermediate 91

HATU (45 mg, 0.12 mmol) and 6-Methyl-2-picolinic acid (12 mg, 0.09 mmol) were mixed in 2 mL of DMF and the reaction mixture was stirred for ten minutes before intermediate 90 (20 mg, 0.06 mmol) and triethylamine (33 µL, 0.24 mmol) were added to the solution. The reaction mixture was stirred for one hour at room temperature, was diluted with CH$_3$CN/H$_2$O (2/2 mL), and was then purified by prep HPLC (15-100% Acetonitrile (with 0.1% trifluoroacetic acid) in water (with 0.1% trifluoroacetic acid)) to yield intermediate 91 (12 mg, 63%) as a solid, trifluoroacetic acid salt, after lyophilization.

LCMS m/z [M+H]+ C18H18ClN5O requires: 356.12. Found 356.14.

HPLC Tr (min), purity %: 1.89, 98%

Example 90: Preparation of Intermediate 92

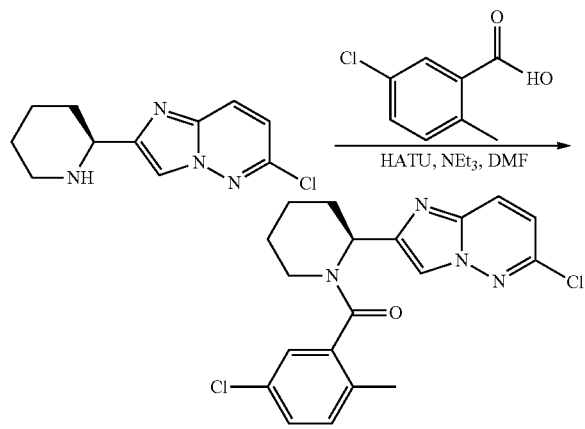

HATU (45 mg, 0.12 mmol) and 2-methyl-5-chlorobenzoic acid (16 mg, 0.09 mmol) were mixed in 2 mL of DMF and the reaction mixture was stirred for ten minutes before intermediate 90 (20 mg, 0.06 mmol) and triethylamine (33 μL, 0.24 mmol) were added to the solution. The reaction mixture was stirred for 1 h at room temperature, was diluted with CH3CN/H2O (2/2 mL), and was then purified by prep HPLC (15-100% acetonitrile (with 0.1% trifluoroacetic acid) in water (with 0.1% trifluoroacetic acid)) to yield intermediate 92 (14 mg, 64%) as a solid, trifluoroacetic acid salt, after lyophilization.

LCMS m/z [M+H]+ C19H18Cl2N4O requires: 389.09. Found 389.13.

HPLC Tr (min), purity %: 2.34, 98%

Example 91: Preparation of Intermediate 93

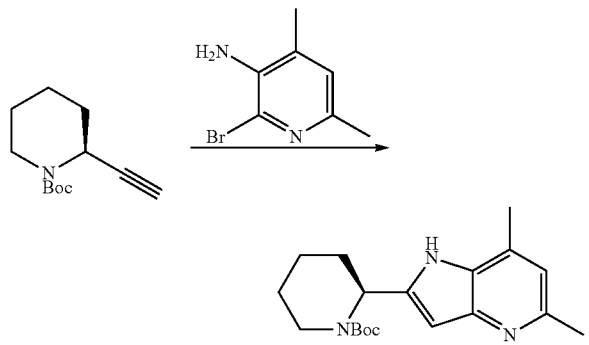

A solution of (S)-tert-butyl 2-ethynylpiperidine-1-carboxylate (Anichem LLC, North Brunswick, N.J., USA) (100 mg, 0.48 mmol), 2-bromo-4,6-dimethylpyridin-3-amine (96 mg, 0.48 mmol), CuI (4.3 mg, 0.0225 mmol) and Pd(Cl)2(PPh3)2 (16 mg, 0.025 mmol) in 5 mL of triethylamine was stirred under nitrogen at 0° C. for 5 minutes followed by heating to 90° C. for 1 hour. After cooling to room temperature, the volatiles were removed under reduce pressure and the crude product was purified via silica gel column chromatography (0-60% ethyl acetate in hexanes) to afford intermediate 93 (78 mg, 49%) as a colorless oil.

LCMS m/z [M+H]+ 330.02.

HPLC Tr (min), purity %: 2.41, 95%

Example 92: Preparation of Intermediate 94

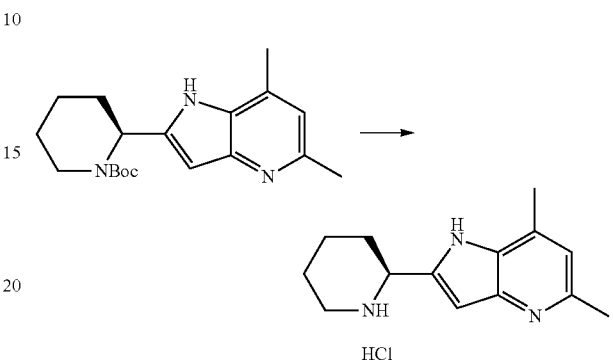

A solution of hydrogen chloride in dioxane (4N, 8 mL, 32 mmol) was added to a mixture of intermediate 93 (429 mg, 1.3 mmol) in 10 mL of dioxane. After stirring for 1 hour, the volatiles were removed under reduced pressure and the resulting residue was freeze-dried from acetonitrile and water to afford intermediate 94 (366 mg, >100%) as an off-white powder, hydrochloric acid salt.

LCMS m/z [M+H]+ 229.97

HPLC Tr (min), purity %: 1.57, 95%

Example 93: Preparation of Intermediate 95

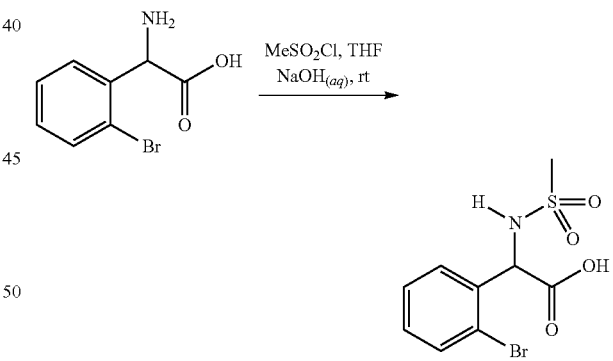

Methanesulfonyl chloride (0.7 mL, 9.14 mmol) was added slowly to a mixture of 2-amino-2-(2-bromophenyl)acetic acid (660 mg, 2.87 mmol) in 8 mL of THF and 7 mL of aqueous 1N sodium hydroxide (7 mmol). The mixture was stirred vigorously at room temperature overnight and was then poured into 5 mL of water. The material was extracted three times with ethyl acetate and combined organics were washed with brine, dried (MgSO4), filtered, and concentrated under reduced pressure to yield intermediate 95 (742 mg, 84%) as a white solid.

$^1$H-NMR (DMSO, 400 MHz): δ 13.2 (s, 1H), 8.24 (d, J=8.8 Hz, 1H), 7.64 (m, 1H), 7.44 (m, 1H), 7.39 (m, 1H), 7.27 (m, 1H), 5.42 (d, J=8.8 Hz, 1H), 2.84 (s, 3H).

Example 94: Preparation of Intermediate 96

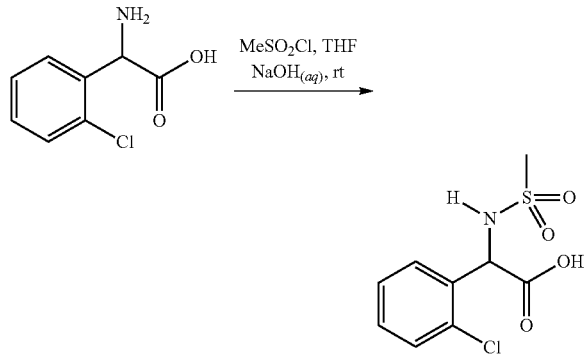

Following the procedure of intermediate 95, beginning with 2-amino-2-(2-chlorophenyl)acetic acid (535 mg, 2.88 mmol), intermediate 96 (397 mg, 52%) was synthesized as a white solid.

$^1$H-NMR (DMSO, 400 MHz): δ 13.2 (s, 1H), 8.21 (d, J=8.8 Hz, 1H), 7.51-7.25 (m, 4H), 5.42 (d, J=8.8 Hz, 1H), 2.84 (s, 3H).

Example 95: Preparation of Intermediate 97

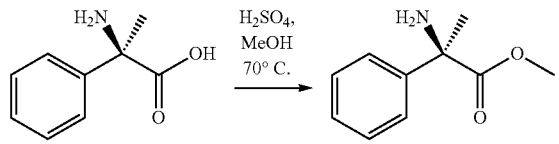

A solution of (R)-2-amino-2-phenylpropanoic acid (304 mg, 1.84 mmol) and 0.7 mL of concentrated H$_2$SO$_4$ in 6.5 mL of anhydrous methanol was heated overnight. After cooling to room temperature, the methanol was concentrated under reduced pressure. The residue was taken up in 40 mL of water and added to a separatory funnel. Solid sodium carbonate was added slowly until gas evolution ceased (pH 9-10). The aqueous layer was extracted with ethyl acetate (3×50 mL). The combined organic layers were washed with 100 mL sat. NaHCO$_{3(aq)}$ and 100 mL of Brine, separated, dried (MgSO$_4$), filtered, and concentrated under reduced pressure to yield intermediate 97 (225 mg, 68%) as an oily residue that was used in the next step without further purification.

$^1$H-NMR (DMSO, 400 MHz): δ 7.44 (m, 2H), 7.30 (m, 2H), 7.22 (m, 1H), 3.58 (s, 3H), 2.36 (s, 2H), 1.50 (s, 3H)

Example 96: Preparation of Intermediate 98

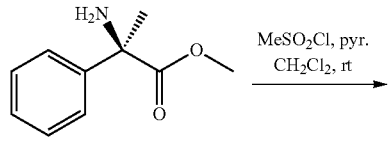

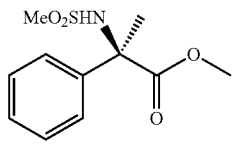

To a solution of intermediate 97 (225 mg, 1.25 mmol) and pyridine (0.30 mL, 3.75 mmol) in 4 mL of anhydrous CH$_2$CL$_2$, was added slowly methane sulfonylchloride (0.15 mL, 1.91 mmol). After stirring overnight, the reaction mixture was quenched with 30 mL of 1N HCl$_{(aq)}$. The aqueous mixture was extracted with ethyl acetate (3×30 mL) and combined organic layers were washed with 1N HCl$_{(aq)}$ and then brine. The organics were dried (MgSO$_4$), filtered, and concentrated under reduced pressure to yield intermediate 98 (312 mg, 97%) as a yellow-green oily residue that was used in the next step without further purification.

LCMS m/z [M+H]$^+$ C$_{11}$H$_{15}$NO$_4$S requires: 258.08. Found 258.31.

Example 97: Preparation of Intermediate 99

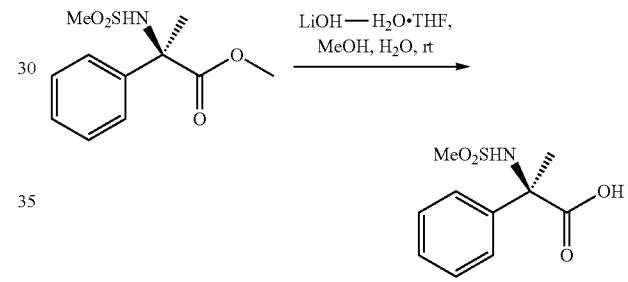

Lithium hydroxide monohydrate (507 mg, 12.1 mmol) was added to a solution of intermediate 98 (310 mg, 1.2 mmol) in 15 mL of 1:1:1 THF:MeOH:H$_2$O at room temperature. The reaction mixture was stirred overnight and then was acidified with 40 mL of 1N HCl$_{(aq)}$ and extracted with ethyl acetate (3×50 mL). The combined organic layers were washed 100 mL of brine, separated, dried (MgSO$_4$), filtered, and concentrated under reduced pressure to yield intermediate 99 as an oily residue (285 mg, 98%).

$^1$H-NMR (DMSO, 400 MHz): δ 13.1 (s, 1H), 7.50 (m, 2H), 7.39 (m, 2H), 7.31 (m, 1H), 2.80 (s, 3H), 1.86 (s, 3H).

Example 98: Preparation of Intermediate 100

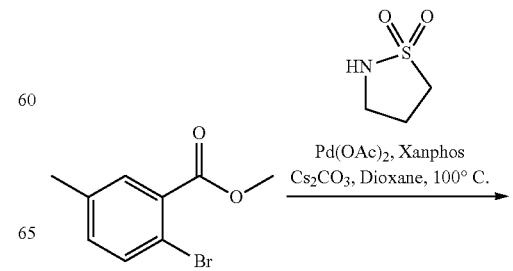

-continued

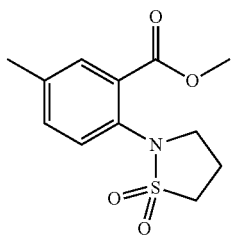

To an oven dried 50 mL round-bottom flask, methyl 2-bromo-5-methylbenzoate (352 mg, 1.54 mmol), sultam (236 mg, 1.95 mmol), cesium carbonate (732 mg, 2.25 mmol), palladium acetate (40.4 mg, 0.18 mmol), and Xanphos (136 mg, 0.235 mmol) were added and flask was placed under argon. The reagents were suspended in 8 mL of anhydrous dioxane and mixture was heated at 100° C. overnight. After cooling to room temperature, the reaction mixture was filtered, washing with ethyl acetate. The combined filtrate was concentrated under reduced pressure and resulting film was purified by silica gel column chromatography (25-100% ethyl Acetate in hexanes) to yield intermediate 100 (322 mg, 78%) as a yellow off-white solid.

$^1$H-NMR (DMSO, 400 MHz): δ 7.75 (d, 1H), 7.44 (m, 1H), 7.35 (m, 1H), 3.89 (s, 3H), 3.81 (t, 2H), 3.28 (t, 2H), 2.55 (m, 2H), 2.39 (s, 3H).

LCMS m/z [M+H]$^+$ $C_{12}H_{15}NO_4S$ requires: 270.07. Found 270.12.

Example 99: Preparation of Intermediate 101

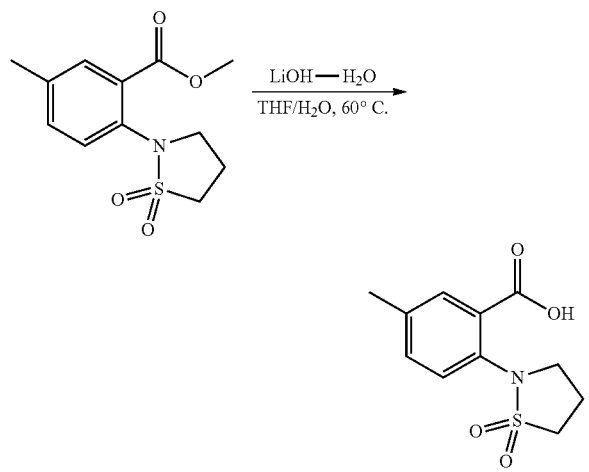

Lithium hydroxide monohydrate (496 mg, 11.8 mmol) was added to a solution of intermediate 100 (316 mg, 1.17 mmol) in 22 mL of THF and 12 mL of water at room temperature. The reaction mixture was heated at 60° C. for two hours. After cooling to room temperature, the reaction mixture was acidified with 40 mL of 1N HCl$_{(aq)}$ and extracted with ethyl acetate (3×30 mL). The combined organic layers were washed 50 mL of brine, separated, dried (MgSO$_4$), filtered, and concentrated under reduced pressure to yield intermediate 101 as an off-white solid (293 mg, 98%).

$^1$H-NMR (DMSO, 400 MHz): δ 12.9 (s, 1H), 7.57 (d, J=1.6 Hz, 1H), 7.41-7.34 (m, 2H), 3.66 (t, J=6.8 Hz, 2H), 3.28 (m, 2H), 2.37 (m, 2H), 2.33 (s, 3H).

LCMS m/z [M+H]$^-$ $C_{11}H_{13}NO_4S$ requires: 254.06. Found 254.18.

Example 100: Preparation of Intermediate 102

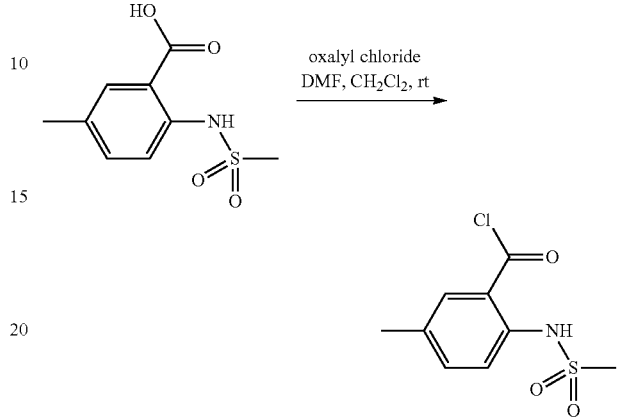

DMF (0.070 mL, 0.908 mmol) was added slowly to a suspension of 5-methyl-2-(methylsulfonamido)benzoic acid (1.01 g, 4.59 mmol) and oxalyl chloride (1.6 mL, 18.3 mmol) in 11 mL of anhydrous dichloromethane. After 3 hours, the reaction mixture was concentrated and dried in-vacuo to yield intermediate 102 as a yellow solid (987 mg, 90%) which was used in the next step without further purification.

$^1$H-NMR (CDCl$_3$, 400 MHz): δ 10.2 (s, 1H), 7.92 (s, 1H), 7.64 (m, 1H), 7.39 (m, 1H), 3.03 (s, 3H), 2.35 (s, 3H).

Example 101: Preparation of Intermediate 103

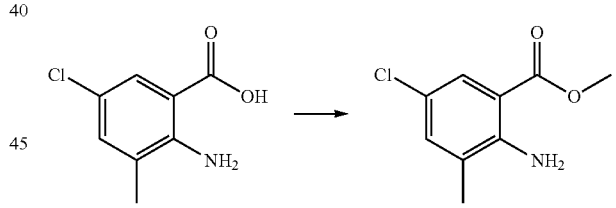

A solution of 2-amino-5-chloro-3-methylbenzoic acid (928 mg, 4.99 mmol) and 2.0 mL of concentrated H$_2$SO$_4$ in 15 mL of anhydrous methanol was heated for 66 hours. After cooling to room temperature, the methanol was concentrated under reduced pressure. The residue was taken up in 50 mL of water and added to a separatory funnel. Solid sodium carbonate was added slowly until gas evolution ceased (pH 9-10). The aqueous layer was extracted with ethyl acetate (3×50 mL). The combined organic layers were washed with 100 mL sat. NaHCO$_{3(aq)}$ and 100 mL of brine, separated, dried (MgSO$_4$), filtered, and concentrated under reduced pressure to yield intermediate 103 (817 mg, 83%) as a brown solid, which was used without further purification.

$^1$H-NMR (CDCl$_3$, 300 MHz): δ 7.75 (d, J=2.7 Hz, 1H), 7.17 (d, J=2.7 Hz, 1H), 5.83 (br s, 2H), 3.88 (s, 3H), 2.16 (s, 3H)

LCMS m/z [M+H]$^+$ $C_9H_{10}ClNO_2$ requires: 200.04. Found 200.10.

Example 102: Preparation of Intermediate 104

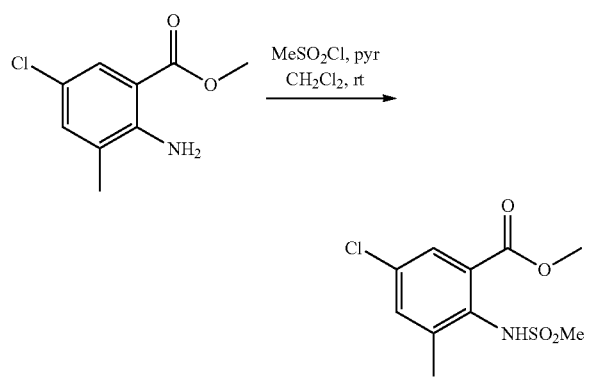

To a solution of intermediate 103 (392 mg, 1.97 mmol) and pyridine (0.45 mL, 5.68 mmol) in 9 mL of anhydrous CH$_2$CL$_2$, was added slowly methane sulfonylchloride (0.46 mL, 5.66 mmol). After stirring overnight, an additional 0.7 mL of pyridine and methane sulfonylchloride were each added and the reaction mixture stirred for two hour. The reaction mixture was then quenched with 30 mL of 1N HCl$_{(aq)}$. The aqueous mixture was extracted with ethyl acetate (3×40 mL) and the combined organic layers were washed with 1N HCl$_{(aq)}$ and then brine. The organics were dried (MgSO$_4$), filtered, and concentrated under reduced pressure to yield a light yellow film. Purification of the residue by silica gel column chromatography (0-50% ethyl Acetate in hexanes) yielded intermediate 104 (330, 60%) as a light yellow solid.

$^1$H-NMR (CDCl$_3$, 300 MHz): δ 8.47 (s, 1H), 7.86 (d, J=2.4 Hz, 1H), 7.50 (d, J=2.4 Hz, 1H), 3.96 (s, 3H), 2.90 (s, 3H), 2.53 (s, 3H)

LCMS m/z [M+H]$^+$ C$_{10}$H$_{12}$ClNO$_4$S requires: 278.03. Found 278.08.

Example 103: Preparation of Intermediate 105

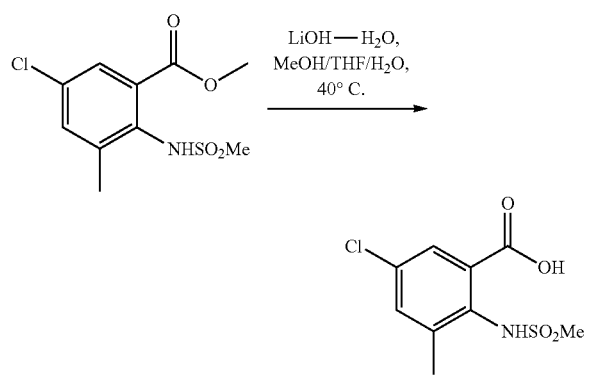

Lithium hydroxide monohydrate (228 mg, 5.43 mmol) was added to a solution of intermediate 104 (120 mg, 0.433 mmol) in 3 mL of 1:1:1 THF:MeOH:H$_2$O at room temperature. The reaction mixture was heated at 50° C. for four hours. After cooling to room temperature, the reaction mixture was acidified with 20 mL of 1N HCl$_{(aq)}$ and extracted with ethyl acetate (3×20 mL). The combined organic layers were washed 50 mL of brine, separated, dried (MgSO$_4$), filtered, and concentrated under reduced pressure to yield intermediate 105 as a white solid (114 mg, 100%).

$^1$H-NMR (DMSO, 300 MHz): δ 9.2 (s, 1H), 7.59 (m, 2H), 2.96 (s, 3H), 2.37 (s, 3H)

LCMS m/z [M+H]$^-$ C$_9$H$_{13}$ClNO$_4$S requires: 264.00. Found 264.09.

Example 104: Preparation of Intermediate 106

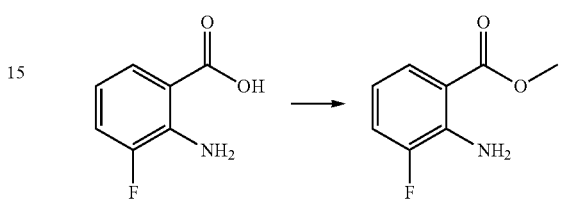

A solution of 2-amino-3-fluorobenzoic acid (559 mg, 3.62 mmol) and 1.7 mL of concentrated H$_2$SO$_4$ in 11 mL of anhydrous methanol was heated for 66 hours. After cooling to room temperature, methanol was concentrated under reduced pressure. The residue was taken up in 30 mL of water and added to a separatory funnel. Solid sodium carbonate was added slowly until gas evolution ceased (pH 9-10). The aqueous layer was extracted with ethyl acetate (3×40 mL). The combined organic layers were washed with 100 mL sat. NaHCO$_{3(aq)}$ and 100 mL of brine, separated, dried (MgSO$_4$), filtered, and concentrated under reduced pressure. Column chromatography (5% ethyl acetate in hexanes) yielded intermediate 106 (491 mg, 80%) as a white solid.

$^1$H-NMR (CDCl$_3$, 300 MHz): δ 7.66-7.63 (m, 1H), 7.15-7.08 (m, 1H), 6.60-6.55 (m, 1H), 5.40 (br s, 2H), 3.89 (s, 3H), LCMS m/z [M+H]$^+$ C$_8$H$_8$FNO$_2$ requires: 170.05. Found 170.10.

Example 105: Preparation of Intermediate 107

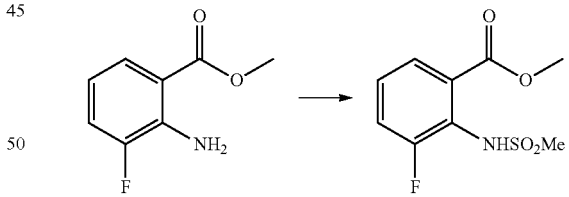

To a mixture intermediate 106 (334 mg, 1.97 mmol) and pyridine (0.41 mL, 4.95 mmol) in 5.5 mL of dichloromethane at 0° C., was added slowly methanesulfonyl chloride (0.40 mL, 4.95 mmol). The mixture was warmed to room temperature and stirred overnight. HPLC indicated ~48% conversion to desired product. Pyridine (0.55 mL) and 0.50 mL of methanesulfonyl chloride (approximately 6.8 mmol each) was then added at room temperature. After a total of 40 hours, reaction mixture was quenched with 10 mL of 1N HCl. After 5 minutes of stirring, mixture was poured into 20 mL of water. The aqueous layer was extracted with ethyl acetate (3×30 mL). The combined organic layers were washed with 100 mL of 1N HCl$_{(aq)}$ and 100 mL brine, separated, dried (MgSO$_4$), filtered, and concentrated under reduced pressure. Column chromatography (15-50% ethyl acetate in hexanes) yielded intermediate 107 (360 mg, 74%) as a white solid.

¹H-NMR (CDCl₃, 300 MHz): δ 9.79 (s, 1H), 7.83 (d, J=7.8 Hz, 1H), 7.35 (m, 1H), 7.19-7.17 (m, 1H), 3.96 (s, 3H), 7.21-3.35 (s, 3H)

LCMS m/z [M+H]⁺ C₉H₁₀FNO₄S requires: 248.03. Found 248.08.

Example 106: Preparation of Intermediate 108

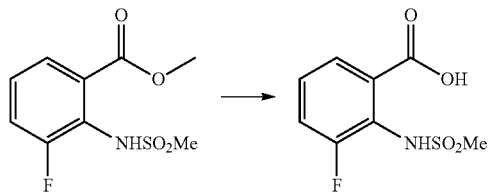

A solution of NaOH in water (2.85 M, 3 mL, 8.55 mmol) was added to a solution of intermediate 107 in 8.5 mL of THF with strong stirring. The reaction mixture was stirred at room temperature overnight. The mixture was then acidified with 15 mL of 1N HCl and extracted with ethyl acetate (3×30 mL). The combined organic layers were washed 80 mL of brine, separated, dried (MgSO₄), filtered, and concentrated under reduced pressure to yield intermediate 108 as a white solid (284 mg, 91%).

¹H-NMR (DMSO, 300 MHz): δ 9.77 (s, 1H), 7.70-7.68 (m, 1H), 7.57-7.50 (m, 1H), 7.38-7.33 (m, 1H), 3.15 (s, 3H)

LCMS m/z [M+H]⁺ C₉H₁₀FNO₄S requires: 234.02. Found 234.09.

Example 107: Preparation of Intermediate 109

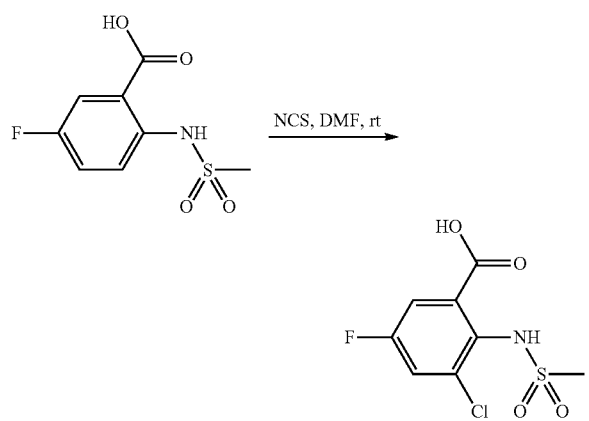

N-chlorosuccinimide (528 mg, 3.95 mmol) was added to a solution of 5-fluoro-2-(methylsulfonamido)benzoic acid (705 mg, 3.03 mmol) in 9 mL of anhydrous DMF. After stirring overnight, the reaction mixture was poured into 100 mL of water and 50 mL of brine and extracted with ethyl acetate (3×100 mL). The combined organic layers were washed with 300 mL of 1:1 water:brine, dried (MgSO₄), filtered, and concentrated under reduced pressure to yield intermediate 109 (746 mg, 93%).

¹H-NMR (DMSO, 400 MHz): δ 9.5 (s, 1H), 7.76 (dd, $J_{HF}$=8 Hz, $J_{HH}$=3 Hz, 1H), 7.52 (dd, $J_{HF}$=8 Hz, $J_{HH}$=3 Hz, 1H), 3.01 (s, 3H)

LCMS m/z [M+H]⁻ C₈H₇ClFNO₄S requires: 265.98. Found 265.09.

Example 108: Preparation of Intermediate 112

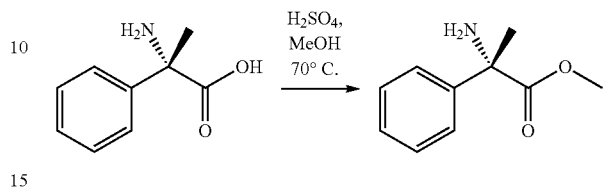

A solution of (S)-2-amino-2-phenylpropanoic acid (246.2 mg, 1.49 mmol) and 0.6 mL of concentrated H₂SO₄ in 6 mL of anhydrous methanol was heated overnight. After cooling to room temperature, the methanol was concentrated under reduced pressure. The residue was taken up in 20 mL of water and added to a separatory funnel. Solid sodium carbonate was added slowly until gas evolution ceased (pH 9-10). The aqueous layer was extracted with ethyl acetate (3×30 mL). The combined organic layers were washed with 80 mL sat. NaHCO₃(aq) and 80 mL of Brine, separated, dried (MgSO₄), filtered, and concentrated under reduced pressure to yield intermediate 112 (117 mg, 44%) as a yellow-green oily residue.

¹H-NMR (DMSO, 400 MHz): δ 7.44 (m, 2H), 7.32 (m, 2H), 7.24 (m, 1H), 3.59 (s, 3H), 2.37 (s, 2H), 1.51 (s, 3H)

LCMS m/z [M+H]⁺ C₁₀H₁₃NO₂ requires: 180.09. Found 180.19.

Example 109: Preparation of Intermediate 113

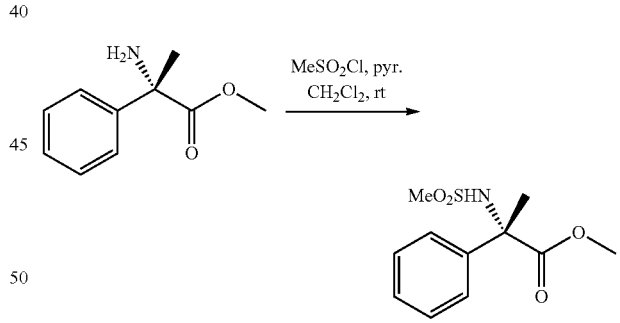

To a solution of intermediate 112 (116 mg, 0.647 mmol) and pyridine (0.16 mL, 1.98 mmol) in 4 mL of anhydrous CH₂CL₂, was added slowly methane sulfonylchloride (0.070 mL, 0.91 mmol). After stirring overnight, the reaction mixture was quenched with 20 mL of 1N HCl(aq). The aqueous mixture was extracted with ethyl acetate (3×20 mL) and combined organic layers were washed with 1N HCl(aq) and then brine. The organics were dried (MgSO₄), filtered, and concentrated under reduced pressure to yield intermediate 113 (312 mg, 97%) as a yellow-green oily residue that was used in the next step without further purification.

LCMS m/z [M+H]⁺ C₁₁H₁₅NO₄S requires: 258.08. Found 258.19.

Example 110: Preparation of Intermediate 114

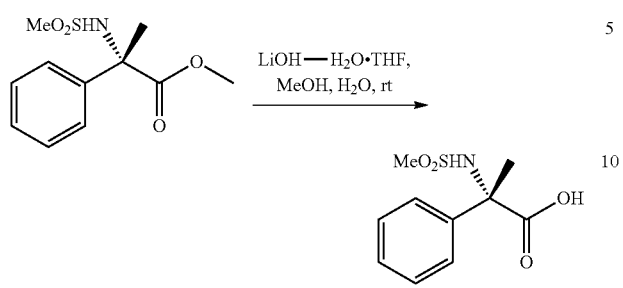

Lithium hydroxide monohydrate (169 mg, 4.02 mmol) was added to a solution of intermediate 113 (102 mg, 0.397 mmol) in 6 mL of 1:1:1 THF:MeOH:H$_2$O at room temperature. The reaction mixture was stirred overnight and then was acidified with 15 mL of 1N HCl$_{(aq)}$ and extracted with ethyl acetate (3×20 mL). The combined organic layers were washed 50 mL of brine, separated, dried (MgSO$_4$), filtered, and concentrated under reduced pressure to yield intermediate 114 as a light green film (93.6 mg, 97%).

LCMS m/z [M+H]$^-$ C$_{10}$H$_{13}$NO$_4$S requires: 242.06. Found 242.10.

Example 111: Preparation of Intermediate 115

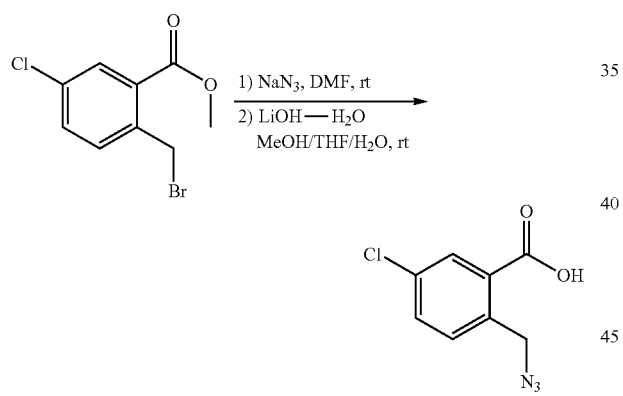

Step 1: Sodium azide (158 mg, 2.43 mmol) was added to a solution of methyl 2-(bromomethyl)-5-chlorobenzoate (518 mg, 1.97 mmol) in 3 mL of DMF at room temperature. After stirring overnight, reaction mixture was quenched with 25 mL of water. The aqueous was extracted with ethyl acetate (3×30 mL) and the combined organics were washed with water (2×40 mL) and 50 mL of brine. The organics were dried (Na$_2$SO$_4$), filtered, and concentrated under reduced pressure to yield methyl 2-(azidomethyl)-5-chlorobenzoate (429 mg, 97%) as an off-white solid, which was used in the next step without further purification.

Step 2: Lithium hydroxide monohydrate (794 mg, 18.9 mmol) was added to a solution of methyl 2-(azidomethyl)-5-chlorobenzoate (426 mg, 1.88 mmol), from the previous step, in 27 mL of 1:1:1 THF:methanol:water at room temperature. After stirring overnight, the reaction mixture was quenched with 20 mL of 2N HCl$_{(aq)}$, and extracted with ethyl acetate (3×30 mL). The combined organics were washed with brine, dried (MgSO$_4$), filtered, and concentrated under reduced pressure to yield intermediate 115 (395 mg, 99%) as a white solid.

$^1$H-NMR (DMSO, 400 MHz): δ 7.88 (m, 1H), 7.70-7.65 (m, 1H), 7.54 (m, 1H), 4.78 (s, 2H).

Example 112: Preparation of Intermediate 116

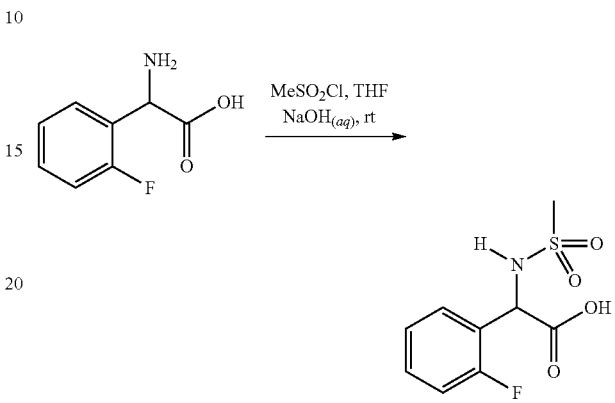

Following the procedure of intermediate 95, beginning with 2-amino-2-(2-fluorophenyl)acetic acid (1.27 g, 7.51 mmol), intermediate 116 (1.33 g, 72%) was synthesized as a yellow solid.

Example 113: Preparation of Intermediate 117

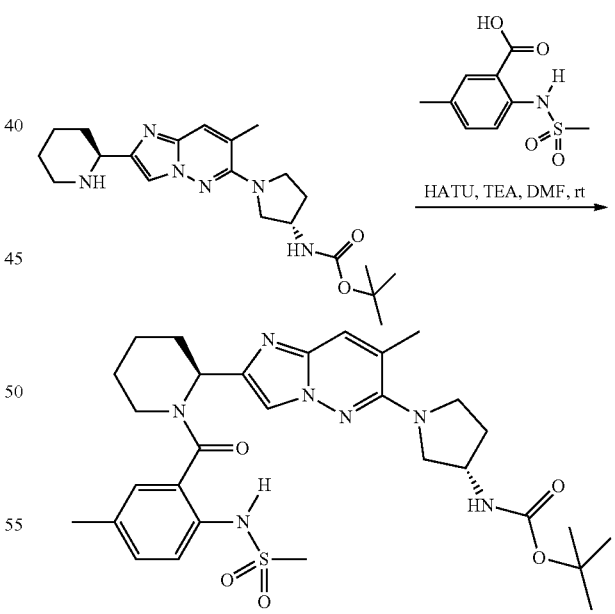

Following the procedure for synthesis of intermediate 88, but beginning with intermediate 87 (53 mg, 0.133 mmol) and 5-methyl-2-(methylsulfonamido)benzoic acid (42 mg, 0.183 mmol), intermediate 117 (31 mg, 38%) was recovered as a clear film.

LCMS m/z [M+H]$^+$ C$_{30}$H$_{41}$N$_7$O$_5$S requires: 612.29. Found 612.31.

Example 114: Preparation of Intermediate 118

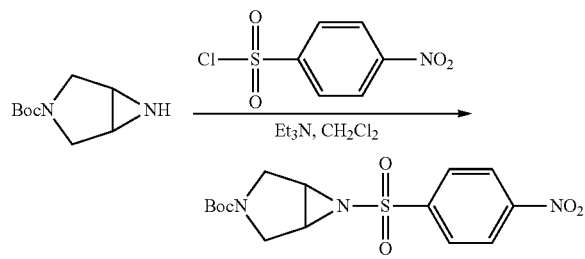

To mixture of tert-butyl 3,6-diazabicyclo[3.1.0]hexane-3-carboxylate (50 mg, 0.271 mmol) and triethylamine (38 μL, 0.271 mmol) in dichloromethane (1.4 ml) was added 4-nitrobenzene-1-sulfonyl chloride (60 mg, 0.271 mol). After 6.5 h, the reaction mixture was purified directly by silica gel chromatography using a gradient of hexanes/ethyl acetate 1:0 to 0:1 to afford intermediate 118 (57 mg, 52%) as a colorless oil.

$^1$H NMR (400 MHz, CDCl$_3$) δ 8.41 (d, J=8.9 Hz, 2H), 8.16 (d, J=8.9 Hz, 2H), 3.76-3.67 (m, 3H), 3.62 (dd, J=5.6, 2.6 Hz, 1H), 3.45-3.37 (m, 1H), 1.41 (s, 9H).

Example 115: Preparation of Intermediate 119

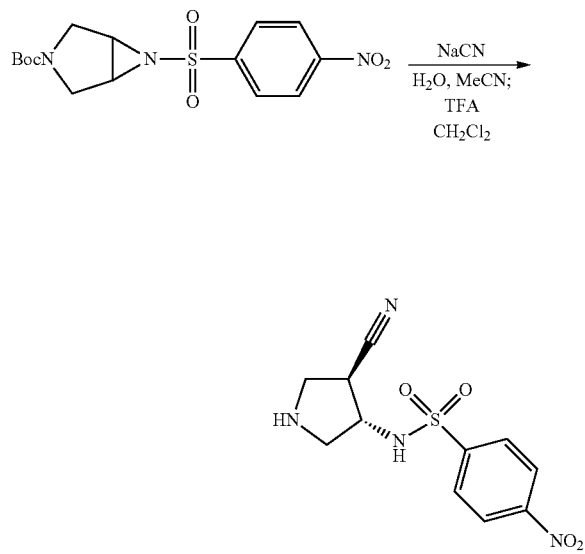

To mixture of intermediate 118 (57 mg, 0.141 mmol) in acetonitrile (564 μL) and water (141 μL) was added sodium cyanide (10.4 mg, 0.21 mmol). After 24 h, the reaction mixture was purified directly by silica preparatory HPLC (Gemini C18, 100×30 mm, 5 micron column) using a gradient of water/acetonitrile (with 0.1% TFA modifier) 75:15 to 0:1. To the resulting intermediate in dichloromethane (1 mL) was added trifluoroacetic acid (1 mL). After 2 h, the reaction mixture was concentrated to afford intermediate 119 (20 mg, 37%) as a colorless oil.

LCMS (m/z) 297.04 [M+H], t$_r$=1.63 min.

Example 116: Preparation of Intermediate 120

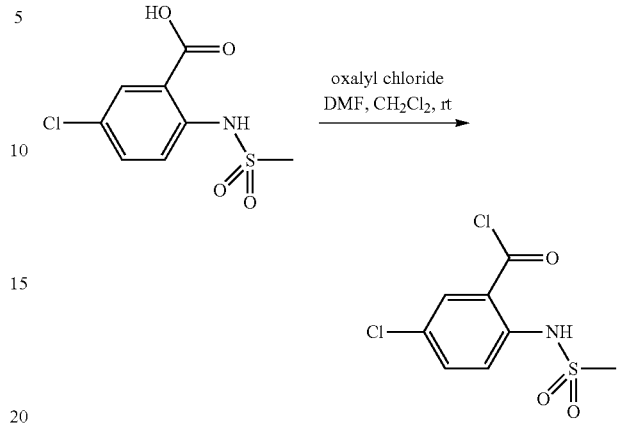

To a suspension of (5-chloro-2-(methylsulfonamido)benzoic acid) (0.7 g, 2.8 mmol) in DCM (6 ml) was added oxalylchloride (2 M in DCM, 6 ml, 12 mmol) and DMF (5 microliter) and the material was stirred for 3 h at room temperature. The volatiles were removed under vacuum to afford intermediate 120 as a crude residue that was used without further purification.

Example 117: Preparation of Compound 1

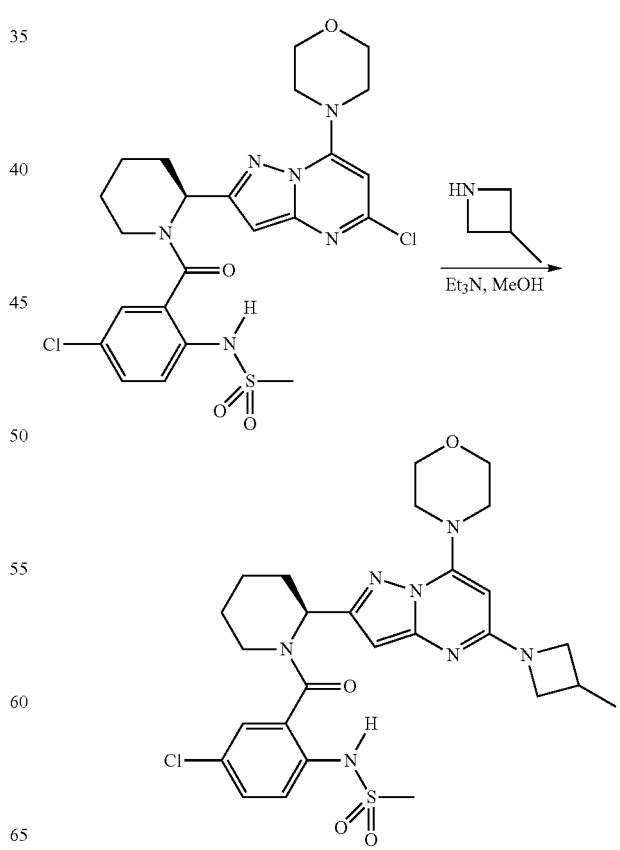

To a solution of intermediate 32 (20.0 mg, 0.036 mmol) in MeOH (1.00 mL) was added 3-methylazetidine hydrochloride (165 mg, 0.72 mmol) and triethylamine (200 μL, 1.44 mmol), and the reaction mixture was stirred at 70° C. After 2 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 1 (28 mg, 96%) as a white solid.

LCMS (m/z) 588.20 [M+H]$^+$

MW 587.21

Example 118: Preparation of Compound 2

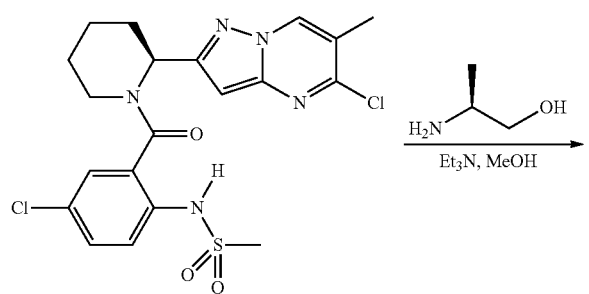

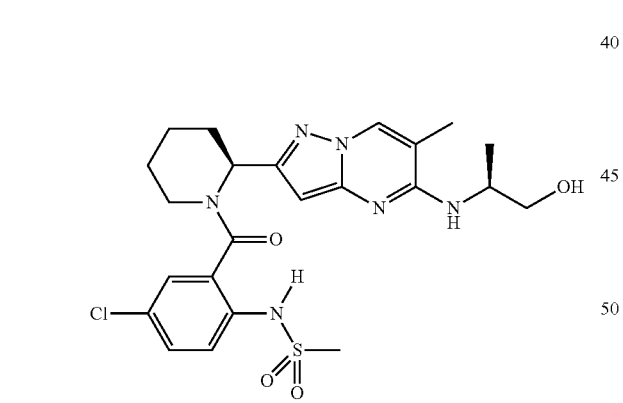

To a solution of intermediate 11 (30.0 mg, 0.06 mmol) in MeOH (1.0 mL) was added (S)-2-aminopropan-1-ol (47 mg, 0.62 mmol) and triethylamine (174 μL, 1.25 mmol), and the reaction mixture was stirred at 70° C. After 2 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 2 (6.7 mg, 22%) as a white solid. (TFA Salt).

LCMS (m/z) 521.10 [M+H]$^+$

MW 520.17

Example 119: Preparation of Compound 3

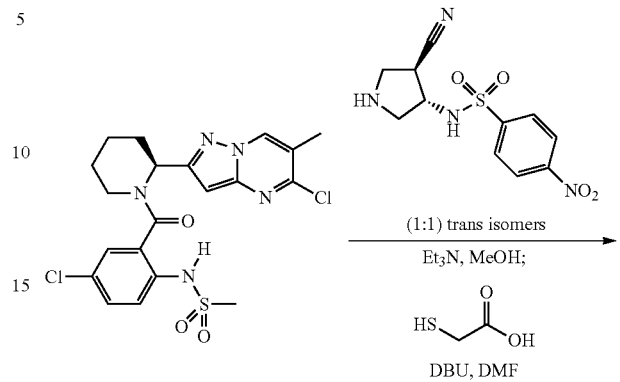

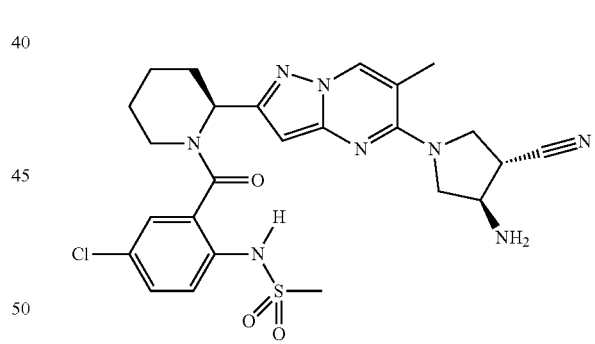

To a solution of intermediate 11 (25 mg, 0.05 mmol) in MeOH (0.5 mL) was added intermediate 119 (20 mg, 0.047 mmol) and triethylamine (174 μL, 1.25 mmol), and the reaction mixture was stirred at 70° C. After 2 h, the reaction mixture was allowed to cool to room temperature and was concentrated under reduced pressure. To the resulting residue was added DMF (0.5 mL) and DBU (40.0 μl, 0.268 mmol) followed by 2-mercaptoacetic acid (5 μL, 0.07 mmol). After 18 h, the reaction mixture was purified by preparatory HPLC (5-100% MeCN/H—$_2$O, 0.1% trifluoroacetic acid modifier) to afford compound 3 (4.2 mg, 14%, 1:1 diastereomeric mixture) as a white solid. (TFA Salt)

LCMS (m/z) 557.10 [M+H]$^+$

MW 556.18

Example 120: General Procedure for the Preparation of Compounds 4-18

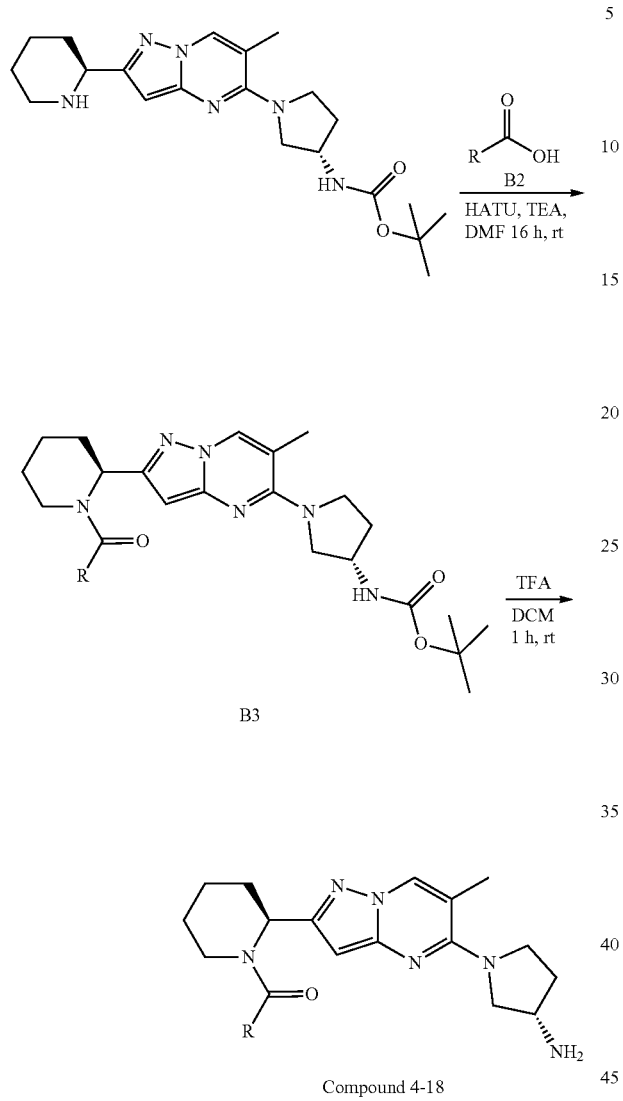

B3

Compound 4-18

In 50 mL, singled necked, round bottomed flask was placed intermediate 12 (2640 mg, 6.59 mmol) and TEA (1.83 mL, 13.2 mmol) in DMF (8.8 mL). The carboxylic acids (B2) (between 0.10 mmol and 0.50 mmol) were placed in separate 2-ml vials. Then, into each vial was dispensed a solution of intermediate 12 (0.050 mmol) followed by the addition of HATU (38 mg, 0.10 mmol). The resulting reaction mixtures were stirred at room temperature for 16 h. Then, to each reaction mixture was added EtOAc (4 mL), washed with sat. NaHCO$_3$ (2 mL×2), and concentrated to give the coupled products (B3) as a crude solid. The crude product was redissolved in dichloromethane (0.5 mL) followed by the addition of TFA (0.2 mL). After the reaction mixture was stirred at room temperature for 1 h, it was loaded onto the CUBCX column. The mixture was washed with MeOH:EtOAc (1:4, 4 mL) and MeOH:dichloromethane (1:4, 4 mL), eluted with 7 N NH$_4$OMe:EtOAc (3:7, 4 mL), and concentrated to afford the final compound (i.e. compounds 4-18).

Example 121: Preparation of Compound 4

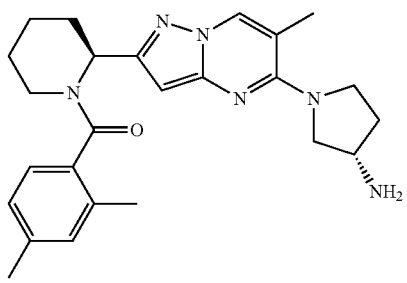 [SMILES: Cc1ccc(C(=O)N2CCCC[C@H]2c2cc3nc(N4CC[C@H](N)C4)c(C)cn3n2)c(C)c1]

The title compound was prepared in 15% yield according to the general procedure of Example 120 starting from intermediate 12 and 2,4-dimethylbenzoic acid.

LCMS (m/z) 433.46 [M+H]$^+$
MW 432.26

Example 122: Preparation of Compound 5

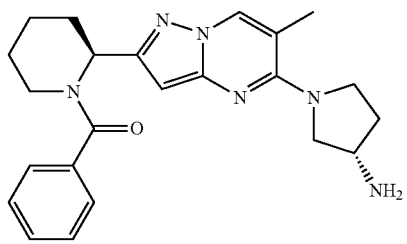 [SMILES: Cc1cn2nc([C@@H]3CCCCN3C(=O)c3ccccc3)cc2nc1N1CC[C@H](N)C1]

The title compound was prepared in 65% yield according to the general procedure of Example 120 starting from intermediate 12 and benzoic acid.

LCMS (m/z) 405.48 [M+H]$^+$
MW 404.23

Example 123: Preparation of Compound 6

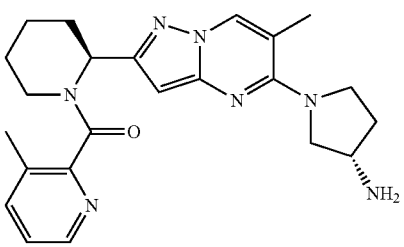 [SMILES: Cc1cccnc1C(=O)N1CCCC[C@H]1c1cc2nc(N3CC[C@H](N)C3)c(C)cn2n1]

The title compound was prepared in 95% yield according to the general procedure of Example 120 starting from intermediate 12 and 3-methylpicolinic acid.

LCMS (m/z) 420.33 [M+H]$^+$
MW 419.24

Example 124: Preparation of Compound 7

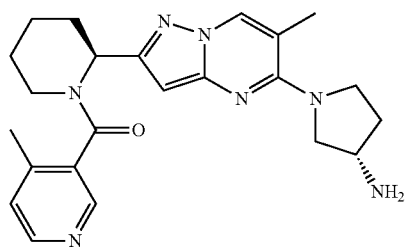 [SMILES: Cc1ccncc1C(=O)N1CCCC[C@H]1c1cc2nc(N3CC[C@H](N)C3)c(C)cn2n1]

The title compound was prepared in 80% yield according to the general procedure of Example 120 starting from intermediate 12 and 4-methylnicotinic acid.

LCMS (m/z) 420.41 [M+H]$^+$
MW 419.24

Example 125: Preparation of Compound 8

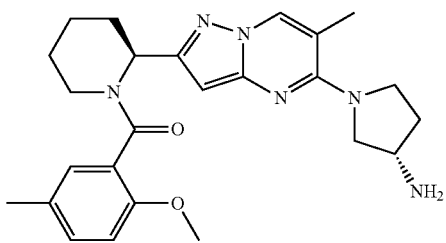 [SMILES: COc1ccc(C)cc1C(=O)N1CCCC[C@H]1c1cc2nc(N3CC[C@H](N)C3)c(C)cn2n1]

The title compound was prepared in 89% yield according to the general procedure of Example 120 starting from intermediate 12 and 2-methoxy-5-methylbenzoic acid.

LCMS (m/z) 449.36 [M+H]$^+$
MW 448.26

Example 126: Preparation of Compound 9

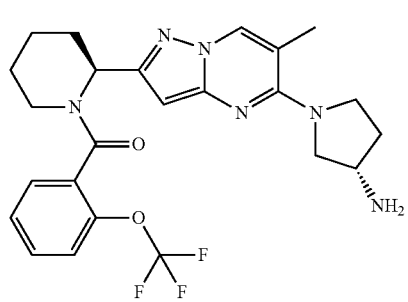 [SMILES: Cc1cn2nc([C@@H]3CCCCN3C(=O)c3ccccc3OC(F)(F)F)cc2nc1N1CC[C@H](N)C1]

The title compound was prepared in 68% yield according to the general procedure starting from intermediate 12 and 2-(trifluoromethoxy)benzoic acid.

LCMS (m/z) 489.30 [M+H]$^+$
MW 448.21

Example 127: Preparation of Compound 10

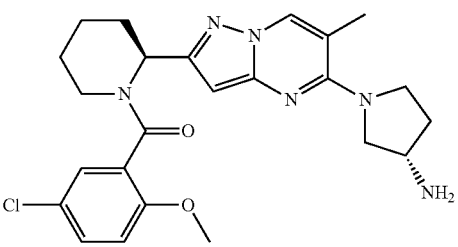 [SMILES: COc1ccc(Cl)cc1C(=O)N1CCCC[C@H]1c1cc2nc(N3CC[C@H](N)C3)c(C)cn2n1]

The title compound was prepared in 39% yield according to the general procedure of Example 120 starting from intermediate 12 and 5-chloro-2-methoxybenzoic acid.

LCMS (m/z) 469.30 [M+H]$^+$
MW 468.20

Example 128: Preparation of Compound 11

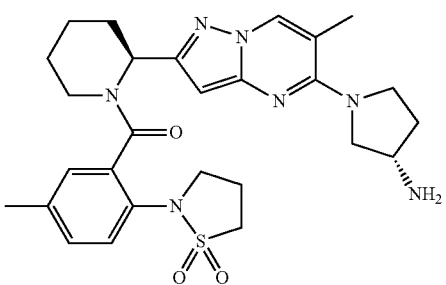 [SMILES: Cc1ccc(N2CCCS2(=O)=O)c(C(=O)N2CCCC[C@H]2c2cc3nc(N4CC[C@H](N)C4)c(C)cn3n2)c1]

The title compound was prepared in 67% yield according to the general procedure of Example 120 starting from intermediate 12 and intermediate 101

LCMS (m/z) 538.14 [M+H]$^+$
MW 537.25

Example 129: Preparation of Compound 12

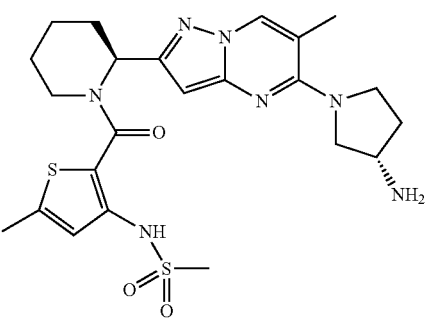 [SMILES: Cc1cc(NS(C)(=O)=O)c(C(=O)N2CCCC[C@H]2c2cc3nc(N4CC[C@H](N)C4)c(C)cn3n2)s1]

The title compound was prepared in 23% yield according to the general procedure of Example 120 starting from intermediate 12 and 5-methyl-3-(methylsulfonamido)thiophene-2-carboxylic acid.

LCMS (m/z) 518.04 [M+H]$^+$
MW 517.19

Example 130: Preparation of Compound 13

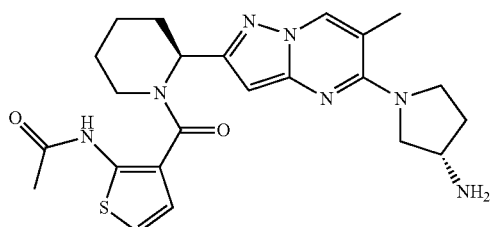

The title compound was prepared according to the general procedure of Example 120 starting from intermediate 12 and 2-acetamidothiophene-3-carboxylic acid.

LCMS (m/z) 468.4 [M+H]$^+$
MW 467.21

Example 131: Preparation of Compound 14

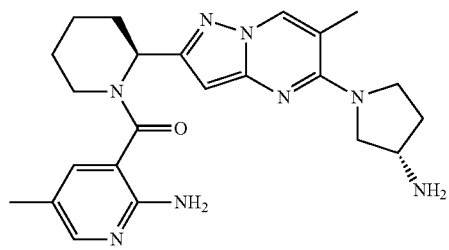 [SMILES: Cc1cnc(N)c(C(=O)N2CCCC[C@H]2c2cc3nc(N4CC[C@H](N)C4)c(C)cn3n2)c1]

The title compound was prepared according to the general procedure of Example 120 starting from intermediate 12 and 2-amino-5-methylnicotinic acid.

LCMS (m/z) 435.4 [M+H]$^+$
MW 434.25

Example 132: Preparation of Compound 15

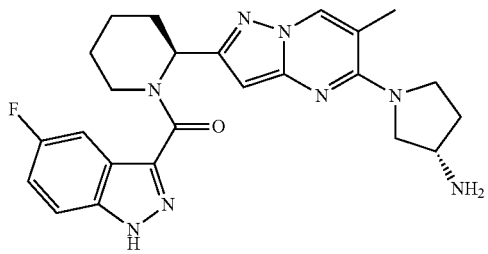 [SMILES: Cc1cn2nc([C@@H]3CCCCN3C(=O)c3n[nH]c4ccc(F)cc34)cc2nc1N1CC[C@H](N)C1]

The title compound was prepared according to the general procedure of Example 120 starting from intermediate 12 and 5-fluoro-1H-indazole-3-carboxylic acid.

LCMS (m/z) 463.4 [M+H]$^+$
MW 462.23

Example 133: Preparation of Compound 16

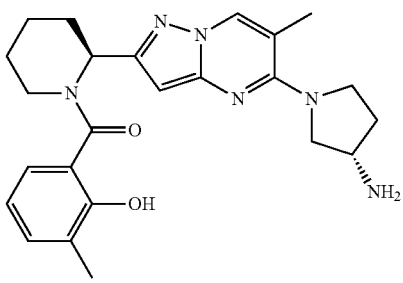 [SMILES: Cc1cn2nc([C@@H]3CCCCN3C(=O)c3cccc(C)c3O)cc2nc1N1CC[C@H](N)C1]

The title compound was prepared according to the general procedure of Example 120 starting from intermediate 12 and 2-hydroxy-3-methylbenzoic acid.

LCMS (m/z) 435.4 [M+H]$^+$
MW 434.24

Example 134: Preparation of Compound 17

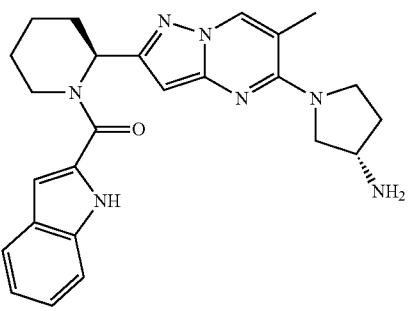 [SMILES: Cc1cn2nc([C@@H]3CCCCN3C(=O)c3cc4ccccc4[nH]3)cc2nc1N1CC[C@H](N)C1]

The title compound was prepared according to the general procedure of Example 120 starting from intermediate 12 and 1H-indole-2-carboxylic acid.

LCMS (m/z) 444.4 [M+H]$^+$
MW 443.24

Example 135: Preparation of Compound 18

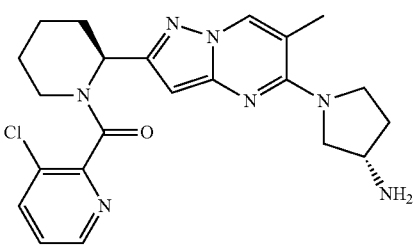 [SMILES: Cc1cn2nc([C@@H]3CCCCN3C(=O)c3ncccc3Cl)cc2nc1N1CC[C@H](N)C1]

The title compound was prepared in 92% yield according to the general procedure of Example 120 starting from intermediate 12 and 3-chloropicolinic acid.

LCMS (m/z) 440.05 [M+H]$^+$
MW 439.19

Example 136: Preparation of Compound 19

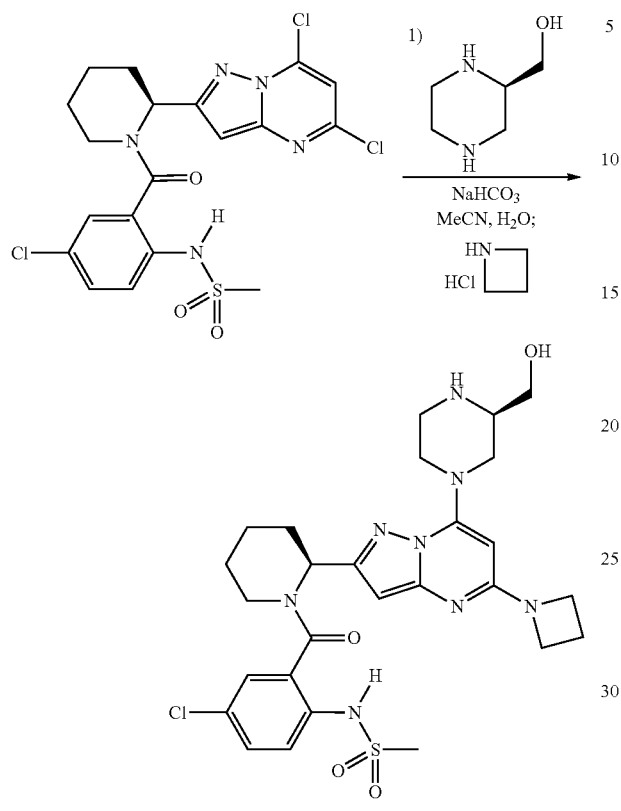

(R)-piperazin-2-ylmethanol (11.6 uL, 0.10 mmol) and sodium bicarbonate (16.0 mg, 0.20 mmol) were added to a solution of intermediate 33 (50 mg, 0.10 mmol) in acetonitrile (0.50 mL) and water (0.50 mL) and the reaction mixture was stirred at room temperature. After 12 h, azetidine hydrochloride (46.0 mg, 0.50 mmol) was added and the reaction mixture was stirred at 70° C. After 5 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 19 (16 mg, 22%) as a white solid.
LCMS (m/z) 603.14 [M+H]$^+$
MW 602.22

Example 137: Preparation of Compound 20

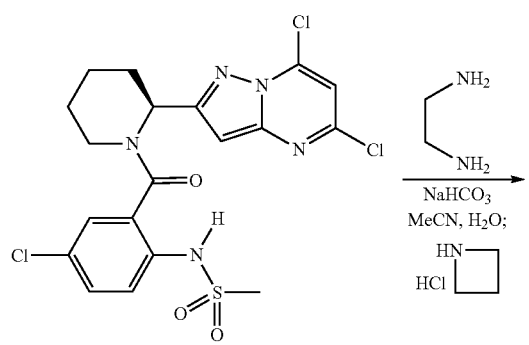

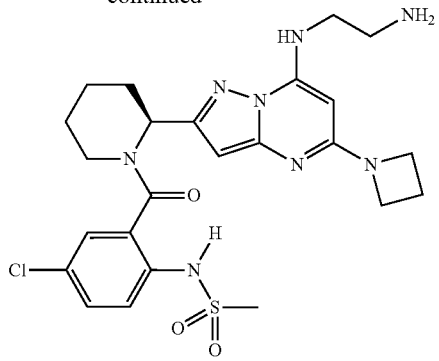

Ethane-1,2-diamine (6.7 µL, 0.10 mmol) and sodium bicarbonate (16.0 mg, 0.20 mmol) were added to a solution of intermediate 33 (50 mg, 0.10 mmol) in acetonitrile (0.50 mL) and water (0.50 mL) and the reaction mixture was stirred at room temperature. After 12 h, azetidine hydrochloride (46.0 mg, 0.50 mmol) was added and the reaction mixture was stirred at 70° C. After 5 h, the reaction mixture was allowed to cool to room temperature and was concentrated under reduced pressure. The crude residue was purified by preparatory HPLC (5-100% MeCN/H$_2$O, 0.1% trifluoroacetic acid modifier) to afford compound 20 (2 mg, 3%) as a white solid.
LCMS (m/z) 547.13 [M+H]$^+$
MW 546.19

Example 138: Preparation of Compound 21

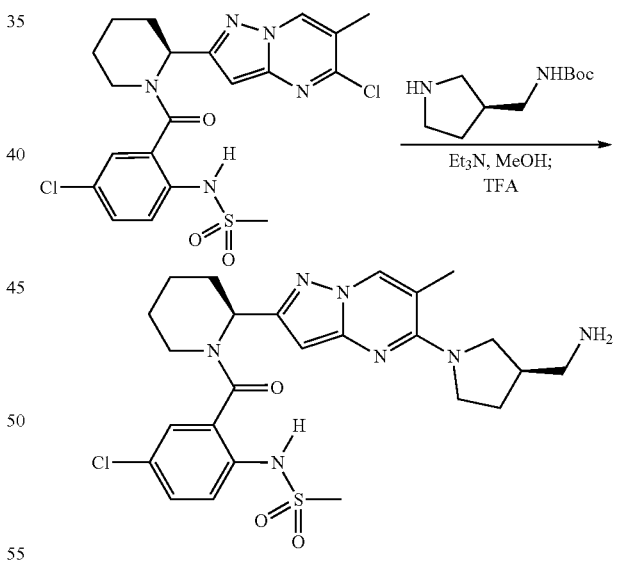

To a solution of intermediate 11 (30.0 mg, 62.0 µmol) in MeOH (1 mL) was added (S)-tert-butyl-pyrrolidin-3-ylmethylcarbamate (146 mg, 0.62 mmol) and triethylamine (174 µL, 1.25 mmol) at room temperature, and the reaction mixture was heated to 70° C. After 12 h, the reaction mixture was allowed to cool to room temperature and was purified by preparatory HPLC (5-100% MeCN/H$_2$O, 0.1% trifluoroacetic acid modifier). Trifluoroacetic acid (1 mL) was added at room temperature. After 30 min, the resulting mixture was concentrated to afford compound 21 (40.0 mg, 98%) as a light yellow solid trifluoroacetate salt.

LCMS (ESI) m/z 546.19 [M+H]+, $t_R$=1.95 min. MW 545.20

Example 139: Preparation of Compound 22

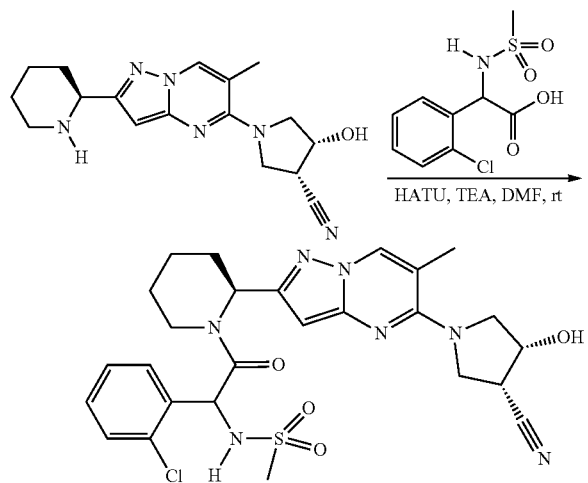

HATU (57 mg, 0.149 mmol) was added to a solution of intermediate 96 (34 mg, 0.129 mmol) 1.2 mL of DMF at room temperature. After 60 minutes of stirring, intermediate 7 (22 mg, 0.067 mmol) was added followed immediately by triethylamine (0.023 mL, 0.168 mmol). Reaction mixture stirred at room temperature overnight under argon. Mixture was then poured into 30 mL of H₂O and extracted three times with 30 mL of ethyl acetate. The combined organic layers were washed with 50 mL brine, dried (MgSO₄), filtered, and concentrated under reduced pressure leaving a residue that was purified by prep HPLC (15-100% Acetonitrile (with 0.1% trifluoroacetic acid) in water (with 0.1% trifluoroacetic acid)) to yield compound 22 as a solid (5 mg, 11%) trifluoroacetic acid salt (~1:1 mixture of diastereomers), after lyophilization LCMS m/z [M+H]+ $C_{26}H_{30}ClN_7O_4S$ requires: 572.18. Found 572.08.

HPLC Tr (min), purity %: 5.65, 88%.

Example 140: Preparation of Compound 23

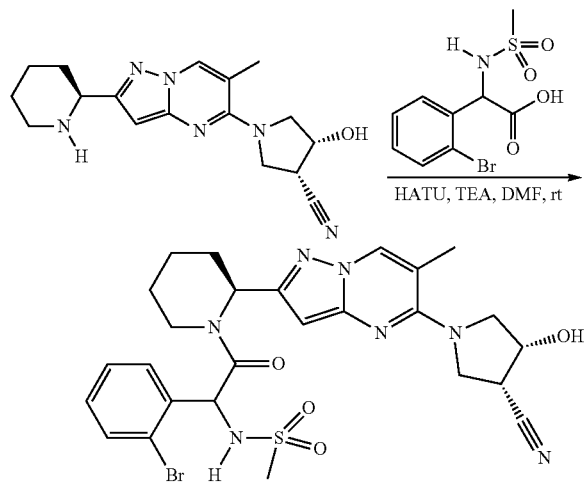

Following the procedure for the synthesis of compound 22, beginning with intermediate 95 (40 mg, 0.130 mmol) and intermediate 7 (25 mg, 0.076 mmol), compound 23 was synthesized as a solid (7 mg, 13%) trifluoroacetic acid salt (~1:1 mixture of diastereomers), after lyophilization LCMS m/z [M+H]+ $C_{26}H_{30}BrN_7O_4S$ requires: 616.13. Found 615.98.

HPLC Tr (min), purity %: 5.69, 93%.

Example 141: Preparation of Compound 24

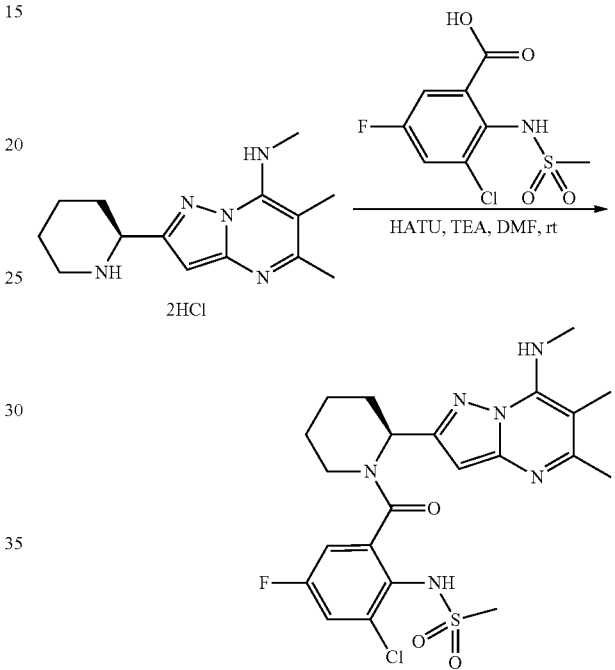

Following the synthesis of compound 22, beginning with intermediate 109 (31.4 mg, 0.117 mmol), and intermediate 24 (30.6 mg, 0.09 mmol) and triethylamine (0.045 mL, 0.315 mmol), compound 24 (38 mg, 68%) was synthesized as a white solid, trifluoroacetic acid salt after lyophilization.

LCMS m/z [M+H]+ $C_{22}H_{26}ClN_6O_3S$ requires: 509.15. Found 509.30.

HPLC Tr (min), purity %: 5.00, 99%.

Example 142: Preparation of Compound 25

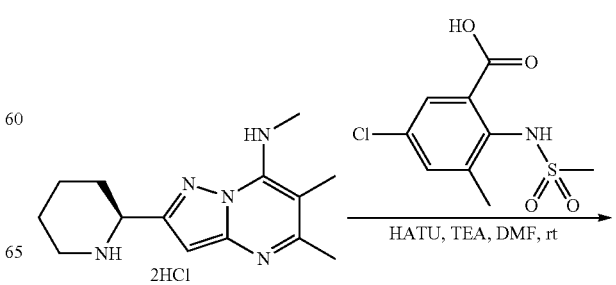

-continued

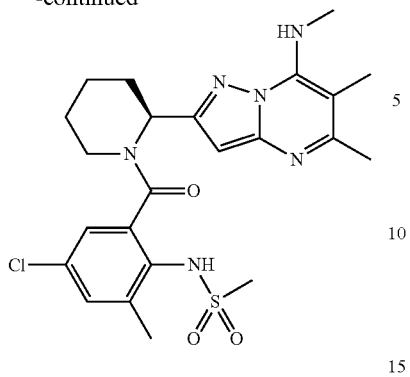

Following the synthesis of compound 22, beginning with intermediate 105 (21.5 mg, 0.081 mmol), and intermediate 24 (20.1 mg, 0.06 mmol) and triethylamine (0.030 mL, 0.210 mmol), compound 25 (29 mg, 77%) was synthesized as a white solid, trifluoroacetic acid salt after lyophilization.

LCMS m/z [M+H]⁺ C₂₃H₂₉ClN₆O₃S requires: 505.17. Found 505.32.

HPLC Tr (min), purity %: 5.58, 99%.

Example 143: Preparation of Compound 26

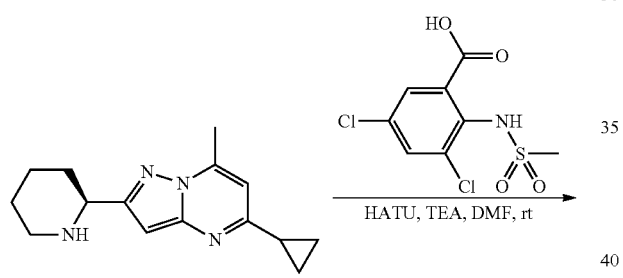

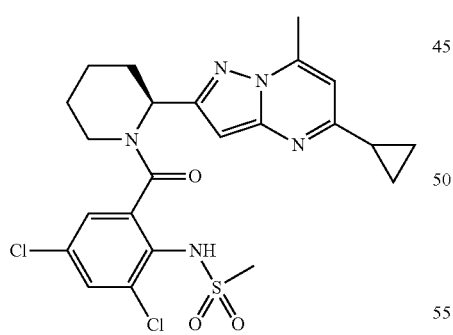

Following the synthesis of compound 22, beginning with 3,5-dichloro-2-(methylsulfonamido)benzoic acid (58 mg, 0.204 mmol), a 0.5 M DMF solution of intermediate 26 (0.3 mL, 0.15 mmol) and triethylamine (0.060 mL, 0.420 mmol), compound 26 (69 mg, 72%) was synthesized as a white solid, trifluoroacetic acid salt after lyophilization.

LCMS m/z [M+H]⁺ C₂₃H₂₅Cl₂N₅O₃S requires: 522.11. Found 522.41.

HPLC Tr (min), purity %: 7.19, 99%.

Example 144: Preparation of Compound 27

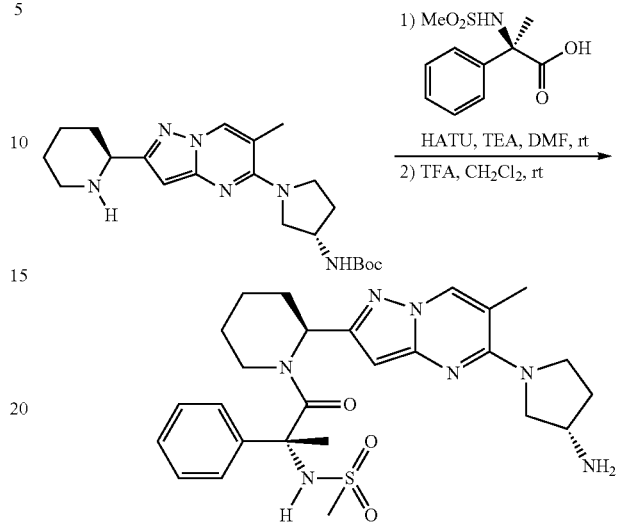

HATU (150 mg, 0.394 mmol) was added to a solution of intermediate 99 (80 mg, 0.33 mmol) in 3.3 mL of DMF at room temperature. After 45 min of stirring, intermediate 12 (106 mg, 0.266 mmol) was added followed immediately by triethylamine (0.090 mL, 0.639 mmol). Reaction mixture stirred at room temperature overnight under argon. Mixture was then poured into 30 mL of H₂O and extracted three times with 30 mL of ethyl acetate. The combined organic layers were washed with 50 mL brine, dried (MgSO₄), filtered, and concentrated under reduced pressure leaving a residue, which was dissolved in 7 mL of dichloromethane. Trifluoroacetic acid (0.7 mL, 8.9 mmol) was added and reaction mixture stirred at room temperature for 18 hours. Mixture was then concentrated under reduced pressure and purified by prep HPLC (15-100% Acetonitrile (with 0.1% trifluoroacetic acid) in water (with 0.1% trifluoroacetic acid)) to yield compound 27 (7.5 mg, 5%) as a white solid, trifluoroacetic acid salt, after lyophilization.

LCMS m/z [M+H]⁺ C₂₆H₃₅N₇O₃S requires: 526.25. Found 526.18.

HPLC Tr (min), purity %: 4.87, 96%.

Example 145: Preparation of Compound 28

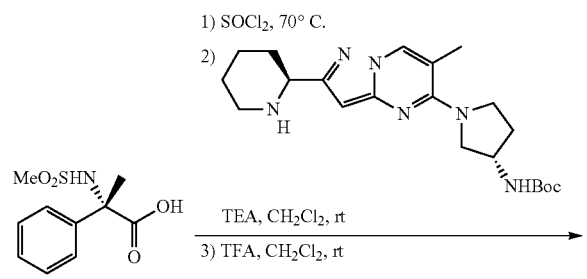

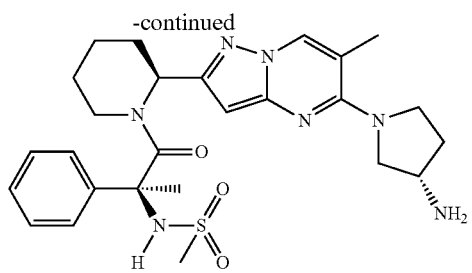

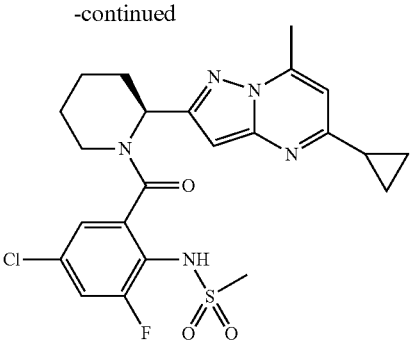

Intermediate 114 (59 mg, 0.243 mmol) was suspended in neat thionyl chloride (2 mL, 27.5 mmol) at room temperature. Mixture was heated at 70° C. overnight. After cooling to room temperature, reaction mixture was concentrated, yielding a residue. To a solution of this residue in 2 mL of dichloromethane, was added intermediate 12 (78 mg, 0.195 mmol) and triethylamine (0.040 mL, 0.283 mmol) and mixture was stirred at room temperature overnight. Reaction mixture was concentrated under reduced pressure and residue was purified by silica gel column chromatography (10-80% ethyl acetate in hexanes) to yield 27 mg of desired precursor, which was dissolved in 2 mL of dichloromethane and treated with trifluoroacetic acid (0.150 mL, 1.95 mmol). After stirring for one hour at room temperature, reaction mixture was concentrated under reduced pressure to yield compound 28 (26 mg, 17% over 3 steps), as an orange-yellow solid, trifluoroacetic acid salt.

LCMS m/z [M+H]$^+$ C$_{26}$H$_{35}$N$_7$O$_3$S requires: 526.25. Found 526.19.

HPLC Tr (min), purity %: 4.88, 97%.

Example 146: Preparation of Compound 29

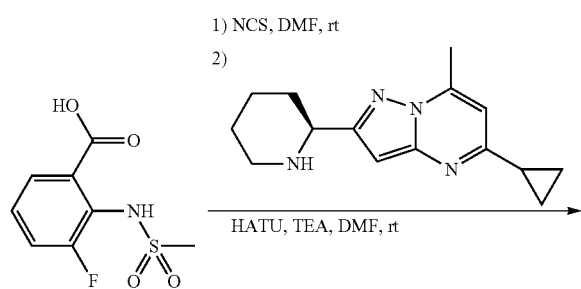

N-chlorosuccinimde (99.4 mg, 0.744 mmol) was added to a solution of intermediate 108 (142 mg, 0.609 mmol) in 3.5 mL of DMF at room temperature. After stirring overnight, reaction mixture was poured into water and extracted three times with ethyl acetate. Combined organics were washed with water and brine, dried (MgSO$_4$), filtered and concentrated under reduced pressure to yield 5-chloro-3-fluoro-2-(methylsulfonamido)benzoic acid (142 mg, 87%, 90% HPLC purity) which was used without further purification. HATU (87.4 mg, 0.230 mmol) was added to a solution of 5-chloro-3-fluoro-2-(methylsulfonamido)benzoic acid (55.1 mg, 0.206 mmol) in 5 mL of DMF at room temperature. After 45 minutes, a 0.5 M DMF solution of intermediate 26 (0.3 mL, 0.15 mmol) and triethylamine (0.050 mL, 0.375 mmol) were added. Reaction mixture stirred at room temperature overnight under argon. Mixture was then poured into 50 mL of H$_2$O and extracted three times with 30 mL of ethyl acetate. The combined organic layers were washed with 50 mL brine, dried (MgSO$_4$), filtered, and concentrated under reduced pressure leaving a residue. Product was purified by prep HPLC (15-100% Acetonitrile (with 0.1% trifluoroacetic acid) in water (with 0.1% trifluoroacetic acid)) to yield compound 29 (28 mg, 31%) as a white solid trifluoroacetic acid salt, after lyophilization.

LCMS m/z [M+H]$^+$ C$_{23}$H$_{25}$ClFN$_5$O$_3$S requires: 506.14. Found 506.07.

HPLC Tr (min), purity %: 7.52, 99%.

Example 147: Preparation of Compound 30 and Compound 31

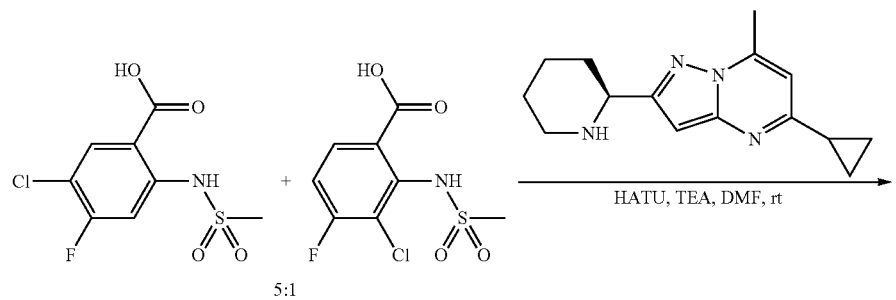

5:1

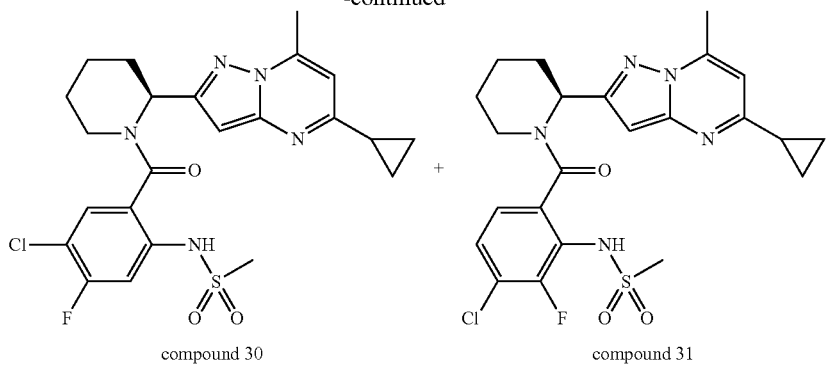

compound 30          compound 31

Following the procedure of compound 29, beginning with an 5:1 mixture of 5-chloro-4-fluoro-2-(methylsulfonamido)benzoic acid and intermediate 43 (53 mg, 0.198 mmol), a 0.5 M DMF solution of intermediate 26 (0.3 mL, 0.15 mmol) and triethylamine (0.060 mL, 0.420 mmol), compound 30 (36 mg, 39%) and compound 31 (7 mg, 8%) were synthesized as white solids, trifluoroacetic acid salts after lyophilization.

Compound 30: LCMS m/z [M+H]$^+$ $C_{23}H_{25}ClFN_5O_3S$ requires: 506.14. Found 506.12.

HPLC Tr (min), purity %: 7.62, 98%.

Compound 31: LCMS m/z [M+H]$^+$ $C_{23}H_{25}ClFN_5O_3S$ requires: 506.14. Found 506.10.

HPLC Tr (min), purity %: 6.73, 99%.

Example 148: Preparation of Compound 32

Following the synthesis of compound 22, beginning with intermediate 109 (15.1 mg, 0.056 mmol), and intermediate 22 and triethylamine (0.020 mL, 0.137 mmol), compound 32 (13 mg, 55%) was synthesized as a white solid, trifluoroacetic acid salt after lyophilization.

LCMS m/z [M+H]$^+$ $C_{22}H_{25}ClFN_5O_3S$ requires: 494.14. Found 494.30.

HPLC Tr (min), purity %: 6.19, 95%.

Example 149: Preparation of Compound 33

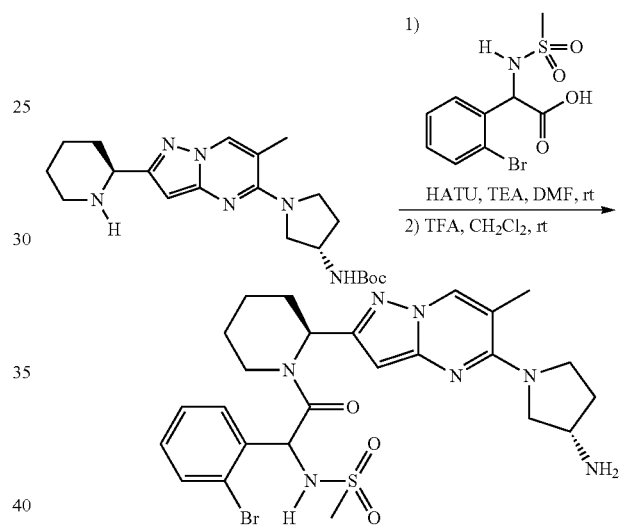

Following the synthesis of compound 27, beginning with intermediate 95 (148 mg, 0.795 mmol) and intermediate 12 (82 mg, 0.151 mmol), compound 33 (89 mg, 84% over two steps) was synthesized as a white solid, trifluoroacetic acid salt (~1:1 mixture of diastereomers).

LCMS m/z [M+H]$^+$ $C_{25}H_{32}BrN_7O_3S$ requires: 590.15. Found 590.33.

HPLC Tr (min), purity %: 4.93, 99%.

Example 150: Preparation of Compound 34

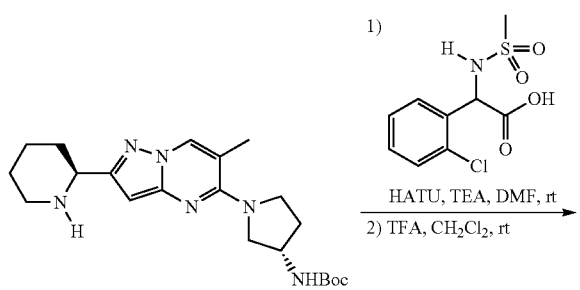

-continued

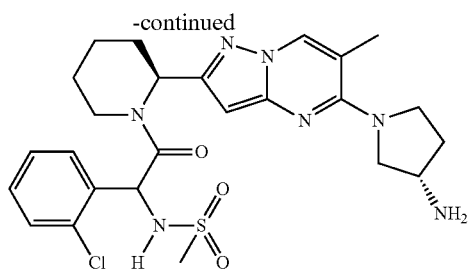

Following the synthesis of compound 27, beginning with intermediate 96 (48 mg, 0.183 mmol) and intermediate 12 (49 mg, 0.122 mmol), compound 34 (47 mg, 58% over two steps) was synthesized as a white solid, trifluoroacetic acid salt (~1:1 mixture of diastereomers).

LCMS m/z [M+H]$^+$ C$_{25}$H$_{32}$ClN$_7$O$_3$S requires: 546.20. Found 546.32.

HPLC Tr (min), purity %: 4.88, 96%.

Example 151: Preparation of Compound 35

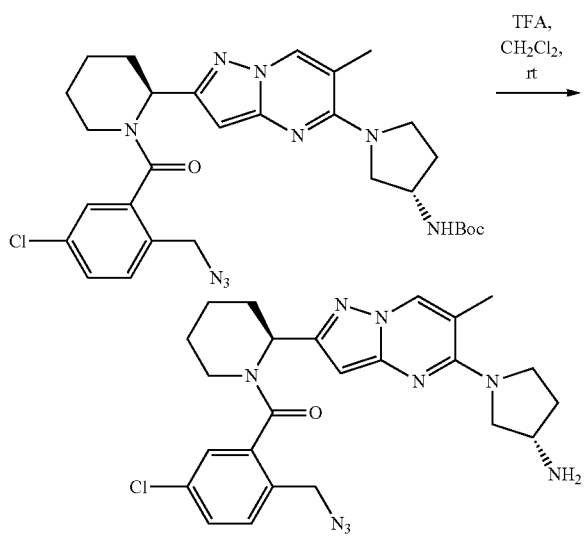

Following the BOC deprotection step in the synthesis of compound 27, but beginning with intermediate 38 (11 mg), compound 35 (11 mg, 99%) was synthesized as a white solid film.

LCMS m/z [M+H]$^+$ C$_{24}$H$_{28}$ClN$_9$O requires: 494.21. Found 494.09.

HPLC Tr (min), purity %: 5.24, 99%.

Example 152: Preparation of Compound 36

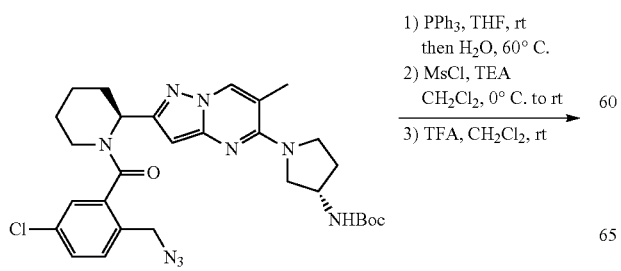

-continued

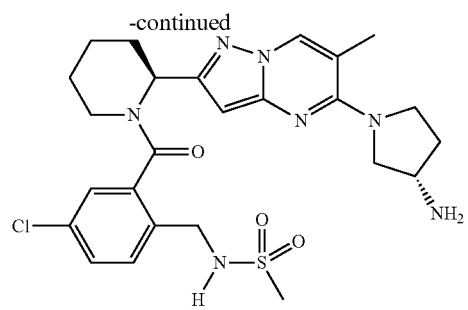

Step 1: Triphenylphosphine (87 mg, 0.332 mmol) was added to a solution of intermediate 38 (97 mg, 0.163 mmol) in 5 mL of THF at room temperature. After 90 minutes, 0.2 mL of water was added and mixture was heated at 60° C. overnight. Reaction mixture was concentrated under reduced pressure and purified by silica gel column chromatography (0-10% methanol in dichloromethane) to yield the intermediate benzylamine (44 mg, 48%).

Step 2: Previous intermediate from step 1 was dissolved in 2 mL of dichloromethane and triethylamine (0.035 mL, 0.249 mmol) was added. Solution was cooled to 0° C. and methane sulfonylchloride (0.020 mL, 0.238 mmol) was added. Reaction mixture was warmed to room temperature, stirred overnight, then concentrated under reduced pressure. Residue was purified by silica gel column chromatography (10-90% ethyl acetate in hexanes) to yield the intermediate benzylsulfonamide (35 mg, 78%).

Step 3: Previous intermediate from step 2 (27 mg, 0.042 mmol) was dissolved in 1.5 mL of dichloromethane at room temperature. Trifluoroacetic acid (0.135 mL, 1.74 mmol) was added and reaction mixture stirred overnight. Reaction mixture was concentrated under reduced pressure to yield compound 36 (26 mg, 99%) as a white solid film, trifluoroacetic acid salt.

LCMS m/z [M+H]$^+$ C$_{25}$H$_{32}$ClN$_7$O$_3$S requires: 546.20. Found 546.32.

HPLC Tr (min), purity %: 4.96, 99%.

Example 153: Preparation of Compound 37

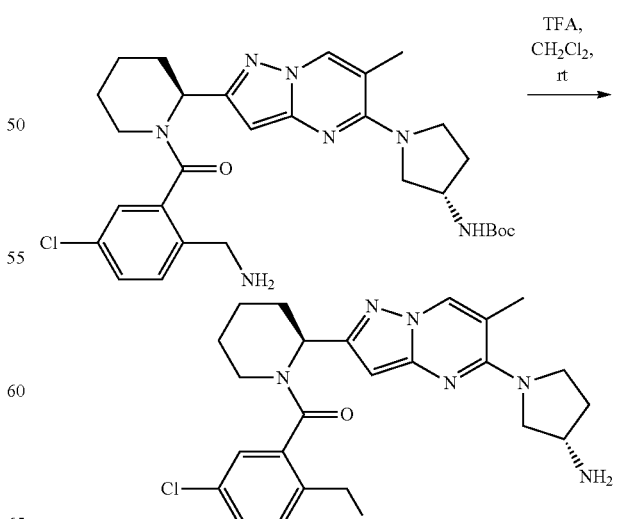

Intermediate 39 (5 mg, 0.00882 mmol) was dissolved in 0.5 mL of dichloromethane at room temperature. Trifluoroacetic acid (0.03 mL, 0.386 mmol) was added and mixture stirred at room temperature for one hour. Reaction mixture was then concentrated under reduced pressure to yield compound 37 (6.6 mg, 93%) as the bis-trifluoroacetic acid salt.

LCMS m/z [M+H]$^+$ C$_{24}$H$_3$ClN$_7$O requires: 468.22. Found 468.09.

HPLC Tr (min), purity %: 4.32, 97%.

Example 154: Preparation of Compound 38 and Compound 39

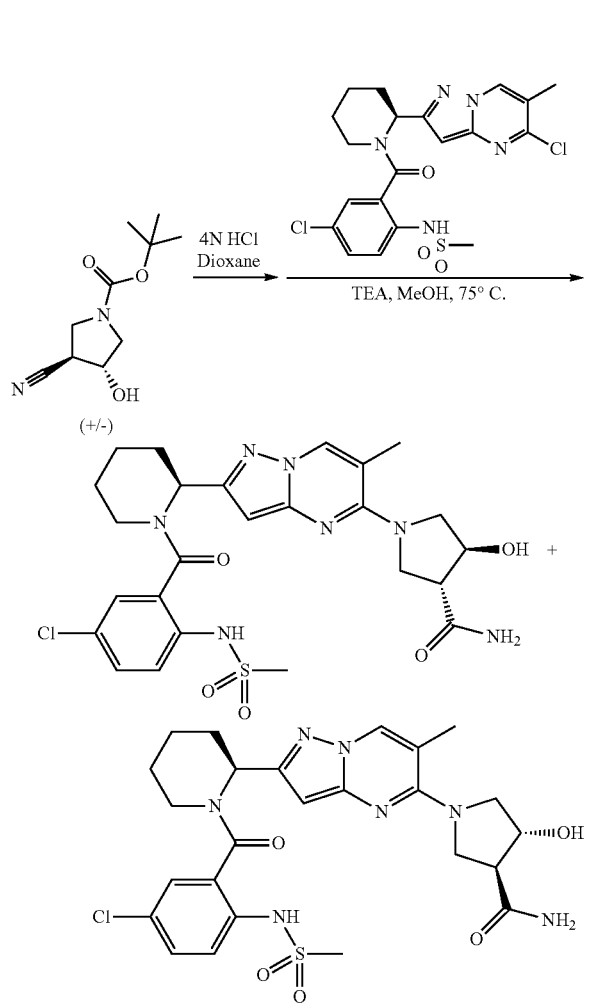

A dioxane solution of hydrochloric acid (4N, 1.25 mL, 5 mmol) was added to a solution of intermediate 54 (106 mg, 0.5 mmol) in 6 mL of dioxane. After stirring for eighteen hours, solvent was concentrated under reduced pressure resulting in a residue that was dissolved in 4 mL of methanol and treated with intermediate 11 (41.4 mg, 0.0858 mmol) and triethylamine (0.14 mL, 1.00 mmol). Mixture was heated at 75° C. overnight. After cooing to room temperature, reaction mixture was concentrated under reduced pressure, resulting in a residue. Purification via prep HPLC (15-100% Acetonitrile (with 0.1% trifluoroacetic acid) in water (with 0.1% trifluoroacetic acid)) yielded compound 38 (18 mg, 19%) and compound 39 (3 mg, 3%) as white solids, trifluoroacetic acid salts, after lyophilization.

Compound 38: LCMS m/z [M+H]$^+$ C$_{25}$H$_{30}$ClN$_7$O$_5$S requires: 576.17. Found 576.44.

HPLC Tr (min), purity %: 5.36, 99%

Compound 39: LCMS m/z [M+H]$^+$ C$_{25}$H$_{30}$ClN$_7$O$_5$S requires: 576.17. Found 576.43.

HPLC Tr (min), purity %: 5.51, 76%

Example 155: Preparation of Compound 40

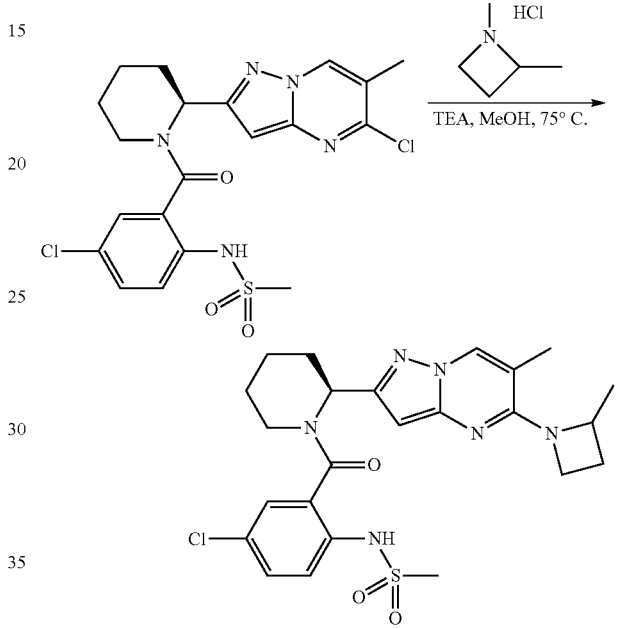

Following the procedure of the second step of Example 154, beginning with intermediate 11 (50 mg, 0.104 mmol) and 2-methylazetidine hydrochloride (72 mg, 0.669 mmol), compound 40 (43 mg, 80%) was synthesized as a white solid (~1:1 mixture of diastereomers).

LCMS m/z [M+H]$^+$ C$_{24}$H$_{29}$ClN$_6$O$_3$S requires: 517.17. Found 517.06.

HPLC Tr (min), purity %: 6.62, 96%.

Example 156: Preparation of Compound 41

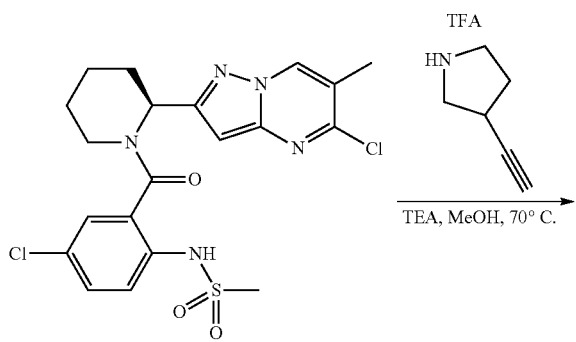

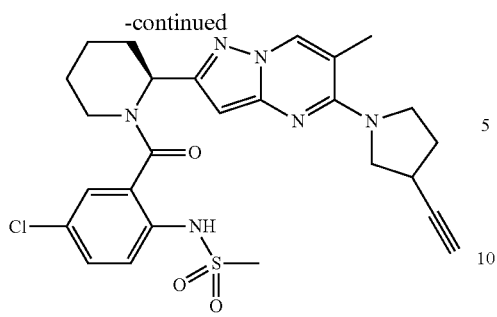

Following the procedure of the second step of Example 154, beginning with intermediate 11 (54 mg, 0.112 mmol) and 3-ethynylpyrrolidine 2,2,2-trifluoroacetate (108 mg, 0.519 mmol), compound 41 (59 mg, 96%) was synthesized as a white solid (~1:1 mixture of diastereomers).

LCMS m/z [M+H]$^+$ C$_{26}$H$_{29}$ClN$_6$O$_3$S requires: 541.17. Found 541.07.

HPLC Tr (min), purity %: 7.25, 99%.

Example 157: Preparation of Compound 42

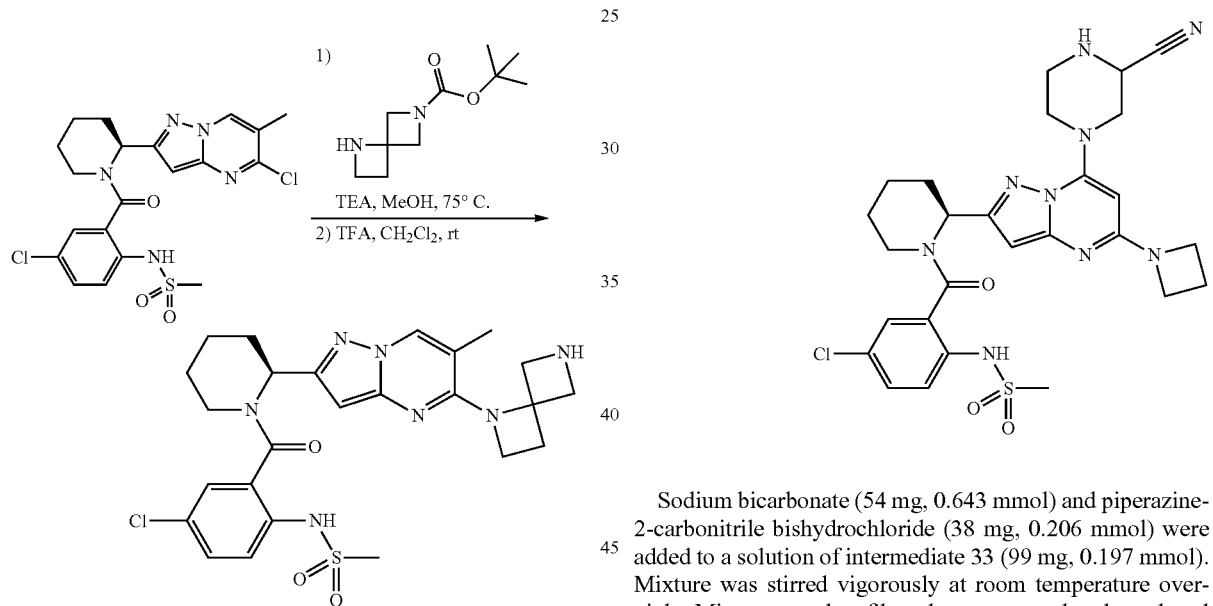

Triethylamine (0.100 mL, 0.717 mmol) was added to a mixture of intermediate 11 (71 mg, 0.147 mmol) and tert-butyl 1,6-diazaspiro[3.3]heptane-6-carboxylate (114 mg, 0.575 mmol) in 5 mL of methanol at room temperature. After heating at 75° C. overnight, reaction mixture was cooled to room temperature and concentrated under reduced pressure. The remaining residue was purified by silica gel column chromatography (5-75% ethyl acetate in hexanes) to yield (S)-tert-butyl 1-(2-(1-(5-chloro-2-(methylsulfonamido)benzoyl)piperidin-2-yl)-6-methylpyrazolo[1,5-a]pyrimidin-5-yl)-1,6-diazaspiro[3.3]heptane-6-carboxylate as a solid (33 mg, 35%). This solid was dissolved in 3 mL of dichloromethane and trifluoroacetic acid (0.15 mL, 1.95 mmol) was added. After stirring overnight and reaction mixture was concentrated under reduced pressure to yield compound 42 (33 mg, 99%) as a white solid.

LCMS m/z [M+H]$^+$ C$_{25}$H$_{30}$ClN$_7$O$_3$ requires: 544.18. Found 544.37.

HPLC Tr (min), purity %: 5.67, 96%.

Example 158: Preparation of Compound 43

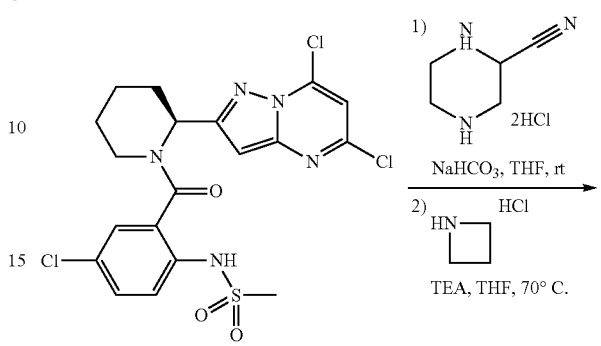

Sodium bicarbonate (54 mg, 0.643 mmol) and piperazine-2-carbonitrile bishydrochloride (38 mg, 0.206 mmol) were added to a solution of intermediate 33 (99 mg, 0.197 mmol). Mixture was stirred vigorously at room temperature overnight. Mixture was then filtered, concentrated under reduced pressure, and residue was purified by silica gel column chromatography to yield N-(4-chloro-2-((2S)-2-(5-chloro-7-(3-cyanopiperazin-1-yl)pyrazolo[1,5-a]pyrimidin-2-yl)piperidine-1-carbonyl)phenyl)methanesulfonamide (30 mg, 26%). This yellow film (27 mg, 0.047 mmol) was dissolved in 3 mL of THF and azetidine hydrochloride (22 mg, 0.237 mmol) and triethylamine (0.066 mL, 0.470 mmol) were added. Reaction mixture was heated at 70° C. overnight. Reaction mixture was then cooled to room temperature, concentrated under reduced pressure, and resulting residue was purified by prep HPLC (15-100% Acetonitrile (with 0.1% trifluoroacetic acid) in water (with 0.1% trifluoroacetic acid)) to yield compound 43 (10 mg, 30%) as a light yellow solid trifluoroacetic acid salt, after lyophilization (~1:1 mixture of diastereomers).

LCMS m/z [M+H]$^+$ C$_{27}$H$_{32}$ClN$_9$O$_3$S requires: 597.21. Found 597.17.

HPLC Tr (min), purity %: 4.79, 91%.

Example 159: Preparation of Compound 44

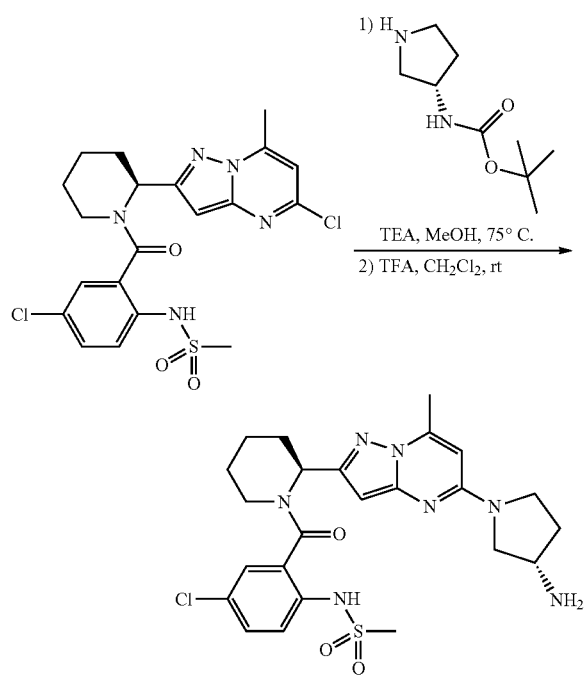

Following the procedure of compound 42, beginning with intermediate 28 (49.7 mg, 0.103 mmol) and (S)-tert-butyl pyrrolidin-3-ylcarbamate (144 mg, 0.744 mmol), compound 44 (63 mg, 95%) as an off white solid, trifluoroacetic acid salt, after lyophilization.

LCMS m/z [M+H]+ $C_{24}H_{30}ClN_7O_3S$ requires: 532.18. Found 532.03.

HPLC Tr (min), purity %: 4.79, 99%.

Example 160: Preparation of Compound 45

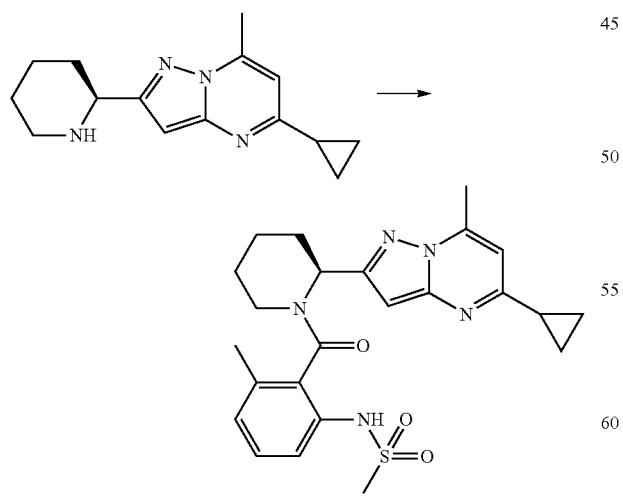

To a solution of intermediate 26 (100 mg, 0.034 mmol) in DMF (5 ml) was added 2-amino-6-methyl benzoic acid (0.5 g, 3.3 mmol), and HATU (1.13 g, 3.9 mmol). After stirring for 5 h at room temperature, volatiles were removed under reduced pressure. The crude residue was purified by preparatory HPLC (5-100% MeCN/H₂O, 0.1% trifluoroacetic acid modifier) to afford the coupled intermediate (44 mg, 33%) as a white solid. This intermediate was then reacted with methansulphonyl chloride (0.3 ml) in DMF (3 ml) at room temperature. After stirring for 0.5 h at room temperature, volatiles were removed under reduced pressure. The crude residue was purified by preparatory HPLC (5-100% MeCN/H₂O, 0.1% trifluoroacetic acid modifier) to afford the product 45 (44 mg, 47%) as a white solid.

LCMS (m/z) 468.15 [M+H]+

MW 467.6

Example 161: Preparation of Compound 46

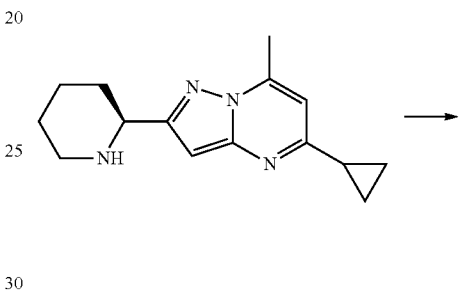

To a solution of intermediate 26 (0.5 mmol) in DMF (1.5 ml) was added the carboxylate (0.1 g, 0.46 mmol) and HATU (0.132 g, 0.46 mmol). After stirring for 1 h at room temperature, volatiles were removed under reduced pressure. The crude residue was purified by preparatory HPLC (5-100% MeCN/H₂O, 0.1% trifluoroacetic acid modifier) to afford the product 46 (66 mg, 32%) as a white solid.

LCMS (m/z) 454.19 [M+H]+

MW 453.6

Example 162: Preparation of Compound 47

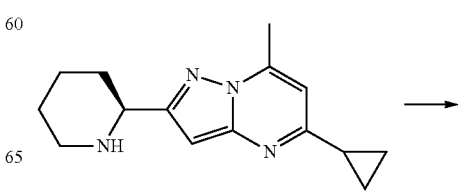

-continued

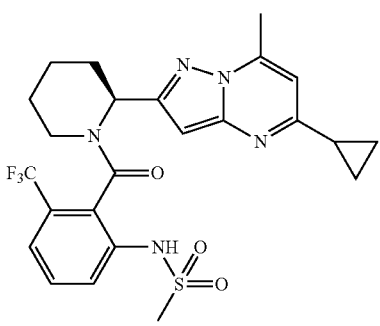

Following the procedure for compound 46, the product was obtained as a white solid (5.4 mg, 12%).

LCMS (m/z) 522.15 [M+H]+

MW 521.6

Example 163: Preparation of Compound 48

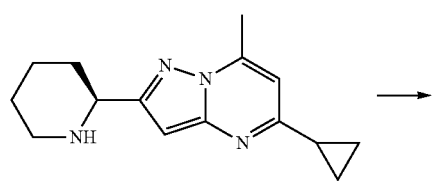

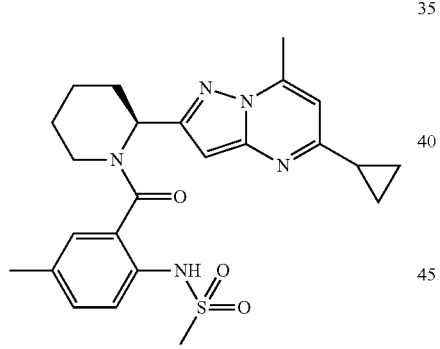

Following the procedure for compound 46, the product was obtained as a white solid (46.1 mg, 24%).

LCMS (m/z) 375.16 [M+H]+

MW 374.5

Example 164: Preparation of Compound 49

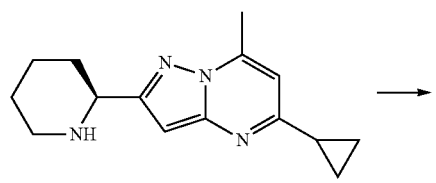

-continued

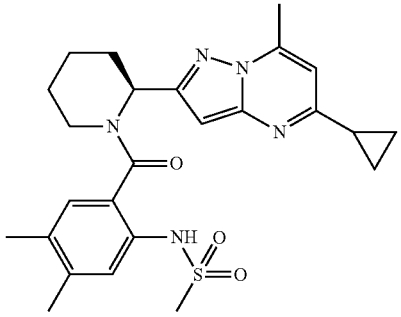

Following the procedure for compound 46, the product was obtained as a white solid (100 mg, 43%).

LCMS (m/z) 389.17 [M+H]+

MW 388.5

Example 165: Preparation of Compound 50

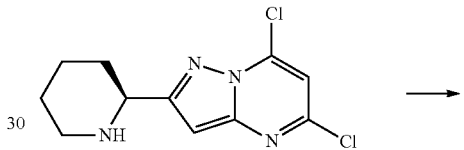

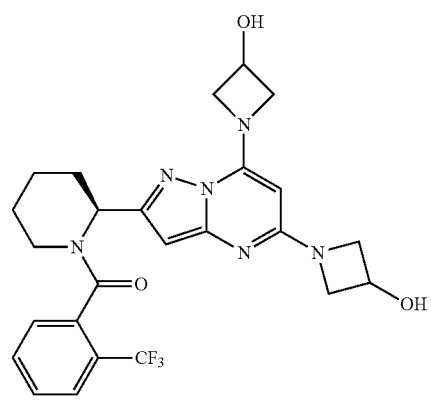

To a solution of intermediate 30 (1 g, 3.68 mmol) in MeOH (5 ml) was added 3-hydroxyazetidine (2 g, 18.4 mmol). After stirring for 16 h at reflux, the volatiles were removed under reduced pressure. The crude residue was purified by preparatory HPLC (5-100% MeCN/H$_2$O, 0.1% trifluoroacetic acid modifier) to afford the bis-adduct (92 mg, 9%) as a white solid. This solid was dissolved in DMF (2.5 ml), NEt$_3$ (0.3 ml) and 2-trifluromethyl-benzoyl chloride (0.2 ml) was added. After stirring for 1 h at room temperature, the volatiles were removed under reduced pressure. The crude residue was purified by preparatory HPLC (5-100% MeCN/H$_2$O, 0.1% trifluoroacetic acid modifier) to afford the product 50 (81 mg, 64%) as a white powder.

LCMS (m/z) 517.3 [M+H]+

MW 516.5

Example 166: Preparation of Compound 51

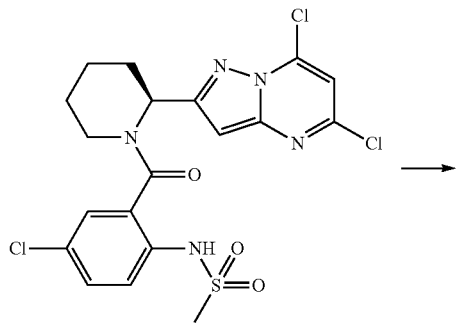

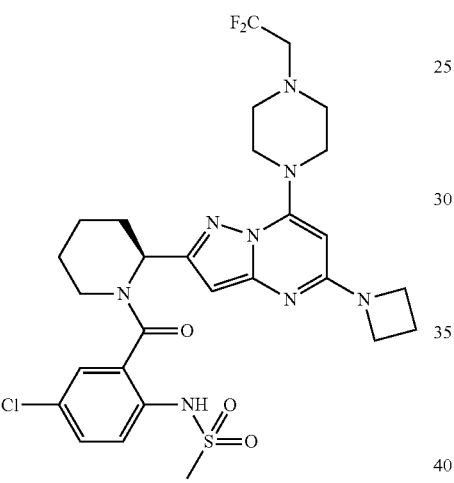

To a solution of intermediate 33 (0.14 g, 0.28 mmol) in MeCN (4 ml) was added the N-difluoroethyl-piperazine (0.062 g, 0.42 mmol). After stirring for 10 min at room temperature, volatiles were removed under reduced pressure. The crude material was dissolved in MeOH (3 ml), azetidine added (1 ml). After stirring for 16 h at room temperature, volatiles were removed under reduced pressure. The crude residue was purified by preparatory HPLC (5-100% MeCN/H$_2$O, 0.1% trifluoroacetic acid modifier) to afford the product 51 (133 mg, 74%) as a white powder.

LCMS (m/z) 637.26 [M+H]$^+$
MW 637.2

Example 167: Preparation of Compound 52

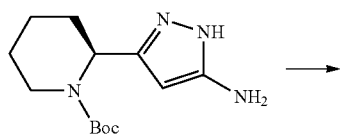

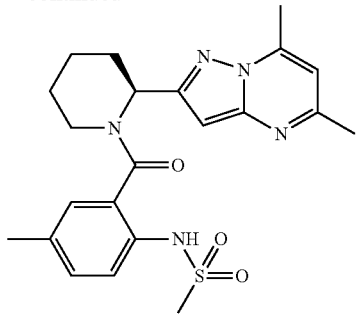

To a solution of intermediate 4 (0.59 g, 2.21 mmol) in EtOH (2 ml) and HOAc (2 ml) was added 2,5-pentanedion (0.332 g). After stirring for 1 h at reflux, the volatiles were removed under reduced pressure. The crude residue was purified by silica gel chromatography using a gradient of hexanes/ethyl acetate 1:0 to 0:1. The residue was dissolved in DCM (2 ml) and TFA (2 ml) and stirred for 2 h. After removal of the solvent, to the resulting amine (0.078 g, 0.34 mmol) in DMF (1.5 ml) was added the carboxylate (0.102 g, 0.44 mmol), HATU (0.146 g, 0.51 mmol) and NEt$_3$ (0.1 ml). After stirring for 1 h at room temperature, the volatiles were removed under reduced pressure. The crude residue was purified by preparatory HPLC (5-100% MeCN/H$_2$O, 0.1% trifluoroacetic acid modifier) to afford the product 52 (108 mg, 95%) as a white solid.

LCMS (m/z) 442.14 [M+H]$^+$
MW 441.6

Example 168: Preparation of Compound 53

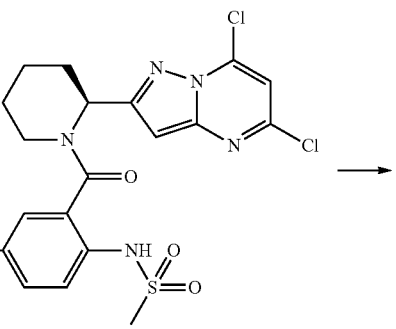

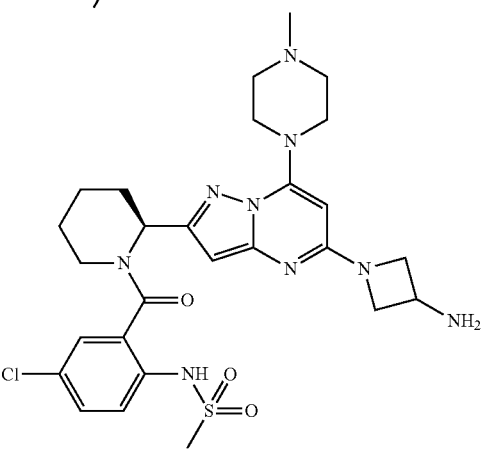

To a solution of intermediate 33 (0.2 g, 0.65 mmol) in MeCN (3 ml) was added the N-methyl-piperazine (0.071 g, 0.65 mmol) and aqueous sat. Na$_2$CO$_3$ to adjust the pH<8. After stirring for 1.5 h at room temperature, the volatiles were removed under reduced pressure. The crude material was dissolved in MeOH (3 ml) and N-Boc-amino-azetidine added (0.167 g). After stirring for 16 h at room temperature, the volatiles were removed under reduced pressure. The residue was dissolved in DCM (2 ml) and TFA (2 ml) added and stirred for 2 h at room temperature. Volatiles were removed and the crude residue was purified by preparatory HPLC (5-100% MeCN/H$_2$O, 0.1% trifluoroacetic acid modifier) to afford the product 53 (49 mg, 12%) as a white powder.

LCMS (m/z) 602.18 [M+H]$^+$
MW 602.2

Example 169: Preparation of Compound 54

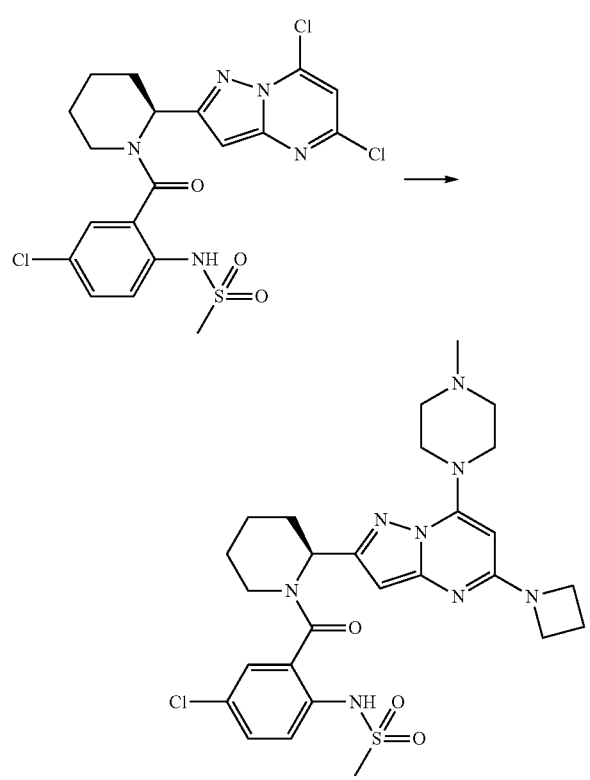

To a solution of intermediate 33 (0.1 g, 0.2 mmol) in MeCN (3 ml) was added N-methyl-piperazine (0.114 g, 0.4 mmol). After stirring for 1.5 h at room temperature, volatiles were removed under reduced pressure. The crude material was dissolved in MeOH (3 ml), azetidine added (1 ml). After stirring for 16 h at room temperature, volatiles were removed under reduced pressure. The residue was dissolved in THF (3 ml) and hydrazine (1 ml) and refluxed for 2 h at room temperature. Volatiles were removed and the crude residue was purified by preparatory HPLC (5-100% MeCN/ H$_2$O, 0.1% trifluoroacetic acid modifier) to afford the corresponding azetidine amide. The amide was subjected to LiOH (1.1 g) in water (5 ml) at reflux for 2 h to afford the product 54 (36 mg) as a white powder after purification by preparatory HPLC (5-100% MeCN/H$_2$O, 0.1% trifluoroacetic acid modifier)

LCMS (m/z) 615.15 [M−H]$^-$
MW 617.1

Example 170: Preparation of Compound 55

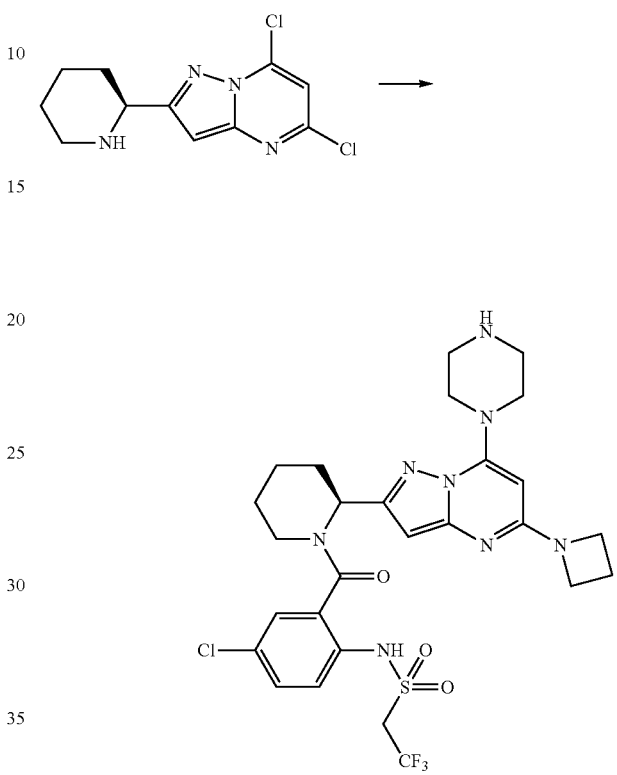

To a solution of intermediate 30 (0.111 g, 0.4 mmol) in MeCN (5 ml) was added N-Boc-piperazine (0.152 g, 0.82 mmol). After stirring for 2 h at room temperature, volatiles were removed under reduced pressure. The crude material was dissolved in MeOH (3 ml), azetidine added (1 ml). After stirring for 16 h at room temperature, the volatiles were removed under reduced pressure. The crude residue was purified by preparatory HPLC (5-100% MeCN/H$_2$O, 0.1% trifluoroacetic acid modifier) to afford the amine as a white solid. To the resulting amine (0.078 g, 0.34 mmol) in DMF (1.5 ml) was added 2-amino-5-chloro-benzoic acid (0.102 g, 0.44 mmol), and HATU (0.146 g, 0.51 mmol) and NEt$_3$ (0.1 ml). After stirring for 1 h at room temperature, volatiles were removed under reduced pressure. The crude residue was purified by preparatory HPLC (5-100% MeCN/H$_2$O, 0.1% trifluoroacetic acid modifier) to afford the aniline (108 mg, 95%) as a white solid. This solid was dissolved in pyridine (2.5 ml) and the sulphonyl chloride added at room temperature drop wise until full conversion was observed. The volatiles were removed and the residue was dissolved in DCM (2 ml) and TFA (2 ml) added and stirred for 2 h at room temperature. The volatiles were removed and the crude residue was purified by preparatory HPLC (5-100% MeCN/ H$_2$O, 0.1% trifluoroacetic acid modifier) to afford the product 55 (49 mg, 12%) as a white powder.

LCMS (m/z) 641.24 [M+H]$^+$
MW 641.1

Example 171: Preparation of Compound 56

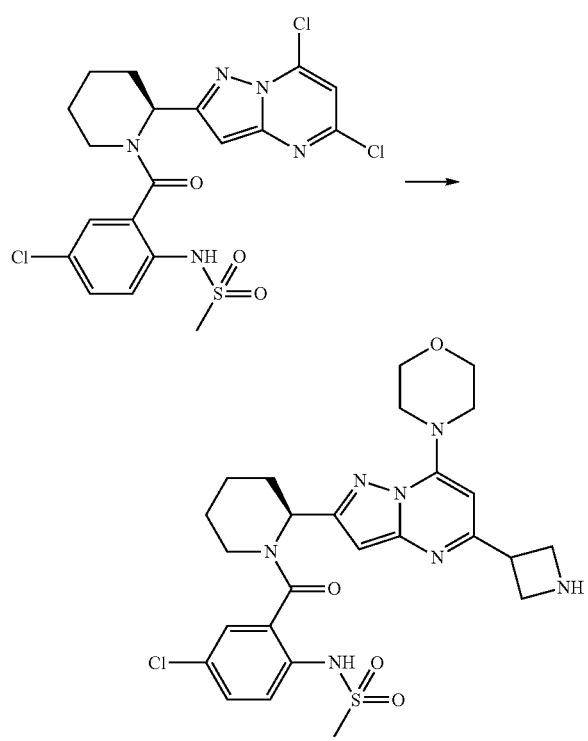

To a solution of intermediate 33 (0.1 g, 0.2 mmol) in MeCN (3 ml) was added morpholine (0.2 mmol). After stirring for 1.5 h at room temperature, volatiles were removed under reduced pressure. The crude residue was purified by preparatory HPLC (5-100% MeCN/H₂O, 0.1% trifluoroacetic acid modifier) to afford the mono adduct. This intermediate (0.06 g) was dissolved in THF (2 ml), NMP (0.2 ml), Fe(acac)3 (0.002 g) and 3-iodo-N-boc-azetidine (0.31 g) was added. A solution of iPrMgCl (1.3 M, 1.7 ml) was added dropwise at −78° C. and the solution warmed slowly to room temperature. The reaction was quenched with aqueous saturated NH₄Cl. The volatiles were removed and the crude residue was purified by preparatory HPLC (5-100% MeCN/H₂O, 0.1% trifluoroacetic acid modifier) to afford the product 56 (16.1 mg) as a white powder.

LCMS (m/z) 574.19 [M+H]⁺
MW 574.1

Example 172: Preparation of Compound 57

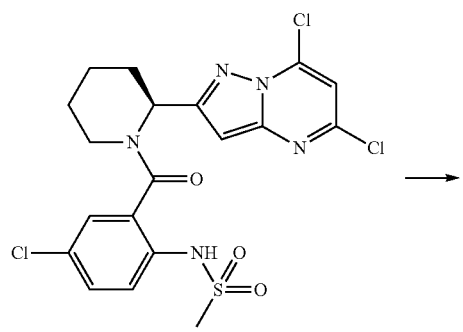

Following the procedure for compound 56 with cylopentylmagnesium bromide, the product 57 was obtained as a white solid (16 mg, 30%).

LCMS (m/z) 587.32 [M+H]⁺
MW 587.1

Example 173: Preparation of Compound 58

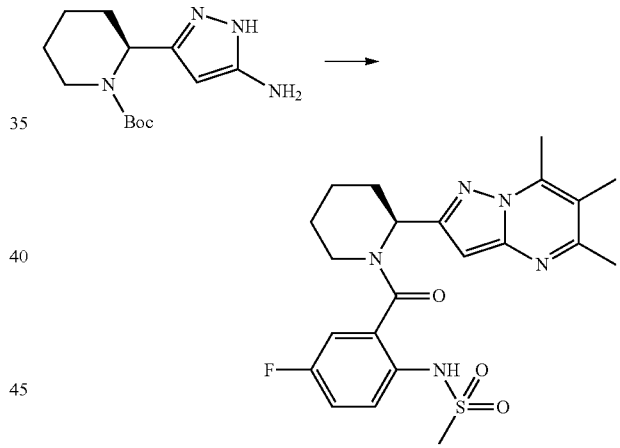

To a solution of intermediate 4 (0.94 g, 4.15 mmol) in HOAc (5 ml) was added 3-methyl-2,5-pentanedion (0.332 g). After stirring for 0.5 h at reflux, volatiles were removed under reduced pressure. The crude residue was purified by silica gel chromatography using a gradient of hexanes/ethyl acetate 1:0 to 0:1. The residue was dissolved in DCM (2 ml) and TFA (2 ml) and stirred for 2 h. After removal of the solvent, to the resulting amine (0.26 g) in DMF (1.5 ml) was added the 5-fluoro-2-(methylsulfonamido)benzoic acid carboxylate (0.26 g), HATU (0.35 g) and NEt3 (0.1 ml). After stirring for 1 h at room temperature, the volatiles were removed under reduced pressure. The crude residue was purified by preparatory HPLC (5-100% MeCN/H₂O, 0.1% trifluoroacetic acid modifier) to afford the product 58 (101 mg, 72%) as a white solid.

LCMS (m/z) 460.12 [M+H]⁺
MW 459.5

Example 174: Preparation of Compound 59

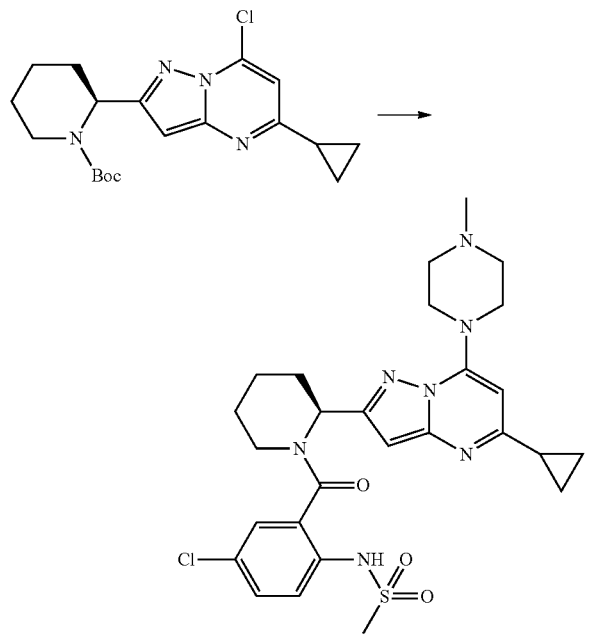

To a solution of intermediate 35 (0.54 g, 1.4 mmol) in MeOH (2 ml) was added N-methyl-piperazine (2 ml) and stirred at room temperature for 4 h. Volatiles were removed and the crude residue purified by silica gel chromatography using a gradient of hexanes/ethyl acetate. The residue was dissolved in DCM (2 ml) and TFA (2 ml) and stirred for 2 h. After removal of the solvent, to the resulting amine (0.09 g) in DMF (1.5 ml) was added the carboxylate (0.26 g), HATU (0.35 g) and NEt3 (0.1 ml). After stirring for 1 h at room temperature, volatiles were removed under reduced pressure. The crude residue was purified by preparatory HPLC (5-100% MeCN/H$_2$O, 0.1% trifluoroacetic acid modifier) to afford the product 59 (70.8 mg, 44%) as a white solid.

LCMS (m/z) 572.24 [M+H]$^+$

MW 572.1

Example 175: Preparation of Compound 60

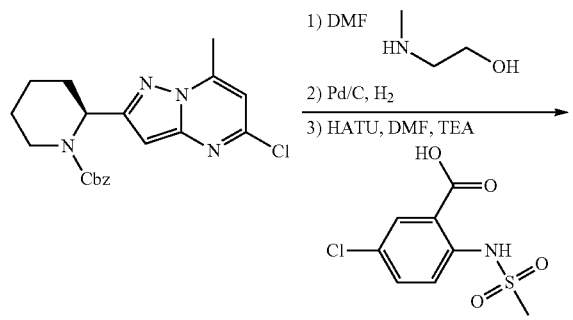

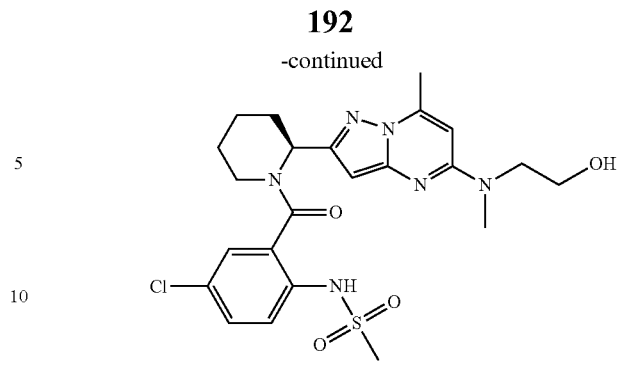

Intermediate 41 (43 mg, 0.109 mmol) was dissolved in DMF (500 uL) and 2-(methylamino)ethanol (88 uL, 1.09 mmol) and TEA (304 uL, 2.18 mmol) were added. The material was stirred at 70° C. for 2 h and then cooled to room temperature. Dissolved with ethyl acetate and washed with saturated aqueous sodium bicarbonate solution twice and saturated aqueous sodium chloride solution. Dried organic extract over anhydrous sodium sulfate and then concentrated under reduced pressure. Dissolved material in MeOH, added Pd/C and stirred under atm H$_2$ (g) for 1 hr. Filtered through Celite and concentrated under reduced pressure. Mixed 5-chloro-2-(methylsulfonamido)benzoic acid (28 mg, 0.109 mmol) with HATU (42 mg, 0.109 mmol) and dissolved in anhydrous DMF (300 uL). Stirred for 1 hr. Dissolved hydrogenation product in anhydrous DMF (300 uL) and added to the reaction. Added TEA (30 uL, 0.218 mmol). Stirred for 12 hrs. Diluted with acetonitrile and purified with Prep HPLC to give title product 60 (19 mg, 27% yield).

$^1$H NMR (400 MHz, CD$_3$OD): δ 7.49 (m, 3H), 6.72 (m, 1H), 6.08 (m, 1H), 4.60 (m, 1H), 3.85 (m, 4H), 3.45-3.30 (m, 4H), 3.02 (m, 4H), 2.79 (s, 3H), 2.40-2.05 (m, 2H), 1.73-1.50 (m, 4H).

LC/MS (m/z): 521.3 [M+H]$^+$

Example 176: Preparation of Compound 61

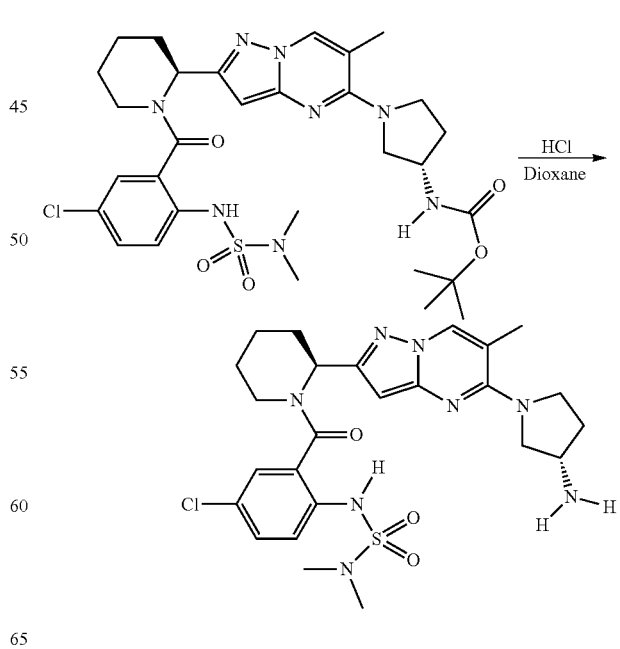

To a solution of intermediate 42 (12 mg, 0.018 mmol) in dioxane (2.00 mL) was added concentrated HCl (50 μL) and the reaction mixture was stirred at room temperature overnight. Then the reaction mixture was allowed to cool to room temperature and was concentrated under reduced pressure. The crude residue was purified by prep HPLC (0-100% CH₃CN/H₂O) to afford compound 61 (8 mg, 86%).

LCMS (m/z) 561.11 [M+H]⁺
MW 560.10

Example 177: Preparation of Compound 62

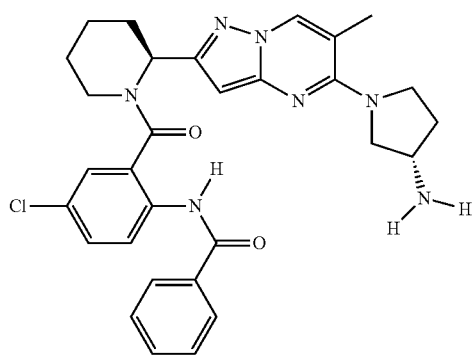 [SMILES: Cc1cn2nc([C@@H]3CCCCN3C(=O)c3cc(Cl)ccc3NC(=O)c3ccccc3)cc2nc1N1CC[C@H](N)C1]

The title compound was prepared in 54% total yield according to the general procedure for compound 61 (i.e. acylation step for the preparation of intermediate 42 and Boc removal step for the preparation of compound 61) starting from intermediate 14 and benzoyl chloride.

LCMS (m/z) 558.12 [M+H]⁺
MW 557.07

Example 178: Preparation of Compound 63

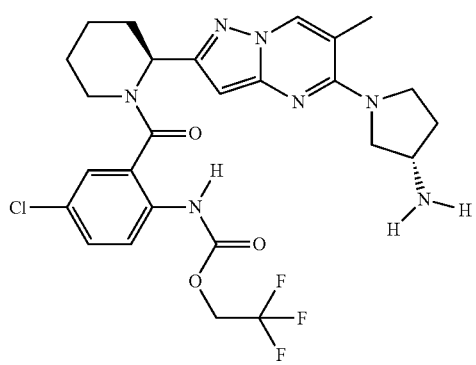 [SMILES: Cc1cn2nc([C@@H]3CCCCN3C(=O)c3cc(Cl)ccc3NC(=O)OCC(F)(F)F)cc2nc1N1CC[C@H](N)C1]

The title compound was prepared in 14% total yield according to the general procedure for compound 61 (i.e. acylation step for the preparation of intermediate 42 and Boc removal step for the preparation of compound 61) starting from intermediate 14 and 2,2,2-trifluoroethyl carbonochloridate.

LCMS (m/z) 580.20 [M+H]⁺
MW 579.00

Example 179: Preparation of Compound 64

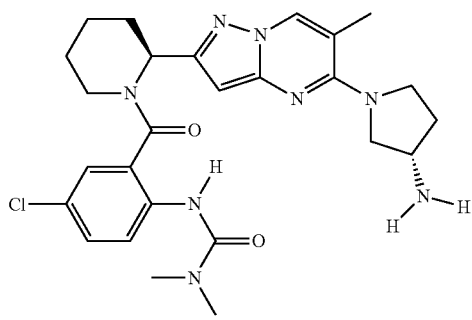 [SMILES: Cc1cn2nc([C@@H]3CCCCN3C(=O)c3cc(Cl)ccc3NC(=O)N(C)C)cc2nc1N1CC[C@H](N)C1]

The title compound was prepared in 27% total yield according to the general procedure for compound 61 (i.e. acylation step for the preparation of intermediate 42 and Boc removal step for the preparation of compound 61) starting from intermediate 14 and dimethylcarbamoyl chloride.

LCMS (m/z) 525.05 [M+H]⁺
MW 524.05

Example 180: Preparation of Compound 65

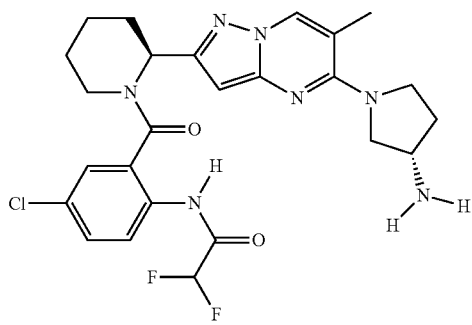 [SMILES: Cc1cn2nc([C@@H]3CCCCN3C(=O)c3cc(Cl)ccc3NC(=O)C(F)F)cc2nc1N1CC[C@H](N)C1]

The title compound was prepared in 47% total yield according to the general procedure for compound 61 (i.e. acylation step for the preparation of intermediate 42 and Boc removal step for the preparation of compound 61) starting from intermediate 14 and difluoroacetic anhydride.

LCMS (m/z) 532.25 [M+H]⁺
MW 530.99

Example 181: Preparation of Compound 66

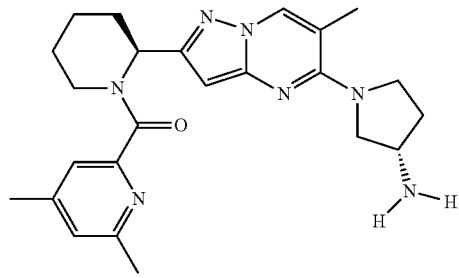 [SMILES: Cc1cc(C)nc(C(=O)N2CCCC[C@H]2c2cc3nc(N4CC[C@H](N)C4)c(C)cn3n2)c1]

The title compound was prepared in 25% total yield according to the general procedure for compounds 4-18 starting from intermediate 12 and 4,6-dimethyl-pyridine-2-carboxylic acid.

LCMS (m/z) 434.27 [M+H]$^+$
MW 433.55

Example 182: Preparation of Compound 67

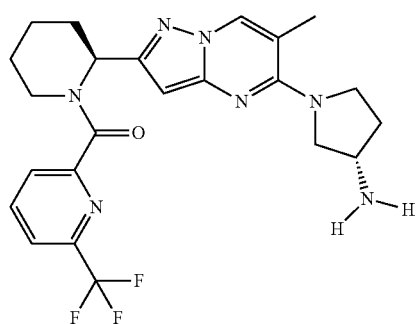 [SMILES: Cc1cn2nc([C@@H]3CCCCN3C(=O)c3cccc(C(F)(F)F)n3)cc2nc1N1CC[C@H](N)C1]

The title compound was prepared in 68% total yield according to the general procedure for compounds 4-18 starting from intermediate 12 and 6-trifluoromethyl-pyridine-2-carboxylic acid.

LCMS (m/z) 473.85 [M+H]$^+$
MW 472.49

Example 183: Preparation of Compound 68

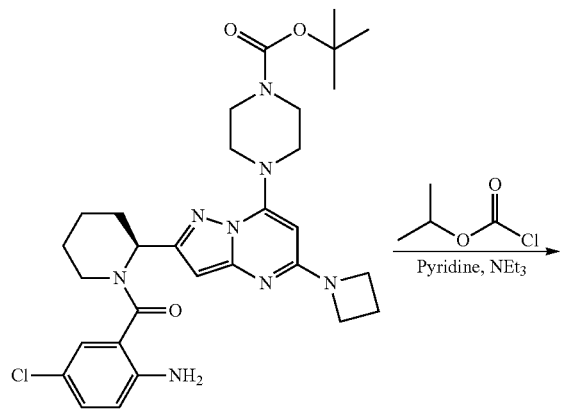

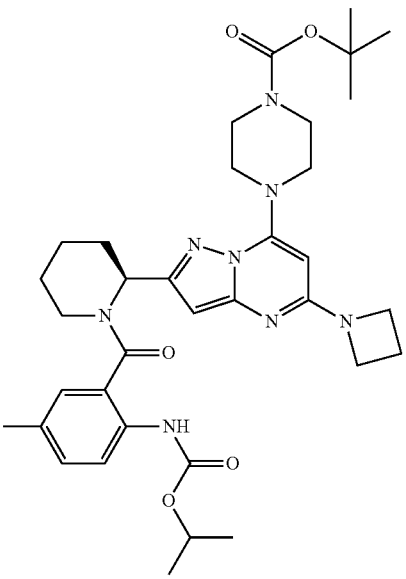

Intermediate 46 (80 mg, 0.13 mmol) was dissolved in pyridine (2 ml), to the solution was added isopropyl chloroformate (331 mg, 2.7 mmol) and NEt$_3$ (54 μl). The reaction was stirred at room temperature overnight and the solvent was evaporated. The residue was purified with combi-flash column chromatography (0-100% EtOAc/Hexane) to afford compound 68 (46 mg, 50%).

LCMS (m/z) 681.21 [M+H]$^+$
MW 680.22

Example 184: Preparation of Compound 69

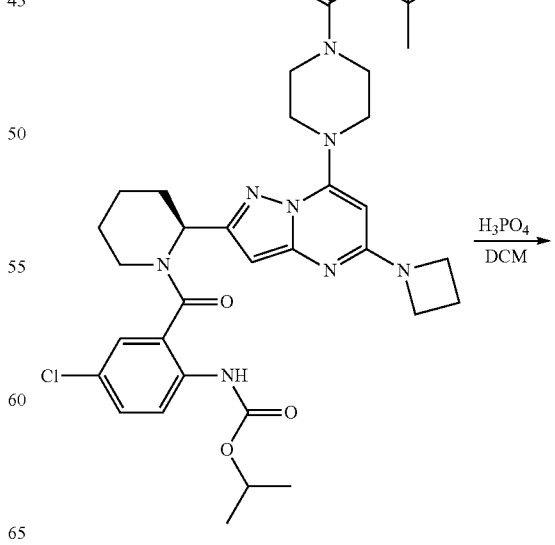

-continued
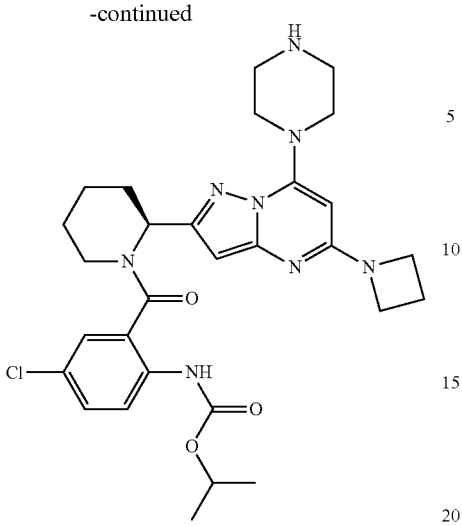
Compound 68 was dissolved in DCM (0.2 mL) and H₃PO₄ (5 μL) was added to the solution. The reaction mixture was stirred at room temperature for 2 h. The solvent was removed under reduced pressure and the residue was purified with prep HPLC (0-100% CH₃CN/H₂O) to afford compound 69 (11 mg, 50%).
LCMS (m/z) 581.26 [M+H]⁺
MW 580.11
Example 185: Preparation of Compound 70
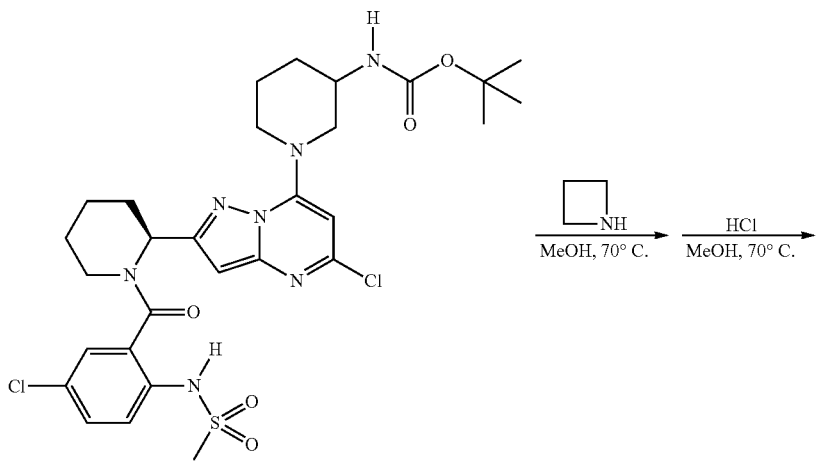
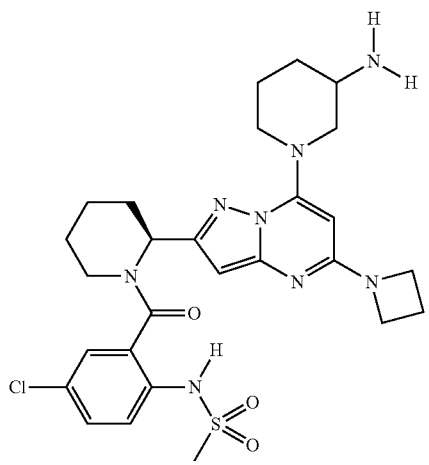

Intermediate 47 (29 mg, 0.04 mmol) was dissolved in MeOH (2 mL), to the solution was added azetidine (0.1 mL). The reaction was heated to 70° C. overnight. Then to the above reaction mixture was added concentrated HCl (0.1 mL) and heated at 70° C. overnight. The reaction was then quenched with NaHCO$_3$ (10 mL) and extracted with EtOAc (20 mL). The organic solvent was removed under reduced pressure and the residue was purified with prep HPLC (0-100% CH$_3$CN/H$_2$O) to afford compound 70 (6 mg, 24%).

LCMS (m/z) 587.20 [M+H]$^+$
MW 586.14

Example 186: Preparation of Compound 71

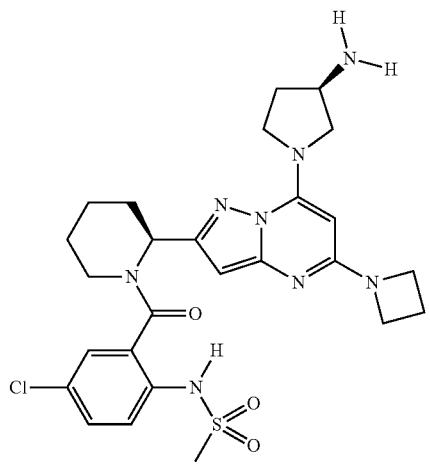 [SMILES: CS(=O)(=O)Nc1ccc(Cl)cc1C(=O)N1CCCC[C@H]1c1cc2nc(N3CCC3)cc(N3CC[C@@H](N)C3)n2n1]

The title compound was prepared in 27% yield according to the general procedure for synthesis of intermediate 47 and compound 70. Thus starting from intermediate 33 the (R)-(+)-3-(Boc-amino)pyrrolidine was installed according to the preparation of intermediate 47 and then the azetidine following the procedure of compound 70 to afford compound 71

LCMS (m/z) 573.31 [M+H]$^+$
MW 572.11

Example 187: Preparation of Compound 72

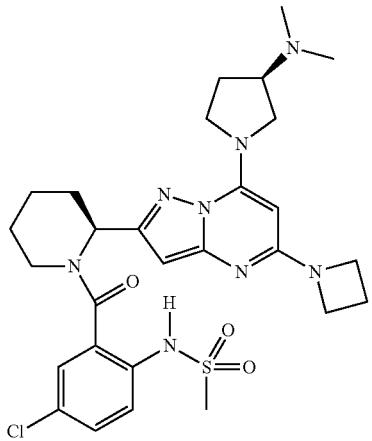 [SMILES: CN(C)[C@@H]1CCN(c2cc(N3CCC3)nc3cc([C@@H]4CCCCN4C(=O)c4cc(Cl)ccc4NS(C)(=O)=O)nn23)C1]

The title compound was prepared in 30% yield according to the general procedure for synthesis of intermediate 47 and compound 70. Thus starting from intermediate 33 the ((R)-(+)-3-(dimethylamino)pyrrolidine was installed according to the preparation of intermediate 47 and then the azetidine following the procedure of compound 70 to afford compound 72

LCMS (m/z) 600.92 [M+H]$^+$
MW 600.16

Example 188: Preparation of Compound 73

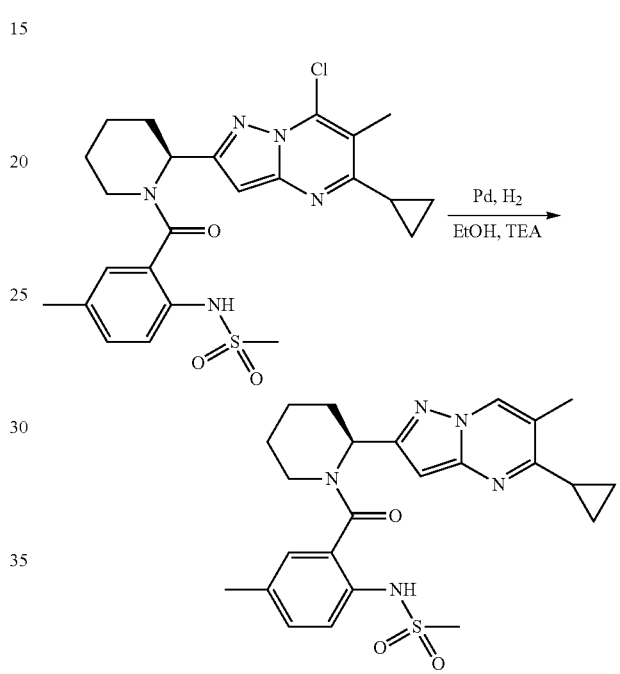

Intermediate 50 (15 mg, 0.03 mmol) was dissolved in EtOH (2 mL). To the solution was added 5% Pd (0.006 mmol) and TEA (17 ul). The reaction was stirred at room temperature for 45 mins. Catalyst was filtered with celite and solvent was concentrated under reduced pressure. The residue was purified with Prep HPLC to yield compound 73 (14 mg, 100%).

LCMS (m/z) 467.75 [M+H]$^+$
MW 466.58

Example 189: Preparation of Compound 74

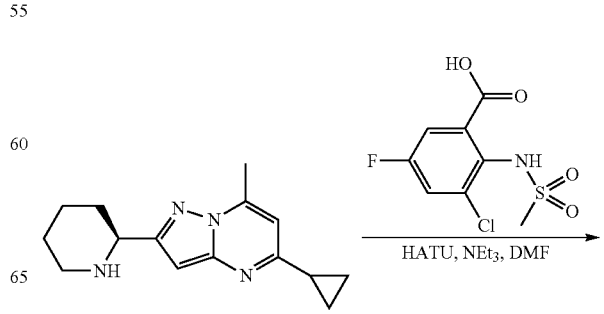

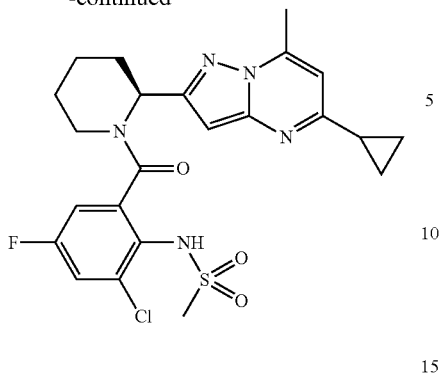

Intermediate 109 (85 mg, 0.32 mmol) and HATU (152 mg, 0.4 mmol) were dissolved in DMF (3 ml). The reaction mixture was stirred at room temperature for 10 mins. To the above solution was added intermediate 26 (50 mg, 0.2 mmol) and NEt₃ (50 μl). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with combi-flash column chromatography (0-100% EtOAc/Hexane) to afford compound 74 (35 mg, 36%).

LCMS (m/z) 506.21 [M+H]⁺

MW 504.99

Example 190: Preparation of Compound 75

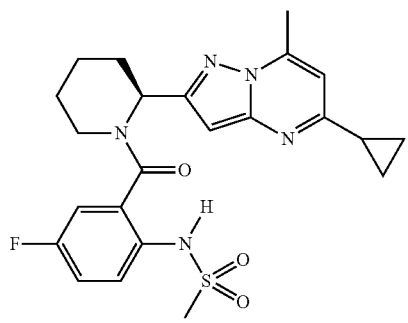 [SMILES: Cc1cc(C2CC2)nc2cc([C@@H]3CCCCN3C(=O)c3cc(F)ccc3NS(C)(=O)=O)nn12]

The title compound was prepared in 16% yield according to the procedure for compound 74 starting from intermediate 26 and 5-fluoro-2-methanesulfonamidobenzoic acid.

LCMS (m/z) 471.68 [M+H]⁺

MW 470.55

Example 191: Preparation of Compound 76

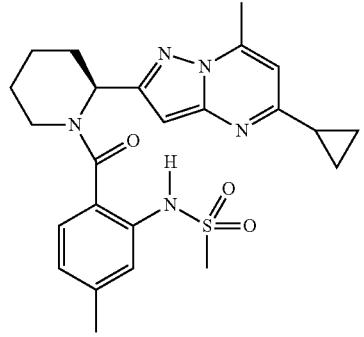 [SMILES: Cc1ccc(C(=O)N2CCCC[C@H]2c2cc3nc(C4CC4)cc(C)n3n2)c(NS(C)(=O)=O)c1]

The title compound was prepared in 32% yield according to the procedure for compound 74 starting from intermediate 26 and 4-methyl-2-methanesulfonamidobenzoic acid.

LCMS (m/z) 467.82 [M+H]⁺

MW 466.58

Example 192: Preparation of Compound 77

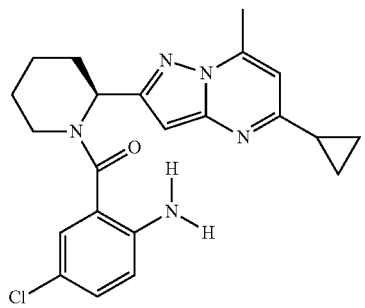 [SMILES: Cc1cc(C2CC2)nc2cc([C@@H]3CCCCN3C(=O)c3cc(Cl)ccc3N)nn12]

The title compound was prepared in 68% yield according to the procedure for compound 74 starting from intermediate 26 and 5-chloro-2-aminobenzoic acid.

LCMS (m/z) 410.10 [M+H]⁺

MW 408.91

Example 193: Preparation of Compound 78

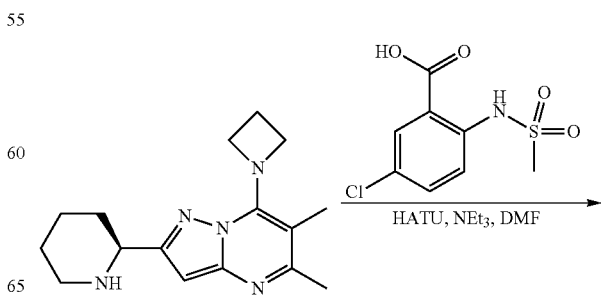

203

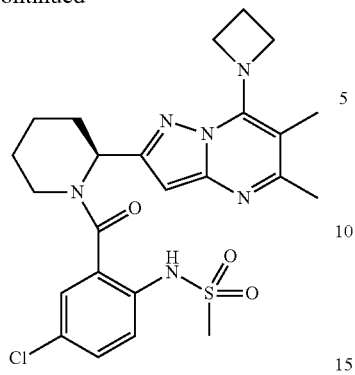

5-Chloro-2-methanesulfonamidobenzoic acid (18 mg, 0.073 mmol) and HATU (32 mg, 0.084 mmol) were dissolved in DMF (3 ml). The reaction mixture was stirred at room temperature for 10 mins. To the above solution was added intermediate 51 (16 mg, 0.056 mmol) and NEt$_3$ (16 µl). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with prep HPLC (0-100% CH$_3$CN/H$_2$O) to afford compound 78 (10 mg, 34%).

LCMS (m/z) 517.17 [M+H]$^+$
MW 516.04

204

Example 194: Preparation of Compound 79

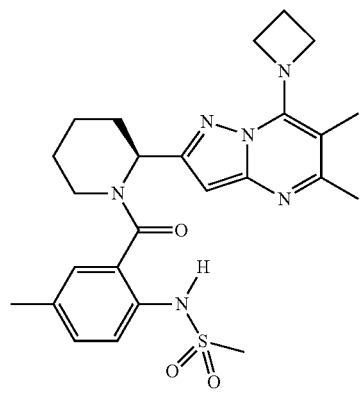

The title compound was prepared in 39% yield according to the procedure for compound 78 starting from intermediate 51 and 5-methyl-2-methanesulfonamidobenzoic acid.

LCMS (m/z) 497.28 [M+H]$^+$
MW 496.62

Example 195: Preparation of Compound 80

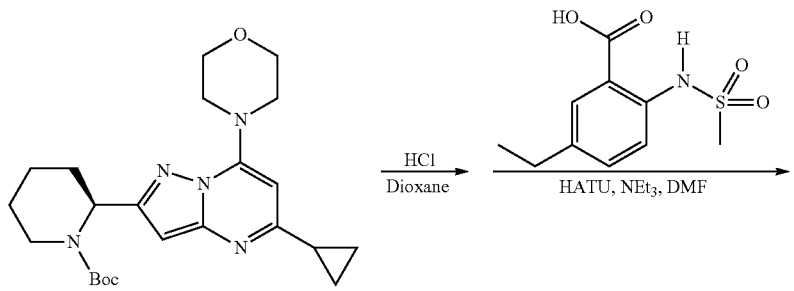

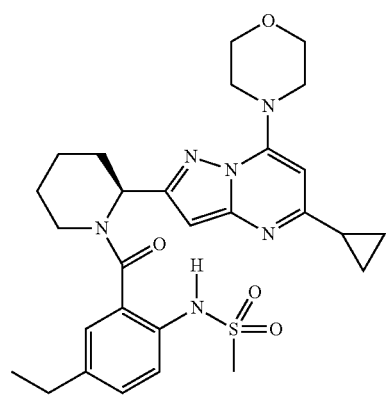

Intermediate 37 (65 mg, 0.13 mmol) was dissolved in 1,4-dioxane (2 mL) and to the solution was added concentrated HCl (0.5 mL). The reaction mixture was stirred at room temperature for 1 h and then the solvent was evaporated. The residue was then added to the DMF solution (3 mL) of 5-ethyl-2-methanesulfonamidobenzoic acid (47 mg, 0.2 mmol) and HATU (95 mg, 0.26 mmol) followed by addition of Net₃ (50 µl). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with combi-flash column chromatography (0-100% EtOAc/Hexane) to afford compound 80 (39 mg, 46%).

LCMS (m/z) 552.94 [M+H]⁺
MW 551.69

Example 196: Preparation of Compound 81

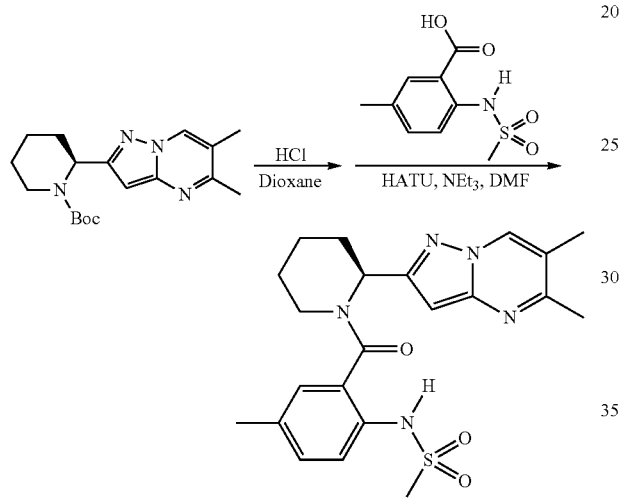

Intermediate 20 (1.08 g, 3.3 mmol) was dissolved in 1,4-dioxane (20 mL) and to the solution was added concentrated HCl (2 mL). The reaction mixture was stirred at room temperature for 1 h and then the solvent was evaporated. The residue was then added to the DMF solution (20 mL) of 5-methyl-2-methanesulfonamidobenzoic acid (1.1 g, 5 mmol) and HATU (2.5 g, 6.6 mmol) followed by addition of NEt₃ (1.4 ml). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with combi-flash column chromatography (0-100% EtOAc/Hexane) to afford compound 81 (652 mg, 45%).

LCMS (m/z) 442.16 [M+H]⁺
MW 441.55

Example 197: Preparation of Compound 82

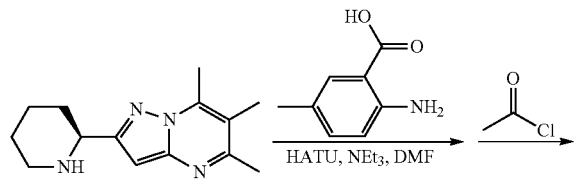

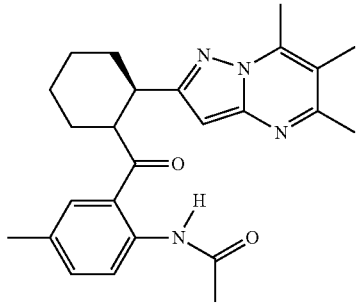

Intermediate 22 added to the DMF solution (2 mL) of 5-methyl-2-aminobenzoic acid (35 mg, 0.19 mmol) and HATU (85 mg, 0.22 mmol) followed by addition of NEt₃ (50 µl). The reaction was stirred at room temperature for 30 mins and was added carbonate resin (50 mg) and was stirred using shaker overnight. Then the resin was filtered and to the filtrate was added acetyl chloride (50 µl). The solvent was evaporated under reduced pressure. The residue was purified with prep HPLC (0-100% CH₃CN/H₂O) to afford compound 82 (54 mg, 59%).

LCMS (m/z) 419.68 [M+H]⁺
MW 418.52

Example 198: Preparation of Compound 83

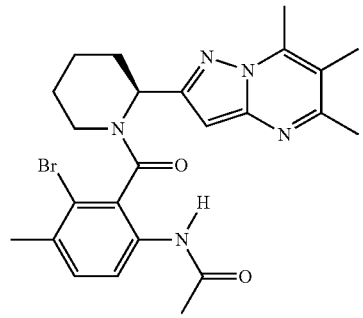

The title compound was prepared in 26% yield according to the procedure for compound 82 starting from intermediate 22 and 2-amino-5-methyl-6-bromobenzoic acid.

LCMS (m/z) 498.35 [M+H]⁺
MW 497.42

Example 199: Preparation of Compound 84

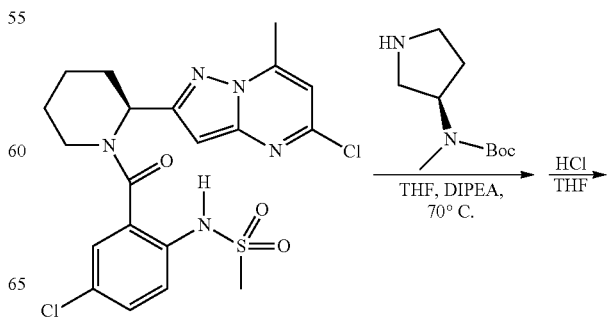

-continued

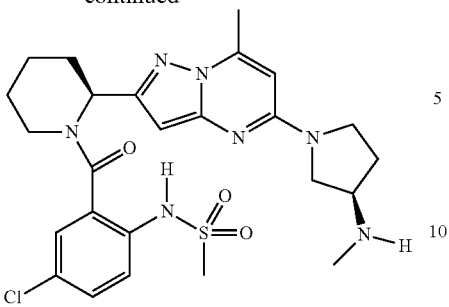

Intermediate 28 (50 mg, 0.1 mmol) was dissolved in THF (2 mL) and to the solution was added (R)-3-N-Boc-N-methylamino-pyrrolidine (200 mg) and DIPEA (0.3 mL). The reaction mixture was heated to 70° C. for 3 h. To the above solution was added concentrated HCl (0.2 mL) and heated at 70° C. for 30 mins. The solvent was removed under reduced pressure and the residue was purified with prep HPLC (0-100% $CH_3CN/H_2O$) to afford compound 84 (20 mg, 35%).

LCMS (m/z) 546.23 [M+H]$^+$
MW 545.08

Example 200: Preparation of Compound 85

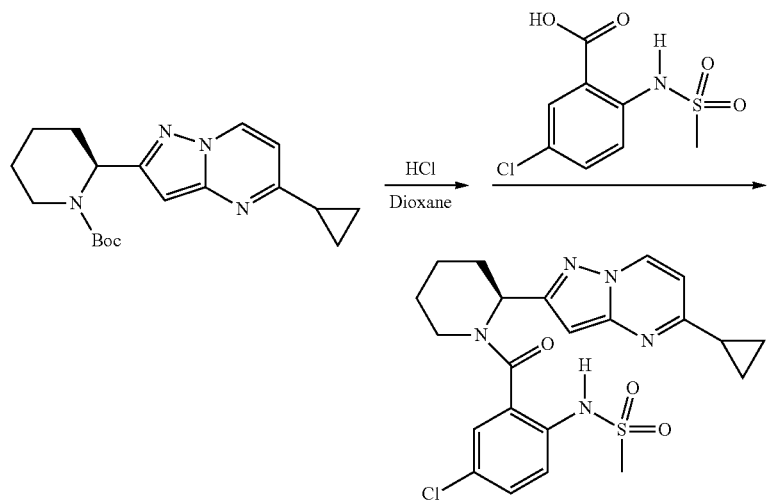

Intermediate 36 (66 mg, 0.16 mmol) was dissolved in 1,4-dioxane (2 mL) and to the solution was added concentrated HCl (0.2 mL). The reaction mixture was stirred at room temperature for 30 mins and then the solvent was evaporated. The residue was then added to the DMF solution (2 mL) of 5-chloro-2-methanesulfonamidobenzoic acid (60 mg, 0.24 mmol) and HATU (122 mg, 0.32 mmol) followed by addition of NEt$_3$ (50 µl). The reaction was stirred at room temperature for 30 mins and was quenched with brine (10 ml) and then extracted with EtOAc (20 ml). The organic layer was washed with brine twice (10 ml) and then was evaporated under reduced pressure. The residue was purified with prep HPLC (0-100% $CH_3CN/H_2O$) to afford compound 85 (39 mg, 52%).

LCMS (m/z) 474.12 [M+H]$^+$
MW 472.98

Example 201: Preparation of Compound 86

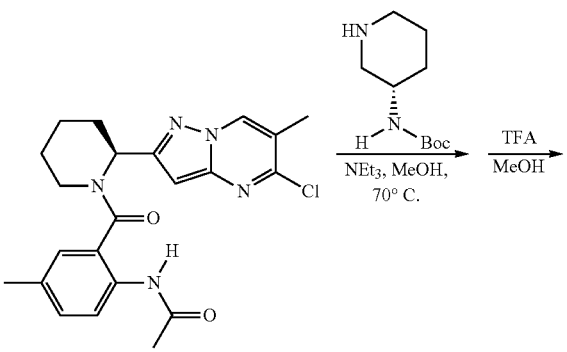

-continued

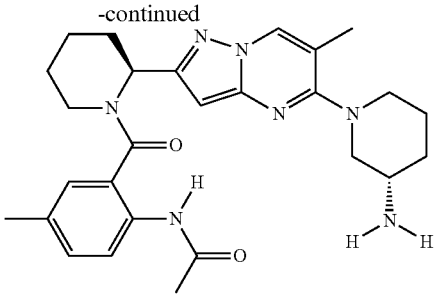

Intermediate 16 (50 mg, 0.11 mmol) was dissolved in MeOH (2 mL) and to the solution was added (S)-3-(Boc-amino)piperidine (65 mg, 0.33 mmol) and Net$_a$ (60 µl). The reaction mixture was heated to 70° C. for 3 h. To the above solution was added TFA (0.2 mL) and stirred at room temperature for 30 mins. The solvent was removed under reduced pressure and the residue was purified with prep HPLC (0-100% CH₃CN/H₂O) to afford compound 86 (10 mg, 18%).

LCMS (m/z) 489.98 [M+H]⁺
MW 488.61

Example 202: Preparation of Compound 87

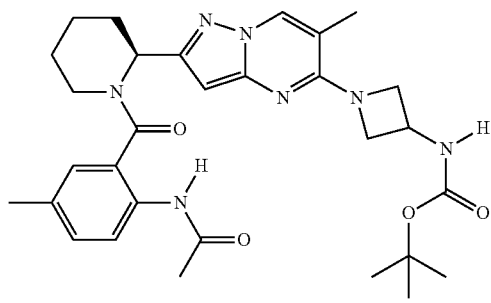 [SMILES: CC(=O)Nc1ccc(C)cc1C(=O)N1CCCC[C@H]1c1cc2nc(N3CC(NC(=O)OC(C)(C)C)C3)c(C)cn2n1]

The title compound was prepared in 56% yield according to the procedure of the second step of Example 154 starting from intermediate 16 and 3-N-Boc-aminoazetidine.

LCMS (m/z) 561.92 [M+H]⁺
MW 560.68

Example 203: Preparation of Compound 88

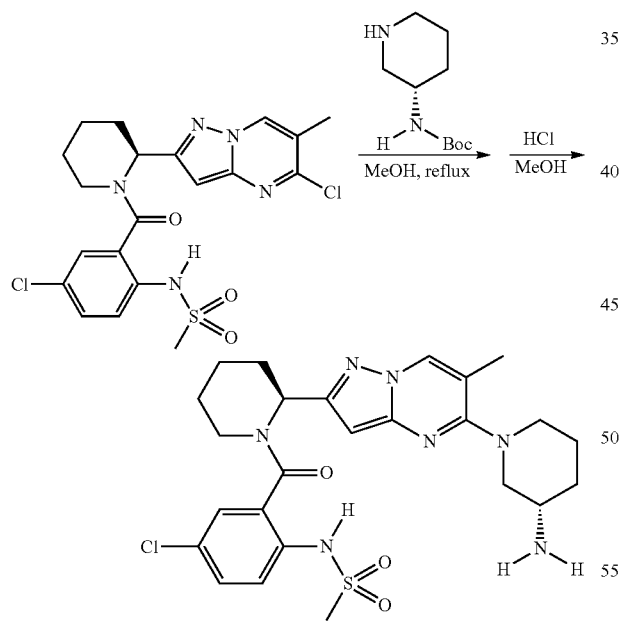

Intermediate 11 (40 mg, 0.083 mmol) was dissolved in MeOH (2 mL) and to the solution was added (S)-3-(Boc-amino)piperidine (166 mg, 0.83 mmol). The reaction mixture was refluxed overnight. To the above solution was added concentrated HCl (0.2 mL) and stirred at room temperature for 30 mins. The solvent was removed under reduced pressure and the residue was purified with prep HPLC (0-100% CH₃CN/H₂O) to afford compound 88 (20 mg, 45%).

LCMS (m/z) 546.21 [M+H]⁺
MW 545.08

Example 204: Preparation of Compound 89

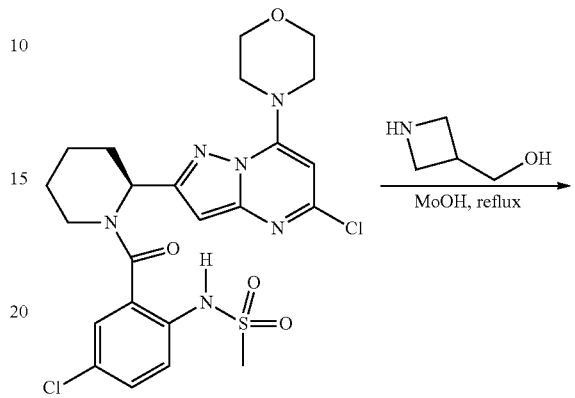

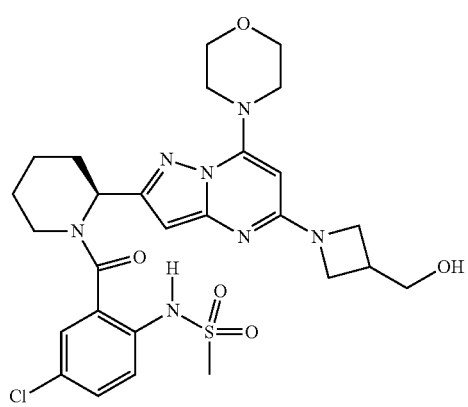

To a solution of intermediate 32 (10.0 mg, 0.018 mmol) in MeOH (1.00 mL) was added 3-hydroxymethylazetidine (20 mg, 0.23 mmol) and triethylamine (55 µl, 0.4 mmol), and the reaction mixture was stirred at 70° C. After 2 h, the reaction mixture was allowed to cool to room temperature and was concentrated under reduced pressure. The crude residue was purified by preparatory HPLC (5-100% MeCN/H₂O) to afford compound 89 (10 mg, 91%) as a white solid.

LCMS (m/z) 604.35 [M+H]⁺
MW 603.12

Example 205: Preparation of Compound 90

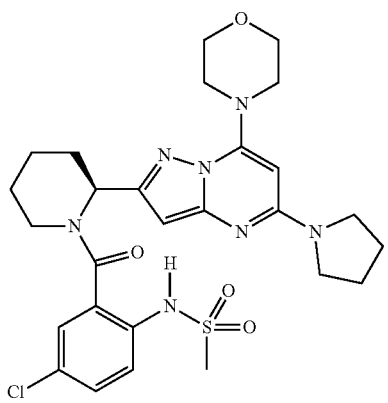 [SMILES: CS(=O)(=O)Nc1ccc(Cl)cc1C(=O)N1CCCC[C@H]1c1cc2nc(N3CCCC3)cc(N3CCOCC3)n2n1]

The title compound was prepared in 92% yield according to the procedure for compound 89 starting from intermediate 32 and pyrrolidine.

LCMS (m/z) 588.31 [M+H]$^+$
MW 587.12

Example 206: Preparation of Compound 91

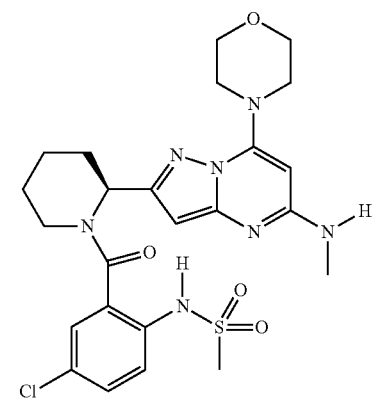 [SMILES: CNc1cc(N2CCOCC2)n2nc([C@@H]3CCCCN3C(=O)c3cc(Cl)ccc3NS(C)(=O)=O)cc2n1]

The title compound was prepared in 31% yield according to the procedure for compound 89 starting from intermediate 32 and methylamine.

LCMS (m/z) 548.16 [M+H]$^+$
MW 547.06

Example 207: Preparation of Compound 92

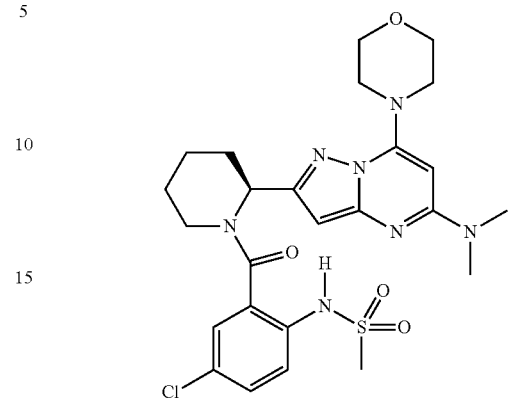

The title compound was prepared in 57% yield according to the procedure for compound 89 starting from intermediate 32 and dimethylamine.

LCMS (m/z) 562.14 [M+H]$^+$
MW 561.08

Example 208: Preparation of Compound 93

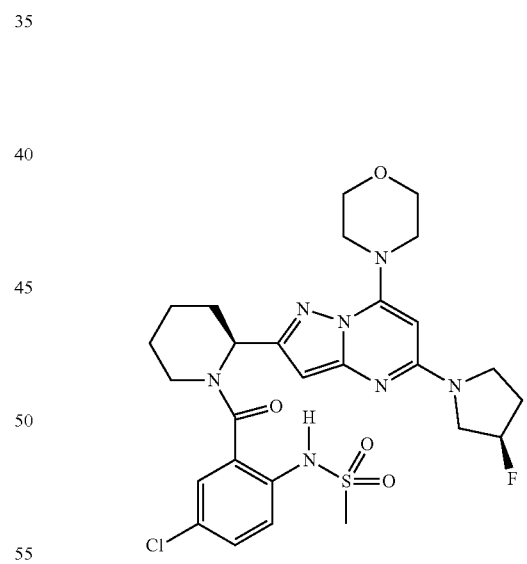

The title compound was prepared in 50% yield according to the procedure for compound 89 starting from intermediate 32 and (R)-(−)-3-fluoropyrrolidine.

LCMS (m/z) 606.21 [M+H]$^+$
MW 605.11

Example 209: Preparation of Compound 94

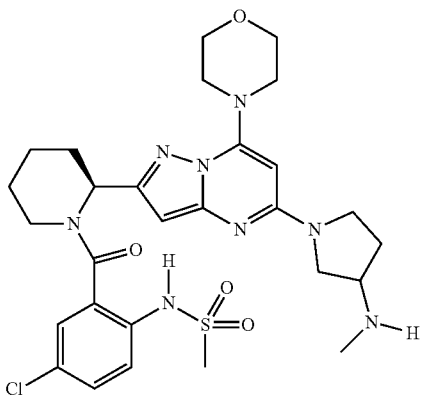 [SMILES: CNC1CCN(c2cc(N3CCOCC3)n3nc([C@@H]4CCCCN4C(=O)c4cc(Cl)ccc4NS(C)(=O)=O)cc3n2)C1]

The title compound was prepared in 27% yield according to the procedure for compound 88 starting from intermediate 32 and 3-N-Boc-3-N-methylamino-pyrrolidine.

LCMS (m/z) 617.25 [M+H]+

MW 616.23

Example 210: Preparation of Compound 95

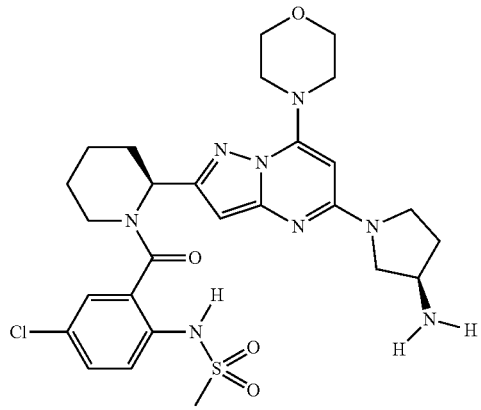 [SMILES: CS(=O)(=O)Nc1ccc(Cl)cc1C(=O)N1CCCC[C@H]1c1cc2nc(N3CC[C@@H](N)C3)cc(N3CCOCC3)n2n1]

The title compound was prepared in 21% yield according to the procedure for compound 88 starting from intermediate 32 and (R)-(−)-3-N-Boc-amino-pyrrolidine.

LCMS (m/z) 603.21 [M+H]+

MW 602.14

Example 211: Preparation of Compound 96

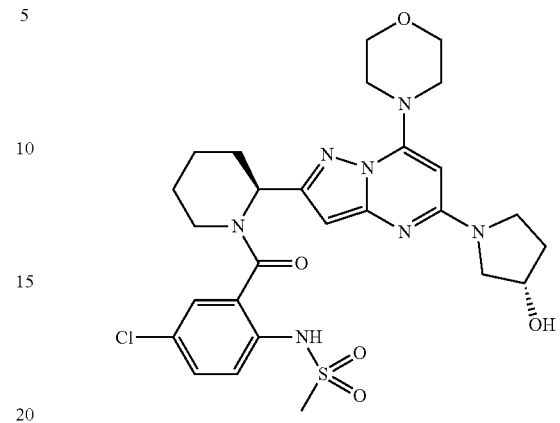

The title compound was prepared in 50% yield according to the procedure for compound 89 starting from intermediate 32 and (S)-(−)-3-hydroxypyrrolidine.

LCMS (m/z) 604.23 [M+H]+

MW 603.12

Example 212: Preparation of Compound 97

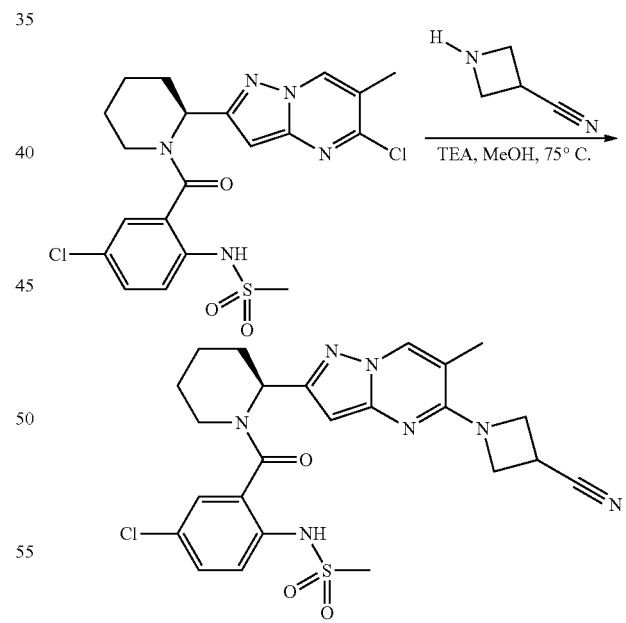

Following the procedure of the second step of Example 154, beginning with intermediate 11 (67 mg, 0.139 mmol) and azetidine-3-carbonitrile (57 mg, 0.695 mmol), compound 97 (10 mg, 14%) was synthesized.

LCMS m/z [M+H]+ $C_{24}H_{26}ClN_7O_3S$ requires: 528.15. Found 528.15.

HPLC Tr (min), purity %: 6.87, 99%.

Example 213: Preparation of Compound 98

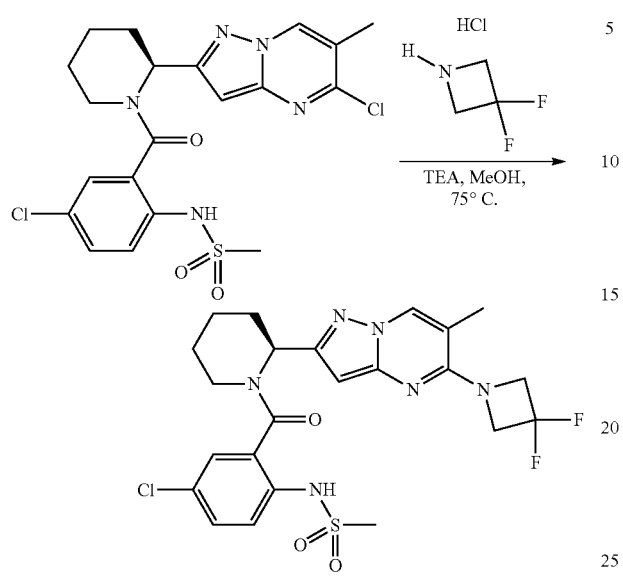

Following the procedure of the second step of Example 154, beginning with intermediate 11 (60 mg, 0.124 mmol) and 3,3-difluoroazetidine hydrochloride (80 mg, 0.618 mmol), compound 98 (21 mg, 31%) was synthesized.

LCMS m/z [M+H]$^+$ $C_{23}H_{25}ClF_2N_6O_3S$ requires: 539.14. Found 517.06.

HPLC Tr (min), purity %: 7.62, 99%.

Example 214: Preparation of Compound 99

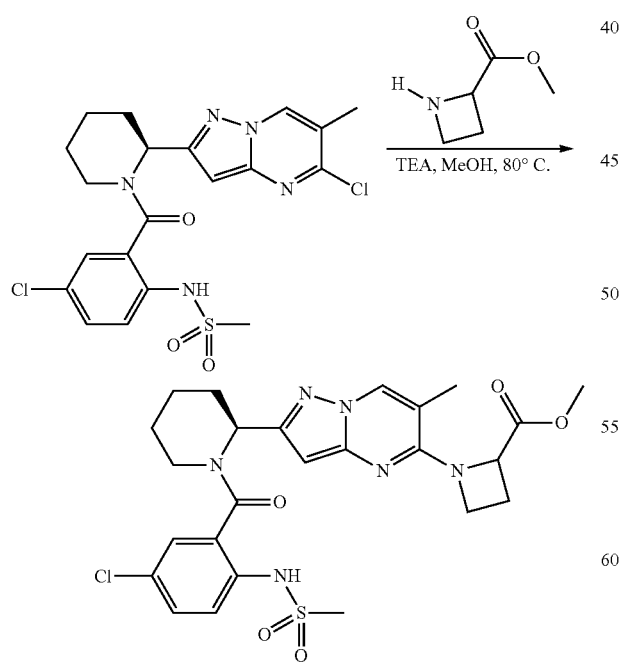

Following the procedure of the second step of Example 154, beginning with intermediate 11 (80 mg, 0.124 mmol) and methyl azetidine-2-carboxylate (98 mg, 0.646 mmol) and heating at 80° C., compound 99 (38 mg, 40%) was synthesized as a mixture of diastereomers.

LCMS m/z [M+H]$^+$ $C_{25}H_{29}ClN_6O_5S$ requires: 561.16. Found 561.37.

HPLC Tr (min), purity %: 7.04, 86%.

Example 215: Preparation of Compound 100

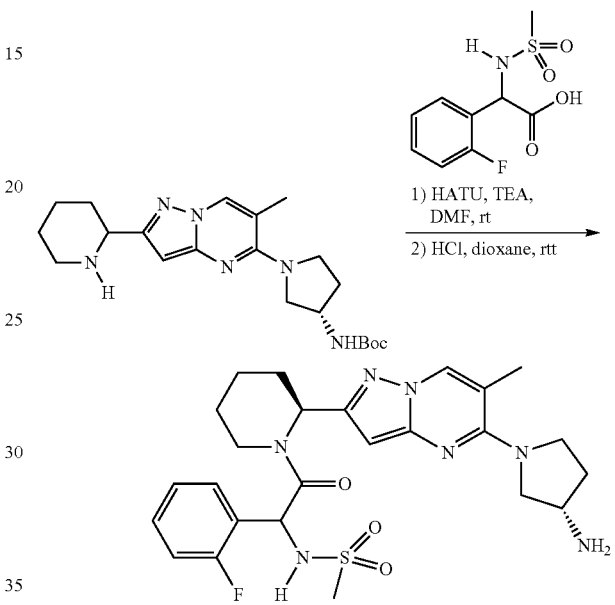

Following the synthesis of compound 27, beginning with intermediate 116 (66 mg, 0.27 mmol) and intermediate 12 (28 mg, 0.07 mmol) and Boc-deprotection with HCl in step 2, compound 100 (10 mg, 25% over two steps) was synthesized (~1:1 mixture of diastereomers).

LCMS m/z [M+H]$^+$ $C_{25}H_{32}FN_7O_3S$ requires: 530.23. Found 530.42.

HPLC Tr (min), purity %: 4.74, 96%.

Example 216: Preparation of Compound 101

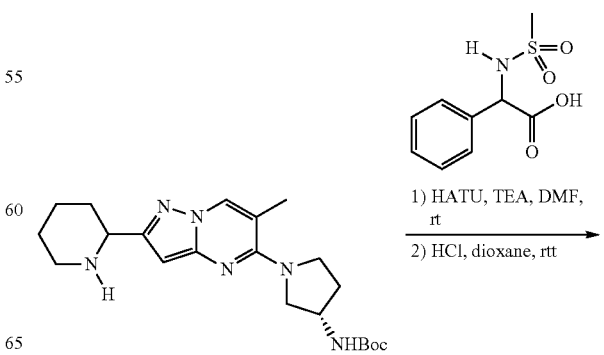

217

-continued

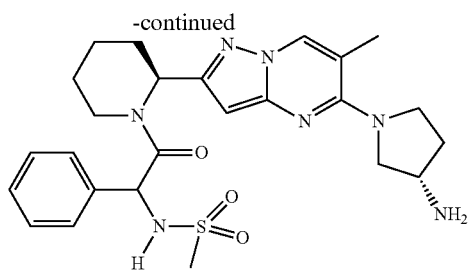

Following the synthesis of compound 27, beginning with 2-(methylsulfonamido)-2-phenylacetic acid (90 mg, 0.39 mmol) and intermediate 12 (60 mg, 0.15 mmol) and Boc-deprotection with HCl in step 2, compound 101 (8 mg, 10% over two steps) was synthesized (~1:1 mixture of diastereomers).

LCMS m/z [M+H]$^+$ C$_{25}$H$_{33}$N$_7$O$_3$S requires: 512.24. Found 512.15.

HPLC Tr (min), purity %: 4.72, 97%.

Example 217: Preparation of Compound 102

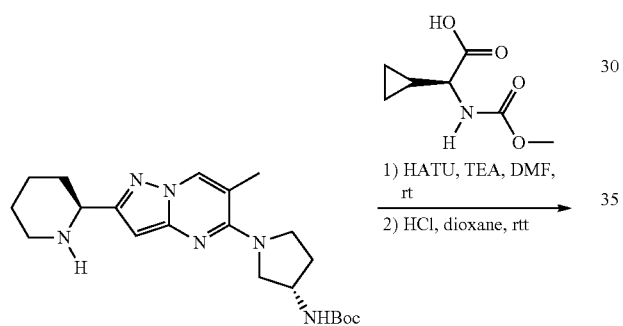

Following the synthesis of compound 27, beginning with (S)-2-cyclopropyl-2-(methoxycarbonylamino)acetic acid (42 mg, 0.243 mmol) and intermediate 12 (75 mg, 0.188 mmol) and Boc-deprotection with HCl in step 2, compound 102 (18 mg, 20% over two steps) was synthesized.

LCMS m/z [M+H]$^+$ C$_{23}$H$_{33}$N$_7$O$_3$ requires: 456.26. Found 546.32.

HPLC Tr (min), purity %: 4.36, 99%.

218

Example 218: Preparation of Compound 103

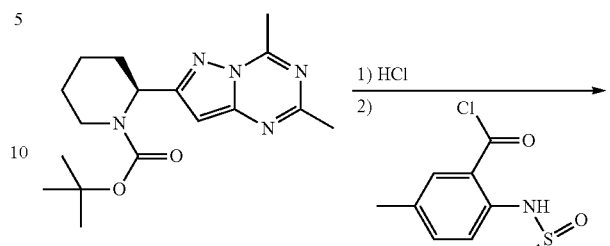

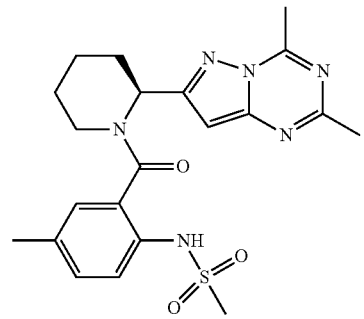

Intermediate 56 (16 mg, 0.048 mmol) was dissolved in methanol (1 mL). HCl (4N in dioxane, 1 mL, 4 mmol) was added and reaction mixture was stirred for 30 minutes. After concentrating under reduced pressure, residue was mixed with anhydrous DCM (2 mL) and TEA (0.020 mL, 0.144 mol) and intermediate 102 (12 mg, 0.048 mmol) was added. After 30 minutes, triethylamine was added (0.020 mL, 0.144 mmol). After 30 minutes, additional methanol was added and then mixture was concentrated under reduced pressure. Purification via prep HPLC (5-95% acetonitrile in water) gave compound 103 (12 mg, 56%).

$^1$H NMR (400 MHz, CD$_3$OD): δ 7.40-7.25 (m, 3H), 6.55-6.45 (m, 1H), 6.21 (m, 1H), 2.95 (m, 7H), 2.60 (s, 3H), 2.45-2.34 (m, 5H), 2.11 (m, 1H), 1.75-1.55 (m, 4H).

LC/MS (m/z): 443.2 [M+H]$^+$

Example 219: Preparation of Compound 104

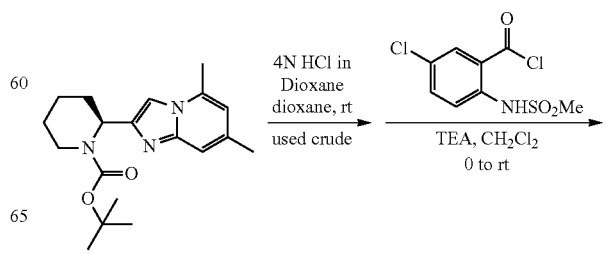

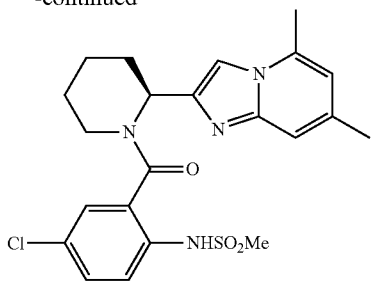

A solution of hydrogen chloride in dioxane (4N, 0.25 mL, 1.0 mmol) was added to a solution of intermediate 59 (5.8 mg, 0.0176 mmol) in 1 mL of dioxane. After stirring overnight, LC/MS indicated full removal of Boc group. Reaction mixture was concentrated under reduced pressure and dried in-vacuo for two hours. To a solution of the resulting residue dissolved in 2 mL of anhydrous $CH_2Cl_2$ was added intermediate 120 (5-chloro-2-(methylsulfonamido)benzoyl chloride) (5.1 mg, 0.020 mmol). After cooling to 0° C., triethylamine (7.0 µL, 0.049 mmol) was added, and resulting mixture was warmed to room temperature and stirred overnight. Reaction mixture was concentrated under reduced pressure and purified by prep HPLC (15-100% Acetonitrile (with 0.1% trifluoroacetic acid) in water (with 0.1% trifluoroacetic acid)) to yield compound 104 (3 mg, 37%) as a yellow solid, trifluoroacetic acid salt, after lyophilization.

LCMS m/z [M+H]$^+$ $C_{22}H_{25}ClN_4O_3S$ requires: 461.13. Found 461.31.

$^1$H-NMR (DMSO, 400 MHz): δ 7.76 (s, 1H), 7.58 (m, 1H), 7.43-7.31 (m, 3H), 6.93 (s, 1H), 6.20 (s, 1H), 3.65 (s, 1H), 3.16 (s, 3H), 3.14 (m, 1H), 2.71 (s, 3H), 2.52 (s, 3H), 2.50 (m, 1H), 2.11 (m, 1H), 1.87 (m, 1H), 1.71-1.45 (m, 4H).

HPLC Tr (min), purity %: 5.15, 99%

Example 220: Preparation of Compound 105

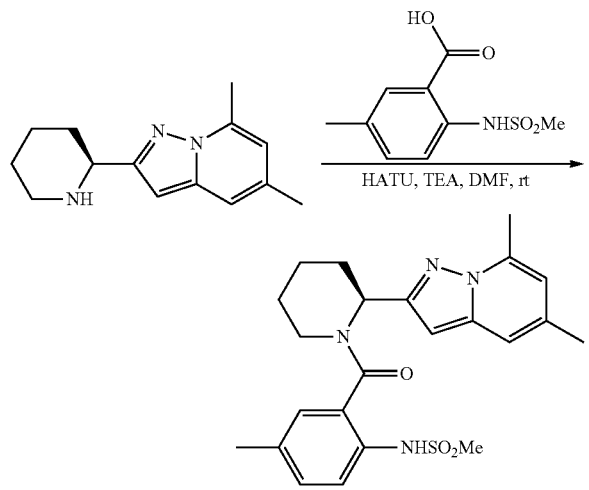

HATU (0.225 mg, 1.49 mmol) was added to a suspension of 5-methyl-2-(methylsulfonamido)benzoic acid (0.15 g, 0.65 mmol) in DMF (2 mL). The suspension was stirred for 30 minutes at room temperature. Intermediate 63 (0.125 g, 0.54 mmol) was dissolved in DMF (2 mL) and triethylamine (0.1 mL, 9.88 mmol) was added. To this, was added the DMF solution of 5-methyl-2-(methylsulfonamido)benzoic acid and HATU. After stirring for 2 h at room temperature, volatiles were removed under reduced pressure and the residue was dissolved in MeCN/water and purified by preparatory HPLC (5-95% $H_2O$/MeCN, 0.1% TFA) to afford compound 105 as a colorless powder (0.134 g, 57%).

$^1$H-NMR (DMSO-$d_6$, 400 MHz): δ 8.95 (s, 1H), 7.31-7.19 (m, 3H), 6.61 (s, 1H0, 6.51 (s, 1H), 6.40 (s, 1H), 6.04 (s, 1H), 4.90 (s, 0.5H), 4.46 (s, 0.5H), 4.22-3.33 (m, 3H), 3.18 (m, 0.5H), 3.04 (m, 1H), 2.99 (s, 3H), 2.63 (s, 3H), 2.48 (s, 3H), 2.19-1.29 (4H)

LCMS m/z [M+H]$^+$ 441.14

HPLC Tr (min), purity %: 2.48, 98%

Example 221: Preparation of Compound 106

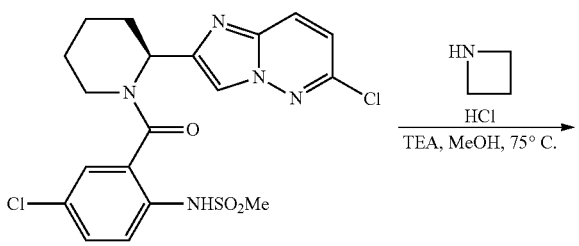

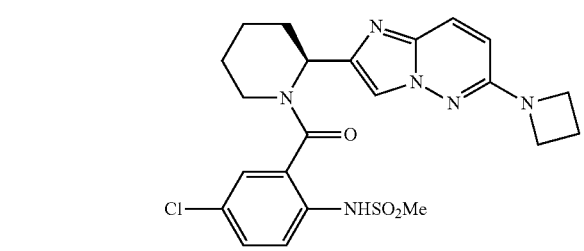

Triethylamine (0.050 mL, 0.363 mmol) was added to a mixture of intermediate 65 (11.2 mg, 0.024 mmol) and azetidine hydrochloride (14 mg, 0.150 mmol) in 2 mL of anhydrous methanol. Mixture was heated at 75° C. overnight. After cooling to room temperature, reaction mixture was concentrated under reduced pressure and residue was purified by prep HPLC (15-100% Acetonitrile (with 0.1% trifluoroacetic acid) in water (with 0.1% trifluoroacetic acid)) to yield compound 106 (5.8 mg, 40%) as a solid, trifluoroacetic acid salt, after lyophilization.

LCMS m/z [M+H]$^+$ $C_{22}H_{25}ClN_6O_3S$ requires: 489.14. Found 489.05.

$^1$H-NMR (DMSO, 400 MHz): δ 9.19 (s, 1H), 8.66 (m, 1H), 7.55-7.36 (m, 3H), 6.32 (s, 1H), 5.98 (m, 1H), 3.88 (m, 2H), 3.57 (m, 1H), 3.22 (m, 2H), 3.04 (s, 3H), 2.89 (t, J=12.4 Hz, 2H), 2.37 (m, 1H), 2.06-1.82 (m, 2H), 1.74-1.41 (m, 4H).

HPLC Tr (min), purity %: 5.49, 85%

Example 222: Preparation of Compound 107

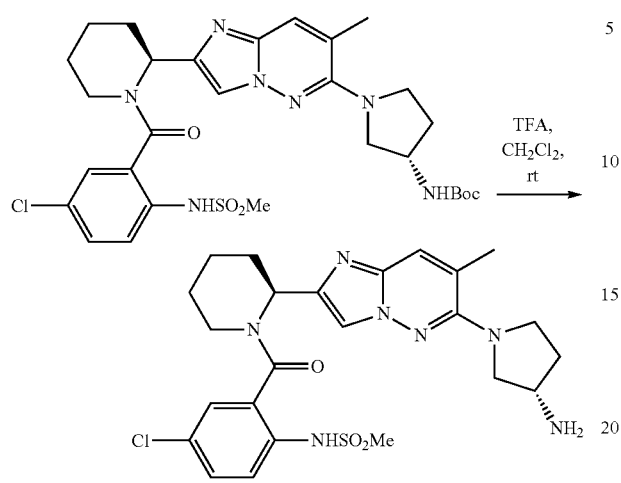

Trifluoroacetic acid (0.45 mL, 5.78 mmol) was added to a solution of intermediate 68 (65 mg, 0.10 mmol) in 6 mL of dichloromethane at room temperature. After 150 minutes, the reaction mixture was concentrated under reduced pressure and dried in-vacuo for twenty four hours to yield compound 107 (66 mg, 99%) as a brown solid, trifluoroacetic acid salt.

LCMS m/z [M+H]$^+$ C$_{24}$H$_{30}$ClN$_7$O$_3$S requires: 532.18. Found 532.01.

$^1$H-NMR (DMSO, 400 MHz): δ 10.1 (s, 1H), 8.05 (s, 3H), 7.85 (s, 1H), 7.61-7.40 (m, 3H), 5.99 (m, 1H), 4.76 (m, 1H), 4.30-3.45 (m, 3H), 3.18 (m, 1H), 2.99 (s, 3H), 2.41 (s, 3H), 2.37-2.17 (m, 3H), 2.04-1.82 (m, 3H), 1.71-1.21 (m, 5H).

HPLC Tr (min), purity %: 4.37, 97%

Example 223: Preparation of Compound 108

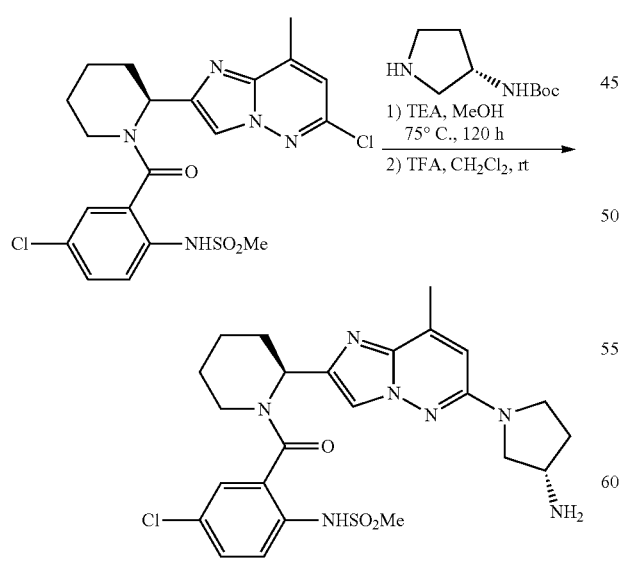

A mixture of intermediate 72 (5.8 mg, 0.012 mmol) and (S)-tert-butyl pyrrolidin-3-ylcarbamate (73 mg, 0.28 mmol) and triethylamine (0.030 mL, 0.21 mmol) in 2.5 mL of methanol was heated at 75° C. for 120 hours. LC/MS analysis showed ~12% conversion to desired product, inseparable from intermediate 72. The reaction mixture was concentrated under reduced pressure to yield a residue that was dissolved in 2 mL of CH$_2$Cl$_2$ and trifluoroacetic acid (0.100 mL, 1.30 mmol) was added. After 1 hour, the reaction mixture was concentrated under reduced pressure and residue was purified by prep HPLC (15-100% Acetonitrile (with 0.1% trifluoroacetic acid) in water (with 0.1% trifluoroacetic acid)) to yield compound 108 (0.8 mg, 10%) as a yellow film, trifluoroacetic acid salt, after lyophilization.

LCMS m/z [M+H]$^+$ C$_{24}$H$_{30}$ClN$_7$O$_3$S requires: 532.18. Found 532.02.

HPLC Tr (min), purity %: 4.33, 99%

Example 224: Preparation of Compound 109

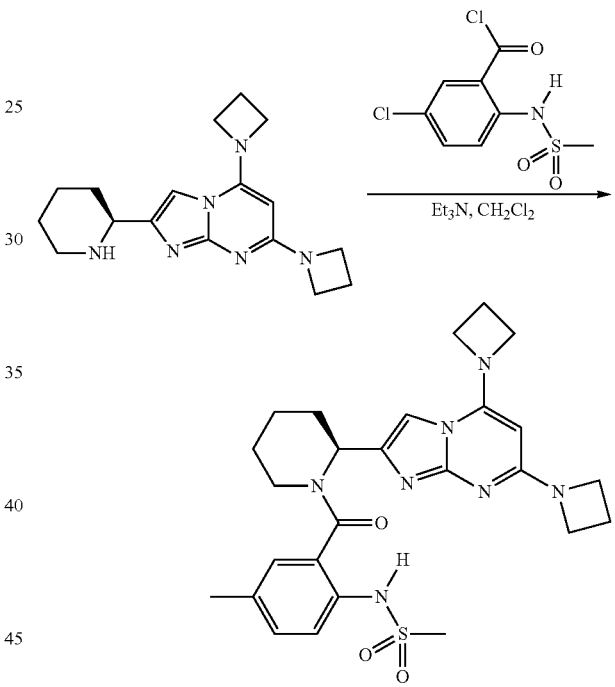

To a solution of intermediate 77 (20 mg, 0.06 mmol) and triethylamine (25 μl, 0.18 mmol) in dichloromethane (0.5 mL) was added intermediate 120 (5-chloro-2-(methylsulfonamido)benzoyl chloride) (16 mg, 0.06 mmol) at room temperature under an argon atmosphere. After 2 h, the reaction mixture was directly purified via SiO$_2$ column chromatography (4 g SiO$_2$ Combiflash HP Gold Column, 0-100% ethyl acetate/hexanes) to afford compound 109 (8.2 mg, 25%) as a colorless solid.

$^1$H NMR (CD$_3$OD, 400 MHz): δ 7.53-7.47 (m, 1H), 7.46-7.39 (m, 3H), 5.85 (s, 1H), 4.39-4.25 (m, 5H), 4.10 (t, J=7.8 Hz, 4H), 3.09 (s, 3H), 2.47 (quint, J=7.7 Hz, 2H), 2.39 (quint, J=7.5 Hz, 2H), 2.05-1.87 (m, 1H), 1.78-1.53 (m, 3H), 1.46-1.24 (m, 4H)

HPLC t$_R$ (min), purity %: 3.55, 85%.

LCMS (ESI) m/z 545.19 [M+H]$^+$, t$_R$=1.97 min.

R$_f$=0.50 (5% methanol/dichloromethane).

Example 225: Preparation of Compound 110

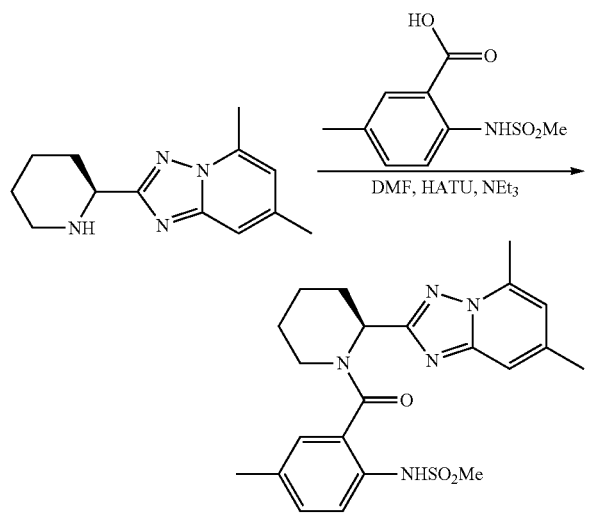

HATU (23 mg, 0.06 mmol) and 5-methyl-2-(methylsulfonamide)benzoic acid (11 mg, 0.05 mmol) were dissolved in anhydrous DMF (1 mL). After activation for 1 hour, intermediate 80 (7 mg, 0.03 mmol) and triethylamine (0.1 mL, 0.72 mmol) were added. The reaction was stirred under nitrogen for 2 hours. Solvents were removed under reduced pressure. The residue was purified with prep HPLC (0-100% acetonitrile in water) to provide compound 110 (2 mg, 15%).

$^1$H-NMR (CD$_3$OD, 400 MHz): δ 7.61 (s, 1H), 7.46 (bs, 1H), 7.34 (d, J=12 Hz, 1H), 7.22-7.19 (m, 1H), 6.80 (bs, 1H), 6.10 (bs, 1H), 2.89-2.81 (m, 2H), 2.65 (s, 3H), 2.37 (s, 3H), 2.29 (s, 3H), 1.93 (bs, 1H), 1.67-1.64 (m, 3H), 1.46 (bs, 2H), 1.19 (s, 3H).

LCMS m/z [M+H]$^+$ C$_{22}$H$_{27}$N$_5$O$_3$S requires: 442.55. Found 442.13

HPLC Tr (min), purity %: 3.35, 98%

Example 226: Preparation of Compound 111

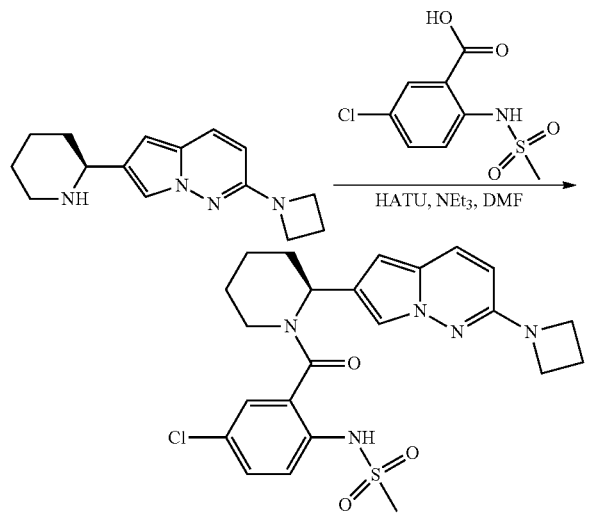

HATU (9.5 mg, 0.038 mmol) and 5-chloro-2-(methylsulfonamide)benzoic acid (7.8 mg, 0.03 mmol) were dissolved in anhydrous DMF (1 mL). After activation for 1 hour, intermediate 83 (5 mg, 0.019 mmol) and triethylamine (0.1 mL, 0.718 mmol) were added. The reaction was stirred under nitrogen for 2 hours. Solvents were removed by reduced pressure and the residue was purified with prep HPLC (0-100% acetonitrile in water) to provide compound 111 (3 mg, 32%).

$^1$H-NMR (CD$_3$OD, 400 MHz): δ 7.94 (d, J=1.8 Hz, 1H), 7.47 (d, J=6.6 Hz, 2H), 7.42-7.36 (m, 2H), 7.30-7.26 (m, 2H), 5.99 (d, J=7.2 Hz, 1H), 3.94 (t, J=5.4 Hz, 4H), 2.96-2.95 (m, 3H), 2.85 (s, 3H), 2.30 (quintet, J=5.7 Hz, 2H), 2.29 (s, 3H), 2.09-1.98 (m, 2H), 1.59-1.48 (m, 4H)

LCMS m/z [M+H]$^+$ C$_{23}$H$_{26}$ClN$_5$O$_3$S requires: 488.00. Found 488.00

HPLC Tr (min), purity %: 2.32, 98%.

Example 227: Preparation of Compound 112

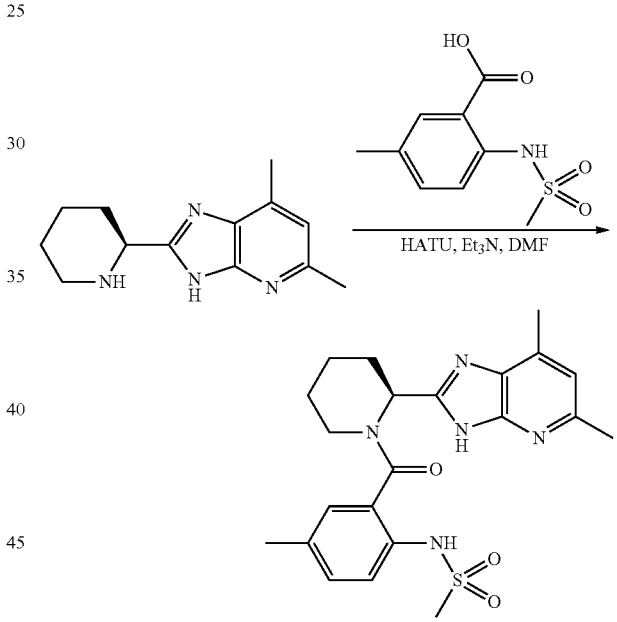

HATU (32 mg, 0.084 mmol) and 5-methyl-2-(methylsulfonamide)benzoic acid (15.5 mg, 0.068 mmol) were dissolved in anhydrous DMF (2 mL). After activation for 1 hour, intermediate 85 (15 mg, 0.056 mmol) and triethylamine (0.1 mL, 0.718 mmol) were added. The reaction mixture was stirred under nitrogen for 2 hours. Solvents were removed by under reduced pressure and the residue was purified with prep HPLC (0-100% acetonitrile in water) to provide compound 112 (16 mg, 57%).

$^1$H-NMR (CD$_3$OD, 400 MHz): δ 7.60 (d, J=6.0 Hz, 1H), 7.31-7.26 (m, 1H), 7.23-7.09 (m, 2H), 6.33 (bs, 1H), 3.54-3.51 (m, 2H), 3.16-3.12 (m, 2H), 2.99 (s, 3H), 2.77 (s, 3H), 2.38 (s, 3H), 2.32 (s, 3H), 1.88 (bs, 2H), 1.55 (bs, 2H).

LCMS m/z [M+H]$^+$ C$_{22}$H$_{27}$N$_5$O$_3$S requires: 442.18. Found 442.12

HPLC Tr (min), purity %: 2.26, 98%.

Example 228: Preparation of Compound 113

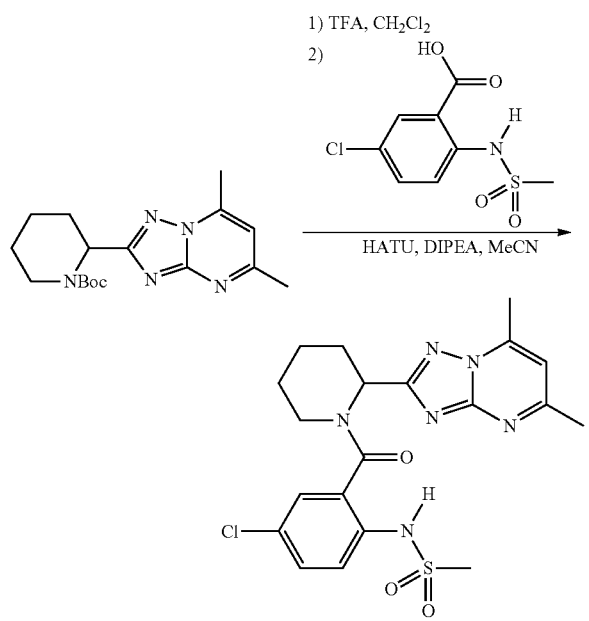

To a solution of intermediate 86 (67 mg, 0.20 mmol) in dichloromethane (2 mL) was added trifluoroacetic acid (2 mL) at room temperature. After 1 h, the resulting mixture was concentrated under reduced pressure. To the residue was added 5-chloro-2-(methylsulfonamido)benzoic acid (54.9 mg, 0.22 mmol), HATU (83.7 mg, 0.22 mmol) followed by acetonitrile (1 mL) and diisopropylethylamine (139 µl, 0.80 mmol), and the resulting mixture was stirred at room temperature. After 16 h, the reaction mixture was partitioned between ethyl acetate (50 mL) and saturated aqueous sodium bicarbonate solution (50 mL). The phases were separated, and the organic layer was washed with saturated sodium chloride solution (2×50 mL). The organic layer was dried over $Na_2SO_4$, and was concentrated under reduced pressure. The crude residue was purified by preparatory HPLC (5-100% $MeCN/H_2O$, 0.1% trifluoroacetic acid modifier) to afford compound 113 (25.8 mg, 28%) as a tan solid.

LCMS (ESI) m/z 463.10 [M+H]$^+$, $t_R$=2.35 min.
$^1$H NMR (CD$_3$OD, 400 MHz): δ 7.71-7.32 (m, 3H), 7.11 (s, 1H), 6.18 (s, 1H), 3.59-3.37 (m, 2H), 3.07 (s, 3H), 2.84 (s, 3H), 2.65 (s, 3H), 2.15-2.01 (m, 1H), 1.84-1.37 (m, 5H).
HPLC $t_R$ (min), purity %: 4.03, 95%.
$R_f$=0.55 (ethyl acetate).

Example 229: Preparation of Compound 114

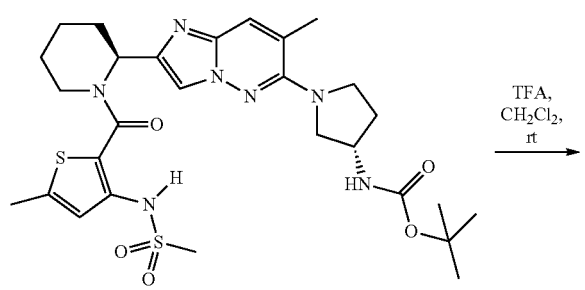

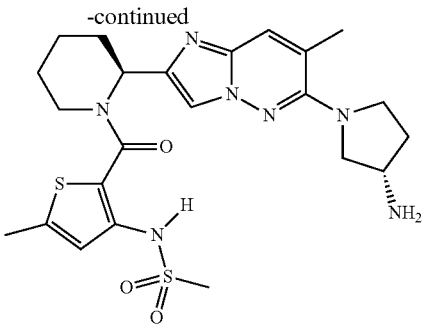

Following the procedure for synthesis of compound 107, but beginning with intermediate 88 (21 mg, 0.034 mmol), compound 114 (20 mg, 99%) was recovered as a light yellow film, trifluoroacetic acid salt.

LCMS m/z [M+H]$^+$ $C_{23}H_{31}N_7O_3S_2$ requires: 518.19. Found 518.19.

$^1$H-NMR (DMSO, 400 MHz): δ 10.4 (s, 1H), 8.01 (s, 3H), 7.94 (m, 1H), 7.73 (s, 1H), 6.89 (s, 1H), 6.51 (br s, 2H), 3.89 (m, 2H), 3.68 (m, 3H), 3.07 (s, 3H), 2.65 (m, 1H), 2.42 (s, 3H), 2.40 (s, 3H), 2.35-2.21 (m, 3H), 1.97 (m, 1H), 1.85 (m, 1H), 1.68-1.38 (m, 3H).

HPLC Tr (min), purity %: 4.36, 98%

Example 230: Preparation of Compound 115

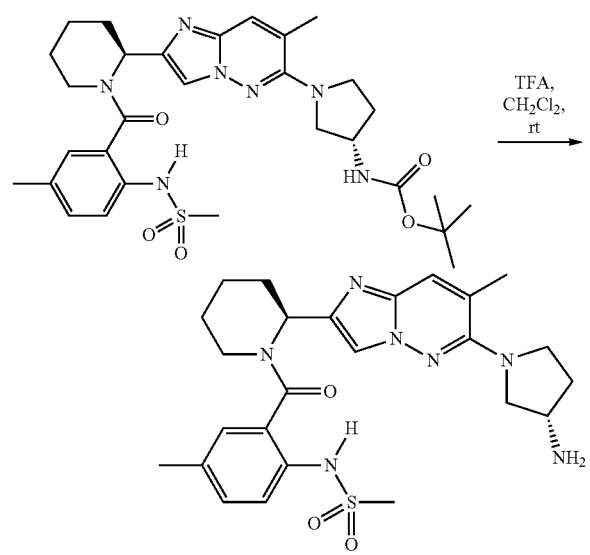

Following the procedure for synthesis of compound 107, but beginning with intermediate 117 (30 mg, 0.049 mmol), compound 115 (27 mg, 88%) was recovered as a light yellow-brown film, trifluoroacetic acid salt.

LCMS m/z [M+H]$^+$ $C_{25}H_{33}N_7O_3S$ requires: 512.24. Found 512.27.

$^1$H-NMR (MeOD, 400 MHz): δ 8.28 (s, 1H), 7.86 (s, 1H), 7.41-7.22 (m, 2H), 7.33 (s, 2H), 6.15 (s, 1H), 4.00 (m, 3H), 3.82 (m, 2H), 3.58 (m, 1H), 3.17 (m, 1H), 3.02 (s, 3H), 3.00 (m, 1H), 2.66 (s, 3H), 2.58-2.32 (m, 4H), 2.40 (s, 3H), 2.19 (m, 2H), 1.85 (m, 1H), 1.78-1.58 (m, 2H).

HPLC Tr (min), purity %: 4.30, 94%

Example 231: Preparation of Compound 116

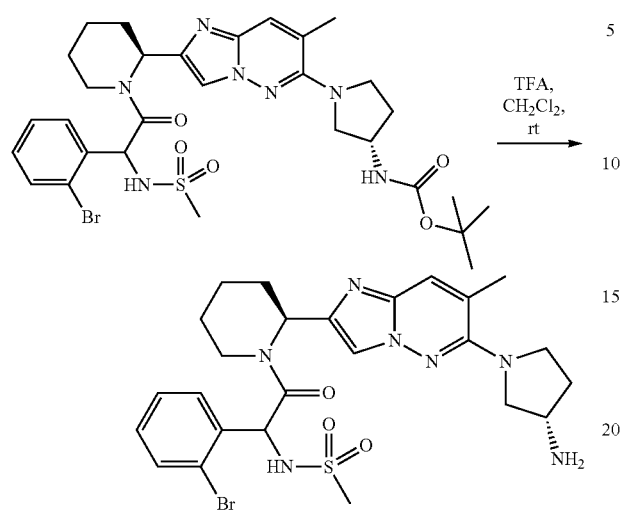

Following the procedure used to prepare compound 107, but beginning with intermediate 89 (11 mg, 0.049 mmol), compound 116 (10.6 mg, 94%) was recovered as a light yellow film, trifluoroacetic acid salt.

LCMS m/z [M+H]+ $C_{25}H_{32}BrN_7O_3S$ requires: 590.15. Found 590.48.

HPLC Tr (min), purity %: 4.84, 95%

Example 232: Preparation of Compound 117

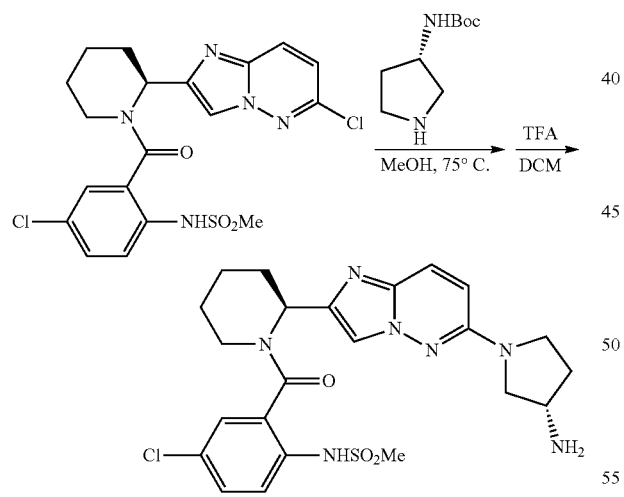

Intermediate 65 (20 mg, 0.043 mmol) and (S)-tert-butyl pyrrolidin-3-ylcarbamate (240 mg, 1.29 mmol) were mixed in 2 mL of anhydrous methanol. Mixture was heated at 75° C. for 3 days. After cooling to room temperature, reaction mixture was concentrated under reduced pressure and residue was dissolved in dichloromethane (1 mL) and TFA (0.1 mL, 1.30 mmol) was added to the solution. The reaction mixture was stirred for two hours and solvent was concentrated under reduced pressure. The residue was purified by prep HPLC (15-100% Acetonitrile (with 0.1% trifluoroacetic acid) in water (with 0.1% trifluoroacetic acid)) to yield compound 117 (10 mg, 45%) as a solid, trifluoroacetic acid salt, after lyophilization.

LCMS m/z [M+H]+ $C_{23}H_{28}ClN_7O_3S$ requires: 518.17. Found 518.22.

$^1$H-NMR (DMSO, 400 MHz): δ 8.01 (d, J=9.2 Hz, 1H), 7.83 (s, 1H), 7.49-7.37 (m, 3H), 6.91 (bs, 1H), 6.04 (s, 1H), 3.99 (s, 2H), 3.75-3.66 (m, 2H), 3.60 (m, 2H), 2.89 (s, 3H), 2.43-2.40 (m, 2H), 2.31-2.13 (m, 2H), 1.89 (bs, 2H), 1.68 (m, 2H), 1.49 (s, 2H).

HPLC Tr (min), purity %: 2.26, 85%

Example 233: Preparation of Compound 118

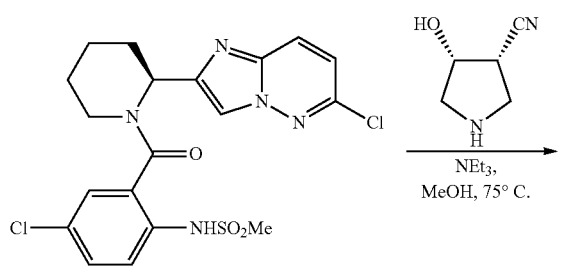

Intermediate 65 (20 mg, 0.043 mmol) and (3S,4R)-4-hydroxypyrrolidine-3-carbonitrile (120 mg, 1.08 mmol) were mixed in 2 mL of anhydrous methanol. To the mixture was added triethylamine (0.12 mL, 0.868 mmol) and the reaction mixture was heated at 75° C. for 5 days. After cooling to room temperature, reaction mixture was concentrated under reduced pressure and residue was purified by prep HPLC (15-100% Acetonitrile (with 0.1% trifluoroacetic acid) in water (with 0.1% trifluoroacetic acid)) to yield compound 118 (10 mg, 45%) as a solid, trifluoroacetic acid salt, after lyophilization.

LCMS m/z [M+H]+ $C_{24}H_{26}ClN_7O_4S$ requires: 544.15. Found 544.21.

$^1$H-NMR (DMSO, 400 MHz): δ 8.20 (s, 1H), 8.15 (s, 1H), 7.52-7.46 (m, 4H), 6.15 (s, 1H), 4.10-3.95 (m, 2H), 3.81-3.62 (m, 4H), 3.61-3.45 (m, 4H), 3.02 (s, 3H), 1.81 (bs, 2H), 1.66 (bs, 3H).

HPLC Tr (min), purity %: 2.07, 90%

Example 234: Preparation of Compound 119

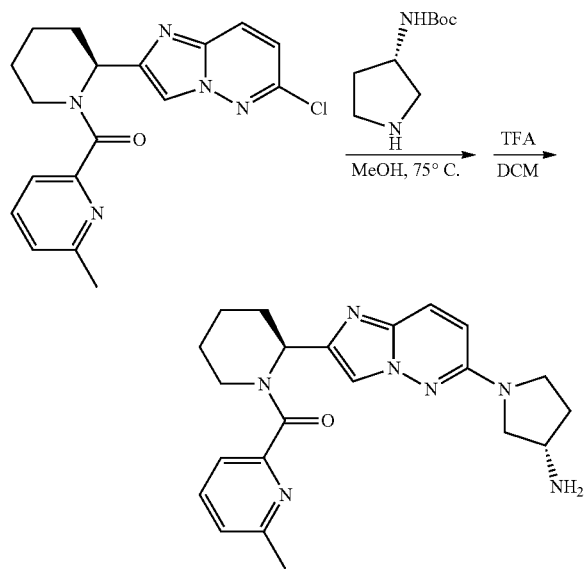

Intermediate 91 (12 mg, 0.034 mmol) and (S)-tert-butyl pyrrolidin-3-ylcarbamate (375 mg, 2.04 mmol) were mixed in 2 mL of anhydrous methanol. Mixture was heated at 75° C. for 5 days. After cooling to room temperature, reaction mixture was concentrated under reduced pressure and residue was dissolved in dichloromethane (1 mL) and TFA (0.1 mL, 1.30 mmol) was added to the solution. The reaction mixture was stirred for two hours and solvent was concentrated under reduced pressure. The residue was purified by prep HPLC (15-100% Acetonitrile (with 0.1% trifluoroacetic acid) in water (with 0.1% trifluoroacetic acid)) to yield compound 119 (8 mg, 56%) as a solid, trifluoroacetic acid salt, after lyophilization.

LCMS m/z [M+H]$^+$ C$_{22}$H$_{27}$N$_7$O requires: 406.23. Found 406.30.

$^1$H-NMR (DMSO, 400 MHz): δ 8.31 (s, 1H), 8.09-8.04 (m, 1H), 7.96-7.88 (m, 1H), 7.61-7.30 (m, 3H), 6.22 (s, 1H), 4.12 (s, 1H), 3.95-3.90 (m, 1H), 3.85-3.66 (m, 4H), 2.60 (s, 3H), 2.55-2.42 (m, 3H), 2.15-2.00 (m, 2H), 1.83-1.60 (m, 5H).

HPLC Tr (min), purity %: 1.52, 90%

Example 235: Preparation of Compound 120

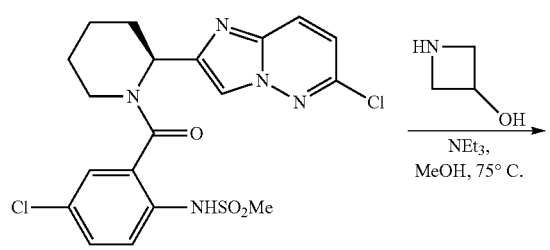

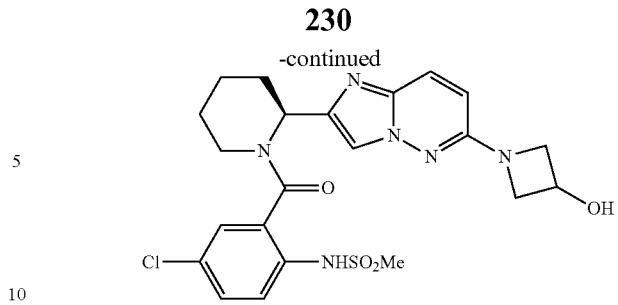

Intermediate 65 (20 mg, 0.043 mmol) and 3-hydroxyazetidine (46 mg, 0.43 mmol) were mixed in 2 mL of anhydrous methanol. To the solution was added triethylamine (0.24 mL, 1.72 mmol). Mixture was heated at 75° C. for 2 days. After cooling to room temperature, reaction mixture was concentrated under reduced pressure and the residue was purified by prep HPLC (15-100% Acetonitrile (with 0.1% trifluoroacetic acid) in water (with 0.1% trifluoroacetic acid)) to yield compound 120 (7 mg, 47%) as a solid, trifluoroacetic acid salt, after lyophilization. LCMS m/z [M+H]$^+$ C$_{22}$H$_{25}$ClN$_6$O$_4$S requires: 505.13. Found 505.19.

$^1$H-NMR (DMSO, 400 MHz): δ 7.95 (s, 1H), 7.76-7.44 (m, 1H), 7.33 (m, 3H), 6.59-6.50 (m, 1H), 6.03 (s, 1H), 4.64-4.59 (m, 2H), 4.23-4.19 (m, 2H), 3.78-3.75 (m, 2H), 2.90 (s, 3H), 2.43-2.16 (m, 2H), 1.94-1.44 (m, 6H).

HPLC Tr (min), purity %: 2.02, 95%

Example 236: Preparation of Compound 121

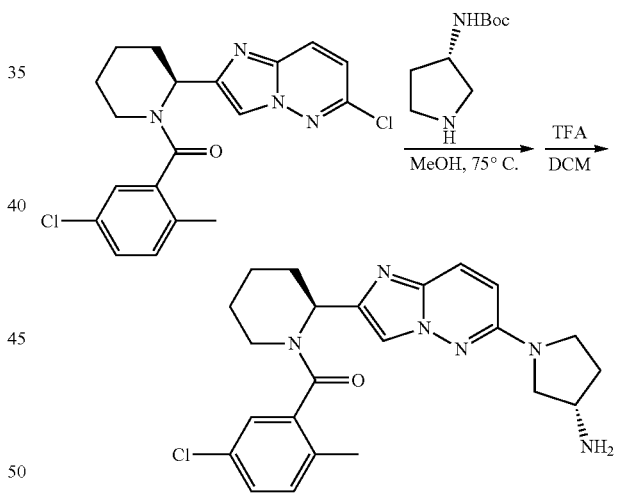

Intermediate 92 (14 mg, 0.036 mmol) and (S)-tert-butyl pyrrolidin-3-ylcarbamate (375 mg, 2.04 mmol) were mixed in 2 mL of anhydrous methanol. Mixture was heated at 75° C. for 5 days. After cooling to room temperature, reaction mixture was concentrated under reduced pressure and residue was dissolved in dichloromethane (1 mL) and TFA (0.1 mL, 1.30 mmol) was added to the solution. The reaction mixture was stirred for two hours and solvent was concentrated under reduced pressure. The residue was purified by prep HPLC (15-100% Acetonitrile (with 0.1% trifluoroacetic acid) in water (with 0.1% trifluoroacetic acid)) to yield compound 121 (12 mg, 73%) as a solid, trifluoroacetic acid salt, after lyophilization.

LCMS m/z [M+H]$^+$ C$_{23}$H$_{27}$ClN$_6$O requires: 439.19. Found 439.30.

¹H-NMR (DMSO, 400 MHz): δ 7.90-7.61 (m, 2H), 7.38-7.19 (m, 3H), 7.02-6.10 (m, 1H), 6.10 (s, 1H), 4.00 (s, 1H), 3.78-3.59 (m, 5H), 2.28 (s, 3H), 2.20-2.05 (m, 2H), 1.93-1.80 (m, 2H), 1.70-1.50 (m, 6H).

HPLC Tr (min), purity %: 1.71, 90%

Example 237: Preparation of Compound 122

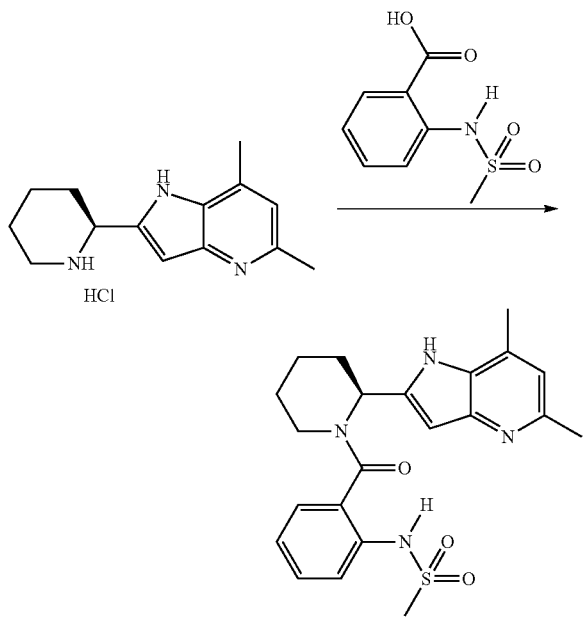

PyBOP (223 mg, 0.78 mmol) was added to a suspension of 2-(methylsulfonamido)benzoic acid (150 mg, 0.69 mmol) in 2 mL of DMF at room temperature. After 30 minutes, intermediate 94 (150 mg, 0.65 mmol) was added, followed by triethylamine until pH was >9. After stirring under nitrogen for 3 hours, volatiles were removed under reduced pressure. The residue was dissolved in MeCN/water and purified by preparatory HPLC (5-95% H₂O/MeCN, 0.1% TFA) to afford compound 122 (154 mg, 54%) as a colorless powder.

¹H NMR (CDCl₃, 400 MHz): δ 9.07 (s, 1H), 7.31-7.23 (m, 5H), 6.85 (s, 1H), 4.93 (s, 1H), 3.31 (m, 5H), 2.98 (s, 3H), 2.29 (s, 3H), 2.08-1.53 (m, 6H).

LCMS m/z [M+H]⁺ 441.12

HPLC Tr (min), purity %: 2.11, 98%

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-virus activity of a compound of the invention after application of the composition can be observed by any method including direct and indirect methods of detecting such activity. Quantitative, qualitative, and semi-quantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Respiratory Syncytial Virus (RSV) Antiviral Activity and Cytotoxicity Assays

Anti-RSV Activity

Antiviral activity against RSV was determined using an in vitro cytoprotection assay in Hep2 cells. In this assay, compounds inhibiting the virus replication exhibit cytoprotective effect against the virus-induced cell killing were quantified using a cell viability reagent. The method used was similar to methods previously described in published literature (Chapman et al., *Antimicrob Agents Chemother.* 2007, 51(9):3346-53.)

Hep2 cells were obtained from ATCC (Manassas, Va.) and maintained in MEM media supplemented with 10% fetal bovine serum and penicillin/streptomycin. Cells were passaged twice a week and kept at subconfluent stage. Commercial stock of RSV strain A2 (Advanced Biotechnologies, Columbia, Md.) was titered before compound testing to determine the appropriate dilution of the virus stock that generated desirable cytopathic effect in Hep2 cells.

For antiviral tests, Hep2 cells were seeded into 96-well plates 24 hours before the assay at a density of 3,000 cells/well. On a separate 96 well plate, compounds to be tested were serially diluted in cell culture media. Eight concentrations in 3-fold serial dilution increments were prepared for each tested compound and 100 uL/well of each dilution was transferred in duplicate onto plates with seeded Hep2 cells. Subsequently, appropriate dilution of virus stock previously determined by titration was prepared in cell culture media and 100 uL/well was added to test plates containing cells and serially diluted compounds. Each plate included three wells of infected untreated cells and three wells of uninfected cells that served as 0% and 100% virus inhibition control, respectively. Following the infection with RSV, testing plates were incubated for 4 days in a tissue culture incubator. After the incubation, RSV-induced cytopathic effect was determined using a Cell TiterGlo reagent (Promega, Madison, Wis.) followed by a luminescence read-out. The percentage inhibition was calculated for each tested concentration relative to the 0% and 100% inhibition controls and the EC50 value for each compound was determined by non-linear regression as a concentration inhibiting the RSV-induced cytopathic effect by 50%. Ribavirin (purchased from Sigma, St. Louis, Mo.) was used as a positive control for antiviral activity.

Compounds were also tested for antiviral activity against RSV in Hep2 cells using a 384 well format. Compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616)

containing 20 µL of media (Mediatech Inc. MEM supplemented with Glutamine, 10% FBS and Pen/Strep). DMSO and a suitable positive control compound, such as 80 µM GS-329467 or 10 µM 427346 was used for the 100% and 0% cell killing controls, respectively.

Hep2 cells ($1.0 \times 10^5$ cells/ml) were prepared as above in batch to at least 40 mls excess of the number of sample plates (8 mls cell mix per plate) and infected with vendor supplied (ABI) RSV strain A2 to arrive at an MOI of 1:1000 (virus:cell #) or 1:3000 (vol virus:cell vol). Immediately after addition of virus, the RSV infected Hep2 cell suspension was added to each stamped 384-well plate at 20 µl per well using a uFlow dispenser, giving a final volume of 40 µL/well, each with 2000 infected cells. The plates were then incubated for 5 days at 37° C. and 5% $CO_2$. Following incubation, the plates were equilibrated to room temperature in a biosafety cabinet hood for 1.5 hrs and 40 µL of Cell-Titer Glo viability reagent (Promega) was added to each well via uFlow. Following a 10-20 minute incubation, the plates were read using an EnVision or Victor Luminescence plate reader (Perkin-Elmer). The data was then uploaded and analyzed on the Bioinformatics portal under the RSV Cell Infectivity and 8-plate EC50-Hep2-384 or 8-plate EC50-Hep2-Envision protocols.

Multiple point data generated in the assay was analysed using Pipeline Pilot (Accelrys, Inc., Version 7.0) to generate a dose response curve based on least squares fit to a 4-parameter curve. The generated formula for the curve was then used to calculate the % inhibition at a given concentration. The % inhibition reported in the table was then adjusted based on the normalization of the bottom and top of the curve % inhibition values to 0% and 100% respectively.

Representative activities for compounds disclosed herein against RSV-induced cytopathic effects are shown in the Table below.

| Compound formula | Percent inhibition at 0.5 µM |
|---|---|
| 1 | 95 |
| 2 | 97 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 98 |
| 14 | 97 |
| 15 | 92 |
| 16 | 100 |
| 17 | 96 |
| 18 | 100 |
| 19 | 100 |
| 20 | 100 |
| 21 | 100 |
| 22 | 100 |
| 23 | 100 |
| 24 | 91 |
| 25 | 97 |
| 26 | 97 |
| 27 | 100 |
| 28 | 100 |
| 29 | 90 |
| 30 | 91 |
| 31 | 86 |
| 32 | 85 |
| 33 | 100 |
| 34 | 100 |
| 35 | 100 |
| 36 | 100 |
| 37 | 100 |
| 38 | 100 |
| 39 | 99 |
| 40 | 100 |
| 41 | 100 |
| 42 | 100 |
| 43 | 100 |
| 44 | 100 |
| 45 | 100 |
| 46 | 97 |
| 47 | 99 |
| 48 | 93 |
| 49 | 94 |
| 50 | 100 |
| 51 | 100 |
| 52 | 99 |
| 53 | 99 |
| 54 | 98 |
| 55 | 98 |
| 56 | 93 |
| 57 | 93 |
| 58 | 89 |
| 59 | 92 |
| 60 | 87 |
| 61 | 100 |
| 62 | 100 |
| 63 | 100 |
| 64 | 100 |
| 65 | 100 |
| 66 | 100 |
| 67 | 99 |
| 68 | 100 |
| 69 | 99 |
| 70 | 100 |
| 71 | 100 |
| 72 | 100 |
| 73 | 100 |
| 74 | 97 |
| 75 | 100 |
| 76 | 99 |
| 77 | 94 |
| 78 | 99 |
| 79 | 100 |
| 80 | 99 |
| 81 | 100 |
| 82 | 97 |
| 83 | 100 |
| 84 | 95 |
| 85 | 86 |
| 86 | 84 |
| 87 | 89 |
| 88 | 89 |
| 89 | 90 |
| 90 | 100 |
| 91 | 91 |
| 92 | 98 |
| 93 | 56 |
| 94 | 89 |
| 95 | 99 |
| 96 | 90 |
| 97 | 97 |
| 98 | 100 |
| 99 | 100 |
| 100 | 100 |
| 101 | 100 |
| 102 | 99 |
| 103 | 27 |
| 104 | 3 |
| 105 | 96 |
| 106 | 100 |
| 107 | 100 |
| 108 | 100 |
| 109 | 64 |

-continued

| Compound formula | Percent inhibition at 0.5 μM |
|---|---|
| 110 | 60 |
| 111 | 56 |
| 112 | 5 |
| 113 | 16 |
| 114 | 100 |
| 115 | 100 |
| 116 | 100 |
| 117 | 100 |
| 118 | 100 |
| 119 | 83 |
| 120 | 100 |
| 121 | 100 |
| 122 | 15 |

Cytotoxicity

Cytotoxicity of tested compounds was determined in uninfected Hep2 cells in parallel with the antiviral activity using the cell viability reagent in a similar fashion as described before for other cell types (Cihlar et al., *Antimicrob Agents Chemother.* 2008, 52(2):655-65.). The same protocol as for the determination of antiviral activity was used for the measurement of compound cytotoxicity except that the cells were not infected with RSV. Instead, fresh cell culture media (100 uL/well) without the virus was added to tested plates with cells and prediluted compounds. Cells were then incubated for 4 days followed by a cell viability test using CellTiter Glo reagent and a luminescence readout. Untreated cell and cells treated with 50 ug/mL puromycin (Sigma, St. Louis, Mo.) were used as 100% and 0% cell viability control, respectively. The percent of cell viability was calculated for each tested compound concentration relative to the 0% and 100% controls and the CC50 value was determined by non-linear regression as a compound concentration reducing the cell viability by 50%.

To test for compound cytotoxicity in Hep2 cells using a 384 well format, compounds were diluted in DMSO using a 10-step serial dilution in 3-fold increments via automation in 4 adjacent replicates each. Eight compounds were tested per dilution plate. 0.4 uL of diluted compounds were then stamped via Biomek into 384-well plates (Nunc 142761 or 164730 w/lid 264616) containing 20 μL of media (Mediatech Inc. MEM supplemented with Glutamine, 10% FBS and Pen/Strep). 50 μg/mL puromycin and DMSO were used for the 100% and 0% cytotoxicity controls, respectively.

Hep2 cells ($1.0\times10^5$ cells/ml) were added to each stamped plate at 20 ul per well to give a total of 2000 cells/well and a final volume of 40 μL/well. Usually, the cells were batch prediluted to $1.0\times10^5$ cells/mL in excess of the number of sample plates and added at 20 ul per well into each assay plate using a uFlow dispenser. The plates were then incubated for 4 days at 37° C. and 5% $CO_2$. Following incubation, the plates were equilibrated to room temperature in a biosafety cabinet hood for 1.5 hrs and 40 μL of Cell-Titer Glo viability reagent (Promega) was added to each well via uFlow. Following a 10-20 minute incubation, the plates were read using an EnVision or Victor Luminescence plate reader (Perkin-Elmer). The data was then uploaded and analyzed on the Bioinformatics portal (Pipeline Pilot) under the Cytotoxicity assay using the 8-plate CC50-Hep2 or 8-plate CC50-Hep2 Envision protocols.

All publications, patents, and patent documents cited herein above are incorporated by reference herein, as though individually incorporated by reference. The invention has been described with reference to various specific and preferred embodiments and techniques. However, one skilled in the art will understand that many variations and modifications may be made while remaining within the spirit and scope of the invention.

What is claimed is:
1. A compound of Formula Ij:

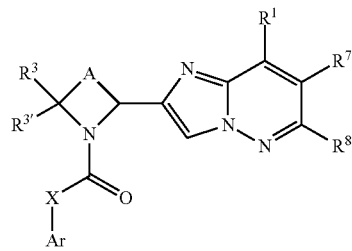

or a pharmaceutically acceptable salt thereof;
wherein:
A is $-(CR^4R^{4'})_n-$;
n is 3, 4, 5 or 6;
each p is 1 or 2;
Ar is a $C_6$-$C_{20}$ aryl group, wherein the $C_6$-$C_{20}$ aryl group is optionally substituted with 1 to 5 $R^6$;
X is $-C(R^{13})(R^{14})-$, $-N(CH_2R^{14})-$ or $-NH-$, or X is absent;
$R^1$ is H, $-OR^{11}$, $-NR^{11}R^{12}$, $-NR^{11}C(O)R^{11}$, $-NR^{11}C(O)OR^{11}$, $-NR^{11}C(O)NR^{11}R^{12}$, $N_3$, CN, $NO_2$, $-SR^{11}$, $-S(O)_pR^a$, $NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $-NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl($C_1$-$C_8)$alkyl, $C_6$-$C_{20}$ aryl, $C_2$-$C_{20}$ heterocyclyl, $C_2$-$C_{20}$ heterocyclyl($C_1$-$C_8$)alkyl, $(C_3$-$C_7)$cycloalkyl or $(C_3$-$C_7)$cycloalkyl($C_1$-$C_8$)alkyl;
$R^3$ is H, $-OR^{11}$, $-NR^{11}R^{12}$, $-NR^{11}C(O)R^{11}$, $-NR^{11}C(O)OR^{11}$, $-NR^{11}C(O)NR^{11}R^{12}$, $N_3$, CN, $NO_2$, $-SR^{11}$, $-S(O)_pR^a$, $-NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $-NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, $(C_3$-$C_7)$cycloalkyl or $(C_3$-$C_7)$cycloalkyl($C_1$-$C_8$)alkyl;
$R^{3'}$ is H, $-OR^{11}$, $(C_1$-$C_8)$alkyl, $(C_2$-$C_8)$alkenyl, $(C_2$-$C_8)$alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, $(C_3$-$C_7)$cycloalkyl or $(C_3$-$C_7)$cycloalkyl($C_1$-$C_8$)alkyl;
each $R^4$ is independently H, $-OR^{11}$, $-NR^{11}R^{12}$, $-NR^{11}C(O)R^{11}$, $-NR^{11}C(O)OR^{11}$, $-NR^{11}C(O)NR^{11}R^{12}$, $N_3$, CN, $NO_2$, $SR^{11}$, $-S(O)_pR^a$, $-NR^{11}S(O)_pR^a$, $-C(=O)R^{11}$, $-C(=O)OR^{11}$, $-C(=O)NR^{11}R^{12}$, $-C(=O)SR^{11}$, $-S(O)_p(OR^{11})$, $-SO_2NR^{11}R^{12}$, $-NR^{11}S(O)_p(OR^{11})$, $-NR^{11}SO_pNR^{11}R^{12}$, $NR^{11}C(=NR^{11})NR^{11}R^{12}$, halogen, $(C_1$-$C_8)$alkyl, $(C_2$-$C_8)$alkenyl, $(C_2$-$C_8)$alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, $(C_3$-$C_7)$cycloalkyl or $(C_3$-$C_7)$cycloalkyl($C_1$-$C_8$)alkyl; and
each $R^{4'}$ is independently H, $OR^{11}$, $(C_1$-$C_8)$alkyl, $(C_2$-$C_8)$alkenyl, $(C_2$-$C_8)$alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

or two $R^4$ on adjacent carbon atoms, when taken together, may form a double bond between the two carbons to which they are attached or may form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —NR$^a$—;

or two $R^4$ on non-adjacent carbon atoms, when taken together, may form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —NR$^a$—;

or two $R^4$ and two $R^{4'}$ on adjacent carbon atoms, when taken together, may form an optionally substituted $C_6$ aryl ring;

or one $R^4$ and one $R^{4'}$ on the same carbon atom, when taken together, may form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —NR$^a$—;

each $R^5$ is independently
H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$ R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

each $R^{5'}$ is independently H, —OR$^{11}$, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

each $R^6$ is independently H,
oxo, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$ R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, —NR$^{11}$C(=NR$^{11}$)NR$^{11}$R$^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

or two $R^6$ on adjacent carbon atoms, when taken together, may form a ($C_3$-$C_7$)cycloalkyl ring wherein one carbon atom of said ($C_3$-$C_7$)cycloalkyl ring may be optionally replaced by —O—, —S—, —S(O)$_p$—, —NH— or —NR$^a$—;

or any $R^6$ adjacent to the obligate carbonyl group of said Ar, when taken together with $R^3$, may form a bond or a —(CR$^5$R$^{5'}$)$_m$— group wherein m is 1 or 2;

or any $R^6$ adjacent to the obligate carbonyl group of said Ar, when taken together with $R^2$ or $R^{2'}$ may form a bond;

$R^7$ is H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$S(O)$_p$NR$^{11}$R$^{12}$, —NR$^{11}$C(=NR$^{11}$)NR$^{11}$R$^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

$R^8$ is H, —OR$^{11}$, —NR$^{11}$R$^{12}$, —NR$^{11}$C(O)R$^{11}$, —NR$^{11}$C(O)OR$^{11}$, —NR$^{11}$C(O)NR$^{11}$R$^{12}$, N$_3$, CN, NO$_2$, —SR$^{11}$, —S(O)$_p$R$^a$, —NR$^{11}$S(O)$_p$R$^a$, —C(=O)R$^{11}$, —C(=O)OR$^{11}$, —C(=O)NR$^{11}$R$^{12}$, —C(=O)SR$^{11}$, —S(O)$_p$(OR$^{11}$), —SO$_2$NR$^{11}$R$^{12}$, —NR$^{11}$S(O)$_p$(OR$^{11}$), —NR$^{11}$SO$_p$NR$^{11}$R$^{12}$, NR$^{11}$C(=NR$^{11}$)NR$^{11}$R$^{12}$, halogen, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl;

each $R^a$ is independently ($C_1$-$C_8$)alkyl, ($C_1$-$C_8$)haloalkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl wherein any ($C_1$-$C_8$)alkyl, ($C_1$-$C_8$)haloalkyl, ($C_2$-$C_8$)alkenyl or ($C_2$-$C_8$)alkynyl of $R^a$ is optionally substituted with one or more OH, NH$_2$, CO$_2$H, $C_2$-$C_{20}$ heterocyclyl, and wherein any aryl($C_1$-$C_8$)alkyl, $C_6$-$C_{20}$ aryl, $C_2$-$C_{20}$ heterocyclyl, ($C_3$-$C_7$)cycloalkyl or ($C_3$-$C_7$)cycloalkyl($C_1$-$C_8$)alkyl of $R^a$ is optionally substituted with one or more —OH, —NH$_2$, CO$_2$H, $C_2$-$C_{20}$ heterocyclyl or ($C_1$-$C_8$)alkyl;

each $R^{11}$ or $R^{12}$ is independently H, ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, ($C_3$-$C_7$)cycloalkyl, ($C_3$-$C_7$)cycloalkyl($C_1$-$C_8$)alkyl, —C(=O)R$^a$ or —S(O)$_p$R$^a$; or when $R^{11}$ and $R^{12}$ are attached to a nitrogen they may optionally be taken together with the nitrogen to which they are both attached to form a 3 to 7 membered heterocyclic ring wherein any one carbon atom of said heterocyclic ring can optionally be replaced with —O—, —S—, —S(O)$_p$—, —NH—, —NR$^a$— or —C(O)—;

$R^{13}$ is H or ($C_1$-$C_8$)alkyl;

$R^{14}$ is H, ($C_1$-$C_8$)alkyl, NR$^{11}$R$^{12}$, NR$^{11}$C(O)R$^{11}$, NR$^{11}$C(O)OR$^{11}$, NR$^{11}$C(O)NR$^{11}$R$^{12}$, NR$^{11}$S(O)$_p$R$^a$, —NR$^{11}$S(O)$_p$(OR$^{11}$) or NR$^{11}$SO$_p$NR$^{11}$R$^{12}$; and wherein each ($C_1$-$C_8$)alkyl, ($C_2$-$C_8$)alkenyl, ($C_2$-$C_8$)alkynyl, aryl($C_1$-$C_8$)alkyl, $C_6$-$C_{20}$ aryl, $C_2$-$C_{20}$ heterocyclyl, $C_2$-$C_{20}$ heterocyclyl($C_1$-$C_8$)alkyl, ($C_3$-$C_7$)cycloalkyl or ($C_3$-$C_7$)cycloalkyl($C_1$-$C_8$)alkyl of each $R^1$, $R^2$, $R^{2'}$, $R^3$, $R^{3'}$, $R^4$, $R^{4'}$, $R^5$, $R^{5'}$, $R^6$, $R^7$, $R^8$, $R^{8'}$, $R^{11}$ or $R^{12}$ is independently, optionally substituted with one or more oxo, halogen, hydroxy, —NH$_2$, CN, N$_3$, —N(R$^a$)$_2$, —NHR$^a$, —SH, —SR$^a$, —S(O)$_p$R$^a$, —OR$^a$, ($C_1$-$C_8$)alkyl, ($C_1$-$C_8$)haloalkyl, —C(O)R$^a$, —C(O)H, —C(=O)OR$^a$, —C(=O)OH, —C(=O)N(R$^a$)$_2$, —C(=O)NHR$^a$, —C(=O)NH$_2$, —NHS(O)$_p$R$^a$, —NR$^a$S(O)$_p$R$^a$, —NHC(O)R$^a$, —NR$^a$C(O)R$^a$, —NHC(O)OR$^a$, —NR$^a$C(O)OR$^a$, —NR$^a$C(O)NHR$^a$, —NR$^a$C(O)N(R$^a$)$_2$, —NR$^a$C(O)NH$_2$, —NHC(O)NHR$^a$, —NHC(O)N(R$^a$)$_2$, —NHC(O)NH$_2$, —NH, =NOH, =NOR$^a$, —NR$^a$S(O)$_p$NHR$^a$, —NR$^a$S(O)$_p$N(R$^a$)$_2$, —NR$^a$S(O)$_p$NH$_2$, —NHS(O)$_p$NHR$^a$, —NHS(O)$_p$N(R$^a$)$_2$, —NHS(O)$_p$NH$_2$, —OC(=O)R$^a$, —OP(O)(OH)$_2$ or R$^a$.

2. The compound of claim 1, wherein the compound of Formula Ij is a compound of Formula Ik:

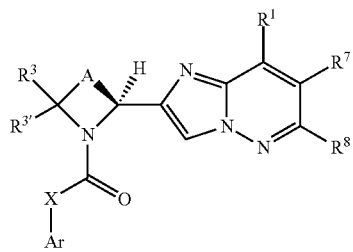

or a pharmaceutically acceptable salt thereof.

3. The compound of claim 1, wherein $R^3$ and $R^{3'}$ are each H, or a pharmaceutically acceptable salt thereof.

4. The compound of claim 1, wherein n is 3, or a pharmaceutically acceptable salt thereof.

5. The compound of claim 1, wherein each $R^4$ and each $R^{4'}$ is H, or a pharmaceutically acceptable salt thereof.

6. The compound of claim 1, wherein A is —$(CH_2)_3$—, or a pharmaceutically acceptable salt thereof.

7. The compound of claim 1, wherein the compound of Formula Ij is a compound of Formula Im:

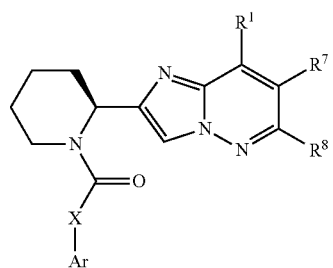

or a pharmaceutically acceptable salt thereof.

8. The compound of claim 1, wherein $R^8$ is a $C_2$-$C_{20}$ heterocyclyl optionally substituted with one of hydroxyl, —$NH_2$, or CN, or a pharmaceutically acceptable salt thereof.

9. The compound of claim 7, wherein R is a $C_2$-$C_{20}$ heterocyclyl, optionally substituted with one of hydroxyl, —$NH_2$, or CN, or a pharmaceutically acceptable salt thereof.

10. The compound of claim 1, wherein $R^1$ is H or $(C_1$-$C_8)$alkyl, or a pharmaceutically acceptable salt thereof.

11. The compound of claim 7, wherein R is H or $(C_1$-$C_8)$ alkyl, or a pharmaceutically acceptable salt thereof.

12. The compound of claim 1, wherein $R^7$ is H or $(C_1$-$C_8)$alkyl, or a pharmaceutically acceptable salt thereof.

13. The compound of claim 7, wherein $R^7$ is H or $(C_1$-$C_8)$alkyl, or a pharmaceutically acceptable salt thereof.

14. The compound of claim 1, wherein X is absent.

15. The compound of claim 7, wherein X is absent, or a pharmaceutically acceptable salt thereof.

16. A compound selected from:

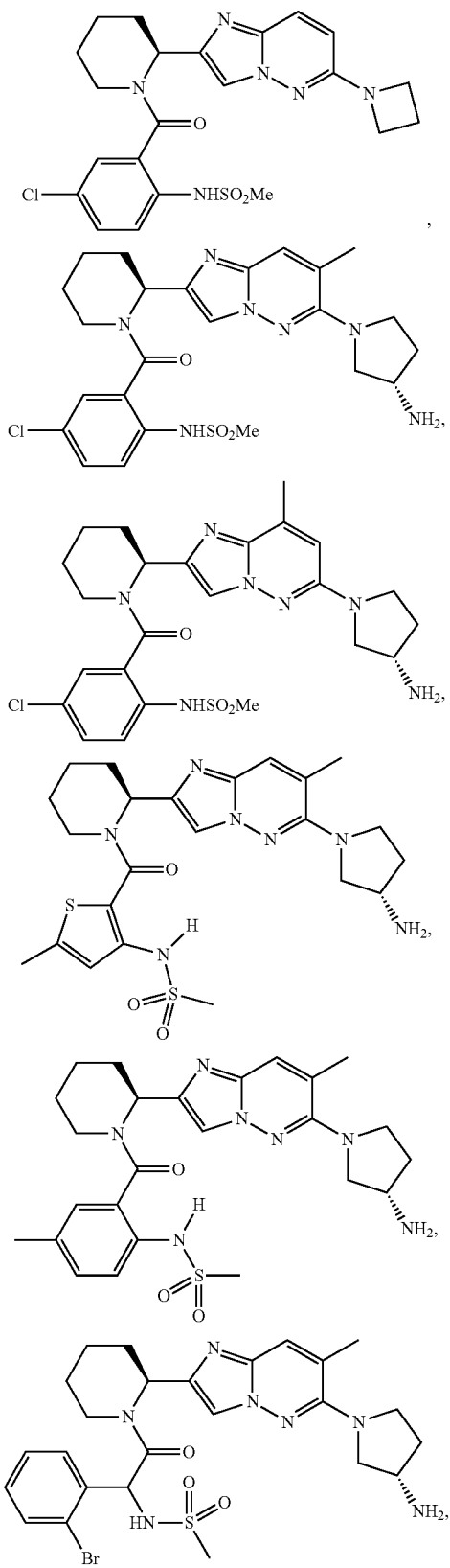

241

-continued

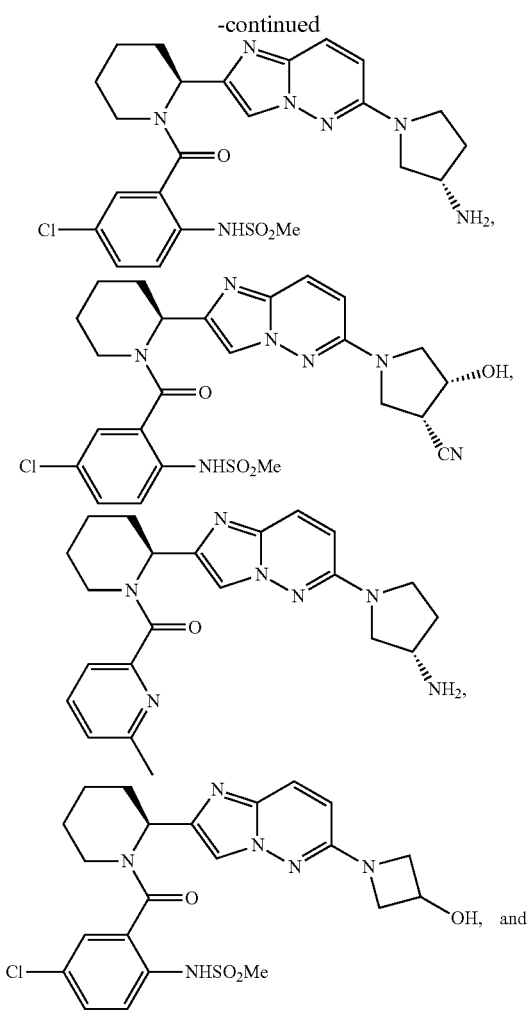

242

-continued

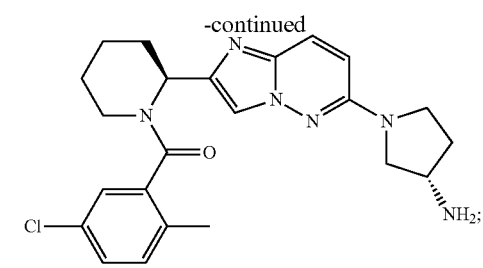

or a pharmaceutically acceptable salt thereof.

17. A pharmaceutical composition comprising a therapeutically effective amount of a compound as described in claim 1 or a pharmaceutically acceptable salt thereof and a pharmaceutically acceptable carrier.

18. A method of treating a Pneumovirinae virus infection in a mammal in need thereof comprising administering to the mammal a therapeutically effective amount of a compound as described in claim 1, or a pharmaceutically acceptable salt thereof.

19. A pharmaceutical composition comprising a therapeutically effective amount of a compound as described in claim 16 or a pharmaceutically acceptable salt thereof and a pharmaceutically acceptable carrier.

20. The method of claim 18, wherein the Pneumovirinae virus infection is a respiratory syncytial virus infection.

* * * * *